(12) United States Patent
Salas et al.

(10) Patent No.: US 10,364,288 B2
(45) Date of Patent: Jul. 30, 2019

(54) ANTI-GPIIB/IIIA ANTIBODIES OR USES THEREOF

(71) Applicant: Biogen MA Inc., Cambridge, MA (US)

(72) Inventors: Joe Salas, Wayland, MA (US); Siyuan Tan, Lexington, MA (US); Robert Peters, Needham, MA (US)

(73) Assignee: Biogen MA Inc., Cambridge, MA (US)

( * ) Notice: Subject to any disclaimer, the term of this patent is extended or adjusted under 35 U.S.C. 154(b) by 598 days.

(21) Appl. No.: 14/890,653

(22) PCT Filed: May 23, 2014

(86) PCT No.: PCT/US2014/039420
§ 371 (c)(1),
(2) Date: Nov. 12, 2015

(87) PCT Pub. No.: WO2014/190305
PCT Pub. Date: Nov. 27, 2014

(65) Prior Publication Data
US 2016/0115234 A1    Apr. 28, 2016

Related U.S. Application Data

(60) Provisional application No. 61/827,165, filed on May 24, 2013.

(51) Int. Cl.
| | | |
|---|---|---|
| A61K 39/395 | (2006.01) | |
| C07K 16/28 | (2006.01) | |
| C12N 9/64 | (2006.01) | |
| C07K 14/755 | (2006.01) | |

(52) U.S. Cl.
CPC ........ *C07K 16/2848* (2013.01); *C07K 14/755* (2013.01); *C12N 9/6408* (2013.01); *C12N 9/6437* (2013.01); *C12Y 304/21021* (2013.01); *C07K 2317/24* (2013.01); *C07K 2317/565* (2013.01); *C07K 2317/92* (2013.01); *C07K 2319/33* (2013.01)

(58) Field of Classification Search
None
See application file for complete search history.

(56) References Cited

U.S. PATENT DOCUMENTS

| | | | |
|---|---|---|---|
| 9,365,650 | B2 | 6/2016 | Peter |
| 9,702,879 | B2 * | 7/2017 | Barneo Serra ......... C07K 16/18 |
| 2002/0009753 | A1 * | 1/2002 | Bednar .............. C07K 16/2848 435/7.1 |
| 2010/0135991 | A1 | 6/2010 | Huang et al. |
| 2011/0045008 | A1 | 2/2011 | Karpatkin et al. |
| 2011/0165175 | A1 | 7/2011 | Linhard et al. |
| 2013/0108629 | A1 | 5/2013 | Dumont et al. |
| 2014/0243502 | A1 | 8/2014 | Peter |
| 2017/0342152 | A1 | 11/2017 | Pearse et al. |
| 2017/0355771 | A1 | 12/2017 | Salas et al. |

FOREIGN PATENT DOCUMENTS

| | | |
|---|---|---|
| EP | 2025685 | 2/2009 |
| WO | 99/19463 | 4/1999 |
| WO | 2004005890 | 4/2004 |
| WO | 2009140593 | 11/2009 |
| WO | WO 2009/140598 | 11/2009 |
| WO | 2010/091122 | 8/2010 |
| WO | 2010115866 | 10/2010 |
| WO | 2011/112549 | 9/2011 |
| WO | 2012/006633 | 1/2012 |
| WO | 2012/078813 | 6/2012 |
| WO | 2012/170969 | 12/2012 |
| WO | 2013/016454 | 1/2013 |
| WO | 2013016454 | 1/2013 |
| WO | 2014/194282 | 12/2014 |
| WO | 2016065301 | 4/2016 |
| WO | 2016070050 | 5/2016 |

OTHER PUBLICATIONS

Stoll et al., Arterioscler Thromb Vasc Biol. May 2007;27(5):1206-12. Epub Feb 22, 2007.*
Janeway et al., Immunobiology, 3rd edition, 1999, Garland Publishing Inc., pp. 3:1-3:11.*
Rudikoff et al., Proc Natl Acad Sci U S A. Mar. 1982;79(6):1979-83.*
Newman et al., "Synergis action of murine monoclonal antibodies that inhibit ADP-induced platelet aggregation without blocking fibrinogen binding," Blood, American Society of Hematology, p. 668-676 (Feb. 1987).
Newman et al., "Quantitation of Membrane Glycoprotein IIIa on Intact Human Platelets Using the Monoclonal Antibody, AP-3," Blood, 66(1):227-232 (Jan. 1985).
Quinn et al., "Quantifying GPIIb/IIIa Receptor Binding Using 2 Monoclonal Antibodies: Discriminating Abciximab and Small Molecular Weight Antagonists," Circulation, 2231-2238 (May 1999).
International Search Report in International Application No. PCT/US2015/057187, dated Feb. 23, 2016, 12 pages.
Shibeko et al., "Predicting dosing advantages of factor VIIa variants with altered tissue factor-dependent and lipid-dependent activities," J Thromb Haemost, 12(8):1302-1312, Aug. 1, 2014.
Anderson et al., "Anti-GPIIb/IIIa (CD41) monoclonal antibody-induced platelet activation requires Fc receptor-dependent cell-cell interaction," British Journal of Haematol, Sep. 1991, 79(1):75-83.
Bi et al., "Targeted disruption of the mouse factor VIII gene produces a model of haemophilia A," Nat. Genet. 1995, 10(1):119-121.
Dumont et al., "Prolonged activity of a recombinant factor VIII-Fc fusion protein in hemophilia A mice and dogs," Blood, 2012, 119(13):3024-3030.

(Continued)

*Primary Examiner* — Michael Szperka
(74) *Attorney, Agent, or Firm* — Fish & Richardson P.C.

(57) ABSTRACT

The present invention provides antibodies and antigen-binding molecules thereof which specifically bind the α and/or β subunits of the non-active form of the GPIIb/IIIa receptor. The antibodies and antigen-binding molecules can be genetically fused and/or conjugated to heterologous moieties and used, for example, as targeting moieties. The invention also includes methods for screening for these antibodies, as well as methods of making and methods of using chimeric molecules derived from the antibodies.

8 Claims, 23 Drawing Sheets
Specification includes a Sequence Listing.

(56) References Cited

OTHER PUBLICATIONS

Emambokus and Frampton, "The glycoprotein IIb molecule is expressed on early murine hematopoietic progenitors and regulates their numbers in sites of hematopoiesis," Immunity, 2003, 19(1):33-45.
Frelinger et al., "Selective Inhibition of Integrin Function by Antibodies Specific for Ligand-occupied Receptor Conformers," The Journal of Biological Chemistry, Apr. 1990, 265(11):6346-6352.
International Preliminary Report on Patentability in International Application No. PCT/US2014/040370, dated Dec. 1, 2015, 9 pages.
International Preliminary Report on Patentability in International Application No. PCT/US2014/039420, dated Nov. 24, 2015, 8 pages.
International Search Report and Written Opinion in International Application No. PCT/US2014/040370, dated Jan. 9, 2015, 13 pages.
International Search Report and Written Opinion in International Application No. PCT/US2014/039420, dated Dec. 9, 2014, 13 pages.
Invitation to Pay Additional Fees in International Application No. PCT/US2015/058326, dated Feb. 8, 2016, 13 pages.
Jurlander et al., "Recombinant activated factor VII (rFVIIa): characterization, manufacturing, and clinical development," Semin. Thromb. Hemost., 2001, 27(4):373-84.
Kosugi, "Platelet-associated anti-GPIIb-IIIa autoantibodies in chronic immune thrombocytopenic purpura recognizing epitopes close to the ligand-binding site of glycoprotein (GP) IIb," Blood, Sep. 2001, 98(6):1819-1827.
Mekrache et al., "Activation of recombinant alphaIIbbeta3 expressed in Chinese hamster ovary cells exposes different binding sites for fibrinogen or von Willebrand factor: evidence using monoclonal antibodies to alphaIIbbeta3," British Journal of Haematol, 2002, 116(3):636-644.
Pan et al., "Enhanced efficacy of recombinant FVIII in noncovalent complex with PEGylated liposome in hemophilia A mice," Blood, Sep. 2009, 114:2802-2811.
Rostin et al., "B-Domain Deleted Recombinant Coagulation Factor VIII Modified with Monomethoxy Polyethylene Glycol," Bioconj. Chem., 2000, 11:387-396.
Schulte, "Use of albumin fusion technology to prolong the half-life of recombinant factor VIIa," Thromb. Res. 2008;122 Suppl 4:S14-19.
Schwarz et al., "Reversibility versus Persistence of GPIIb/IIIa Blocker-Induced Conformational Change of GPIIb/IIIa ($\alpha$IIb$\beta$3), CD41/CD61)," Journal of Pharmacology and Experimental Therapeutics, Aug. 2004, 308(3):1002-1011.

Spira et al., "Prolonged bleeding-free period following prophylactic infusion of recombinant factor VIII reconstituted with pegylated liposomes," Blood, Dec. 2006, 108:3668-3673.
Stennicke et al., "Generation and biochemical characterization of glycoPEGylated factor VIIa derivatives," Thromb Haemost., Nov. 2008, 100:920-928.
Thornton et al., "Identification of distal regulatory regions in the human alpha IIb gene locus necessary for consistent, high-level megakaryocyte expression," Blood, 2002, 100(10):12 pages.
International Preliminary Report on Patentability in International Application No. PCT/US2015/057187, dated Apr. 25, 2017, 7 pages.
International Search Report and Written Opinion in International Application No. PCT/US2015/058326, dated Apr. 20, 2016, 26 pages.
International Preliminary Report on Patentability in International Application No. PCT/US2015/058326, dated May 2, 2017, 17 pages.
Supplementary European Search Report in European Application No. 14801129.9, dated Mar. 30, 2017, 17 pages.
Li et al., "Platelet Fragmentation requires a Specific Structural Conformation of Human Monoclonal Antibody against beta3 Integrin," Journal of Biological Chemistry, 283(6):3224-3230 (Feb. 2008).
O'Toole et al., "Affinity Modulation of the Alpha-I-I-B-Beta-3 Integrin Platelet GPIIB-IIIA is an Intrinsic Property of the Receptor," Cell Regulation, Bethesda, MD, US, 1(12):883-893 (Nov. 1990).
Pidard et al., "Interaction of AP-2, a Monoclonal Antibody Specific for the Human Platelet Glycoprotein IIb-IIIa Complex, with Intact Platelets," The Journal of Biological Chemistry, 12582-12586 (Oct. 1983).
Shattil et al., "changes in the platelet membrane glycoprotein IIb.IIIa complex during platelet activation," Journal of Biological Chemistry, 11107-11114 (Sep. 1985).
European Search Report in European Application No. 14801129.9, dated Dec. 22, 2016, 11 pages.
Schwarz et al., "Conformation-specific blockade of the integrin GPIIb/IIIa: a novel antiplatelet strategy that selectively targets activated platelets," Circulation Research, American Heart Association, 99(1):25-33 (Jul. 2006).
White et al. [online], "Common Bleeding Episodes," National Hemophilia Foundation, 2013, [retrieved on Oct. 22, 2018], retrieved from: URL<http://www.hemophilia.org/sites/default/files/document/files/Nurses-Guide-Chapter-4-Common-Bleeding-Episodes.pdf>, pp. 1-14.
World Health Organization [online], "Blood products and related biologicals," Aug. 2018, [retrieved on Oct. 22, 2018], retrieved from: URL<www.who.int/bloodproducts/ivd/coagulation_disorders/en/>, 2 pages.

* cited by examiner

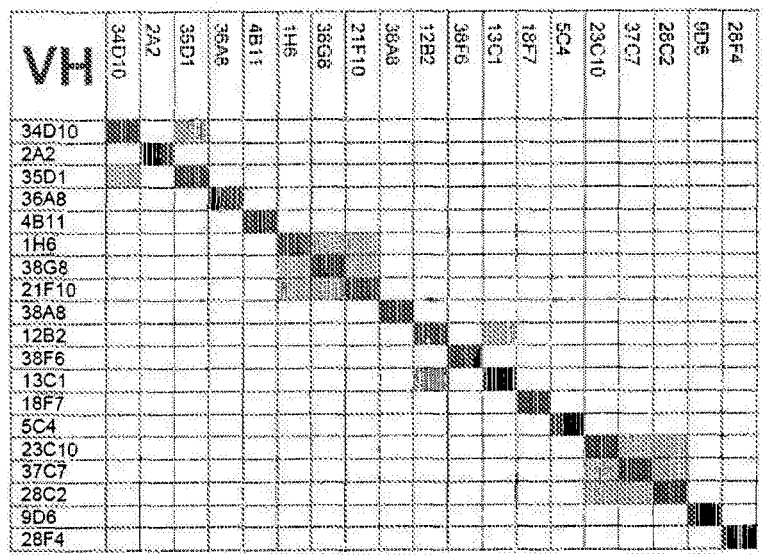
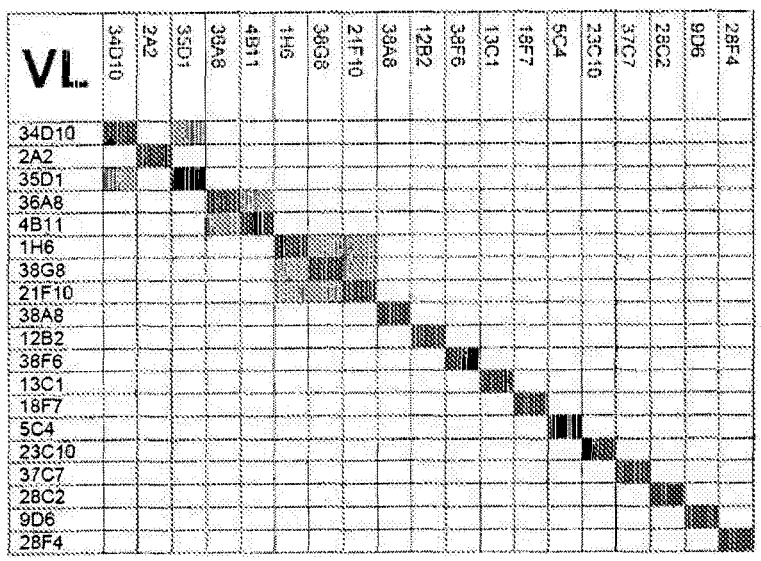
FIG. 4

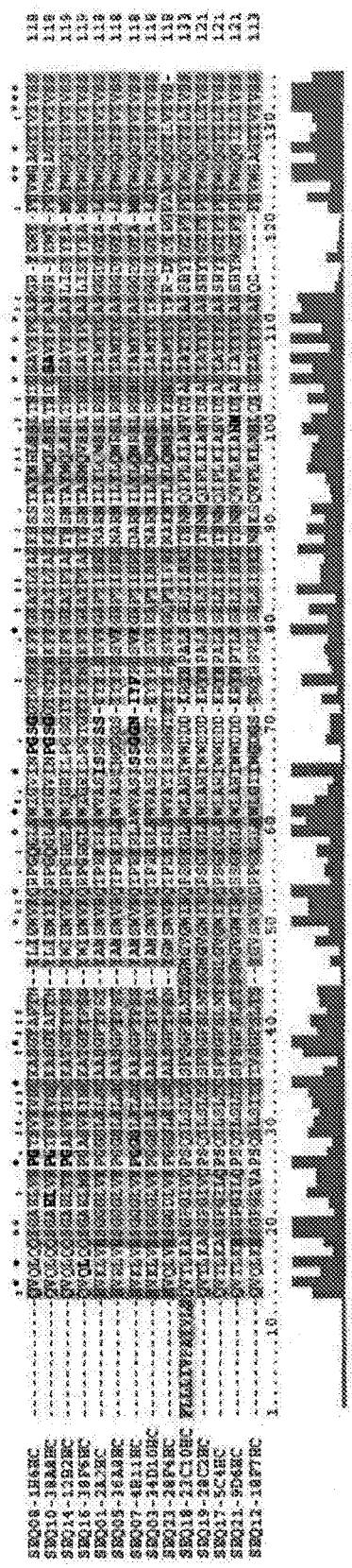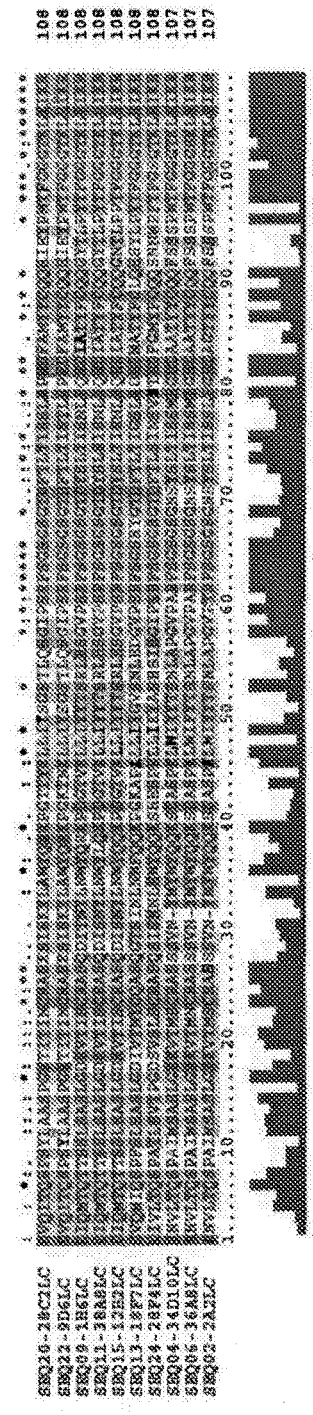
FIG. 5

VH SEQUENCES – Full Alignment (All Sequenced VH and VL Included)

```
CLUSTAL 2.1 multiple sequence alignment

Kabat 31-35
                                                                CDR1
SEQ08-1H6HC       ---------------QVQLQQSGAELVRPGTSVKVSCKASGYAFN--YLIEWVNQRPGQGLE
SEQ10-38A8HC      ---------------QVQLQQSGAELVRPGTSVKVSCKASGYAFN--YLIEWIKQRPGQGLE
SEQ14-12B2HC      ---------------QVQLQQSGAELTKPGASVKISCKATGYTFS--YWIEWVKQRPGHGLE
SEQ16-38F6HC      ---------------QVQLQQSGAELMRPGASVKISCKATGYTFS--YWIEWVKQRPGHGLE
SEQ03-2A2HC       ---------------EVKLVESGGGLVKPGGSLKLSCAASGFTFT--YAMSWVRQTPEKRLE
SEQ05-36A8HC      ---------------EVRLVESGGGLVKPGGSLKLSCAASGFTFT--YAMSWVRQTPEKRLE
SEQ07-4B11HC      ---------------EVKLVESGGGLVKPGGSLKLSCAASGFTFS--YAMSWVRQTPEKRLA
SEQ01-34D10HC     ---------------EVKLVESGGGLVKPGGSLKLSCAASGFTFA--YAMSWVRQTPEKRLE
SEQ23-28F4HC      ---------------EVQLVESGGDLVKPGGSLKLSCAASGFTFN--YGMSWVRQTPDKRLE
SEQ18-23C10HC     FLLLIVPAYVLSQVTLKASGPGIVQPSQTLSLTCSFSGFSLTSGMVGWIRQPSGKGLE
SEQ19-28C2HC      ---------------QVTLKASGPGIVQPSQTLSLTCSFSGFSLTSGMVGWIRQPSGKGLE
SEQ17-5C4HC       ---------------QVTLKASGPGILQPSQTLSLTCSFSGFSLTSGLGVGWIRQPSGKGLE
SEQ21-9D6HC       ---------------QVTLKESGPGILQPSQTLSLTCSFSGFSLTSGMVGWIRQSSGKGLE
SEQ12-18F7HC      ---------------QVQLKESGPGLVAPSQSLSITCTVSGFSLS--YGVSWVRQPPGKGLE
                                 :*  *   **  :   *. ::.::*  :*:::        *  ::**  . : *

Kabat 50-65                                    Kabat 95-102
                        CDR2                                           CDR3
SEQ08-1H6HC       WIGVINPGSGGTNYNEKFKGATLTADKSSSTAYMHLSSLTSDDSAVYFCARGR-YEWY
SEQ10-38A8HC      WIGVINPGSGGTNYNEKFKGATLTADKSSSTAYMQLSSLTSDDSAVYFCARGR-YEWY
SEQ14-12B2HC      WIGEILPGSGITKYNDKFKGATFTADTSSNTAYMQLSSLTSEDSAVYFCARLSYYYA
SEQ16-38F6HC      WIGEILPGTGYTKYNEKFKGATFTAETSSNTASMQVSSLTSEDSAVYFCARLSYYYA
SEQ03-2A2HC       WVASISSGSS-TYYLDSVKGFTISRDNARNILYLQMSSLRSEDTAMYYCARGDYGYA
SEQ05-36A8HC      WVASINGGGS-TYYPDSVKGFTISRDNARNILYLQMRSLRSEDTAMYYCARGDYGYA
SEQ07-4B11HC      WVASISSGGN-IYFPDSVKGFTISRDDARNILYLQMRSLRSEDTAMYYCARGDYGYA
SEQ01-34D10HC     WVASISSGGT-TYYPDSVKGFTISRDNARNILYLQMSSLRSEDTAMYYCTRGDYGYA
SEQ23-28F4HC      WVATISSGGTYTYYPDSVKGFTIFRDNAKNTLYLQMSSLKSEDTAMYYCTR-DYPYG
SEQ18-23C10HC     WLAHIWWDDD-KRYNPALKSLTISKDTSNNQIFLKIASVDTADTATYYCARSHYYGTFY
SEQ19-28C2HC      WLAHIWWDDD-KRYNPALKSLTISKDTSNNQIFLKIASVDTADTATYYCARSHYYGTFY
SEQ17-5C4HC       WLAHIWWDDD-KRYNPALKSLTISKDTSNNQIFLKIASVDTADTATYYCARSHYYGTFY
SEQ21-9D6HC       WLAHIWWDDD-KRYNPTLKSLTISKDTSNNQVFLKIANMDTADIATYYCARSHYNGTFY
SEQ12-18F7HC      WLGIIWGDGS-TNYHSVLKSLSISKDNSKSQVFLKLNSLQTDDTATYYCARQD-----
                  *:  *       :    :  .*    :: :    : *. ::.:  .: : * *  * *:

SEQ08-1H6HC       FDVWGAGTTVTVSS
SEQ10-38A8HC      FDVWGAGTTVTVSS
SEQ14-12B2HC      MDYWGQGTSVTVSS
SEQ16-38F6HC      MDYWGQGTSVTVSS
SEQ03-2A2HC       LDYWGQGTSVTVSS
SEQ05-36A8HC      LDYWGQGTSVTVSS
SEQ07-4B11HC      MDYWGQGTSVTVSS
SEQ01-34D10HC     LDYWGQGTSVTVSS
SEQ23-28F4HC      FAYWGQGTLVTVS-
SEQ18-23C10HC     FDYWGQGTTLTVSS
SEQ19-28C2HC      FDYWGQGTTLTVSS
SEQ17-5C4HC       FDYWGQGTTLTVSS
SEQ21-9D6HC       FDYWGQGITLTVSS
SEQ12-18F7HC      FDVWGAGTTVTVSS
                  :   * *  ;***
```

\* - Identical
: - Conserved
. - Partially conserved

FIG. 6

VL SEQUENCES – Full Alignment (All Sequenced VH and VL Included)

CLUSTAL 2.1 multiple sequence alignment

```
                              Kabat 24-34                  Kabat 50-56
                                 CDR1                         CDR2
SEQ20-28C2LC    DVQITQSPSYLAASPGETITIN RASKSISKYLA NYQEKPGTTYKLLI SGSTLQS IPS
SEQ22-9D6LC     DVQITQSPSYLAASPGETITIN RASKSISKYLA NYQEKPGKTNKLLI SGSTLQS IPS
SEQ09-1H6LC     DIQMTQTTSSLSASLGDRVTISC RASQDITNYLN WYQRKPDGTVKLLI YTSRLHS VPS
SEQ11-38A8LC    DIQMTQTTSSLSASLGDRVTISC RASQDISNYLN WYLQKPDGTVKLLI YTSRLHS VPS
SEQ15-12B2LC    DIQMTQTTSSLSASLGDRVTISC RASQDISNYLN WYQQKPDGTVKLLI YTSRLHS VPS
SEQ13-18F7LC    DVQMIQSPFSLSASLGDIVTMT QASQGTSINLN WYQQKPGKAPKLLI GVSNLED VPS
SEQ24-28F4LC    DIVLTQSPATLSVTPGDSVSLSC RASQSISNNLH WYQQKSHESPRLLI YASHSIS IPS
SEQ02-34D10LC   ENVLTQSPAIMSASLGEKVTMSC RASSSVN-YMY WYQQKSDASPKLWI YTSNLAF VPA
SEQ06-36A8LC    ENVLTQSPAIMSASLGEKVTMN RASSSVN-YMY WYQQKSDASPKLWI YTSNLAF VPA
SEQ04-2A2LC     ENVLTQSPAIMSASLGEKVTMSC RASSSVN-YMY WYQQKSDASPKLWI YTSNLAF VPT Kabat 89-97
                                          CDR3
SEQ20-28C2LC    RFSGSGSGTDFTLTISSLEPEDFAMYYC QQHIEYPWT FGGGTKLEIKR
SEQ22-9D6LC     RFSGSGSGTDFTLTISTLEPEDFAMYYC QQHIEYPWT FGGGTKLEIKR
SEQ09-1H6LC     RFSGSGSGTDYSLTISNLEQEDIATYFC QQGYTLPYT FGGGTKLEIKR
SEQ11-38A8LC    RFSGSGSGTDYSLSISNLEQEDIATYFC QQGYTLPYT FGGGTKLEIKR
SEQ15-12B2LC    RFSGSGSGTDYSLTISNLEQEDIATYFC QQGNTLPPT FGGGTKLEIKR
SEQ13-18F7LC    RFSGSRYGTDFTLTIGSLEDEDMATYFC LQHSYLPYT FGGGTKLEIKR
SEQ24-28F4LC    RFSGSGSGTDFTLSINSVETEDFGMYFC QQSNNWPYT FGSGTKLEIKR
SEQ02-34D10LC   RFSGSGSGNSYSLTISSMEGEDAATYYC QQFSSSPWT FGGGTKLEIKR
SEQ06-36A8LC    RFSGSGSGNSYSLTISSMEGEDAATYYC QQFSSSPWT FGGGTKLEIKR
SEQ04-2A2LC     RFSGSGSGNSYSLTISSLEGEDAGTYYC QQFSSSPWT FGGGTKLEIKR
```

* – Identical
: – Conserved
. – Partially conserved

FIG. 7

VL SEQUENCES - Percent Identity Matrix

|  | | 1 | 2 | 3 | 4 | 5 | 6 | 7 | 8 | 9 | 10 |
|---|---|---|---|---|---|---|---|---|---|---|---|
| 1: | SEQ20-28C2LC | 100 | 97 | 66 | 65 | 67 | 62 | 60 | 59 | 58 | 59 |
| 2: | SEQ22-9D6LC | 97 | 100 | 66 | 65 | 67 | 62 | 59 | 58 | 57 | 58 |
| 3: | SEQ09-1H6LC | 66 | 66 | 100 | 96 | 96 | 66 | 58 | 63 | 60 | 63 |
| 4: | SEQ11-38A8LC | 65 | 65 | 96 | 100 | 96 | 66 | 60 | 62 | 59 | 62 |
| 5: | SEQ15-12B2LC | 67 | 67 | 96 | 96 | 100 | 67 | 61 | 64 | 61 | 64 |
| 6: | SEQ13-18F7LC | 62 | 62 | 66 | 66 | 67 | 100 | 56 | 57 | 55 | 57 |
| 7: | SEQ24-28F4LC | 60 | 59 | 58 | 60 | 61 | 56 | 100 | 56 | 54 | 57 |
| 8: | SEQ02-34D10LC | 59 | 58 | 63 | 62 | 64 | 57 | 56 | 100 | 97 | 97 |
| 9: | SEQ06-36A8LC | 58 | 57 | 60 | 59 | 61 | 55 | 54 | 97 | 100 | 94 |
| 10: | SEQ04-2A2LC | 59 | 58 | 63 | 62 | 64 | 57 | 57 | 97 | 94 | 100 |

VH SEQUENCES - Percent Identity Matrix

Percent Identity Matrix

|  | | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|
| 1: | SEQ08-1H6HC | 100 | 98 | 75 | 74 | 48 | 47 | 44 | 45 | 47 | 37 | 37 | 36 | 33 | 50 |
| 2: | SEQ10-38A8HC | 98 | 100 | 75 | 74 | 48 | 47 | 44 | 45 | 47 | 38 | 38 | 37 | 34 | 49 |
| 3: | SEQ14-12B2HC | 75 | 75 | 100 | 92 | 54 | 53 | 53 | 53 | 52 | 36 | 36 | 36 | 34 | 42 |
| 4: | SEQ16-38F6HC | 74 | 74 | 92 | 100 | 50 | 50 | 49 | 49 | 50 | 36 | 36 | 36 | 33 | 41 |
| 5: | SEQ03-2A2HC | 48 | 48 | 54 | 50 | 100 | 94 | 91 | 94 | 81 | 46 | 46 | 45 | 42 | 50 |
| 6: | SEQ05-36A8HC | 47 | 47 | 53 | 50 | 94 | 100 | 92 | 93 | 81 | 46 | 46 | 45 | 42 | 51 |
| 7: | SEQ07-4B11HC | 44 | 44 | 53 | 49 | 91 | 92 | 100 | 92 | 79 | 43 | 43 | 42 | 40 | 47 |
| 8: | SEQ01-34D10HC | 45 | 45 | 53 | 49 | 94 | 93 | 92 | 100 | 84 | 44 | 44 | 43 | 41 | 49 |
| 9: | SEQ23-28F4HC | 47 | 47 | 52 | 50 | 81 | 81 | 79 | 84 | 100 | 41 | 41 | 40 | 38 | 49 |
| 10: | SEQ18-23C10HC | 37 | 38 | 36 | 36 | 46 | 46 | 43 | 44 | 41 | 100 | 100 | 98 | 90 | 49 |
| 11: | SEQ19-28C2HC | 37 | 38 | 36 | 36 | 46 | 46 | 43 | 44 | 41 | 100 | 100 | 98 | 90 | 65 |
| 12: | SEQ17-5C4HC | 36 | 37 | 36 | 36 | 45 | 45 | 42 | 43 | 40 | 98 | 98 | 100 | 90 | 65 |
| 13: | SEQ21-9D6HC | 33 | 34 | 34 | 33 | 42 | 42 | 40 | 41 | 38 | 90 | 90 | 90 | 100 | 62 |
| 14: | SEQ12-18F7HC | 50 | 49 | 42 | 41 | 50 | 51 | 47 | 49 | 49 | 65 | 65 | 64 | 62 | 100 |

FIG. 8

VH Sequences Clustered According to Alpha/Beta Specificity

Only sequences with both VH and VL sequenced included

CLUSTAL 2.1 multiple sequence alignment

ALPHA SUBUNIT SPECIFIC

```
                                                                    Kabat 31-35
                                                                       CDR1
SEQ09-1H6HC         ------------QVQLQQSGAELVRPGTSVKVSCKASGYAFT---YLIE WVKQRPGQGLE
SEQ10-38A8HC        ------------QVQLQQSGAELVRPGTSVKVSCKASGYAFT N--YLIE WIKQRPGQGLE
SEQ03-2A2HC         ------------EVKLVESGGGLVKPGGSLKLSCAASGFTFF T--YAMS WVRQTPEKRLE
SEQ05-36A8HC        ------------EVRLVESGGGLVKPGGSLKLSCAASGFTFS T--YAMS WVRQTPEKRLE
SEQ01-34D10HC       ------------EVKLVESGGGLVKPGGSLKLSCAASGFTFS A--YAMS WVRQTPEKRLE
SEQ12-18F7HC        ------------QVQLKESGPGLVAPSQSLSITCTVSGFSLT S--YGVS WVRQPPGKGLE Kabat 50-65                                       Kabat 95-102
                      CDR2                                              CDR3
SEQ09-1H6HC         WIG................... KATLTADKSSSTAYMHLSSLTSDDSAVYFCAR GR-YEWY
SEQ10-38A8HC        WIG VINPGSGGTNYNEKFK KATLTADKSSSTAYMQLSSLTSDDSAVYFCAR GR-YEWY-
SEQ03-2A2HC         WVA SISSGSS-TYYLDSVKG RFTISRDNARNILYLQMSSLRSEDTAMYYCAR GGDYGYA-
SEQ05-36A8HC        WVA INGGGS-TYYPDSVKR FTISRDNARNILYLQMRSLRSEDTAMYYCAR GGDYGYA-
SEQ01-34D10HC       WVA ISSGGT-TYYPDSVKR FTISRDNARNILYLQMSSLRSEDTAMYYCTR GGDYGYA-
SEQ12-18F7HC        WLS IWGDGS-TNYHSVLKS LSISKDNSKSQVFLKLNSLQTDDTATYYCAR QD------

SEQ09-1H6HC         FDV WGAGTTVTVSS
SEQ10-38A8HC        FDV WGAGTTVTVSS
SEQ03-2A2HC         LDY WGQGTSVTVSS
SEQ05-36A8HC        LDY WGQGTSVTVSS
SEQ01-34D10HC       LDY WGQGTSVTVSS
SEQ12-18F7HC        FDV WGAGTTVTVSS
```

BETA SUBUNIT SPECIFIC

```
                                                                    Kabat 31-35
                                                                       CDR1
SEQ14-12B2HC        ------------QVQLQQSGAELTKPGASVKISCKATGYTFS S--YWIE WVKQRPGHGLE
SEQ23-28F4HC        ------------EVQLVESGGDLVKPGGSLKLSCAASGFTFS N--YGMS WVRQTPDKRLE
SEQ19-28C2HC        ------------QVTLKASGPGIVQPSQTLSLTCSFSGFSLN TSGMGVG WIRQPSGKGLE
SEQ21-9D6HC         ------------QVTLKESGPGILQPSQTLSLTCSFSGFSLS TSGMGVG WIRQSSGKGLE Kabat 50-65                                       Kabat 95-102
                      CDR2                                              CDR3
SEQ14-12B2HC        WIG ................ KATFTADTSSNTAYMQLSSLTSEDSAVYSCAR LISYYIA-
SEQ23-28F4HC        WVA TISSGGTYTYYPDSVKG QFTIFRDNAKNTLYLQMSSLKSEDTAMYYCTR R-DYDYEG
SEQ19-28C2HC        WLA HIWNDDD-KRYNPALKS RLTISKDTSNNQIFLKIASVDTADTATYYCAR SHYYGTFY
SEQ21-9D6HC         WLA HIWNDDD-KRYNPTLKS RLTISKDTSNNQVFLKIANMDTADIATYYCAR SHYNGTFY SEQ23-28F4HC        FAI WGQGTLVTVS-
SEQ19-28C2HC        FDY WGQGTTLTVSS
SEQ21-9D6HC         FDF WGQGITLTVSS
SEQ14-12B2HC        MDY WGQGTSVTVSS
```

FIG. 9

VL Sequences Clustered According to Alpha/Beta Specificity

Only sequences with both VH and VL sequenced included
CLUSTAL 2.1 multiple sequence alignment

ALPHA SUBUNIT SPECIFIC

```
                           Kabat 24-34                    Kabat 50-56
                              CDR1                           CDR2
SEQ09-1H6LC     DIQMTQTTSSLSASLGDRVTISC RASQDITNYLN WYQRKPDGTVKLLIY YTSRLHS GVPS
SEQ11-38A8LC    DIQMTQTTSSLSASLGDRVTISC RASQDISNYLN WYLQKPDGTVKLLIY YTSRLHS GVPS
SEQ13-18F7LC    DVQMIQSPFSLSASLGDIVTMTC QASQGTSINLN WFQQKPGKAPKLLIY GVSNLED GVPS
SEQ02-34D10LC   ENVLTQSPAIMSASLGEKVTMSC RASSSVN-YMY WYQQKSDASPKLWIY YTSNLAP GVPA
SEQ06-36A8LC    ENVLTQSPAIMSASLGEKVTMNC RASSSVN-YMY WYQQKSDASPKLWIF YTSNLAP GVPA
SEQ04-2A2LC     ENVLTQSPAIMSASLGEKVTMSC RASSSVN-YMY WYQQKSDASPKLWIY YTSNLAP GVPT
                                       **                                *

Kabat 89-97
                              CDR3
SEQ09-1H6LC     RFSGSGSGTDYSLTISNLEQEDIATYFC QQGYTLFYT FGGGTKLEIKR
SEQ11-38A8LC    RFSGSGSGTDYSLSISNLEQEDIATYFC QQGYTLPYT FGGGTKLEIKR
SEQ13-18F7LC    RFSGSRYGTDFTLTIGSLEDEDMATYFC LQHSYLPYT FGGGTKLEIKR
SEQ02-34D10LC   RFSGSGSGNSYSLTISSMEGEDAATYYC QQFSSSPWT FGGGTKLEIKR
SEQ06-36A8LC    RFSGSGSGNSYSLTISSMEGEDAATYYC QQFSSSPWT FGGSKLEIKR
SEQ04-2A2LC     RFSGSGSGNSYSLTISSLEGEDAGTYYC QQFSSSPWT FGGGTKLEIKR
                                              *
```

BETA SUBUNIT SPECIFIC

```
                           Kabat 24-34                    Kabat 50-56
                              CDR1                           CDR2
SEQ20-28C2LC    DVQITQSPSYLAASPGETITINC RASKSISKYLA WYQEKPGTTYKLLIY SGSTLQS GIPS
SEQ22-9D6LC     DVQITQSPSYLAASPGETITINC RASKSISKYLA WYQEKPGKTNKLLIY SGSTLQS GIPS
SEQ15-12B2LC    DIQMTQTTSSLSASLGDRVTISC RASQDISNYLN WYQQKPDGTVKLLIY YTSRLHS GVPS
SEQ24-28F4LC    DIVLTQSPATLSVTPGDSVSLSC RASQSISNNLH WYQQKSHESPRLLIK ASHSIS  GIPS
                                       *** **  *                     *  *

Kabat 89-97
                              CDR3
SEQ20-28C2LC    RFSGSGSGTDFTLTISSLEPEDFAMYYC QQHIEYPWT FGGGTKLEIKR
SEQ22-9D6LC     RFSGSGSGTDFTLTISTLEPEDFAMYYC QQHIEYPWT FGGGTKLEIKR
SEQ15-12B2LC    RFSGSGSGTDYSLTISNLEQEDIATYFC QQGNTLPPT FGGGTKLEIKR
SEQ24-28F4LC    RFSGSGSGTDFTLSINSVETEDFGMYFC QQSNNWPPT FGSGTKLEIKR
                                              **        *
```

FIG. 10

VH Sequence Clustered According to Competition with Fibrinogen

Only sequence with both VH and VL included

CLUSTAL O(1.1.0) multiple sequence alignment

No Fibrinogen Competition

```
                                    Kabat 31-35          Kabat 50-65
                                      CDR1                 CDR2
SEQ04-2A2HC     EVKLVESGGGLVKPGGSLKLSCAASGFTFR TYAMS WVRQTPEKRLEWVA SI-SSGSSTYY
SEQ01-34D10HC   EVKLVESGGGLVKPGGSLKLSCAASGFTFS AYAMS WVRQTPEKRLEWVA SI-SSGGTTYY
SEQ05-36A8HC    EVRLVESGGGLVKPGGSLKLSCAASGFTFS TYAMS WVRQTPEKRLEWVA SI-NGGGSTYY
SEQ14-12B2HC    QVQLQQSGAELTKPGASVKISCKATGYTFS SYWIE WVKQRPGHGLEWIG EILPGSGITKY
                                       *                       *   *  *

Kabat 95-102
                                                 CDR3
SEQ04-2A2HC     LDSVKG RFTISRDNARNILYLQMSSLRSEDTAMYYCAR GDYGYALDY WGQGTSVTVSS
SEQ01-34D10HC   PDSVKG RFTISRDNARNILYLQMSSLRSEDTAMYYCTR GDYGYALDY WGQGTSVTVSS
SEQ05-36A8HC    PDSVKG RFTISRDNARNILYLQMRSLRSEDTAMYYCAR GDYGYALDY WGQGTSVTVSS
SEQ14-12B2HC    NDKFKG KATFTADTSSNTAYMQLSSLTSEDSAVYSCAR LISYYYAMDY WGQGTSVTVSS
                   *                                     * ** **
```

Fibrinogen Competition

```
                                    Kabat 31-35          Kabat 50-65
                                      CDR1                 CDR2
SEQ08-1H6HC     QVQLQQSGAELVRPGTSVKVSCKASGYAFT N--YLIE WVKQRPGQGLEWIG VINPGSGGT
SEQ10-38A8HC    QVQLQQSGAELVRPGTSVKVSCKASGYAFT N--YLIE WIKQRPGQGLEWIG VINPGSGGT
SEQ12-18F7HC    QVQLKESGPGLVAPSQSLSITCTVSGFSLT S--YGVS WVRQPPGKGLEWLG IIW-GDGST
SEQ23-28F4HC    EVQLVESGGDLVKPGGSLKLSCAASGFTFS N--YGMS WVRQTPDKRLEWVA TISSGGTYT
SEQ19-28C2HC    QVTLKASGPGIVQPSQTLSLTCSFSGFSLN TSGMGVG WIRQPSGKGLEWLA HIW-WDDDK
SEQ21-9D6HC     QVTLKESGPGILQPSQTLSLTCSFSGFSLS ISGMGVG WIRQSSGKGLEWLA HIW-WDDDK
                  *  *    **     *   **        *              ***      *

Kabat 95-102
                                                 CDR3
SEQ08-1H6HC     NYNEKFKG KATLTADKSSSTAYMHLSSLTSDDSAVYFCAR GRY--EWYFDV WGAGTTVTV
SEQ10-38A8HC    NYNEKFKG KATLTADKSSSTAYMQLSSLTSDDSAVYFCAR GRY--EWYFDV WGAGTTVTV
SEQ12-18F7HC    NYHSVLKS RLSISKDNSKSQVFLKLNSLQTDDTATYYCAK QD------FDV WGAGTTVTV
SEQ23-28F4HC    YYPDSVKG QFTIFRDNAKNTLYLQMSSLKSEDTAMYYCTR RDYDY-EGFAY WGQGTLVTV
SEQ19-28C2HC    RYNPALKS RLTISKDTSNNQIFLKIASVDTADTATYYCAR SHYYGTFYFDV WGQGTLTV
SEQ21-9D6HC     RYNPTLKS RLTISKDTSNNQVFLKIANMDTADIATYYCAR SHYNGTFYFDV WGQGITLTV
                  *   *     *                 * * **          *  ** *    **

SEQ08-1H6HC     SS
SEQ10-38A8HC    SS
SEQ12-18F7HC    SS
SEQ23-28F4HC    S-
SEQ19-28C2HC    SS
SEQ21-9D6HC     SS
                 *
```

FIG. 11

VL Sequence Clustered According to Competition with Fibrinogen

Only sequence with both VH and VL included

CLUSTAL O (1.1.0) multiple sequence alignment

No Fibrinogen Competition

```
                              Kabat 24-34              Kabat 50-56
                                CDR1                      CDR2
SEQ04-2A2LC      ENVLTQSPAIMSASLGEKVTMSCKSSS-VNYMHWYQQKSDASPKLWIYYTSNLAFGVPT
SEQ02-34D10LC    ENVLTQSPAIMSASLGEKVTMSCKASSS-VNYMHWYQQKSDASPKLWIYYTSNLAFGVPA
SEQ06-36A8LC     ENVLTQSPAIMSASLGEKVTMNCRASSS-VNYMHYYQQKSDASPKLWIFYTSNLAFGVPA
SEQ15-12B2LC     DIQMTQTTSSLSASLGDRVTISCRASQDISNYLNWYQQKPDGTVKLLIYYTSRLHSGVPS
                                      **   **                   ***  *
```

```
                              Kabat 89-97
                                 CDR3
SEQ04-2A2LC      RFSGSGSGNSYSLTISSLEGEDAGTYYCQQFSSSPWTFGGGTKLEIKR
SEQ02-34D10LC    RFSGSGSGNSYSLTISSMEGEDAATYYCQQFSSSPWTFGGGSKLEIKR
SEQ06-36A8LC     RFSGSGSGNSYSLTISSMEGEDAATYYCQQFSSSPWTFGGGSKLEIKR
SEQ15-12B2LC     RFSGSGSGTDYSLTISNLEQEDIATYFCQQGNTLPPTFGGGTKLEIKR
                                             **    * *
```

Fibrinogen Competition

```
                              Kabat 24-34              Kabat 50-56
                                CDR1                      CDR2
SEQ09-1H6LC      DIQMTQTTSSLSASLGDRVTISCRASQDITNYLNWYQRKPDGTVKLLIYYTSKLHSGVPS
SEQ13-18F7LC     DVQMIQSPFSLSASLGDIVTMTCQASQGTSINLNWFQQKPGKAPKLLIYYSNLEDGVPS
SEQ11-38A8LC     DIQMTQTTSSLSASLGDRVTISCRASQDISNYLNWYLQKPDGTVKLLIYYTSRLHSGVPS
SEQ20-28C2LC     DVQITQSPSYLAASPGETITINCRASKSISKYLAWYQEKPGTTYNKLIYGSTLQSIPS
SEQ22-9D6LC      DVQITQSPSYLAASPGETITINCRASKSISKYLAWYQEKPGKTNKLLIYGSTLQSIPS
SEQ24-28F4LC     DIVLTQSPATLSVTPGDSVSLSCRASQSISNNLHWYQQKSHESPRLLIKASHSISIPS
                                        **     *                       *
```

```
                              Kabat 89-97
                                 CDR3
SEQ09-1H6LC      RFSGSGSGTDYSLTISNLEQEDIATYFCQQGYTLPYTFGGGTKLEIKR
SEQ13-18F7LC     RFSGSRYGTDFTLTIGSLEDEDMATYFCLQHSYLPYTFGGGTKLEIKR
SEQ11-38A8LC     RFSGSGSGTDYSLSISNLEQEDIATYFCQQGYTLPYTFGGGTKLEIKR
SEQ20-28C2LC     RFSGSGSGTDFTLTISSLEPEDFAMYYCQQHIEYPWTFGGGTKLEIKR
SEQ22-9D6LC      RFSGSGSGTDFTLTISTLEPEDFAMYYCQQHIEYPWTFGGGTKLEIKR
SEQ24-28F4LC     RFSGSGSGTDFTLSINSVETEDFGMYFCQQSNNWPTFGSGTKLEIKR
                                             *    *  *
```

FIG. 12

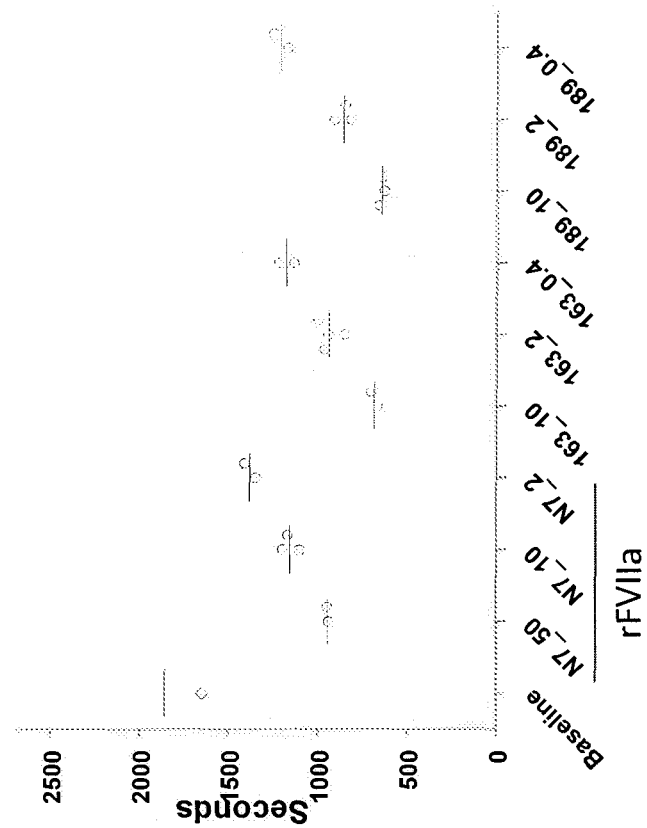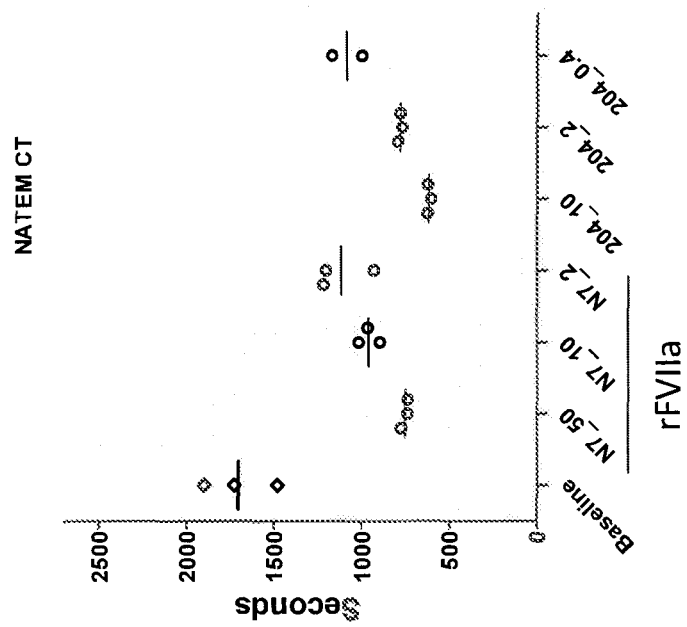
FIG. 17

VH-VL: scFv derived, *e.g.*, from 34D10
H1: *E.g.*, half-life extending peptide
H2: *E.g.*, clotting factor (*e.g.*, FVIIa)

SEQUENCE LISTING

<160> NUMBER OF SEQ ID NOS: 250

<210> SEQ ID NO 1
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:

<223> OTHER INFORMATION: 34D10 HC

<400> SEQUENCE: 1

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ala Tyr
            20                  25                  30

Ala Met Ser Trp Val Arg Gln Thr Pro Glu Lys Arg Leu Glu Trp Val
        35                  40                  45

Ala Ser Ile Ser Ser Gly Gly Thr Thr Tyr Tyr Pro Asp Ser Val Lys
    50                  55                  60

Arg Arg Phe Thr Ile Ser Arg Asp Asn Ala Arg Asn Ile Leu Tyr Leu
65                  70                  75                  80

Gln Met Ser Ser Leu Arg Ser Glu Asp Thr Ala Met Tyr Tyr Cys Thr
                85                  90                  95

Arg Gly Gly Asp Tyr Gly Tyr Ala Leu Asp Tyr Trp Gly Gln Gly Thr
            100                 105                 110

Ser Val Thr Val Ser Ser
        115

<210> SEQ ID NO 2
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 34D10 LC

<400> SEQUENCE: 2

Glu Asn Val Leu Thr Gln Ser Pro Ala Ile Met Ser Ala Ser Leu Gly
1               5                   10                  15

Glu Lys Val Thr Met Ser Cys Arg Ala Ser Ser Ser Val Asn Tyr Met
            20                  25                  30

Tyr Trp Tyr Gln Gln Lys Ser Asp Ala Ser Pro Lys Leu Trp Ile Tyr
        35                  40                  45

Tyr Thr Ser Asn Leu Ala Pro Gly Val Pro Ala Arg Phe Ser Gly Ser
    50                  55                  60

Gly Ser Gly Asn Ser Tyr Ser Leu Thr Ile Ser Ser Met Glu Gly Glu
65                  70                  75                  80

Asp Ala Ala Thr Tyr Tyr Cys Gln Gln Phe Ser Ser Ser Pro Trp Thr
                85                  90                  95

Phe Gly Gly Gly Thr Lys Leu Glu Ile Lys Arg
            100                 105

<210> SEQ ID NO 3
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 2A2 HC

<400> SEQUENCE: 3

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Arg Thr Tyr

```
                20                  25                  30
Ala Met Ser Trp Val Arg Gln Thr Pro Glu Lys Arg Leu Glu Trp Val
            35                  40                  45

Ala Ser Ile Ser Ser Gly Ser Ser Thr Tyr Tyr Leu Asp Ser Val Lys
        50                  55                  60

Gly Arg Phe Thr Ile Ser Arg Asp Asn Ala Arg Asn Ile Leu Tyr Leu
65                  70                  75                  80

Gln Met Ser Ser Leu Arg Ser Glu Asp Thr Ala Met Tyr Tyr Cys Ala
                85                  90                  95

Arg Gly Gly Asp Tyr Gly Tyr Ala Leu Asp Tyr Trp Gly Gln Gly Thr
            100                 105                 110

Ser Val Thr Val Ser Ser
        115

<210> SEQ ID NO 4
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 2A2 LC

<400> SEQUENCE: 4

Glu Asn Val Leu Thr Gln Ser Pro Ala Ile Met Ser Ala Ser Leu Gly
1               5                   10                  15

Glu Lys Val Thr Met Ser Cys Arg Ala Ser Ser Val Asn Tyr Met
            20                  25                  30

Tyr Trp Tyr Gln Gln Lys Ser Asp Ala Ser Pro Lys Leu Trp Ile Tyr
        35                  40                  45

Tyr Thr Ser Asn Leu Ala Pro Gly Val Pro Thr Arg Phe Ser Gly Ser
    50                  55                  60

Gly Ser Gly Asn Ser Tyr Ser Leu Thr Ile Ser Ser Leu Glu Gly Glu
65                  70                  75                  80

Asp Ala Gly Thr Tyr Tyr Cys Gln Gln Phe Ser Ser Ser Pro Trp Thr
                85                  90                  95

Phe Gly Gly Gly Thr Lys Leu Glu Ile Lys Arg
            100                 105

<210> SEQ ID NO 5
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 36A8 HC

<400> SEQUENCE: 5

Glu Val Arg Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Thr Tyr
            20                  25                  30

Ala Met Ser Trp Val Arg Gln Thr Pro Glu Lys Arg Leu Glu Trp Val
        35                  40                  45

Ala Ser Ile Asn Gly Gly Gly Ser Thr Tyr Tyr Pro Asp Ser Val Lys
    50                  55                  60
```

```
Gly Arg Phe Thr Ile Ser Arg Asp Asn Ala Arg Asn Ile Leu Tyr Leu
65                  70                  75                  80

Gln Met Arg Ser Leu Arg Ser Glu Asp Thr Ala Met Tyr Tyr Cys Ala
                85                  90                  95

Arg Gly Gly Asp Tyr Gly Tyr Ala Leu Asp Tyr Trp Gly Gln Gly Thr
            100                 105                 110

Ser Val Thr Val Ser Ser
            115

<210> SEQ ID NO 6
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 36A8 LC

<400> SEQUENCE: 6

Glu Asn Val Leu Thr Gln Ser Pro Ala Ile Met Ser Ala Ser Leu Gly
1               5                   10                  15

Glu Lys Val Thr Met Asn Cys Arg Ala Ser Ser Ser Val Asn Tyr Met
                20                  25                  30

Tyr Trp Tyr Gln Gln Lys Ser Asp Ala Ser Pro Lys Leu Trp Ile Phe
            35                  40                  45

Tyr Thr Ser Asn Leu Ala Pro Gly Val Pro Ala Arg Phe Ser Gly Ser
        50                  55                  60

Gly Ser Gly Asn Ser Tyr Ser Leu Thr Ile Ser Ser Met Glu Gly Glu
65                  70                  75                  80

Asp Ala Ala Thr Tyr Tyr Cys Gln Gln Phe Ser Ser Ser Pro Trp Thr
                85                  90                  95

Phe Gly Gly Gly Ser Lys Leu Glu Ile Lys Arg
            100                 105

<210> SEQ ID NO 7
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4B11 LC

<400> SEQUENCE: 7

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
                20                  25                  30

Ala Met Ser Trp Val Arg Gln Thr Pro Glu Lys Arg Leu Ala Trp Val
            35                  40                  45

Ala Ser Ile Ser Ser Gly Gly Asn Ile Tyr Phe Pro Asp Ser Val Lys
        50                  55                  60

Gly Arg Phe Thr Ile Ser Arg Asp Asp Ala Arg Asn Ile Leu Tyr Leu
65                  70                  75                  80

Gln Met Arg Ser Leu Arg Ser Glu Asp Thr Ala Met Tyr Tyr Cys Ala
                85                  90                  95

Arg Gly Gly Asp Tyr Gly Tyr Ala Met Asp Tyr Trp Gly Gln Gly Thr
            100                 105                 110
```

Ser Val Thr Val Ser Ser
        115

<210> SEQ ID NO 8
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 1H6 HC

<400> SEQUENCE: 8

Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Thr Asn Tyr
            20                  25                  30

Leu Ile Glu Trp Val Lys Gln Arg Pro Gly Gln Gly Leu Glu Trp Ile
        35                  40                  45

Gly Val Ile Asn Pro Gly Ser Gly Gly Thr Asn Tyr Asn Glu Lys Phe
    50                  55                  60

Lys Gly Lys Ala Thr Leu Thr Ala Asp Lys Ser Ser Ser Thr Ala Tyr
65                  70                  75                  80

Met His Leu Ser Ser Leu Thr Ser Asp Asp Ser Ala Val Tyr Phe Cys
                85                  90                  95

Ala Arg Gly Arg Tyr Glu Trp Tyr Phe Asp Val Trp Gly Ala Gly Thr
            100                 105                 110

Thr Val Thr Val Ser Ser
        115

<210> SEQ ID NO 9
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 1H6 LC

<400> SEQUENCE: 9

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Thr Asn Tyr
            20                  25                  30

Leu Asn Trp Tyr Gln Arg Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Tyr Thr Leu Pro Tyr
                85                  90                  95

Thr Phe Gly Gly Gly Thr Lys Leu Glu Ile Lys Arg
            100                 105

<210> SEQ ID NO 10
<211> LENGTH: 118
<212> TYPE: PRT

```
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 38A8 HC

<400> SEQUENCE: 10

Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Thr Asn Tyr
            20                  25                  30

Leu Ile Glu Trp Ile Lys Gln Arg Pro Gly Gln Gly Leu Glu Trp Ile
        35                  40                  45

Gly Val Ile Asn Pro Gly Ser Gly Gly Thr Asn Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Asp Asp Ser Ala Val Tyr Phe Cys
                85                  90                  95

Ala Arg Gly Arg Tyr Glu Trp Tyr Phe Asp Val Trp Gly Ala Gly Thr
            100                 105                 110

Thr Val Thr Val Ser Ser
            115

<210> SEQ ID NO 11
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 38A8 LC

<400> SEQUENCE: 11

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Leu Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Ser Ile Ser Asn Leu Glu Gln
65                  70                  75                  80

Glu Asp Ile Ala Thr Tyr Phe Cys Gln Gln Gly Tyr Thr Leu Pro Tyr
                85                  90                  95

Thr Phe Gly Gly Gly Thr Lys Leu Glu Ile Lys Arg
            100                 105

<210> SEQ ID NO 12
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 18F7 HC

<400> SEQUENCE: 12
```

```
Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
                20                  25                  30

Gly Val Ser Trp Val Arg Gln Pro Pro Gly Lys Gly Leu Glu Trp Leu
            35                  40                  45

Gly Ile Ile Trp Gly Asp Gly Ser Thr Asn Tyr His Ser Val Leu Lys
        50                  55                  60

Ser Arg Leu Ser Ile Ser Lys Asp Asn Ser Lys Ser Gln Val Phe Leu
65                  70                  75                  80

Lys Leu Asn Ser Leu Gln Thr Asp Thr Ala Thr Tyr Tyr Cys Ala
                85                  90                  95

Lys Gln Asp Phe Asp Val Trp Gly Ala Gly Thr Thr Val Thr Val Ser
            100                 105                 110

Ser
```

<210> SEQ ID NO 13
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 18F7 LC

<400> SEQUENCE: 13

```
Asp Val Gln Met Ile Gln Ser Pro Phe Ser Leu Ser Ala Ser Leu Gly
1               5                   10                  15

Asp Ile Val Thr Met Thr Cys Gln Ala Ser Gln Gly Thr Ser Ile Asn
                20                  25                  30

Leu Asn Trp Phe Gln Gln Lys Pro Gly Lys Ala Pro Lys Leu Leu Ile
            35                  40                  45

Tyr Gly Val Ser Asn Leu Glu Asp Gly Val Pro Ser Arg Phe Ser Gly
        50                  55                  60

Ser Arg Tyr Gly Thr Asp Phe Thr Leu Thr Ile Gly Ser Leu Glu Asp
65                  70                  75                  80

Glu Asp Met Ala Thr Tyr Phe Cys Leu Gln His Ser Tyr Leu Pro Tyr
                85                  90                  95

Thr Phe Gly Gly Gly Thr Lys Leu Glu Ile Lys Arg
            100                 105
```

<210> SEQ ID NO 14
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 12B2 HC

<400> SEQUENCE: 14

```
Gln Val Gln Leu Gln Gln Ser Gly Ala Glu Leu Thr Lys Pro Gly Ala
1               5                   10                  15

Ser Val Lys Ile Ser Cys Lys Ala Thr Gly Tyr Thr Phe Ser Ser Tyr
                20                  25                  30

Trp Ile Glu Trp Val Lys Gln Arg Pro Gly His Gly Leu Glu Trp Ile
            35                  40                  45
```

Gly Glu Ile Leu Pro Gly Ser Gly Ile Thr Lys Tyr Asn Asp Lys Phe
            50                  55                  60

Lys Gly Lys Ala Thr Phe Thr Ala Asp Thr Ser Ser Asn Thr Ala Tyr
 65                  70                  75                  80

Met Gln Leu Ser Ser Leu Thr Ser Glu Asp Ser Ala Val Tyr Ser Cys
                 85                  90                  95

Ala Arg Leu Ile Ser Tyr Tyr Tyr Ala Met Asp Tyr Trp Gly Gln Gly
             100                 105                 110

Thr Ser Val Thr Val Ser Ser
            115

<210> SEQ ID NO 15
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 12B2 LC

<400> SEQUENCE: 15

Asp Ile Gln Met Thr Gln Thr Thr Ser Ser Leu Ser Ala Ser Leu Gly
 1               5                  10                  15

Asp Arg Val Thr Ile Ser Cys Arg Ala Ser Gln Asp Ile Ser Asn Tyr
             20                  25                  30

Leu Asn Trp Tyr Gln Gln Lys Pro Asp Gly Thr Val Lys Leu Leu Ile
         35                  40                  45

Tyr Tyr Thr Ser Arg Leu His Ser Gly Val Pro Ser Arg Phe Ser Gly
     50                  55                  60

Ser Gly Ser Gly Thr Asp Tyr Ser Leu Thr Ile Ser Asn Leu Glu Gln
 65                  70                  75                  80

Glu Asp Ile Ala Thr Tyr Phe Cys Gln Gln Gly Asn Thr Leu Pro Pro
                 85                  90                  95

Thr Phe Gly Gly Gly Thr Lys Leu Glu Ile Lys Arg
             100                 105

<210> SEQ ID NO 16
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 38F6 HC

<400> SEQUENCE: 16

Gln Val Gln Leu Gln Gln Ser Gly Ala Glu Leu Met Arg Pro Gly Ala
 1               5                  10                  15

Ser Val Lys Ile Ser Cys Lys Ala Thr Gly Tyr Thr Phe Ser Ser Tyr
             20                  25                  30

Trp Ile Glu Trp Val Lys Gln Arg Pro Gly His Gly Leu Glu Trp Ile
         35                  40                  45

Gly Glu Ile Leu Pro Gly Thr Gly Tyr Thr Lys Tyr Asn Glu Lys Phe
     50                  55                  60

Lys Gly Lys Ala Thr Phe Thr Ala Glu Thr Ser Ser Asn Thr Ala Ser
 65                  70                  75                  80

Met Gln Val Ser Ser Leu Thr Ser Glu Asp Ser Ala Val Tyr Phe Cys

```
                    85                  90                  95

Ala Arg Leu Ile Ser Tyr Tyr Tyr Ala Met Asp Tyr Trp Gln Gly
                100                 105                 110

Thr Ser Val Thr Val Ser Ser
            115

<210> SEQ ID NO 17
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 5C4

<400> SEQUENCE: 17

Gln Val Thr Leu Lys Ala Ser Gly Pro Gly Ile Leu Gln Pro Ser Gln
1               5                   10                  15

Thr Leu Ser Leu Thr Cys Ser Phe Ser Gly Phe Ser Leu Asn Thr Ser
                20                  25                  30

Gly Leu Gly Val Gly Trp Ile Arg Gln Pro Ser Gly Lys Gly Leu Glu
            35                  40                  45

Trp Leu Ala His Ile Trp Trp Asp Asp Lys Arg Tyr Asn Pro Ala
50                  55                  60

Leu Lys Ser Arg Leu Thr Ile Ser Lys Asp Thr Ser Asn Asn Gln Ile
65                  70                  75                  80

Phe Leu Lys Ile Ala Ser Val Asp Thr Ala Asp Thr Ala Thr Tyr Tyr
                85                  90                  95

Cys Ala Arg Ser His Tyr Tyr Gly Thr Phe Tyr Phe Asp Tyr Trp Gly
                100                 105                 110

Gln Gly Thr Thr Leu Thr Val Ser Ser
            115                 120

<210> SEQ ID NO 18
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 23C10 HC

<400> SEQUENCE: 18

Phe Leu Leu Leu Ile Val Pro Ala Tyr Val Leu Ser Gln Val Thr Leu
1               5                   10                  15

Lys Ala Ser Gly Pro Gly Ile Val Gln Pro Ser Gln Thr Leu Ser Leu
                20                  25                  30

Thr Cys Ser Phe Ser Gly Phe Ser Leu Asn Thr Ser Gly Met Gly Val
                35                  40                  45

Gly Trp Ile Arg Gln Pro Ser Gly Lys Gly Leu Glu Trp Leu Ala His
            50                  55                  60

Ile Trp Trp Asp Asp Lys Arg Tyr Asn Pro Ala Leu Lys Ser Arg
65                  70                  75                  80

Leu Thr Ile Ser Lys Asp Thr Ser Asn Asn Gln Ile Phe Leu Lys Ile
                85                  90                  95

Ala Ser Val Asp Thr Ala Asp Thr Ala Thr Tyr Tyr Cys Ala Arg Ser
                100                 105                 110
```

His Tyr Tyr Gly Thr Phe Tyr Phe Asp Tyr Trp Gln Gly Thr Thr
            115                 120                 125

Leu Thr Val Ser Ser
    130

<210> SEQ ID NO 19
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 28C2 HC

<400> SEQUENCE: 19

Gln Val Thr Leu Lys Ala Ser Gly Pro Gly Ile Val Gln Pro Ser Gln
1               5                   10                  15

Thr Leu Ser Leu Thr Cys Ser Phe Ser Gly Phe Ser Leu Asn Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Lys Arg Tyr Asn Pro Ala
    50                  55                  60

Leu Lys Ser Arg Leu Thr Ile Ser Lys Asp Thr Ser Asn Asn Gln Ile
65                  70                  75                  80

Phe Leu Lys Ile Ala Ser Val Asp Thr Ala Asp Thr Ala Thr Tyr Tyr
                85                  90                  95

Cys Ala Arg Ser His Tyr Tyr Gly Thr Phe Tyr Phe Asp Tyr Trp Gly
            100                 105                 110

Gln Gly Thr Thr Leu Thr Val Ser Ser
        115                 120

<210> SEQ ID NO 20
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 28C2 LC

<400> SEQUENCE: 20

Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
            20                  25                  30

Leu Ala Trp Tyr Gln Glu Lys Pro Gly Thr Thr Tyr Lys Leu Leu Ile
        35                  40                  45

Tyr Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Ile Glu Tyr Pro Trp
                85                  90                  95

Thr Phe Gly Gly Gly Thr Lys Leu Glu Ile Lys Arg
            100                 105

<210> SEQ ID NO 21

<211> LENGTH: 121
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: 9D6 HC

<400> SEQUENCE: 21

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Ser Ser Gly Lys Gly Leu Glu
        35                  40                  45

Trp Leu Ala His Ile Trp Trp Asp Asp Lys Arg Tyr Asn Pro Thr
50                  55                  60

Leu Lys Ser Arg Leu Thr Ile Ser Lys Asp Thr Ser Asn Asn Gln Val
65                  70                  75                  80

Phe Leu Lys Ile Ala Asn Met Asp Thr Ala Asp Ile Ala Thr Tyr Tyr
                85                  90                  95

Cys Ala Arg Ser His Tyr Asn Gly Thr Phe Tyr Phe Asp Phe Trp Gly
            100                 105                 110

Gln Gly Ile Thr Leu Thr Val Ser Ser
        115                 120

<210> SEQ ID NO 22
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: 9D6 LC

<400> SEQUENCE: 22

Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
50                  55                  60

Ser Gly Ser Gly Thr Asp Phe Thr Leu Thr Ile Ser Thr Leu Glu Pro
65                  70                  75                  80

Glu Asp Phe Ala Met Tyr Tyr Cys Gln Gln His Ile Glu Tyr Pro Trp
                85                  90                  95

Thr Phe Gly Gly Gly Thr Lys Leu Glu Ile Lys Arg
            100                 105

<210> SEQ ID NO 23
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: 28F4 HC

<400> SEQUENCE: 23

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Asn Tyr
            20                  25                  30

Gly Met Ser Trp Val Arg Gln Thr Pro Asp Lys Arg Leu Glu Trp Val
        35                  40                  45

Ala Thr Ile Ser Ser Gly Gly Thr Tyr Thr Tyr Tyr Pro Asp Ser Val
    50                  55                  60

Lys Gly Gln Phe Thr Ile Phe Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Thr Arg Arg Asp Tyr Asp Tyr Glu Gly Phe Ala Tyr Trp Gly Gln Gly
            100                 105                 110

Thr Leu Val Thr Val Ser
            115

<210> SEQ ID NO 24
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 28F4 LC

<400> SEQUENCE: 24

Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Ser Ile Ser Asn Asn
            20                  25                  30

Leu His Trp Tyr Gln Gln Lys Ser His Glu Ser Pro Arg Leu Leu Ile
        35                  40                  45

Lys Tyr Ala Ser His Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Met Tyr Phe Cys Gln Gln Ser Asn Asn Trp Pro Phe
                85                  90                  95

Thr Phe Gly Ser Gly Thr Lys Leu Glu Ile Lys Arg
            100                 105

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 2A2 HC CDR1

<400> SEQUENCE: 25

Thr Tyr Ala Met Ser
1               5

<210> SEQ ID NO 26

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 2A2 HC CDR2

<400> SEQUENCE: 26

Ser Ile Ser Ser Gly Ser Ser Thr Tyr Tyr Leu Asp Ser Val Lys Gly
1               5                   10                  15

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 2A2 HC CDR3

<400> SEQUENCE: 27

Gly Gly Asp Tyr Gly Tyr Ala Leu Asp Tyr
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 2A2 LC CDR1

<400> SEQUENCE: 28

Arg Ala Ser Ser Ser Val Asn Tyr Met Tyr
1               5                   10

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 2A2 LC CDR2

<400> SEQUENCE: 29

Tyr Thr Ser Asn Leu Ala Pro
1               5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 2A2 LC CDR3

<400> SEQUENCE: 30

Gln Gln Phe Ser Ser Ser Pro Trp Thr
1               5
```

```
<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 34D10 HC CDR1

<400> SEQUENCE: 31

Ala Tyr Ala Met Ser
1               5

<210> SEQ ID NO 32
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 34D10 HC CDR2

<400> SEQUENCE: 32

Ser Ile Ser Ser Gly Gly Thr Thr Tyr Tyr Pro Asp Ser Val Lys Arg
1               5                   10                  15

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 34D10 HC CDR3

<400> SEQUENCE: 33

Gly Gly Asp Tyr Gly Tyr Ala Leu Asp Tyr
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 34D10 LC CDR1

<400> SEQUENCE: 34

Arg Ala Ser Ser Ser Val Asn Tyr Met Tyr
1               5                   10

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 34D10 LC CDR2

<400> SEQUENCE: 35

Tyr Thr Ser Asn Leu Ala Pro
1               5
```

```
<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 34D10 LC CDR3

<400> SEQUENCE: 36

Gln Gln Phe Ser Ser Ser Pro Trp Thr
1               5

<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 36A8 HC CDR1

<400> SEQUENCE: 37

Thr Tyr Ala Met Ser
1               5

<210> SEQ ID NO 38
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 36A8 HC CDR2

<400> SEQUENCE: 38

Ser Ile Asn Gly Gly Gly Ser Thr Tyr Tyr Pro Asp Ser Val Lys Gly
1               5                   10                  15

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 36A8 HC CDR3

<400> SEQUENCE: 39

Gly Gly Asp Tyr Gly Tyr Ala Leu Asp Tyr
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 36A8 LC CDR1

<400> SEQUENCE: 40

Arg Ala Ser Ser Ser Val Asn Tyr Met Tyr
1               5                   10
```

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 36A8 LC CDR2

<400> SEQUENCE: 41

Tyr Thr Ser Asn Leu Ala Pro
1               5

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 36A8 LC CDR3

<400> SEQUENCE: 42

Gln Gln Phe Ser Ser Ser Pro Trp Thr
1               5

<210> SEQ ID NO 43
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4B11 HC CDR1

<400> SEQUENCE: 43

Ser Tyr Ala Met Ser
1               5

<210> SEQ ID NO 44
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4B11 HC CDR2

<400> SEQUENCE: 44

Ser Ile Ser Ser Gly Gly Asn Ile Tyr Phe Pro Asp Ser Val Lys Gly
1               5                   10                  15

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4B11 HC CDR3

<400> SEQUENCE: 45

Gly Gly Asp Tyr Gly Tyr Ala Met Asp Tyr

<210> SEQ ID NO 46
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 1H6 HC CDR1

<400> SEQUENCE: 46

Asn Tyr Leu Ile Glu
1               5

<210> SEQ ID NO 47
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 1H6 HC CDR2

<400> SEQUENCE: 47

Val Ile Asn Pro Gly Ser Gly Gly Thr Asn Tyr Asn Glu Lys Phe Lys
1               5                   10                  15

Gly

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 1H6 HC CDR3

<400> SEQUENCE: 48

Gly Arg Tyr Glu Trp Tyr Phe Asp Val
1               5

<210> SEQ ID NO 49
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 1H6 LC CDR1

<400> SEQUENCE: 49

Arg Ala Ser Gln Asp Ile Thr Asn Tyr Leu Asn
1               5                   10

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 1H6 LC CDR2

```
<400> SEQUENCE: 50

Tyr Thr Ser Arg Leu His Ser
1               5

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 1H6 LC CDR3

<400> SEQUENCE: 51

Gln Gln Gly Tyr Thr Leu Pro Tyr Thr
1               5

<210> SEQ ID NO 52
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 38A8 HC CDR1

<400> SEQUENCE: 52

Asn Tyr Leu Ile Glu
1               5

<210> SEQ ID NO 53
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 38A8 HC CDR2

<400> SEQUENCE: 53

Val Ile Asn Pro Gly Ser Gly Gly Thr Asn Tyr Asn Glu Lys Phe Lys
1               5                   10                  15

Gly

<210> SEQ ID NO 54
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 38A8 HC CDR3

<400> SEQUENCE: 54

Gly Arg Tyr Glu Trp Tyr Phe Asp Val
1               5

<210> SEQ ID NO 55
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

<220> FEATURE:
<223> OTHER INFORMATION: 38A8 LC CDR1

<400> SEQUENCE: 55

Arg Ala Ser Gln Asp Ile Ser Asn Tyr Leu Asn
1               5                   10

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 38A8 LC CDR2

<400> SEQUENCE: 56

Tyr Thr Ser Arg Leu His Ser
1               5

<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 38A8 LC CDR3

<400> SEQUENCE: 57

Gln Gln Gly Tyr Thr Leu Pro Tyr Thr
1               5

<210> SEQ ID NO 58
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 18F7 HC CDR1

<400> SEQUENCE: 58

Ser Tyr Gly Val Ser
1               5

<210> SEQ ID NO 59
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 18F7 HC CDR2

<400> SEQUENCE: 59

Ile Ile Trp Gly Asp Gly Ser Thr Asn Tyr His Ser Val Leu Lys Ser
1               5                   10                  15

<210> SEQ ID NO 60
<211> LENGTH: 5
<212> TYPE: PRT
<213> ORGANISM: Artificial Sequence
<220> FEATURE:
<223> OTHER INFORMATION: Description of Artificial Sequence: Synthetic

```
            peptide
<220> FEATURE:
<223> OTHER INFORMATION: 18F7 HC CDR3

<400> SEQUENCE: 60

Gln Asp Phe Asp Val
1               5

<210> SEQ ID NO 61
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 18F7 LC CDR1

<400> SEQUENCE: 61

Gln Ala Ser Gln Gly Thr Ser Ile Asn Leu Asn
1               5                   10

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 18F7 LC CDR2

<400> SEQUENCE: 62

Gly Val Ser Asn Leu Glu Asp
1               5

<210> SEQ ID NO 63
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 18F7 LC CDR3

<400> SEQUENCE: 63

Leu Gln His Ser Tyr Leu Pro Tyr Thr
1               5

<210> SEQ ID NO 64
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 12B2 HC CDR1

<400> SEQUENCE: 64

Ser Tyr Trp Ile Glu
1               5

<210> SEQ ID NO 65
<211> LENGTH: 17
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: 12B2 HC CDR2

<400> SEQUENCE: 65

Glu Ile Leu Pro Gly Ser Gly Ile Thr Lys Tyr Asn Asp Lys Phe Lys
1               5                   10                  15

Gly

<210> SEQ ID NO 66
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 12B2 HC CDR3

<400> SEQUENCE: 66

Leu Ile Ser Tyr Tyr Tyr Ala Met Asp Tyr
1               5                   10

<210> SEQ ID NO 67
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 12B2 LC CDR1

<400> SEQUENCE: 67

Arg Ala Ser Gln Asp Ile Ser Asn Tyr Leu Asn
1               5                   10

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 12B2 LC CDR2

<400> SEQUENCE: 68

Tyr Thr Ser Arg Leu His Ser
1               5

<210> SEQ ID NO 69
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 12B2 LC CDR3

<400> SEQUENCE: 69

Gln Gln Gly Asn Thr Leu Pro Pro Thr
1               5

<210> SEQ ID NO 70
<211> LENGTH: 5
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 38F6 HC CDR1

<400> SEQUENCE: 70

Ser Tyr Trp Ile Glu
1               5

<210> SEQ ID NO 71
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 38F6 HC CDR2

<400> SEQUENCE: 71

Glu Ile Leu Pro Gly Thr Gly Tyr Thr Lys Tyr Asn Glu Lys Phe Lys
1               5                   10                  15

Gly

<210> SEQ ID NO 72
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 38F6 HC CDR3

<400> SEQUENCE: 72

Leu Ile Ser Tyr Tyr Tyr Ala Met Asp Tyr
1               5                   10

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 5C4 HC CDR1

<400> SEQUENCE: 73

Thr Ser Gly Leu Gly Val Gly
1               5

<210> SEQ ID NO 74
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 5C4 HC CDR2

<400> SEQUENCE: 74

His Ile Trp Trp Asp Asp Asp Lys Arg Tyr Asn Pro Ala Leu Lys Ser
1               5                   10                  15
```

```
<210> SEQ ID NO 75
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 5C4 HC CDR3

<400> SEQUENCE: 75

Ser His Tyr Tyr Gly Thr Phe Tyr Phe Asp Tyr
1               5                   10

<210> SEQ ID NO 76
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 23C10 HC CDR1

<400> SEQUENCE: 76

Thr Ser Gly Met Gly Val Gly
1               5

<210> SEQ ID NO 77
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 23C10 HC CDR2

<400> SEQUENCE: 77

His Ile Trp Trp Asp Asp Asp Lys Arg Tyr Asn Pro Ala Leu Lys Ser
1               5                   10                  15

<210> SEQ ID NO 78
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 23C10 HC CDR3

<400> SEQUENCE: 78

Ser His Tyr Tyr Gly Thr Phe Tyr Phe Asp Tyr
1               5                   10

<210> SEQ ID NO 79
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 28C2 HC CDR1

<400> SEQUENCE: 79

Thr Ser Gly Met Gly Val Gly
1               5
```

```
<210> SEQ ID NO 80
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 28C2 HC CDR2

<400> SEQUENCE: 80

His Ile Trp Trp Asp Asp Lys Arg Tyr Asn Pro Ala Leu Lys Ser
1               5                   10                  15

<210> SEQ ID NO 81
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 28C2 HC CDR3

<400> SEQUENCE: 81

Ser His Tyr Tyr Gly Thr Phe Tyr Phe Asp Tyr
1               5                   10

<210> SEQ ID NO 82
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 28C2 LC CDR1

<400> SEQUENCE: 82

Arg Ala Ser Lys Ser Ile Ser Lys Tyr Leu Ala
1               5                   10

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 28C2 LC CDR2

<400> SEQUENCE: 83

Ser Gly Ser Thr Leu Gln Ser
1               5

<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 28C2 LC CDR3

<400> SEQUENCE: 84

Gln Gln His Ile Glu Tyr Pro Trp Thr
```

```
<210> SEQ ID NO 85
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 9D6 HC CDR1

<400> SEQUENCE: 85

Thr Ser Gly Met Gly Val Gly
1               5

<210> SEQ ID NO 86
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 9D6 HC CDR2

<400> SEQUENCE: 86

His Ile Trp Trp Asp Asp Asp Lys Arg Tyr Asn Pro Thr Leu Lys Ser
1               5                   10                  15

<210> SEQ ID NO 87
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 9D6 HC CDR3

<400> SEQUENCE: 87

Ser His Tyr Asn Gly Thr Phe Tyr Phe Asp Phe
1               5                   10

<210> SEQ ID NO 88
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 9D6 LC CDR1

<400> SEQUENCE: 88

Arg Ala Ser Lys Ser Ile Ser Lys Tyr Leu Ala
1               5                   10

<210> SEQ ID NO 89
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 9D6 LC CDR2

<400> SEQUENCE: 89
```

```
Ser Gly Ser Thr Leu Gln Ser
1               5

<210> SEQ ID NO 90
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 9D6 LC CDR3

<400> SEQUENCE: 90

Gln Gln His Ile Glu Tyr Pro Trp Thr
1               5

<210> SEQ ID NO 91
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 28F4 HC CDR1

<400> SEQUENCE: 91

Asn Tyr Gly Met Ser
1               5

<210> SEQ ID NO 92
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 28F4 HC CDR2

<400> SEQUENCE: 92

Thr Ile Ser Ser Gly Gly Thr Tyr Thr Tyr Tyr Pro Asp Ser Val Lys
1               5                   10                  15
Gly

<210> SEQ ID NO 93
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 28F4 HC CDR3

<400> SEQUENCE: 93

Arg Asp Tyr Asp Tyr Glu Gly Phe Ala Tyr
1               5                   10

<210> SEQ ID NO 94
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 28F4 LC CDR1
```

<400> SEQUENCE: 94

Arg Ala Ser Gln Ser Ile Ser Asn Asn Leu His
1               5                   10

<210> SEQ ID NO 95
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 28F4 LC CDR2

<400> SEQUENCE: 95

Tyr Ala Ser His Ser Ile Ser
1               5

<210> SEQ ID NO 96
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 28F4 LC CDR3

<400> SEQUENCE: 96

Gln Gln Ser Asn Asn Trp Pro Phe Thr
1               5

<210> SEQ ID NO 97
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 35D1 HC

<400> SEQUENCE: 97

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ala Tyr
            20                  25                  30

Ala Met Ser Trp Val Arg Gln Thr Pro Glu Lys Arg Leu Glu Trp Val
        35                  40                  45

Ala Ser Ile Ser Ser Gly Gly Thr Thr Tyr Tyr Pro Asp Ser Val Lys
    50                  55                  60

Arg Arg Phe Thr Ile Ser Arg Asp Asn Ala Arg Asn Ile Leu Tyr Leu
65                  70                  75                  80

Gln Met Ser Ser Leu Arg Ser Glu Asp Thr Ala Met Tyr Tyr Cys Thr
                85                  90                  95

Arg Gly Gly Asp Tyr Gly Tyr Ala Leu Asp Tyr Trp Gly Gln Gly Thr
            100                 105                 110

Ser Val Thr Val Ser Ser
        115

<210> SEQ ID NO 98
<211> LENGTH: 107
<212> TYPE: PRT

<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 35D1 LC

<400> SEQUENCE: 98

Glu Asn Val Leu Thr Gln Ser Pro Ala Ile Met Ser Ala Ser Leu Gly
1               5                   10                  15

Glu Lys Val Thr Met Ser Cys Arg Ala Ser Ser Ser Val Asn Tyr Met
                20                  25                  30

Tyr Trp Tyr Gln Gln Lys Ser Asp Ala Ser Pro Lys Leu Trp Ile Tyr
            35                  40                  45

Tyr Thr Ser Asn Leu Ala Pro Gly Val Pro Ala Arg Phe Ser Gly Ser
        50                  55                  60

Gly Ser Gly Asn Ser Tyr Ser Leu Thr Ile Ser Ser Met Glu Gly Glu
65                  70                  75                  80

Asp Ala Ala Thr Tyr Tyr Cys Gln Gln Phe Ser Ser Pro Trp Thr
                85                  90                  95

Phe Gly Gly Gly Thr Lys Leu Glu Ile Lys Arg
            100                 105

<210> SEQ ID NO 99
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4B11 LC

<400> SEQUENCE: 99

Glu Asn Val Leu Thr Gln Ser Pro Ala Ile Met Ser Ala Ser Leu Gly
1               5                   10                  15

Glu Lys Val Thr Met Asn Cys Arg Ala Ser Ser Ser Val Asn Tyr Met
                20                  25                  30

Tyr Trp Tyr Gln Gln Lys Ser Asp Ala Ser Pro Lys Leu Trp Ile Phe
            35                  40                  45

Tyr Thr Ser Asn Leu Ala Pro Gly Val Pro Ala Arg Phe Ser Gly Ser
        50                  55                  60

Gly Ser Gly Asn Ser Tyr Ser Leu Thr Ile Ser Ser Met Glu Gly Glu
65                  70                  75                  80

Asp Ala Ala Thr Tyr Tyr Cys Gln Gln Phe Ser Ser Pro Trp Thr
                85                  90                  95

Phe Gly Gly Gly Ser Lys Leu Glu Ile Lys Arg
            100                 105

<210> SEQ ID NO 100
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 38G8 HC

<400> SEQUENCE: 100

Gln Val Gln Leu Gln Gln Ser Gly Ala Glu Leu Val Arg Pro Gly Thr
1               5                   10                  15

-continued

```
Ser Val Lys Val Ser Cys Lys Ala Ser Gly Tyr Ala Phe Thr Asn Tyr
            20                  25                  30

Leu Ile Glu Trp Val Lys Gln Arg Pro Gly Gln Gly Leu Glu Trp Ile
        35                  40                  45

Gly Val Ile Asn Pro Gly Ser Gly Gly Thr Tyr Asn Glu Lys Phe
50                  55                  60

Lys Gly Lys Ala Thr Leu Thr Ala Asp Lys Ser Ser Thr Ala Tyr
65                  70                  75                  80

Met His Leu Ser Ser Leu Thr Ser Asp Asp Ser Ala Val Tyr Phe Cys
                85                  90                  95

Ala Arg Gly Arg Tyr Glu Trp Tyr Phe Asp Val Trp Gly Ala Gly Thr
            100                 105                 110

Thr Val Thr Val Ser Ser
            115

<210> SEQ ID NO 101
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 38G8 LC

<400> SEQUENCE: 101

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Thr Asn Tyr
            20                  25                  30

Leu Asn Trp Tyr Gln Arg Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Tyr Thr Leu Pro Tyr
                85                  90                  95

Thr Phe Gly Gly Gly Thr Lys Leu Glu Ile Lys Arg
            100                 105

<210> SEQ ID NO 102
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 21F10 HC

<400> SEQUENCE: 102

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Thr Asn Tyr
            20                  25                  30

Leu Asn Trp Tyr Gln Arg Lys Pro Asp Gly Thr Val Lys Leu Leu Ile
        35                  40                  45

Tyr Tyr Thr Ser Arg Leu His Ser Gly Val Pro Ser Arg Phe Ser Gly
```

```
                         50                  55                  60
Ser Gly Ser Gly Thr Asp Tyr Ser Leu Thr Ile Ser Asn Leu Glu Gln
 65                  70                  75                  80

Glu Asp Ile Ala Thr Tyr Phe Cys Gln Gln Gly Tyr Thr Leu Pro Tyr
                 85                  90                  95

Thr Phe Gly Gly Gly Thr Lys Leu Glu Ile Lys Arg
            100                 105

<210> SEQ ID NO 103
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 21F10 LC

<400> SEQUENCE: 103

Asp Ile Gln Met Thr Gln Thr Thr Ser Ser Leu Ser Ala Ser Leu Gly
 1               5                  10                  15

Asp Arg Val Thr Ile Ser Cys Arg Ala Ser Gln Asp Ile Thr Asn Tyr
                20                  25                  30

Leu Asn Trp Tyr Gln Arg Lys Pro Asp Gly Thr Val Lys Leu Leu Ile
            35                  40                  45

Tyr Tyr Thr Ser Arg Leu His Ser Gly Val Pro Ser Arg Phe Ser Gly
        50                  55                  60

Ser Gly Ser Gly Thr Asp Tyr Ser Leu Thr Ile Ser Asn Leu Glu Gln
 65                  70                  75                  80

Glu Asp Ile Ala Thr Tyr Phe Cys Gln Gln Gly Tyr Thr Leu Pro Tyr
                 85                  90                  95

Thr Phe Gly Gly Gly Thr Lys Leu Glu Ile Lys Arg
            100                 105

<210> SEQ ID NO 104

<400> SEQUENCE: 104

000

<210> SEQ ID NO 105
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 13C1 HC

<400> SEQUENCE: 105

Gln Val Gln Leu Gln Gln Ser Gly Ala Glu Leu Thr Lys Pro Gly Ala
 1               5                  10                  15

Ser Val Lys Ile Ser Cys Lys Ala Thr Gly Tyr Thr Phe Ser Ser Tyr
                20                  25                  30

Trp Ile Glu Trp Val Lys Gln Arg Pro Gly His Gly Leu Glu Trp Ile
            35                  40                  45

Gly Glu Ile Leu Pro Gly Ser Gly Ile Thr Tyr Asn Asp Lys Phe
        50                  55                  60

Lys Gly Lys Ala Thr Phe Thr Ala Asp Thr Ser Ser Asn Thr Ala Tyr
 65                  70                  75                  80
```

```
Met Gln Leu Ser Ser Leu Thr Ser Glu Asp Ser Ala Val Tyr Ser Cys
                85                  90                  95

Ala Arg Leu Ile Ser Tyr Tyr Ala Met Asp Tyr Trp Gly Gln Gly
            100                 105                 110

Thr Ser Val Thr Val Ser Ser
        115

<210> SEQ ID NO 106

<400> SEQUENCE: 106

000

<210> SEQ ID NO 107

<400> SEQUENCE: 107

000

<210> SEQ ID NO 108

<400> SEQUENCE: 108

000

<210> SEQ ID NO 109
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 37C7 HC

<400> SEQUENCE: 109

Phe Leu Leu Ile Val Pro Ala Tyr Val Leu Ser Gln Val Thr Leu
1               5                   10                  15

Lys Ala Ser Gly Pro Gly Ile Val Gln Pro Ser Gln Thr Leu Ser Leu
            20                  25                  30

Thr Cys Ser Phe Ser Gly Phe Ser Leu Asn Thr Ser Gly Met Gly Val
            35                  40                  45

Gly Trp Ile Arg Gln Pro Ser Gly Lys Gly Leu Glu Trp Leu Ala His
        50                  55                  60

Ile Trp Trp Asp Asp Asp Lys Arg Tyr Asn Pro Ala Leu Lys Ser Arg
65                  70                  75                  80

Leu Thr Ile Ser Lys Asp Thr Ser Asn Asn Gln Ile Phe Leu Lys Ile
                85                  90                  95

Ala Ser Val Asp Thr Ala Asp Thr Ala Thr Tyr Tyr Cys Ala Arg Ser
            100                 105                 110

His Tyr Tyr Gly Thr Phe Tyr Phe Asp Tyr Trp Gly Gln Gly Thr Thr
            115                 120                 125

Leu Thr Val Ser Ser
        130

<210> SEQ ID NO 110

<400> SEQUENCE: 110

000
```

```
<210> SEQ ID NO 111
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 35D1 HC CDR1

<400> SEQUENCE: 111

Ala Tyr Ala Met Ser
1               5

<210> SEQ ID NO 112
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 35D1 HC CDR2

<400> SEQUENCE: 112

Ser Ile Ser Ser Gly Gly Thr Thr Tyr Tyr Pro Asp Ser Val Lys Arg
1               5                   10                  15

<210> SEQ ID NO 113
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 35D1 HC CDR3

<400> SEQUENCE: 113

Gly Gly Asp Tyr Gly Tyr Ala Leu Asp Tyr
1               5                   10

<210> SEQ ID NO 114
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 35D2 LC CDR1

<400> SEQUENCE: 114

Arg Ala Ser Ser Ser Val Asn Tyr Met Tyr
1               5                   10

<210> SEQ ID NO 115
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 35D2 LC CDR2

<400> SEQUENCE: 115

Tyr Thr Ser Asn Leu Ala Pro
1               5
```

```
<210> SEQ ID NO 116
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 35D2 LC CDR3

<400> SEQUENCE: 116

Gln Gln Phe Ser Ser Ser Pro Trp Thr
1               5

<210> SEQ ID NO 117
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4B11 LC CDR1

<400> SEQUENCE: 117

Arg Ala Ser Ser Ser Val Asn Tyr Met Tyr
1               5                   10

<210> SEQ ID NO 118
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4B11 LC CDR2

<400> SEQUENCE: 118

Tyr Thr Ser Asn Leu Ala Pro
1               5

<210> SEQ ID NO 119
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4B11 LC CDR3

<400> SEQUENCE: 119

Gln Gln Phe Ser Ser Ser Pro Trp Thr
1               5

<210> SEQ ID NO 120
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 38G8 HC CDR1

<400> SEQUENCE: 120

Asn Tyr Leu Ile Glu
1               5
```

<210> SEQ ID NO 121
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 38G8 HC CDR2

<400> SEQUENCE: 121

Val Ile Asn Pro Gly Ser Gly Gly Thr Asn Tyr Asn Glu Lys Phe Lys
1               5                   10                  15

Gly

<210> SEQ ID NO 122
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 38G8 HC CDR3

<400> SEQUENCE: 122

Gly Arg Tyr Glu Trp Tyr Phe Asp Val
1               5

<210> SEQ ID NO 123
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 38G8 LC CDR1

<400> SEQUENCE: 123

Arg Ala Ser Gln Asp Ile Thr Asn Tyr Leu Asn
1               5                   10

<210> SEQ ID NO 124
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 38G8 LC CDR2

<400> SEQUENCE: 124

Tyr Thr Ser Arg Leu His Ser
1               5

<210> SEQ ID NO 125
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 38G8 LC CDR3

<400> SEQUENCE: 125

Gln Gln Gly Tyr Thr Leu Pro Tyr Thr
1               5

<210> SEQ ID NO 126
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 21F10 HC CDR1

<400> SEQUENCE: 126

Asn Tyr Leu Ile Glu
1               5

<210> SEQ ID NO 127
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 21F10 HC CDR2

<400> SEQUENCE: 127

Val Ile Asn Pro Gly Ser Gly Gly Thr Asn Tyr Asn Glu Lys Phe Lys
1               5                   10                  15

Gly

<210> SEQ ID NO 128
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 21F10 HC CDR3

<400> SEQUENCE: 128

Gly Arg Tyr Glu Trp Tyr Phe Asp Val
1               5

<210> SEQ ID NO 129
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 21F10 LC CDR1

<400> SEQUENCE: 129

Arg Ala Ser Gln Asp Ile Thr Asn Tyr Leu Asn
1               5                   10

<210> SEQ ID NO 130
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:

<223> OTHER INFORMATION: 21F10 LC CDR2

<400> SEQUENCE: 130

Tyr Thr Ser Arg Leu His Ser
1               5

<210> SEQ ID NO 131
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 21F10 LC CDR3

<400> SEQUENCE: 131

Gln Gln Gly Tyr Thr Leu Pro Tyr Thr
1               5

<210> SEQ ID NO 132

<400> SEQUENCE: 132

000

<210> SEQ ID NO 133

<400> SEQUENCE: 133

000

<210> SEQ ID NO 134

<400> SEQUENCE: 134

000

<210> SEQ ID NO 135
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 13C1 HC CDR1

<400> SEQUENCE: 135

Ser Tyr Trp Ile Glu
1               5

<210> SEQ ID NO 136
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 13C1 HC CDR2

<400> SEQUENCE: 136

Glu Ile Leu Pro Gly Ser Gly Ile Thr Lys Tyr Asn Asp Lys Phe Lys
1               5                   10                  15

Gly

```
<210> SEQ ID NO 137
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 13C1 HC CDR3

<400> SEQUENCE: 137

Leu Ile Ser Tyr Tyr Tyr Ala Met Asp Tyr
1               5                   10

<210> SEQ ID NO 138

<400> SEQUENCE: 138

000

<210> SEQ ID NO 139

<400> SEQUENCE: 139

000

<210> SEQ ID NO 140

<400> SEQUENCE: 140

000

<210> SEQ ID NO 141

<400> SEQUENCE: 141

000

<210> SEQ ID NO 142

<400> SEQUENCE: 142

000

<210> SEQ ID NO 143

<400> SEQUENCE: 143

000

<210> SEQ ID NO 144

<400> SEQUENCE: 144

000

<210> SEQ ID NO 145

<400> SEQUENCE: 145

000

<210> SEQ ID NO 146

<400> SEQUENCE: 146

000
```

```
<210> SEQ ID NO 147
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 37C7 HC CDR1

<400> SEQUENCE: 147

Thr Ser Gly Met Gly Val Gly
1               5

<210> SEQ ID NO 148
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 37C7 HC CDR2

<400> SEQUENCE: 148

His Ile Trp Trp Asp Asp Asp Lys Arg Tyr Asn Pro Ala Leu Lys Ser
1               5                   10                  15

<210> SEQ ID NO 149
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 37C7 HC CDR3

<400> SEQUENCE: 149

Ser His Tyr Tyr Gly Thr Phe Tyr Phe Asp Tyr
1               5                   10

<210> SEQ ID NO 150

<400> SEQUENCE: 150

000

<210> SEQ ID NO 151

<400> SEQUENCE: 151

000

<210> SEQ ID NO 152

<400> SEQUENCE: 152

000

<210> SEQ ID NO 153
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CTP peptide 1
```

```
<400> SEQUENCE: 153

Asp Pro Arg Phe Gln Asp Ser Ser Ser Lys Ala Pro Pro Pro Ser
1               5                   10                  15

Leu Pro Ser Pro Ser Arg Leu Pro Gly Pro Ser Asp Thr Pro Ile Leu
                20                  25                  30

<210> SEQ ID NO 154
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CTP peptide 2

<400> SEQUENCE: 154

Ser Ser Ser Ser Lys Ala Pro Pro Pro Ser Leu Pro Ser Pro Ser Arg
1               5                   10                  15

Leu Pro Gly Pro Ser Asp Thr Pro Ile Leu Pro Gln
                20                  25

<210> SEQ ID NO 155
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: PAS peptide 1

<400> SEQUENCE: 155

Ala Ser Pro Ala Ala Pro Ala Pro Ala Ser Pro Ala Ala Pro Ala Pro
1               5                   10                  15

Ser Ala Pro Ala
                20

<210> SEQ ID NO 156
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: PAS peptide 2

<400> SEQUENCE: 156

Ala Ala Pro Ala Ser Pro Ala Pro Ala Ala Pro Ser Ala Pro Ala Pro
1               5                   10                  15

Ala Ala Pro Ser
                20

<210> SEQ ID NO 157
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: PAS peptide 3

<400> SEQUENCE: 157

Ala Pro Ser Ser Pro Ser Pro Ser Ala Pro Ser Ser Pro Ser Pro Ala
```

```
                        1               5                  10                  15

Ser Pro Ser Ser
            20

<210> SEQ ID NO 158
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: PAS peptide 4

<400> SEQUENCE: 158

Ala Pro Ser Ser Pro Ser Pro Ser Ala Pro Ser Ser Pro Ser Pro Ala
1               5                   10                  15

Ser Pro Ser

<210> SEQ ID NO 159
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: PAS peptide 5

<400> SEQUENCE: 159

Ser Ser Pro Ser Ala Pro Ser Pro Ser Ser Pro Ala Ser Pro Ser Pro
1               5                   10                  15

Ser Ser Pro Ala
            20

<210> SEQ ID NO 160
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: PAS peptide 6

<400> SEQUENCE: 160

Ala Ala Ser Pro Ala Ala Pro Ser Ala Pro Pro Ala Ala Ala Ser Pro
1               5                   10                  15

Ala Ala Pro Ser Ala Pro Pro Ala
            20

<210> SEQ ID NO 161
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: PAS peptide 7

<400> SEQUENCE: 161

Ala Ser Ala Ala Ala Pro Ala Ala Ser Ala Ala Ala Ser Ala Pro
1               5                   10                  15

Ser Ala Ala Ala
            20
```

```
<210> SEQ ID NO 162
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Albumin Binding Peptide Core Sequence

<400> SEQUENCE: 162

Asp Ile Cys Leu Pro Arg Trp Gly Cys Leu Trp
1               5                   10

<210> SEQ ID NO 163
<211> LENGTH: 264
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GFP protein sequence

<400> SEQUENCE: 163

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Gly Tyr Gly Val Gln Cys Phe Ala Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys Ser Arg
225                 230                 235                 240

Thr Ser Gly Ser Pro Gly Leu Gln Glu Phe Asp Ile Lys Leu Ile Asp
                245                 250                 255

Thr Val Asp Leu Glu Ser Cys Asn
            260
```

<210> SEQ ID NO 164
<211> LENGTH: 474
<212> TYPE: PRT
<213> ORGANISM: Homo sapiens

<400> SEQUENCE: 164

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Gly Ser Gly Gly Gly Gly Ser Gly Gly Gly
225                 230                 235                 240

Gly Ser Gly Gly Gly Ser Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365
```

```
Gln Pro Arg Glu Pro Gln Val Tyr Thr Leu Pro Pro Ser Arg Asp Glu
    370                 375                 380

Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
                420                 425                 430

Leu Tyr Ser Lys Leu Thr Val Asp Lys Ser Arg Trp Gln Gln Gly Asn
                435                 440                 445

Val Phe Ser Cys Ser Val Met His Glu Ala Leu His Asn His Tyr Thr
450                 455                 460

Gln Lys Ser Leu Ser Leu Ser Pro Gly Lys
465                 470

<210> SEQ ID NO 165
<211> LENGTH: 591
<212> TYPE: PRT
<213> ORGANISM: Homo sapiens

<400> SEQUENCE: 165

Arg Gly Val Phe Arg Arg Asp Ala His Lys Ser Glu Val Ala His Arg
1               5                   10                  15

Phe Lys Asp Leu Gly Glu Glu Asn Phe Lys Ala Leu Val Leu Ile Ala
                20                  25                  30

Phe Ala Gln Tyr Leu Gln Gln Cys Pro Phe Glu Asp His Val Lys Leu
                35                  40                  45

Val Asn Glu Val Thr Glu Phe Ala Lys Thr Cys Val Ala Asp Glu Ser
50                  55                  60

Ala Glu Asn Cys Asp Lys Ser Leu His Thr Leu Phe Gly Asp Lys Leu
65                  70                  75                  80

Cys Thr Val Ala Thr Leu Arg Glu Thr Tyr Gly Glu Met Ala Asp Cys
                85                  90                  95

Cys Ala Lys Gln Glu Pro Glu Arg Asn Glu Cys Phe Leu Gln His Lys
                100                 105                 110

Asp Asp Asn Pro Asn Leu Pro Arg Leu Val Arg Pro Glu Val Asp Val
                115                 120                 125

Met Cys Thr Ala Phe His Asp Asn Glu Glu Thr Phe Leu Lys Lys Tyr
130                 135                 140

Leu Tyr Glu Ile Ala Arg Arg His Pro Tyr Phe Tyr Ala Pro Glu Leu
145                 150                 155                 160

Leu Phe Phe Ala Lys Arg Tyr Lys Ala Ala Phe Thr Glu Cys Cys Gln
                165                 170                 175

Ala Ala Asp Lys Ala Ala Cys Leu Leu Pro Lys Leu Asp Glu Leu Arg
                180                 185                 190

Asp Glu Gly Lys Ala Ser Ser Ala Lys Gln Arg Leu Lys Cys Ala Ser
                195                 200                 205

Leu Gln Lys Phe Gly Glu Arg Ala Phe Lys Ala Trp Ala Val Ala Arg
    210                 215                 220

Leu Ser Gln Arg Phe Pro Lys Ala Glu Phe Ala Glu Val Ser Lys Leu
225                 230                 235                 240

Val Thr Asp Leu Thr Lys Val His Thr Glu Cys Cys His Gly Asp Leu
                245                 250                 255

Leu Glu Cys Ala Asp Asp Arg Ala Asp Leu Ala Lys Tyr Ile Cys Glu
                260                 265                 270
```

Asn Gln Asp Ser Ile Ser Ser Lys Leu Lys Glu Cys Cys Glu Lys Pro
            275                 280                 285

Leu Leu Glu Lys Ser His Cys Ile Ala Glu Val Glu Asn Asp Glu Met
        290                 295                 300

Pro Ala Asp Leu Pro Ser Leu Ala Ala Asp Phe Val Glu Ser Lys Asp
305                 310                 315                 320

Val Cys Lys Asn Tyr Ala Glu Ala Lys Asp Val Phe Leu Gly Met Phe
                325                 330                 335

Leu Tyr Glu Tyr Ala Arg Arg His Pro Asp Tyr Ser Val Val Leu Leu
            340                 345                 350

Leu Arg Leu Ala Lys Thr Tyr Glu Thr Thr Leu Glu Lys Cys Cys Ala
        355                 360                 365

Ala Ala Asp Pro His Glu Cys Tyr Ala Lys Val Phe Asp Glu Phe Lys
    370                 375                 380

Pro Leu Val Glu Glu Pro Gln Asn Leu Ile Lys Gln Asn Cys Glu Leu
385                 390                 395                 400

Phe Glu Gln Leu Gly Glu Tyr Lys Phe Gln Asn Ala Leu Leu Val Arg
                405                 410                 415

Tyr Thr Lys Lys Val Pro Gln Val Ser Thr Pro Thr Leu Val Glu Val
            420                 425                 430

Ser Arg Asn Leu Gly Lys Val Gly Ser Lys Cys Cys Lys His Pro Glu
        435                 440                 445

Ala Lys Arg Met Pro Cys Ala Glu Asp Tyr Leu Ser Val Val Leu Asn
    450                 455                 460

Gln Leu Cys Val Leu His Glu Lys Thr Pro Val Ser Asp Arg Val Thr
465                 470                 475                 480

Lys Cys Cys Thr Glu Ser Leu Val Asn Arg Arg Pro Cys Phe Ser Ala
                485                 490                 495

Leu Glu Val Asp Glu Thr Tyr Val Pro Lys Glu Phe Asn Ala Glu Thr
            500                 505                 510

Phe Thr Phe His Ala Asp Ile Cys Thr Leu Ser Glu Lys Glu Arg Gln
        515                 520                 525

Ile Lys Lys Gln Thr Ala Leu Val Glu Leu Val Lys His Lys Pro Lys
    530                 535                 540

Ala Thr Lys Glu Gln Leu Lys Ala Val Met Asp Asp Phe Ala Ala Phe
545                 550                 555                 560

Val Glu Lys Cys Cys Lys Ala Asp Asp Lys Glu Thr Cys Phe Ala Glu
                565                 570                 575

Glu Gly Lys Lys Leu Val Ala Ala Ser Gln Ala Ala Leu Gly Leu
            580                 585                 590

<210> SEQ ID NO 166
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Linker

<400> SEQUENCE: 166

Gly Gly Gly Ser
1

<210> SEQ ID NO 167

```
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Albumin binding peptide 1

<400> SEQUENCE: 167

Arg Leu Ile Glu Asp Ile Cys Leu Pro Arg Trp Gly Cys Leu Trp Glu
1               5                   10                  15

Asp Asp

<210> SEQ ID NO 168
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Albumin binding peptide 2

<400> SEQUENCE: 168

Gln Arg Leu Met Glu Asp Ile Cys Leu Pro Arg Trp Gly Cys Leu Trp
1               5                   10                  15

Glu Asp Asp Phe
            20

<210> SEQ ID NO 169
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Albumin binding peptide 3

<400> SEQUENCE: 169

Gln Gly Leu Ile Gly Asp Ile Cys Leu Pro Arg Trp Gly Cys Leu Trp
1               5                   10                  15

Gly Asp Ser Val Lys
            20

<210> SEQ ID NO 170
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Albumin binding peptide 4

<400> SEQUENCE: 170

Gly Glu Trp Trp Glu Asp Ile Cys Leu Pro Arg Trp Gly Cys Leu Trp
1               5                   10                  15

Glu Glu Glu Asp
            20

<210> SEQ ID NO 171
<211> LENGTH: 10
<212> TYPE: PRT
<213> ORGANISM: Artificial Sequence
<220> FEATURE:
```

<223> OTHER INFORMATION: Description of Artificial Sequence: Synthetic
peptide
<220> FEATURE:
<223> OTHER INFORMATION: Cysteine-containing peptide

<400> SEQUENCE: 171

Gly Gly Gly Ser Gly Cys Gly Gly Ser
1               5               10

<210> SEQ ID NO 172
<211> LENGTH: 4544
<212> TYPE: PRT
<213> ORGANISM: Homo sapiens

<400> SEQUENCE: 172

Met Leu Thr Pro Pro Leu Leu Leu Leu Pro Leu Leu Ser Ala Leu
1               5                   10                  15

Val Ala Ala Ala Ile Asp Ala Pro Lys Thr Cys Ser Pro Lys Gln Phe
                20                  25                  30

Ala Cys Arg Asp Gln Ile Thr Cys Ile Ser Lys Gly Trp Arg Cys Asp
            35                  40                  45

Gly Glu Arg Asp Cys Pro Asp Gly Ser Asp Glu Ala Pro Glu Ile Cys
        50                  55                  60

Pro Gln Ser Lys Ala Gln Arg Cys Gln Pro Asn Glu His Asn Cys Leu
65                  70                  75                  80

Gly Thr Glu Leu Cys Val Pro Met Ser Arg Leu Cys Asn Gly Val Gln
                85                  90                  95

Asp Cys Met Asp Gly Ser Asp Glu Gly Pro His Cys Arg Glu Leu Gln
            100                 105                 110

Gly Asn Cys Ser Arg Leu Gly Cys Gln His His Cys Val Pro Thr Leu
        115                 120                 125

Asp Gly Pro Thr Cys Tyr Cys Asn Ser Ser Phe Gln Leu Gln Ala Asp
130                 135                 140

Gly Lys Thr Cys Lys Asp Phe Asp Glu Cys Ser Val Tyr Gly Thr Cys
145                 150                 155                 160

Ser Gln Leu Cys Thr Asn Thr Asp Gly Ser Phe Ile Cys Gly Cys Val
                165                 170                 175

Glu Gly Tyr Leu Leu Gln Pro Asp Asn Arg Ser Cys Lys Ala Lys Asn
            180                 185                 190

Glu Pro Val Asp Arg Pro Pro Val Leu Leu Ile Ala Asn Ser Gln Asn
        195                 200                 205

Ile Leu Ala Thr Tyr Leu Ser Gly Ala Gln Val Ser Thr Ile Thr Pro
210                 215                 220

Thr Ser Thr Arg Gln Thr Thr Ala Met Asp Phe Ser Tyr Ala Asn Glu
225                 230                 235                 240

Thr Val Cys Trp Val His Val Gly Asp Ser Ala Ala Gln Thr Gln Leu
                245                 250                 255

Lys Cys Ala Arg Met Pro Gly Leu Lys Gly Phe Val Asp Glu His Thr
            260                 265                 270

Ile Asn Ile Ser Leu Ser Leu His His Val Glu Gln Met Ala Ile Asp
        275                 280                 285

Trp Leu Thr Gly Asn Phe Tyr Phe Val Asp Ile Asp Asp Arg Ile
        290                 295                 300

Phe Val Cys Asn Arg Asn Gly Asp Thr Cys Val Thr Leu Leu Asp Leu
305                 310                 315                 320

Glu Leu Tyr Asn Pro Lys Gly Ile Ala Leu Asp Pro Ala Met Gly Lys

-continued

```
                325                 330                 335
Val Phe Phe Thr Asp Tyr Gly Gln Ile Pro Lys Val Glu Arg Cys Asp
                340                 345                 350
Met Asp Gly Gln Asn Arg Thr Lys Leu Val Asp Ser Lys Ile Val Phe
                355                 360                 365
Pro His Gly Ile Thr Leu Asp Leu Val Ser Arg Leu Val Tyr Trp Ala
                370                 375                 380
Asp Ala Tyr Leu Asp Tyr Ile Glu Val Val Asp Tyr Glu Gly Lys Gly
385                 390                 395                 400
Arg Gln Thr Ile Ile Gln Gly Ile Leu Ile Glu His Leu Tyr Gly Leu
                405                 410                 415
Thr Val Phe Glu Asn Tyr Leu Tyr Ala Thr Asn Ser Asp Asn Ala Asn
                420                 425                 430
Ala Gln Gln Lys Thr Ser Val Ile Arg Val Asn Arg Phe Asn Ser Thr
                435                 440                 445
Glu Tyr Gln Val Val Thr Arg Val Asp Lys Gly Gly Ala Leu His Ile
                450                 455                 460
Tyr His Gln Arg Arg Gln Pro Arg Val Arg Ser His Ala Cys Glu Asn
465                 470                 475                 480
Asp Gln Tyr Gly Lys Pro Gly Cys Ser Asp Ile Cys Leu Leu Ala
                485                 490                 495
Asn Ser His Lys Ala Arg Thr Cys Arg Cys Arg Ser Gly Phe Ser Leu
                500                 505                 510
Gly Ser Asp Gly Lys Ser Cys Lys Lys Pro Glu His Glu Leu Phe Leu
                515                 520                 525
Val Tyr Gly Lys Gly Arg Pro Gly Ile Ile Arg Gly Met Asp Met Gly
                530                 535                 540
Ala Lys Val Pro Asp Glu His Met Ile Pro Ile Glu Asn Leu Met Asn
545                 550                 555                 560
Pro Arg Ala Leu Asp Phe His Ala Glu Thr Gly Phe Ile Tyr Phe Ala
                565                 570                 575
Asp Thr Thr Ser Tyr Leu Ile Gly Arg Gln Lys Ile Asp Gly Thr Glu
                580                 585                 590
Arg Glu Thr Ile Leu Lys Asp Gly Ile His Asn Val Glu Gly Val Ala
                595                 600                 605
Val Asp Trp Met Gly Asp Asn Leu Tyr Trp Thr Asp Asp Gly Pro Lys
                610                 615                 620
Lys Thr Ile Ser Val Ala Arg Leu Glu Lys Ala Ala Gln Thr Arg Lys
625                 630                 635                 640
Thr Leu Ile Glu Gly Lys Met Thr His Pro Arg Ala Ile Val Val Asp
                645                 650                 655
Pro Leu Asn Gly Trp Met Tyr Trp Thr Asp Trp Glu Glu Asp Pro Lys
                660                 665                 670
Asp Ser Arg Arg Gly Arg Leu Glu Arg Ala Trp Met Asp Gly Ser His
                675                 680                 685
Arg Asp Ile Phe Val Thr Ser Lys Thr Val Leu Trp Pro Asn Gly Leu
                690                 695                 700
Ser Leu Asp Ile Pro Ala Gly Arg Leu Tyr Trp Val Asp Ala Phe Tyr
705                 710                 715                 720
Asp Arg Ile Glu Thr Ile Leu Leu Asn Gly Thr Asp Arg Lys Ile Val
                725                 730                 735
Tyr Glu Gly Pro Glu Leu Asn His Ala Phe Gly Leu Cys His His Gly
                740                 745                 750
```

```
Asn Tyr Leu Phe Trp Thr Glu Tyr Arg Ser Gly Ser Val Tyr Arg Leu
        755                 760                 765

Glu Arg Gly Val Gly Gly Ala Pro Pro Thr Val Thr Leu Leu Arg Ser
770                 775                 780

Glu Arg Pro Pro Ile Phe Glu Ile Arg Met Tyr Asp Ala Gln Gln Gln
785                 790                 795                 800

Gln Val Gly Thr Asn Lys Cys Arg Val Asn Asn Gly Gly Cys Ser Ser
                805                 810                 815

Leu Cys Leu Ala Thr Pro Gly Ser Arg Gln Cys Ala Cys Ala Glu Asp
                820                 825                 830

Gln Val Leu Asp Ala Asp Gly Val Thr Cys Leu Ala Asn Pro Ser Tyr
                835                 840                 845

Val Pro Pro Pro Gln Cys Gln Pro Gly Glu Phe Ala Cys Ala Asn Ser
850                 855                 860

Arg Cys Ile Gln Glu Arg Trp Lys Cys Asp Gly Asp Asn Asp Cys Leu
865                 870                 875                 880

Asp Asn Ser Asp Glu Ala Pro Ala Leu Cys His Gln His Thr Cys Pro
                885                 890                 895

Ser Asp Arg Phe Lys Cys Glu Asn Asn Arg Cys Ile Pro Asn Arg Trp
                900                 905                 910

Leu Cys Asp Gly Asp Asn Asp Cys Gly Asn Ser Glu Asp Glu Ser Asn
                915                 920                 925

Ala Thr Cys Ser Ala Arg Thr Cys Pro Pro Asn Gln Phe Ser Cys Ala
                930                 935                 940

Ser Gly Arg Cys Ile Pro Ile Ser Trp Thr Cys Asp Leu Asp Asp Asp
945                 950                 955                 960

Cys Gly Asp Arg Ser Asp Glu Ser Ala Ser Cys Ala Tyr Pro Thr Cys
                965                 970                 975

Phe Pro Leu Thr Gln Phe Thr Cys Asn Asn Gly Arg Cys Ile Asn Ile
                980                 985                 990

Asn Trp Arg Cys Asp Asn Asp Asn Asp Cys Gly Asp Asn Ser Asp Glu
                995                 1000                1005

Ala Gly Cys Ser His Ser Cys Ser Ser Thr Gln Phe Lys Cys Asn
        1010                1015                1020

Ser Gly Arg Cys Ile Pro Glu His Trp Thr Cys Asp Gly Asp Asn
        1025                1030                1035

Asp Cys Gly Asp Tyr Ser Asp Glu Thr His Ala Asn Cys Thr Asn
        1040                1045                1050

Gln Ala Thr Arg Pro Pro Gly Gly Cys His Thr Asp Glu Phe Gln
        1055                1060                1065

Cys Arg Leu Asp Gly Leu Cys Ile Pro Leu Arg Trp Arg Cys Asp
        1070                1075                1080

Gly Asp Thr Asp Cys Met Asp Ser Ser Asp Glu Lys Ser Cys Glu
        1085                1090                1095

Gly Val Thr His Val Cys Asp Pro Ser Val Lys Phe Gly Cys Lys
        1100                1105                1110

Asp Ser Ala Arg Cys Ile Ser Lys Ala Trp Val Cys Asp Gly Asp
        1115                1120                1125

Asn Asp Cys Glu Asp Asn Ser Asp Glu Glu Asn Cys Glu Ser Leu
        1130                1135                1140

Ala Cys Arg Pro Pro Ser His Pro Cys Ala Asn Asn Thr Ser Val
        1145                1150                1155
```

```
Cys Leu Pro Pro Asp Lys Leu Cys Asp Gly Asn Asp Asp Cys Gly
    1160            1165                1170

Asp Gly Ser Asp Glu Gly Glu Leu Cys Asp Gln Cys Ser Leu Asn
    1175            1180                1185

Asn Gly Gly Cys Ser His Asn Cys Ser Val Ala Pro Gly Glu Gly
    1190            1195                1200

Ile Val Cys Ser Cys Pro Leu Gly Met Glu Leu Gly Pro Asp Asn
    1205            1210                1215

His Thr Cys Gln Ile Gln Ser Tyr Cys Ala Lys His Leu Lys Cys
    1220            1225                1230

Ser Gln Lys Cys Asp Gln Asn Lys Phe Ser Val Lys Cys Ser Cys
    1235            1240                1245

Tyr Glu Gly Trp Val Leu Glu Pro Asp Gly Glu Ser Cys Arg Ser
    1250            1255                1260

Leu Asp Pro Phe Lys Pro Phe Ile Ile Phe Ser Asn Arg His Glu
    1265            1270                1275

Ile Arg Arg Ile Asp Leu His Lys Gly Asp Tyr Ser Val Leu Val
    1280            1285                1290

Pro Gly Leu Arg Asn Thr Ile Ala Leu Asp Phe His Leu Ser Gln
    1295            1300                1305

Ser Ala Leu Tyr Trp Thr Asp Val Val Glu Asp Lys Ile Tyr Arg
    1310            1315                1320

Gly Lys Leu Leu Asp Asn Gly Ala Leu Thr Ser Phe Glu Val Val
    1325            1330                1335

Ile Gln Tyr Gly Leu Ala Thr Pro Glu Gly Leu Ala Val Asp Trp
    1340            1345                1350

Ile Ala Gly Asn Ile Tyr Trp Val Glu Ser Asn Leu Asp Gln Ile
    1355            1360                1365

Glu Val Ala Lys Leu Asp Gly Thr Leu Arg Thr Thr Leu Leu Ala
    1370            1375                1380

Gly Asp Ile Glu His Pro Arg Ala Ile Ala Leu Asp Pro Arg Asp
    1385            1390                1395

Gly Ile Leu Phe Trp Thr Asp Trp Asp Ala Ser Leu Pro Arg Ile
    1400            1405                1410

Glu Ala Ala Ser Met Ser Gly Ala Gly Arg Arg Thr Val His Arg
    1415            1420                1425

Glu Thr Gly Ser Gly Gly Trp Pro Asn Gly Leu Thr Val Asp Tyr
    1430            1435                1440

Leu Glu Lys Arg Ile Leu Trp Ile Asp Ala Arg Ser Asp Ala Ile
    1445            1450                1455

Tyr Ser Ala Arg Tyr Asp Gly Ser Gly His Met Glu Val Leu Arg
    1460            1465                1470

Gly His Glu Phe Leu Ser His Pro Phe Ala Val Thr Leu Tyr Gly
    1475            1480                1485

Gly Glu Val Tyr Trp Thr Asp Trp Arg Thr Asn Thr Leu Ala Lys
    1490            1495                1500

Ala Asn Lys Trp Thr Gly His Asn Val Thr Val Val Gln Arg Thr
    1505            1510                1515

Asn Thr Gln Pro Phe Asp Leu Gln Val Tyr His Pro Ser Arg Gln
    1520            1525                1530

Pro Met Ala Pro Asn Pro Cys Glu Ala Asn Gly Gly Gln Gly Pro
    1535            1540                1545

Cys Ser His Leu Cys Leu Ile Asn Tyr Asn Arg Thr Val Ser Cys
```

-continued

```
            1550                1555                1560
Ala Cys Pro His Leu Met Lys Leu His Lys Asp Asn Thr Thr Cys
    1565                1570                1575
Tyr Glu Phe Lys Lys Phe Leu Leu Tyr Ala Arg Gln Met Glu Ile
    1580                1585                1590
Arg Gly Val Asp Leu Asp Ala Pro Tyr Tyr Asn Tyr Ile Ile Ser
    1595                1600                1605
Phe Thr Val Pro Asp Ile Asp Asn Val Thr Val Leu Asp Tyr Asp
    1610                1615                1620
Ala Arg Glu Gln Arg Val Tyr Trp Ser Asp Val Arg Thr Gln Ala
    1625                1630                1635
Ile Lys Arg Ala Phe Ile Asn Gly Thr Gly Val Glu Thr Val Val
    1640                1645                1650
Ser Ala Asp Leu Pro Asn Ala His Gly Leu Ala Val Asp Trp Val
    1655                1660                1665
Ser Arg Asn Leu Phe Trp Thr Ser Tyr Asp Thr Asn Lys Lys Gln
    1670                1675                1680
Ile Asn Val Ala Arg Leu Asp Gly Ser Phe Lys Asn Ala Val Val
    1685                1690                1695
Gln Gly Leu Glu Gln Pro His Gly Leu Val Val His Pro Leu Arg
    1700                1705                1710
Gly Lys Leu Tyr Trp Thr Asp Gly Asp Asn Ile Ser Met Ala Asn
    1715                1720                1725
Met Asp Gly Ser Asn Arg Thr Leu Leu Phe Ser Gly Gln Lys Gly
    1730                1735                1740
Pro Val Gly Leu Ala Ile Asp Phe Pro Glu Ser Lys Leu Tyr Trp
    1745                1750                1755
Ile Ser Ser Gly Asn His Thr Ile Asn Arg Cys Asn Leu Asp Gly
    1760                1765                1770
Ser Gly Leu Glu Val Ile Asp Ala Met Arg Ser Gln Leu Gly Lys
    1775                1780                1785
Ala Thr Ala Leu Ala Ile Met Gly Asp Lys Leu Trp Trp Ala Asp
    1790                1795                1800
Gln Val Ser Glu Lys Met Gly Thr Cys Ser Lys Ala Asp Gly Ser
    1805                1810                1815
Gly Ser Val Val Leu Arg Asn Ser Thr Thr Leu Val Met His Met
    1820                1825                1830
Lys Val Tyr Asp Glu Ser Ile Gln Leu Asp His Lys Gly Thr Asn
    1835                1840                1845
Pro Cys Ser Val Asn Asn Gly Asp Cys Ser Gln Leu Cys Leu Pro
    1850                1855                1860
Thr Ser Glu Thr Thr Arg Ser Cys Met Cys Thr Ala Gly Tyr Ser
    1865                1870                1875
Leu Arg Ser Gly Gln Gln Ala Cys Glu Gly Val Gly Ser Phe Leu
    1880                1885                1890
Leu Tyr Ser Val His Glu Gly Ile Arg Gly Ile Pro Leu Asp Pro
    1895                1900                1905
Asn Asp Lys Ser Asp Ala Leu Val Pro Val Ser Gly Thr Ser Leu
    1910                1915                1920
Ala Val Gly Ile Asp Phe His Ala Glu Asn Asp Thr Ile Tyr Trp
    1925                1930                1935
Val Asp Met Gly Leu Ser Thr Ile Ser Arg Ala Lys Arg Asp Gln
    1940                1945                1950
```

```
Thr Trp Arg Glu Asp Val Val Thr Asn Gly Ile Gly Arg Val Glu
    1955                1960                1965

Gly Ile Ala Val Asp Trp Ile Ala Gly Asn Ile Tyr Trp Thr Asp
    1970                1975                1980

Gln Gly Phe Asp Val Ile Glu Val Ala Arg Leu Asn Gly Ser Phe
    1985                1990                1995

Arg Tyr Val Val Ile Ser Gln Gly Leu Asp Lys Pro Arg Ala Ile
    2000                2005                2010

Thr Val His Pro Glu Lys Gly Tyr Leu Phe Trp Thr Glu Trp Gly
    2015                2020                2025

Gln Tyr Pro Arg Ile Glu Arg Ser Arg Leu Asp Gly Thr Glu Arg
    2030                2035                2040

Val Val Leu Val Asn Val Ser Ile Ser Trp Pro Asn Gly Ile Ser
    2045                2050                2055

Val Asp Tyr Gln Asp Gly Lys Leu Tyr Trp Cys Asp Ala Arg Thr
    2060                2065                2070

Asp Lys Ile Glu Arg Ile Asp Leu Glu Thr Gly Glu Asn Arg Glu
    2075                2080                2085

Val Val Leu Ser Ser Asn Asn Met Asp Met Phe Ser Val Ser Val
    2090                2095                2100

Phe Glu Asp Phe Ile Tyr Trp Ser Asp Arg Thr His Ala Asn Gly
    2105                2110                2115

Ser Ile Lys Arg Gly Ser Lys Asp Asn Ala Thr Asp Ser Val Pro
    2120                2125                2130

Leu Arg Thr Gly Ile Gly Val Gln Leu Lys Asp Ile Lys Val Phe
    2135                2140                2145

Asn Arg Asp Arg Gln Lys Gly Thr Asn Val Cys Ala Val Ala Asn
    2150                2155                2160

Gly Gly Cys Gln Gln Leu Cys Leu Tyr Arg Gly Arg Gly Gln Arg
    2165                2170                2175

Ala Cys Ala Cys Ala His Gly Met Leu Ala Glu Asp Gly Ala Ser
    2180                2185                2190

Cys Arg Glu Tyr Ala Gly Tyr Leu Leu Tyr Ser Glu Arg Thr Ile
    2195                2200                2205

Leu Lys Ser Ile His Leu Ser Asp Glu Arg Asn Leu Asn Ala Pro
    2210                2215                2220

Val Gln Pro Phe Glu Asp Pro Glu His Met Lys Asn Val Ile Ala
    2225                2230                2235

Leu Ala Phe Asp Tyr Arg Ala Gly Thr Ser Pro Gly Thr Pro Asn
    2240                2245                2250

Arg Ile Phe Phe Ser Asp Ile His Phe Gly Asn Ile Gln Gln Ile
    2255                2260                2265

Asn Asp Asp Gly Ser Arg Arg Ile Thr Ile Val Glu Asn Val Gly
    2270                2275                2280

Ser Val Glu Gly Leu Ala Tyr His Arg Gly Trp Asp Thr Leu Tyr
    2285                2290                2295

Trp Thr Ser Tyr Thr Thr Ser Thr Ile Thr Arg His Thr Val Asp
    2300                2305                2310

Gln Thr Arg Pro Gly Ala Phe Glu Arg Glu Thr Val Ile Thr Met
    2315                2320                2325

Ser Gly Asp Asp His Pro Arg Ala Phe Val Leu Asp Glu Cys Gln
    2330                2335                2340
```

```
Asn Leu Met Phe Trp Thr Asn  Trp Asn Glu Gln His  Pro Ser Ile
    2345             2350                  2355

Met Arg Ala Ala Leu Ser Gly  Ala Asn Val Leu Thr  Leu Ile Glu
    2360             2365                  2370

Lys Asp Ile Arg Thr Pro Asn  Gly Leu Ala Ile Asp  His Arg Ala
    2375             2380                  2385

Glu Lys Leu Tyr Phe Ser Asp  Ala Thr Leu Asp Lys  Ile Glu Arg
    2390             2395                  2400

Cys Glu Tyr Asp Gly Ser His  Arg Tyr Val Ile Leu  Lys Ser Glu
    2405             2410                  2415

Pro Val His Pro Phe Gly Leu  Ala Val Tyr Gly Glu  His Ile Phe
    2420             2425                  2430

Trp Thr Asp Trp Val Arg Arg  Ala Val Gln Arg Ala  Asn Lys His
    2435             2440                  2445

Val Gly Ser Asn Met Lys Leu  Leu Arg Val Asp Ile  Pro Gln Gln
    2450             2455                  2460

Pro Met Gly Ile Ile Ala Val  Ala Asn Asp Thr Asn  Ser Cys Glu
    2465             2470                  2475

Leu Ser Pro Cys Arg Ile Asn  Asn Gly Gly Cys Gln  Asp Leu Cys
    2480             2485                  2490

Leu Leu Thr His Gln Gly His  Val Asn Cys Ser Cys  Arg Gly Gly
    2495             2500                  2505

Arg Ile Leu Gln Asp Asp Leu  Thr Cys Arg Ala Val  Asn Ser Ser
    2510             2515                  2520

Cys Arg Ala Gln Asp Glu Phe  Glu Cys Ala Asn Gly  Glu Cys Ile
    2525             2530                  2535

Asn Phe Ser Leu Thr Cys Asp  Gly Val Pro His Cys  Lys Asp Lys
    2540             2545                  2550

Ser Asp Glu Lys Pro Ser Tyr  Cys Asn Ser Arg Arg  Cys Lys Lys
    2555             2560                  2565

Thr Phe Arg Gln Cys Ser Asn  Gly Arg Cys Val Ser  Asn Met Leu
    2570             2575                  2580

Trp Cys Asn Gly Ala Asp Asp  Cys Gly Asp Gly Ser  Asp Glu Ile
    2585             2590                  2595

Pro Cys Asn Lys Thr Ala Cys  Gly Val Gly Glu Phe  Arg Cys Arg
    2600             2605                  2610

Asp Gly Thr Cys Ile Gly Asn  Ser Ser Arg Cys Asn  Gln Phe Val
    2615             2620                  2625

Asp Cys Glu Asp Ala Ser Asp  Glu Met Asn Cys Ser  Ala Thr Asp
    2630             2635                  2640

Cys Ser Ser Tyr Phe Arg Leu  Gly Val Lys Gly Val  Leu Phe Gln
    2645             2650                  2655

Pro Cys Glu Arg Thr Ser Leu  Cys Tyr Ala Pro Ser  Trp Val Cys
    2660             2665                  2670

Asp Gly Ala Asn Asp Cys Gly  Asp Tyr Ser Asp Glu  Arg Asp Cys
    2675             2680                  2685

Pro Gly Val Lys Arg Pro Arg  Cys Pro Leu Asn Tyr  Phe Ala Cys
    2690             2695                  2700

Pro Ser Gly Arg Cys Ile Pro  Met Ser Trp Thr Cys  Asp Lys Glu
    2705             2710                  2715

Asp Asp Cys Glu His Gly Glu  Asp Glu Thr His Cys  Asn Lys Phe
    2720             2725                  2730

Cys Ser Glu Ala Gln Phe Glu  Cys Gln Asn His Arg  Cys Ile Ser
```

-continued

|  | 2735 |  |  | 2740 |  |  | 2745 |  |  |
| --- | --- | --- | --- | --- | --- | --- | --- | --- | --- |
| Lys | Gln | Trp | Leu | Cys | Asp | Gly | Ser | Asp | Cys |
|  | 2750 |  |  | 2755 |  |  | 2760 |  |  |
| Asp | Gly | Ser |  |  |  |  |  |  |  |

Asp Glu Ala Ala His Cys Glu Gly Lys Thr Cys Gly Pro Ser Ser
      2765              2770              2775

Phe Ser Cys Pro Gly Thr His Val Cys Val Pro Glu Arg Trp Leu
      2780              2785              2790

Cys Asp Gly Asp Lys Asp Cys Ala Asp Gly Ala Asp Glu Ser Ile
      2795              2800              2805

Ala Ala Gly Cys Leu Tyr Asn Ser Thr Cys Asp Asp Arg Glu Phe
      2810              2815              2820

Met Cys Gln Asn Arg Gln Cys Ile Pro Lys His Phe Val Cys Asp
      2825              2830              2835

His Asp Arg Asp Cys Ala Asp Gly Ser Asp Glu Ser Pro Glu Cys
      2840              2845              2850

Glu Tyr Pro Thr Cys Gly Pro Ser Glu Phe Arg Cys Ala Asn Gly
      2855              2860              2865

Arg Cys Leu Ser Ser Arg Gln Trp Glu Cys Asp Gly Glu Asn Asp
      2870              2875              2880

Cys His Asp Gln Ser Asp Glu Ala Pro Lys Asn Pro His Cys Thr
      2885              2890              2895

Ser Pro Glu His Lys Cys Asn Ala Ser Ser Gln Phe Leu Cys Ser
      2900              2905              2910

Ser Gly Arg Cys Val Ala Glu Ala Leu Leu Cys Asn Gly Gln Asp
      2915              2920              2925

Asp Cys Gly Asp Ser Ser Asp Glu Arg Gly Cys His Ile Asn Glu
      2930              2935              2940

Cys Leu Ser Arg Lys Leu Ser Gly Cys Ser Gln Asp Cys Glu Asp
      2945              2950              2955

Leu Lys Ile Gly Phe Lys Cys Arg Cys Arg Pro Gly Phe Arg Leu
      2960              2965              2970

Lys Asp Asp Gly Arg Thr Cys Ala Asp Val Asp Glu Cys Ser Thr
      2975              2980              2985

Thr Phe Pro Cys Ser Gln Arg Cys Ile Asn Thr His Gly Ser Tyr
      2990              2995              3000

Lys Cys Leu Cys Val Glu Gly Tyr Ala Pro Arg Gly Gly Asp Pro
      3005              3010              3015

His Ser Cys Lys Ala Val Thr Asp Glu Glu Pro Phe Leu Ile Phe
      3020              3025              3030

Ala Asn Arg Tyr Tyr Leu Arg Lys Leu Asn Leu Asp Gly Ser Asn
      3035              3040              3045

Tyr Thr Leu Leu Lys Gln Gly Leu Asn Asn Ala Val Ala Leu Asp
      3050              3055              3060

Phe Asp Tyr Arg Glu Gln Met Ile Tyr Trp Thr Asp Val Thr Thr
      3065              3070              3075

Gln Gly Ser Met Ile Arg Arg Met His Leu Asn Gly Ser Asn Val
      3080              3085              3090

Gln Val Leu His Arg Thr Gly Leu Ser Asn Pro Asp Gly Leu Ala
      3095              3100              3105

Val Asp Trp Val Gly Gly Asn Leu Tyr Trp Cys Asp Lys Gly Arg
      3110              3115              3120

Asp Thr Ile Glu Val Ser Lys Leu Asn Gly Ala Tyr Arg Thr Val
      3125              3130              3135

```
Leu Val Ser Ser Gly Leu Arg Glu Pro Arg Ala Leu Val Val Asp
    3140                3145                3150

Val Gln Asn Gly Tyr Leu Tyr Trp Thr Asp Trp Gly Asp His Ser
    3155                3160                3165

Leu Ile Gly Arg Ile Gly Met Asp Gly Ser Ser Arg Ser Val Ile
    3170                3175                3180

Val Asp Thr Lys Ile Thr Trp Pro Asn Gly Leu Thr Leu Asp Tyr
    3185                3190                3195

Val Thr Glu Arg Ile Tyr Trp Ala Asp Ala Arg Glu Asp Tyr Ile
    3200                3205                3210

Glu Phe Ala Ser Leu Asp Gly Ser Asn Arg His Val Val Leu Ser
    3215                3220                3225

Gln Asp Ile Pro His Ile Phe Ala Leu Thr Leu Phe Glu Asp Tyr
    3230                3235                3240

Val Tyr Trp Thr Asp Trp Glu Thr Lys Ser Ile Asn Arg Ala His
    3245                3250                3255

Lys Thr Thr Gly Thr Asn Lys Thr Leu Leu Ile Ser Thr Leu His
    3260                3265                3270

Arg Pro Met Asp Leu His Val Phe His Ala Leu Arg Gln Pro Asp
    3275                3280                3285

Val Pro Asn His Pro Cys Lys Val Asn Asn Gly Gly Cys Ser Asn
    3290                3295                3300

Leu Cys Leu Leu Ser Pro Gly Gly Gly His Lys Cys Ala Cys Pro
    3305                3310                3315

Thr Asn Phe Tyr Leu Gly Ser Asp Gly Arg Thr Cys Val Ser Asn
    3320                3325                3330

Cys Thr Ala Ser Gln Phe Val Cys Lys Asn Asp Lys Cys Ile Pro
    3335                3340                3345

Phe Trp Trp Lys Cys Asp Thr Glu Asp Asp Cys Gly Asp His Ser
    3350                3355                3360

Asp Glu Pro Pro Asp Cys Pro Glu Phe Lys Cys Arg Pro Gly Gln
    3365                3370                3375

Phe Gln Cys Ser Thr Gly Ile Cys Thr Asn Pro Ala Phe Ile Cys
    3380                3385                3390

Asp Gly Asp Asn Asp Cys Gln Asp Asn Ser Asp Glu Ala Asn Cys
    3395                3400                3405

Asp Ile His Val Cys Leu Pro Ser Gln Phe Lys Cys Thr Asn Thr
    3410                3415                3420

Asn Arg Cys Ile Pro Gly Ile Phe Arg Cys Asn Gly Gln Asp Asn
    3425                3430                3435

Cys Gly Asp Gly Glu Asp Glu Arg Asp Cys Pro Glu Val Thr Cys
    3440                3445                3450

Ala Pro Asn Gln Phe Gln Cys Ser Ile Thr Lys Arg Cys Ile Pro
    3455                3460                3465

Arg Val Trp Val Cys Asp Arg Asp Asn Asp Cys Val Asp Gly Ser
    3470                3475                3480

Asp Glu Pro Ala Asn Cys Thr Gln Met Thr Cys Gly Val Asp Glu
    3485                3490                3495

Phe Arg Cys Lys Asp Ser Gly Arg Cys Ile Pro Ala Arg Trp Lys
    3500                3505                3510

Cys Asp Gly Glu Asp Asp Cys Gly Asp Gly Ser Asp Glu Pro Lys
    3515                3520                3525
```

-continued

| | | | | | | | | | | | |
|---|---|---|---|---|---|---|---|---|---|---|---|
|Glu|Glu|Cys|Asp|Glu|Arg|Thr|Cys|Glu|Pro|Tyr|Gln|Phe|Arg|Cys|
| |3530| | | | |3535| | | |3540| | | | |

Glu Glu Cys Asp Glu Arg Thr Cys Glu Pro Tyr Gln Phe Arg Cys
    3530                3535              3540

Lys Asn Asn Arg Cys Val Pro Gly Arg Trp Gln Cys Asp Tyr Asp
    3545                3550              3555

Asn Asp Cys Gly Asp Asn Ser Asp Glu Glu Ser Cys Thr Pro Arg
    3560                3565              3570

Pro Cys Ser Glu Ser Glu Phe Ser Cys Ala Asn Gly Arg Cys Ile
    3575                3580              3585

Ala Gly Arg Trp Lys Cys Asp Gly Asp His Asp Cys Ala Asp Gly
    3590                3595              3600

Ser Asp Glu Lys Asp Cys Thr Pro Arg Cys Asp Met Asp Gln Phe
    3605                3610              3615

Gln Cys Lys Ser Gly His Cys Ile Pro Leu Arg Trp Arg Cys Asp
    3620                3625              3630

Ala Asp Ala Asp Cys Met Asp Gly Ser Asp Glu Glu Ala Cys Gly
    3635                3640              3645

Thr Gly Val Arg Thr Cys Pro Leu Asp Glu Phe Gln Cys Asn Asn
    3650                3655              3660

Thr Leu Cys Lys Pro Leu Ala Trp Lys Cys Asp Gly Glu Asp Asp
    3665                3670              3675

Cys Gly Asp Asn Ser Asp Glu Asn Pro Glu Glu Cys Ala Arg Phe
    3680                3685              3690

Val Cys Pro Pro Asn Arg Pro Phe Arg Cys Lys Asn Asp Arg Val
    3695                3700              3705

Cys Leu Trp Ile Gly Arg Gln Cys Asp Gly Thr Asp Asn Cys Gly
    3710                3715              3720

Asp Gly Thr Asp Glu Glu Asp Cys Glu Pro Pro Thr Ala His Thr
    3725                3730              3735

Thr His Cys Lys Asp Lys Lys Glu Phe Leu Cys Arg Asn Gln Arg
    3740                3745              3750

Cys Leu Ser Ser Ser Leu Arg Cys Asn Met Phe Asp Asp Cys Gly
    3755                3760              3765

Asp Gly Ser Asp Glu Glu Asp Cys Ser Ile Asp Pro Lys Leu Thr
    3770                3775              3780

Ser Cys Ala Thr Asn Ala Ser Ile Cys Gly Asp Glu Ala Arg Cys
    3785                3790              3795

Val Arg Thr Glu Lys Ala Ala Tyr Cys Ala Cys Arg Ser Gly Phe
    3800                3805              3810

His Thr Val Pro Gly Gln Pro Gly Cys Gln Asp Ile Asn Glu Cys
    3815                3820              3825

Leu Arg Phe Gly Thr Cys Ser Gln Leu Cys Asn Asn Thr Lys Gly
    3830                3835              3840

Gly His Leu Cys Ser Cys Ala Arg Asn Phe Met Lys Thr His Asn
    3845                3850              3855

Thr Cys Lys Ala Glu Gly Ser Glu Tyr Gln Val Leu Tyr Ile Ala
    3860                3865              3870

Asp Asp Asn Glu Ile Arg Ser Leu Phe Pro Gly His Pro His Ser
    3875                3880              3885

Ala Tyr Glu Gln Ala Phe Gln Gly Asp Glu Ser Val Arg Ile Asp
    3890                3895              3900

Ala Met Asp Val His Val Lys Ala Gly Arg Val Tyr Trp Thr Asn
    3905                3910              3915

Trp His Thr Gly Thr Ile Ser Tyr Arg Ser Leu Pro Pro Ala Ala

```
                    3920                3925                3930
Pro Pro Thr Thr Ser Asn Arg His Arg Arg Gln Ile Asp Arg Gly
    3935                3940                3945

Val Thr His Leu Asn Ile Ser Gly Leu Lys Met Pro Arg Gly Ile
    3950                3955                3960

Ala Ile Asp Trp Val Ala Gly Asn Val Tyr Trp Thr Asp Ser Gly
    3965                3970                3975

Arg Asp Val Ile Glu Val Ala Gln Met Lys Gly Glu Asn Arg Lys
    3980                3985                3990

Thr Leu Ile Ser Gly Met Ile Asp Glu Pro His Ala Ile Val Val
    3995                4000                4005

Asp Pro Leu Arg Gly Thr Met Tyr Trp Ser Asp Trp Gly Asn His
    4010                4015                4020

Pro Lys Ile Glu Thr Ala Ala Met Asp Gly Thr Leu Arg Glu Thr
    4025                4030                4035

Leu Val Gln Asp Asn Ile Gln Trp Pro Thr Gly Leu Ala Val Asp
    4040                4045                4050

Tyr His Asn Glu Arg Leu Tyr Trp Ala Asp Ala Lys Leu Ser Val
    4055                4060                4065

Ile Gly Ser Ile Arg Leu Asn Gly Thr Asp Pro Ile Val Ala Ala
    4070                4075                4080

Asp Ser Lys Arg Gly Leu Ser His Pro Phe Ser Ile Asp Val Phe
    4085                4090                4095

Glu Asp Tyr Ile Tyr Gly Val Thr Tyr Ile Asn Asn Arg Val Phe
    4100                4105                4110

Lys Ile His Lys Phe Gly His Ser Pro Leu Val Asn Leu Thr Gly
    4115                4120                4125

Gly Leu Ser His Ala Ser Asp Val Val Leu Tyr His Gln His Lys
    4130                4135                4140

Gln Pro Glu Val Thr Asn Pro Cys Asp Arg Lys Lys Cys Glu Trp
    4145                4150                4155

Leu Cys Leu Leu Ser Pro Ser Gly Pro Val Cys Thr Cys Pro Asn
    4160                4165                4170

Gly Lys Arg Leu Asp Asn Gly Thr Cys Val Pro Val Pro Ser Pro
    4175                4180                4185

Thr Pro Pro Pro Asp Ala Pro Arg Pro Gly Thr Cys Asn Leu Gln
    4190                4195                4200

Cys Phe Asn Gly Gly Ser Cys Phe Leu Asn Ala Arg Arg Gln Pro
    4205                4210                4215

Lys Cys Arg Cys Gln Pro Arg Tyr Thr Gly Asp Lys Cys Glu Leu
    4220                4225                4230

Asp Gln Cys Trp Glu His Cys Arg Asn Gly Gly Thr Cys Ala Ala
    4235                4240                4245

Ser Pro Ser Gly Met Pro Thr Cys Arg Cys Pro Thr Gly Phe Thr
    4250                4255                4260

Gly Pro Lys Cys Thr Gln Gln Val Cys Ala Gly Tyr Cys Ala Asn
    4265                4270                4275

Asn Ser Thr Cys Thr Val Asn Gln Gly Asn Gln Pro Gln Cys Arg
    4280                4285                4290

Cys Leu Pro Gly Phe Leu Gly Asp Arg Cys Gln Tyr Arg Gln Cys
    4295                4300                4305

Ser Gly Tyr Cys Glu Asn Phe Gly Thr Cys Gln Met Ala Ala Asp
    4310                4315                4320
```

```
Gly Ser Arg Gln Cys Arg Cys Thr Ala Tyr Phe Glu Gly Ser Arg
    4325            4330                4335
Cys Glu Val Asn Lys Cys Ser Arg Cys Leu Glu Gly Ala Cys Val
    4340            4345                4350
Val Asn Lys Gln Ser Gly Asp Val Thr Cys Asn Cys Thr Asp Gly
    4355            4360                4365
Arg Val Ala Pro Ser Cys Leu Thr Cys Val Gly His Cys Ser Asn
    4370            4375                4380
Gly Gly Ser Cys Thr Met Asn Ser Lys Met Met Pro Glu Cys Gln
    4385            4390                4395
Cys Pro Pro His Met Thr Gly Pro Arg Cys Glu Glu His Val Phe
    4400            4405                4410
Ser Gln Gln Gln Pro Gly His Ile Ala Ser Ile Leu Ile Pro Leu
    4415            4420                4425
Leu Leu Leu Leu Leu Leu Val Leu Val Ala Gly Val Val Phe Trp
    4430            4435                4440
Tyr Lys Arg Arg Val Gln Gly Ala Lys Gly Phe Gln His Gln Arg
    4445            4450                4455
Met Thr Asn Gly Ala Met Asn Val Glu Ile Gly Asn Pro Thr Tyr
    4460            4465                4470
Lys Met Tyr Glu Gly Gly Glu Pro Asp Asp Val Gly Gly Leu Leu
    4475            4480                4485
Asp Ala Asp Phe Ala Leu Asp Pro Asp Lys Pro Thr Asn Phe Thr
    4490            4495                4500
Asn Pro Val Tyr Ala Thr Leu Tyr Met Gly Gly His Gly Ser Arg
    4505            4510                4515
His Ser Leu Ala Ser Thr Asp Glu Lys Arg Glu Leu Leu Gly Arg
    4520            4525                4530
Gly Pro Glu Asp Glu Ile Gly Asp Pro Leu Ala
    4535            4540

<210> SEQ ID NO 173
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Biotin Acceptor Peptide (BAP)

<400> SEQUENCE: 173

Leu Asn Asp Ile Phe Glu Ala Gln Lys Ile Glu Trp His
1               5                   10

<210> SEQ ID NO 174
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Lipoate Acceptor Peptide 2 (LAP2)

<400> SEQUENCE: 174

Gly Phe Glu Ile Asp Lys Val Trp Tyr Asp Leu Asp Ala
1               5                   10
```

```
<210> SEQ ID NO 175
<211> LENGTH: 2000
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: HAPylation motif
<220> FEATURE:
<221> NAME/KEY: MISC_FEATURE
<222> LOCATION: (1)..(2000)
<223> OTHER INFORMATION: This sequence may encompass 1-400 "Gly Gly Gly
      Gly Ser" repeating units

<400> SEQUENCE: 175
```

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser Gly Gly Gly Gly
    50                  55                  60

Ser Gly Gly Gly Gly Ser Gly Gly Gly Gly Ser Gly Gly Gly Gly Ser
65                  70                  75                  80

Gly Gly Gly Gly Ser Gly Gly Gly Gly Ser Gly Gly Gly Gly Ser Gly
                85                  90                  95

Gly Gly Gly Ser Gly Gly Gly Gly Ser Gly Gly Gly Gly Ser Gly Gly
            100                 105                 110

Gly Gly Ser Gly Gly Gly Gly Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Gly Gly Gly Gly Ser Gly Gly Gly Gly Ser
145                 150                 155                 160

Gly Gly Gly Gly Ser Gly Gly Gly Gly Ser Gly Gly Gly Gly Ser Gly
                165                 170                 175

Gly Gly Gly Ser Gly Gly Gly Gly Ser Gly Gly Gly Gly Ser Gly Gly
            180                 185                 190

Gly Gly Ser Gly Gly Gly Gly Ser Gly Gly Gly Gly Ser Gly Gly Gly
        195                 200                 205

Gly Ser Gly Gly Gly Gly Ser Gly Gly Gly Gly Ser Gly Gly Gly Gly
    210                 215                 220

Ser Gly Gly Gly Gly Ser Gly Gly Gly Gly Ser Gly Gly Gly Gly Ser
225                 230                 235                 240

Gly Gly Gly Gly Ser Gly Gly Gly Gly Ser Gly Gly Gly Gly Ser Gly
                245                 250                 255

Gly Gly Gly Ser Gly Gly Gly Gly Ser Gly Gly Gly Gly Ser Gly Gly
            260                 265                 270

Gly Gly Ser Gly Gly Gly Gly Ser Gly Gly Gly Gly Ser Gly Gly Gly
        275                 280                 285

Gly Ser Gly Gly Gly Gly Ser Gly Gly Gly Gly Ser Gly Gly Gly Gly
    290                 295                 300

Ser Gly Gly Gly Gly Ser Gly Gly Gly Gly Ser Gly Gly Gly Gly Ser
305                 310                 315                 320

Gly Gly Gly Gly Ser Gly Gly Gly Gly Ser Gly Gly Gly Gly Ser Gly
                325                 330                 335

```
Gly Gly Gly Ser Gly Gly Gly Ser Gly Gly Ser Gly
            340             345             350
Gly Gly Ser Gly Gly Gly Ser Gly Gly Gly Ser Gly Gly
            355             360             365
Gly Ser Gly Gly Gly Ser Gly Gly Gly Ser Gly Gly Gly
    370             375             380
Ser Gly Gly Gly Ser Gly Gly Gly Ser Gly Gly Gly Ser
385             390             395             400
Gly Gly Gly Ser Gly Gly Gly Ser Gly Gly Gly Ser Gly
            405             410             415
Gly Gly Gly Ser Gly Gly Gly Ser Gly Gly Gly Ser Gly Gly
            420             425             430
Gly Gly Ser Gly Gly Gly Ser Gly Gly Gly Ser Gly Gly
            435             440             445
Gly Ser Gly Gly Gly Ser Gly Gly Gly Ser Gly Gly Gly
    450             455             460
Ser Gly Gly Gly Ser Gly Gly Gly Ser Gly Gly Gly Ser
465             470             475             480
Gly Gly Gly Gly Ser Gly Gly Gly Ser Gly Gly Gly Ser Gly
            485             490             495
Gly Gly Ser Gly Gly Gly Ser Gly Gly Gly Ser Gly Gly
            500             505             510
Gly Gly Ser Gly Gly Gly Ser Gly Gly Gly Ser Gly Gly Gly
        515             520             525
Gly Ser Gly Gly Gly Ser Gly Gly Gly Ser Gly Gly Gly
    530             535             540
Ser Gly Gly Gly Ser Gly Gly Gly Ser Gly Gly Gly Ser
545             550             555             560
Gly Gly Gly Gly Ser Gly Gly Gly Ser Gly Gly Gly Ser Gly
            565             570             575
Gly Gly Gly Ser Gly Gly Gly Ser Gly Gly Gly Ser Gly Gly
            580             585             590
Gly Gly Ser Gly Gly Gly Ser Gly Gly Gly Ser Gly Gly
            595             600             605
Gly Ser Gly Gly Gly Ser Gly Gly Gly Ser Gly Gly Gly Gly
    610             615             620
Ser Gly Gly Gly Ser Gly Gly Gly Ser Gly Gly Gly Ser
625             630             635             640
Gly Gly Gly Gly Ser Gly Gly Gly Ser Gly Gly Gly Ser Gly
            645             650             655
Gly Gly Ser Gly Gly Gly Ser Gly Gly Gly Ser Gly Gly
            660             665             670
Gly Gly Ser Gly Gly Gly Ser Gly Gly Gly Ser Gly Gly Gly
            675             680             685
Gly Ser Gly Gly Gly Ser Gly Gly Gly Ser Gly Gly Gly
    690             695             700
Ser Gly Gly Gly Ser Gly Gly Gly Ser Gly Gly Gly Ser
705             710             715             720
Gly Gly Gly Gly Ser Gly Gly Gly Ser Gly Gly Gly Ser Gly
            725             730             735
Gly Gly Gly Ser Gly Gly Gly Ser Gly Gly Gly Ser Gly Gly
            740             745             750
```

```
Gly Gly Ser Gly Gly Gly Ser Gly Gly Gly Ser Gly Gly Gly
        755                 760                 765

Gly Ser Gly Gly Gly Ser Gly Gly Gly Ser Gly Gly Gly
    770                 775                 780

Ser Gly Gly Gly Ser Gly Gly Gly Ser Gly Gly Gly Ser
785                 790                 795             800

Gly Gly Gly Gly Ser Gly Gly Gly Ser Gly Gly Gly Ser Gly
            805                 810                 815

Gly Gly Gly Ser Gly Gly Gly Ser Gly Gly Gly Ser Gly Gly
            820                 825                 830

Gly Gly Ser Gly Gly Gly Ser Gly Gly Gly Ser Gly Gly Gly
        835                 840                 845

Gly Ser Gly Gly Gly Ser Gly Gly Gly Ser Gly Gly Gly
    850                 855                 860

Ser Gly Gly Gly Ser Gly Gly Gly Ser Gly Gly Gly Ser
865                 870                 875             880

Gly Gly Gly Gly Ser Gly Gly Gly Ser Gly Gly Gly Ser Gly
            885                 890                 895

Gly Gly Gly Ser Gly Gly Gly Ser Gly Gly Gly Ser Gly Gly
            900                 905                 910

Gly Gly Ser Gly Gly Gly Ser Gly Gly Gly Ser Gly Gly Gly
        915                 920                 925

Gly Ser Gly Gly Gly Ser Gly Gly Gly Ser Gly Gly Gly
    930                 935                 940

Ser Gly Gly Gly Ser Gly Gly Gly Ser Gly Gly Gly Ser
945                 950                 955             960

Gly Gly Gly Gly Ser Gly Gly Gly Ser Gly Gly Gly Ser Gly
            965                 970                 975

Gly Gly Gly Ser Gly Gly Gly Ser Gly Gly Gly Ser Gly Gly
            980                 985                 990

Gly Gly Ser Gly Gly Gly Ser  Gly Gly Gly Gly Ser  Gly Gly Gly
        995                 1000                1005

Gly Ser  Gly Gly Gly Gly Ser  Gly Gly Gly Gly Ser  Gly Gly Gly
    1010                1015                1020

Gly Ser  Gly Gly Gly Gly Ser  Gly Gly Gly Gly Ser  Gly Gly Gly
    1025                1030                1035

Gly Ser  Gly Gly Gly Gly Ser  Gly Gly Gly Gly Ser  Gly Gly Gly
    1040                1045                1050

Gly Ser  Gly Gly Gly Gly Ser  Gly Gly Gly Gly Ser  Gly Gly Gly
    1055                1060                1065

Gly Ser  Gly Gly Gly Gly Ser  Gly Gly Gly Gly Ser  Gly Gly Gly
    1070                1075                1080

Gly Ser  Gly Gly Gly Gly Ser  Gly Gly Gly Gly Ser  Gly Gly Gly
    1085                1090                1095

Gly Ser  Gly Gly Gly Gly Ser  Gly Gly Gly Gly Ser  Gly Gly Gly
    1100                1105                1110

Gly Ser  Gly Gly Gly Gly Ser  Gly Gly Gly Gly Ser  Gly Gly Gly
    1115                1120                1125

Gly Ser  Gly Gly Gly Gly Ser  Gly Gly Gly Gly Ser  Gly Gly Gly
    1130                1135                1140

Gly Ser  Gly Gly Gly Gly Ser  Gly Gly Gly Gly Ser  Gly Gly Gly
    1145                1150                1155

Gly Ser  Gly Gly Gly Gly Ser  Gly Gly Gly Gly Ser  Gly Gly Gly
```

```
                1160                1165                1170

Gly Ser Gly Gly Gly Gly Ser Gly Gly Gly Gly Ser Gly Gly Gly
    1175                1180                1185

Gly Ser Gly Gly Gly Gly Ser Gly Gly Gly Gly Ser Gly Gly Gly
    1190                1195                1200

Gly Ser Gly Gly Gly Gly Ser Gly Gly Gly Gly Ser Gly Gly Gly
    1205                1210                1215

Gly Ser Gly Gly Gly Gly Ser Gly Gly Gly Gly Ser Gly Gly Gly
    1220                1225                1230

Gly Ser Gly Gly Gly Gly Ser Gly Gly Gly Gly Ser Gly Gly Gly
    1235                1240                1245

Gly Ser Gly Gly Gly Gly Ser Gly Gly Gly Gly Ser Gly Gly Gly
    1250                1255                1260

Gly Ser Gly Gly Gly Gly Ser Gly Gly Gly Gly Ser Gly Gly Gly
    1265                1270                1275

Gly Ser Gly Gly Gly Gly Ser Gly Gly Gly Gly Ser Gly Gly Gly
    1280                1285                1290

Gly Ser Gly Gly Gly Gly Ser Gly Gly Gly Gly Ser Gly Gly Gly
    1295                1300                1305

Gly Ser Gly Gly Gly Gly Ser Gly Gly Gly Gly Ser Gly Gly Gly
    1310                1315                1320

Gly Ser Gly Gly Gly Gly Ser Gly Gly Gly Gly Ser Gly Gly Gly
    1325                1330                1335

Gly Ser Gly Gly Gly Gly Ser Gly Gly Gly Gly Ser Gly Gly Gly
    1340                1345                1350

Gly Ser Gly Gly Gly Gly Ser Gly Gly Gly Gly Ser Gly Gly Gly
    1355                1360                1365

Gly Ser Gly Gly Gly Gly Ser Gly Gly Gly Gly Ser Gly Gly Gly
    1370                1375                1380

Gly Ser Gly Gly Gly Gly Ser Gly Gly Gly Gly Ser Gly Gly Gly
    1385                1390                1395

Gly Ser Gly Gly Gly Gly Ser Gly Gly Gly Gly Ser Gly Gly Gly
    1400                1405                1410

Gly Ser Gly Gly Gly Gly Ser Gly Gly Gly Gly Ser Gly Gly Gly
    1415                1420                1425

Gly Ser Gly Gly Gly Gly Ser Gly Gly Gly Gly Ser Gly Gly Gly
    1430                1435                1440

Gly Ser Gly Gly Gly Gly Ser Gly Gly Gly Gly Ser Gly Gly Gly
    1445                1450                1455

Gly Ser Gly Gly Gly Gly Ser Gly Gly Gly Gly Ser Gly Gly Gly
    1460                1465                1470

Gly Ser Gly Gly Gly Gly Ser Gly Gly Gly Gly Ser Gly Gly Gly
    1475                1480                1485

Gly Ser Gly Gly Gly Gly Ser Gly Gly Gly Gly Ser Gly Gly Gly
    1490                1495                1500

Gly Ser Gly Gly Gly Gly Ser Gly Gly Gly Gly Ser Gly Gly Gly
    1505                1510                1515

Gly Ser Gly Gly Gly Gly Ser Gly Gly Gly Gly Ser Gly Gly Gly
    1520                1525                1530

Gly Ser Gly Gly Gly Gly Ser Gly Gly Gly Gly Ser Gly Gly Gly
    1535                1540                1545

Gly Ser Gly Gly Gly Gly Ser Gly Gly Gly Gly Ser Gly Gly Gly
    1550                1555                1560
```

Gly Ser Gly Gly Gly Gly Ser Gly Gly Gly Gly Ser Gly Gly Gly
1565                1570                1575

Gly Ser Gly Gly Gly Gly Ser Gly Gly Gly Gly Ser Gly Gly Gly
1580                1585                1590

Gly Ser Gly Gly Gly Gly Ser Gly Gly Gly Gly Ser Gly Gly Gly
1595                1600                1605

Gly Ser Gly Gly Gly Gly Ser Gly Gly Gly Gly Ser Gly Gly Gly
1610                1615                1620

Gly Ser Gly Gly Gly Gly Ser Gly Gly Gly Gly Ser Gly Gly Gly
1625                1630                1635

Gly Ser Gly Gly Gly Gly Ser Gly Gly Gly Gly Ser Gly Gly Gly
1640                1645                1650

Gly Ser Gly Gly Gly Gly Ser Gly Gly Gly Gly Ser Gly Gly Gly
1655                1660                1665

Gly Ser Gly Gly Gly Gly Ser Gly Gly Gly Gly Ser Gly Gly Gly
1670                1675                1680

Gly Ser Gly Gly Gly Gly Ser Gly Gly Gly Gly Ser Gly Gly Gly
1685                1690                1695

Gly Ser Gly Gly Gly Gly Ser Gly Gly Gly Gly Ser Gly Gly Gly
1700                1705                1710

Gly Ser Gly Gly Gly Gly Ser Gly Gly Gly Gly Ser Gly Gly Gly
1715                1720                1725

Gly Ser Gly Gly Gly Gly Ser Gly Gly Gly Gly Ser Gly Gly Gly
1730                1735                1740

Gly Ser Gly Gly Gly Gly Ser Gly Gly Gly Gly Ser Gly Gly Gly
1745                1750                1755

Gly Ser Gly Gly Gly Gly Ser Gly Gly Gly Gly Ser Gly Gly Gly
1760                1765                1770

Gly Ser Gly Gly Gly Gly Ser Gly Gly Gly Gly Ser Gly Gly Gly
1775                1780                1785

Gly Ser Gly Gly Gly Gly Ser Gly Gly Gly Gly Ser Gly Gly Gly
1790                1795                1800

Gly Ser Gly Gly Gly Gly Ser Gly Gly Gly Gly Ser Gly Gly Gly
1805                1810                1815

Gly Ser Gly Gly Gly Gly Ser Gly Gly Gly Gly Ser Gly Gly Gly
1820                1825                1830

Gly Ser Gly Gly Gly Gly Ser Gly Gly Gly Gly Ser Gly Gly Gly
1835                1840                1845

Gly Ser Gly Gly Gly Gly Ser Gly Gly Gly Gly Ser Gly Gly Gly
1850                1855                1860

Gly Ser Gly Gly Gly Gly Ser Gly Gly Gly Gly Ser Gly Gly Gly
1865                1870                1875

Gly Ser Gly Gly Gly Gly Ser Gly Gly Gly Gly Ser Gly Gly Gly
1880                1885                1890

Gly Ser Gly Gly Gly Gly Ser Gly Gly Gly Gly Ser Gly Gly Gly
1895                1900                1905

Gly Ser Gly Gly Gly Gly Ser Gly Gly Gly Gly Ser Gly Gly Gly
1910                1915                1920

Gly Ser Gly Gly Gly Gly Ser Gly Gly Gly Gly Ser Gly Gly Gly
1925                1930                1935

Gly Ser Gly Gly Gly Gly Ser Gly Gly Gly Gly Ser Gly Gly Gly
1940                1945                1950

-continued

```
Gly Ser Gly Gly Gly Gly Ser Gly Gly Gly Gly Ser Gly Gly Gly
    1955                1960                1965

Gly Ser Gly Gly Gly Gly Ser Gly Gly Gly Gly Ser Gly Gly Gly
    1970                1975                1980

Gly Ser Gly Gly Gly Gly Ser Gly Gly Gly Gly Ser Gly Gly Gly
    1985                1990                1995

Gly Ser
    2000

<210> SEQ ID NO 176
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Alternative linker

<400> SEQUENCE: 176

Pro Glu Ala Pro Thr Asp Pro Glu Ala Pro Thr Asp
1               5                   10

<210> SEQ ID NO 177
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CTP

<400> SEQUENCE: 177

Asp Ser Ser Ser Ser Lys Ala Pro Pro Pro Ser Leu Pro Ser Pro Ser
1               5                   10                  15

Arg Leu Pro Gly Pro Ser Asp Thr Pro Ile Leu Pro Gln
            20                  25

<210> SEQ ID NO 178
<211> LENGTH: 254
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: FVII-HC

<400> SEQUENCE: 178

Ile Val Gly Gly Lys Val Cys Pro Lys Gly Glu Cys Pro Trp Gln Val
1               5                   10                  15

Leu Leu Leu Val Asn Gly Ala Gln Leu Cys Gly Gly Thr Leu Ile Asn
            20                  25                  30

Thr Ile Trp Val Val Ser Ala Ala His Cys Phe Asp Lys Ile Lys Asn
        35                  40                  45

Trp Arg Asn Leu Ile Ala Val Leu Gly Glu His Asp Leu Ser Glu His
    50                  55                  60

Asp Gly Asp Glu Gln Ser Arg Arg Val Ala Gln Val Ile Ile Pro Ser
65                  70                  75                  80

Thr Tyr Val Pro Gly Thr Thr Asn His Asp Ile Ala Leu Leu Arg Leu
                85                  90                  95

His Gln Pro Val Val Leu Thr Asp His Val Val Pro Leu Cys Leu Pro
```

```
                    100                 105                 110
Glu Arg Thr Phe Ser Glu Arg Thr Leu Ala Phe Val Arg Phe Ser Leu
                115                 120                 125
Val Ser Gly Trp Gly Gln Leu Leu Asp Arg Gly Ala Thr Ala Leu Glu
            130                 135                 140
Leu Met Val Leu Asn Val Pro Arg Leu Met Thr Gln Asp Cys Leu Gln
145                 150                 155                 160
Gln Ser Arg Lys Val Gly Asp Ser Pro Asn Ile Thr Glu Tyr Met Phe
                165                 170                 175
Cys Ala Gly Tyr Ser Asp Gly Ser Lys Asp Ser Cys Lys Gly Asp Ser
            180                 185                 190
Gly Gly Pro His Ala Thr His Tyr Arg Gly Thr Trp Tyr Leu Thr Gly
        195                 200                 205
Ile Val Ser Trp Gly Gln Gly Cys Ala Thr Val Gly His Phe Gly Val
            210                 215                 220
Tyr Thr Arg Val Ser Gln Tyr Ile Glu Trp Leu Gln Lys Leu Met Arg
225                 230                 235                 240
Ser Glu Pro Arg Pro Gly Val Leu Leu Arg Ala Pro Phe Pro
                245                 250
```

<210> SEQ ID NO 179
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: FVII-LC

<400> SEQUENCE: 179

```
Ala Asn Ala Phe Leu Glu Glu Leu Arg Pro Gly Ser Leu Glu Arg Glu
1               5                   10                  15
Cys Lys Glu Glu Gln Cys Ser Phe Glu Glu Ala Arg Glu Ile Phe Lys
            20                  25                  30
Asp Ala Glu Arg Thr Lys Leu Phe Trp Ile Ser Tyr Ser Asp Gly Asp
        35                  40                  45
Gln Cys Ala Ser Ser Pro Cys Gln Asn Gly Gly Ser Cys Lys Asp Gln
    50                  55                  60
Leu Gln Ser Tyr Ile Cys Phe Cys Leu Pro Ala Phe Glu Gly Arg Asn
65                  70                  75                  80
Cys Glu Thr His Lys Asp Asp Gln Leu Ile Cys Val Asn Glu Asn Gly
                85                  90                  95
Gly Cys Glu Gln Tyr Cys Ser Asp His Thr Gly Thr Lys Arg Ser Cys
            100                 105                 110
Arg Cys His Glu Gly Tyr Ser Leu Leu Ala Asp Gly Val Ser Cys Thr
        115                 120                 125
Pro Thr Val Glu Tyr Pro Cys Gly Lys Ile Pro Ile Leu Glu Lys Arg
    130                 135                 140
Asn Ala Ser Lys Pro Gln Gly Arg
145                 150
```

<210> SEQ ID NO 180
<211> LENGTH: 466
<212> TYPE: PRT
<213> ORGANISM: Artificial Sequence
<220> FEATURE:
<223> OTHER INFORMATION: Description of Artificial Sequence: Synthetic

```
                            polypeptide
<220> FEATURE:
<223> OTHER INFORMATION: FVII zymogen

<400> SEQUENCE: 180

Met Val Ser Gln Ala Leu Arg Leu Leu Cys Leu Leu Leu Gly Leu Gln
1               5                   10                  15

Gly Cys Leu Ala Ala Gly Gly Val Ala Lys Ala Ser Gly Gly Glu Thr
            20                  25                  30

Arg Asp Met Pro Trp Lys Pro Gly Pro His Arg Val Phe Val Thr Gln
        35                  40                  45

Glu Glu Ala His Gly Val Leu His Arg Arg Arg Ala Asn Ala Phe
50                  55                  60

Leu Glu Glu Leu Arg Pro Gly Ser Leu Glu Arg Glu Cys Lys Glu Glu
65                  70                  75                  80

Gln Cys Ser Phe Glu Glu Ala Arg Glu Ile Phe Lys Asp Ala Glu Arg
                85                  90                  95

Thr Lys Leu Phe Trp Ile Ser Tyr Ser Asp Gly Asp Gln Cys Ala Ser
            100                 105                 110

Ser Pro Cys Gln Asn Gly Gly Ser Cys Lys Asp Gln Leu Gln Ser Tyr
        115                 120                 125

Ile Cys Phe Cys Leu Pro Ala Phe Glu Gly Arg Asn Cys Glu Thr His
130                 135                 140

Lys Asp Asp Gln Leu Ile Cys Val Asn Glu Asn Gly Gly Cys Glu Gln
145                 150                 155                 160

Tyr Cys Ser Asp His Thr Gly Thr Lys Arg Ser Cys Arg Cys His Glu
                165                 170                 175

Gly Tyr Ser Leu Leu Ala Asp Gly Val Ser Cys Thr Pro Thr Val Glu
            180                 185                 190

Tyr Pro Cys Gly Lys Ile Pro Ile Leu Glu Lys Arg Asn Ala Ser Lys
        195                 200                 205

Pro Gln Gly Arg Ile Val Gly Gly Lys Val Cys Pro Lys Gly Glu Cys
210                 215                 220

Pro Trp Gln Val Leu Leu Leu Val Asn Gly Ala Gln Leu Cys Gly Gly
225                 230                 235                 240

Thr Leu Ile Asn Thr Ile Trp Val Val Ser Ala Ala His Cys Phe Asp
                245                 250                 255

Lys Ile Lys Asn Trp Arg Asn Leu Ile Ala Val Leu Gly Glu His Asp
            260                 265                 270

Leu Ser Glu His Asp Gly Asp Glu Gln Ser Arg Arg Val Ala Gln Val
        275                 280                 285

Ile Ile Pro Ser Thr Tyr Val Pro Gly Thr Thr Asn His Asp Ile Ala
290                 295                 300

Leu Leu Arg Leu His Gln Pro Val Val Leu Thr Asp His Val Val Pro
305                 310                 315                 320

Leu Cys Leu Pro Glu Arg Thr Phe Ser Glu Arg Thr Leu Ala Phe Val
                325                 330                 335

Arg Phe Ser Leu Val Ser Gly Trp Gly Gln Leu Leu Asp Arg Gly Ala
            340                 345                 350

Thr Ala Leu Glu Leu Met Val Leu Asn Val Pro Arg Leu Met Thr Gln
        355                 360                 365

Asp Cys Leu Gln Gln Ser Arg Lys Val Gly Asp Ser Pro Asn Ile Thr
370                 375                 380

Glu Tyr Met Phe Cys Ala Gly Tyr Ser Asp Gly Ser Lys Asp Ser Cys
```

```
                385                 390                 395                 400
Lys Gly Asp Ser Gly Gly Pro His Ala Thr His Tyr Arg Gly Thr Trp
            405                 410                 415

Tyr Leu Thr Gly Ile Val Ser Trp Gly Gln Gly Cys Ala Thr Val Gly
            420                 425                 430

His Phe Gly Val Tyr Thr Arg Val Ser Gln Tyr Ile Glu Trp Leu Gln
            435                 440                 445

Lys Leu Met Arg Ser Glu Pro Arg Pro Gly Val Leu Leu Arg Ala Pro
            450                 455                 460

Phe Pro
465

<210> SEQ ID NO 181
<211> LENGTH: 461
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: FIX zymogen

<400> SEQUENCE: 181

Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
            35                  40                  45

Ser Gly Lys Leu Glu Glu Phe Val Gln Gly Asn Leu Glu Arg Glu Cys
        50                  55                  60

Met Glu Glu Lys Cys Ser Phe Glu Glu Ala Arg Glu Val Phe Glu Asn
65              70                  75                  80

Thr Glu Arg Thr Thr Glu Phe Trp Lys Gln Tyr Val Asp Gly Asp Gln
            85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
            115                 120                 125

Glu Leu Asp Val Thr Cys Asn Ile Lys Asn Gly Arg Cys Glu Gln Phe
        130                 135                 140

Cys Lys Asn Ser Ala Asp Asn Lys Val Val Cys Ser Cys Thr Glu Gly
145             150                 155                 160

Tyr Arg Leu Ala Glu Asn Gln Lys Ser Cys Glu Pro Ala Val Pro Phe
            165                 170                 175

Pro Cys Gly Arg Val Ser Val Ser Gln Thr Ser Lys Leu Thr Arg Ala
            180                 185                 190

Glu Thr Val Phe Pro Asp Val Asp Tyr Val Asn Ser Thr Glu Ala Glu
            195                 200                 205

Thr Ile Leu Asp Asn Ile Thr Gln Ser Thr Gln Ser Phe Asn Asp Phe
        210                 215                 220

Thr Arg Val Val Gly Gly Glu Asp Ala Lys Pro Gly Gln Phe Pro Trp
225             230                 235                 240

Gln Val Val Leu Asn Gly Lys Val Asp Ala Phe Cys Gly Gly Ser Ile
            245                 250                 255

Val Asn Glu Lys Trp Ile Val Thr Ala Ala His Cys Val Glu Thr Gly
```

```
                260             265             270
Val Lys Ile Thr Val Val Ala Gly Glu His Asn Ile Glu Glu Thr Glu
            275             280             285

His Thr Glu Gln Lys Arg Asn Val Ile Arg Ile Ile Pro His His Asn
        290             295             300

Tyr Asn Ala Ala Ile Asn Lys Tyr Asn His Asp Ile Ala Leu Leu Glu
305             310             315             320

Leu Asp Glu Pro Leu Val Leu Asn Ser Tyr Val Thr Pro Ile Cys Ile
            325             330             335

Ala Asp Lys Glu Tyr Thr Asn Ile Phe Leu Lys Phe Gly Ser Gly Tyr
        340             345             350

Val Ser Gly Trp Gly Arg Val Phe His Lys Gly Arg Ser Ala Leu Val
        355             360             365

Leu Gln Tyr Leu Arg Val Pro Leu Val Asp Arg Ala Thr Cys Leu Arg
        370             375             380

Ser Thr Lys Phe Thr Ile Tyr Asn Asn Met Phe Cys Ala Gly Phe His
385             390             395             400

Glu Gly Gly Arg Asp Ser Cys Gln Gly Asp Ser Gly Gly Pro His Val
            405             410             415

Thr Glu Val Glu Gly Thr Ser Phe Leu Thr Gly Ile Ile Ser Trp Gly
            420             425             430

Glu Glu Cys Ala Met Lys Gly Lys Tyr Gly Ile Tyr Thr Lys Val Ser
        435             440             445

Arg Tyr Val Asn Trp Ile Lys Glu Lys Thr Lys Leu Thr
    450             455             460

<210> SEQ ID NO 182
<211> LENGTH: 488
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: FX zymogen

<400> SEQUENCE: 182

Met Gly Arg Pro Leu His Leu Val Leu Leu Ser Ala Ser Leu Ala Gly
1               5                   10                  15

Leu Leu Leu Leu Gly Glu Ser Leu Phe Ile Arg Arg Glu Gln Ala Asn
            20                  25                  30

Asn Ile Leu Ala Arg Val Thr Arg Ala Asn Ser Phe Leu Glu Glu Met
        35                  40                  45

Lys Lys Gly His Leu Glu Arg Glu Cys Met Glu Glu Thr Cys Ser Tyr
    50                  55                  60

Glu Glu Ala Arg Glu Val Phe Glu Asp Ser Asp Lys Thr Asn Glu Phe
65                  70                  75                  80

Trp Asn Lys Tyr Lys Asp Gly Asp Gln Cys Glu Thr Ser Pro Cys Gln
                85                  90                  95

Asn Gln Gly Lys Cys Lys Asp Gly Leu Gly Glu Tyr Thr Cys Thr Cys
            100                 105                 110

Leu Glu Gly Phe Glu Gly Lys Asn Cys Glu Leu Phe Thr Arg Lys Leu
        115                 120                 125

Cys Ser Leu Asp Asn Gly Asp Cys Asp Gln Phe Cys His Glu Glu Gln
    130                 135                 140

Asn Ser Val Val Cys Ser Cys Ala Arg Gly Tyr Thr Leu Ala Asp Asn
```

```
                145                 150                 155                 160
Gly Lys Ala Cys Ile Pro Thr Gly Pro Tyr Pro Cys Gly Lys Gln Thr
                165                 170                 175

Leu Glu Arg Arg Lys Arg Ser Val Ala Gln Ala Thr Ser Ser Ser Gly
                180                 185                 190

Glu Ala Pro Asp Ser Ile Thr Trp Lys Pro Tyr Asp Ala Ala Asp Leu
                195                 200                 205

Asp Pro Thr Glu Asn Pro Phe Asp Leu Leu Asp Phe Asn Gln Thr Gln
        210                 215                 220

Pro Glu Arg Gly Asp Asn Asn Leu Thr Arg Ile Val Gly Gly Gln Glu
225                 230                 235                 240

Cys Lys Asp Gly Glu Cys Pro Trp Gln Ala Leu Leu Ile Asn Glu Glu
                245                 250                 255

Asn Glu Gly Phe Cys Gly Gly Thr Ile Leu Ser Glu Phe Tyr Ile Leu
                260                 265                 270

Thr Ala Ala His Cys Leu Tyr Gln Ala Lys Arg Phe Lys Val Arg Val
                275                 280                 285

Gly Asp Arg Asn Thr Glu Gln Glu Glu Gly Gly Glu Ala Val His Glu
        290                 295                 300

Val Glu Val Val Ile Lys His Asn Arg Phe Thr Lys Glu Thr Tyr Asp
305                 310                 315                 320

Phe Asp Ile Ala Val Leu Arg Leu Lys Thr Pro Ile Thr Phe Arg Met
                325                 330                 335

Asn Val Ala Pro Ala Cys Leu Pro Glu Arg Asp Trp Ala Glu Ser Thr
                340                 345                 350

Leu Met Thr Gln Lys Thr Gly Ile Val Ser Gly Phe Gly Arg Thr His
                355                 360                 365

Glu Lys Gly Arg Gln Ser Thr Arg Leu Lys Met Leu Glu Val Pro Tyr
        370                 375                 380

Val Asp Arg Asn Ser Cys Lys Leu Ser Ser Ser Phe Ile Ile Thr Gln
385                 390                 395                 400

Asn Met Phe Cys Ala Gly Tyr Asp Thr Lys Gln Glu Asp Ala Cys Gln
                405                 410                 415

Gly Asp Ser Gly Gly Pro His Val Thr Arg Phe Lys Asp Thr Tyr Phe
                420                 425                 430

Val Thr Gly Ile Val Ser Trp Gly Glu Gly Cys Ala Arg Lys Gly Lys
                435                 440                 445

Tyr Gly Ile Tyr Thr Lys Val Thr Ala Phe Leu Lys Trp Ile Asp Arg
        450                 455                 460

Ser Met Lys Thr Arg Gly Leu Pro Lys Ala Lys Ser His Ala Pro Glu
465                 470                 475                 480

Val Ile Thr Ser Ser Pro Leu Lys
                485

<210> SEQ ID NO 183
<211> LENGTH: 1039
<212> TYPE: PRT
<213> ORGANISM: Homo sapiens

<400> SEQUENCE: 183

Met Ala Arg Ala Leu Cys Pro Leu Gln Ala Leu Trp Leu Leu Glu Trp
1               5                   10                  15

Val Leu Leu Leu Leu Gly Pro Cys Ala Ala Pro Pro Ala Trp Ala Leu
                20                  25                  30
```

```
Asn Leu Asp Pro Val Gln Leu Thr Phe Tyr Ala Gly Pro Asn Gly Ser
         35                  40                  45

Gln Phe Gly Phe Ser Leu Asp Phe His Lys Asp Ser His Gly Arg Val
 50                  55                  60

Ala Ile Val Val Gly Ala Pro Arg Thr Leu Gly Pro Ser Gln Glu Glu
 65                  70                  75                  80

Thr Gly Gly Val Phe Leu Cys Pro Trp Arg Ala Glu Gly Gly Gln Cys
                     85                  90                  95

Pro Ser Leu Leu Phe Asp Leu Arg Asp Glu Thr Arg Asn Val Gly Ser
             100                 105                 110

Gln Thr Leu Gln Thr Phe Lys Ala Arg Gln Gly Leu Gly Ala Ser Val
         115                 120                 125

Val Ser Trp Ser Asp Val Ile Val Ala Cys Ala Pro Trp Gln His Trp
 130                 135                 140

Asn Val Leu Glu Lys Thr Glu Glu Ala Glu Lys Thr Pro Val Gly Ser
 145                 150                 155                 160

Cys Phe Leu Ala Gln Pro Glu Ser Gly Arg Arg Ala Glu Tyr Ser Pro
             165                 170                 175

Cys Arg Gly Asn Thr Leu Ser Arg Ile Tyr Val Glu Asn Asp Phe Ser
             180                 185                 190

Trp Asp Lys Arg Tyr Cys Glu Ala Gly Phe Ser Ser Val Val Thr Gln
         195                 200                 205

Ala Gly Glu Leu Val Leu Gly Ala Pro Gly Gly Tyr Tyr Phe Leu Gly
         210                 215                 220

Leu Leu Ala Gln Ala Pro Val Ala Asp Ile Phe Ser Ser Tyr Arg Pro
225                 230                 235                 240

Gly Ile Leu Leu Trp His Val Ser Ser Gln Ser Leu Ser Phe Asp Ser
                     245                 250                 255

Ser Asn Pro Glu Tyr Phe Asp Gly Tyr Trp Gly Tyr Ser Val Ala Val
             260                 265                 270

Gly Glu Phe Asp Gly Asp Leu Asn Thr Thr Glu Tyr Val Val Gly Ala
             275                 280                 285

Pro Thr Trp Ser Trp Thr Leu Gly Ala Val Glu Ile Leu Asp Ser Tyr
 290                 295                 300

Tyr Gln Arg Leu His Arg Leu Arg Gly Glu Gln Met Ala Ser Tyr Phe
305                 310                 315                 320

Gly His Ser Val Ala Val Thr Asp Val Asn Gly Asp Gly Arg His Asp
                     325                 330                 335

Leu Leu Val Gly Ala Pro Leu Tyr Met Glu Ser Arg Ala Asp Arg Lys
             340                 345                 350

Leu Ala Glu Val Gly Arg Val Tyr Leu Phe Leu Gln Pro Arg Gly Pro
         355                 360                 365

His Ala Leu Gly Ala Pro Ser Leu Leu Leu Thr Gly Thr Gln Leu Tyr
         370                 375                 380

Gly Arg Phe Gly Ser Ala Ile Ala Pro Leu Gly Asp Leu Asp Arg Asp
385                 390                 395                 400

Gly Tyr Asn Asp Ile Ala Val Ala Ala Pro Tyr Gly Gly Pro Ser Gly
                     405                 410                 415

Arg Gly Gln Val Leu Val Phe Leu Gly Gln Ser Glu Gly Leu Arg Ser
             420                 425                 430

Arg Pro Ser Gln Val Leu Asp Ser Pro Phe Pro Thr Gly Ser Ala Phe
         435                 440                 445

Gly Phe Ser Leu Arg Gly Ala Val Asp Ile Asp Asp Asn Gly Tyr Pro
```

```
            450                 455                 460
Asp Leu Ile Val Gly Ala Tyr Gly Ala Asn Gln Val Ala Val Tyr Arg
465                 470                 475                 480

Ala Gln Pro Val Val Lys Ala Ser Val Gln Leu Leu Val Gln Asp Ser
                485                 490                 495

Leu Asn Pro Ala Val Lys Ser Cys Val Leu Pro Gln Thr Lys Thr Pro
                500                 505                 510

Val Ser Cys Phe Asn Ile Gln Met Cys Val Gly Ala Thr Gly His Asn
            515                 520                 525

Ile Pro Gln Lys Leu Ser Leu Asn Ala Glu Leu Gln Leu Asp Arg Gln
        530                 535                 540

Lys Pro Arg Gln Gly Arg Arg Val Leu Leu Gly Ser Gln Gln Ala
545                 550                 555                 560

Gly Thr Thr Leu Asn Leu Asp Leu Gly Lys His Ser Pro Ile Cys
                565                 570                 575

His Thr Thr Met Ala Phe Leu Arg Asp Glu Ala Asp Phe Arg Asp Lys
                580                 585                 590

Leu Ser Pro Ile Val Leu Ser Leu Asn Val Ser Leu Pro Pro Thr Glu
            595                 600                 605

Ala Gly Met Ala Pro Ala Val Val Leu His Gly Asp Thr His Val Gln
        610                 615                 620

Glu Gln Thr Arg Ile Val Leu Asp Cys Gly Glu Asp Val Cys Val
625                 630                 635                 640

Pro Gln Leu Gln Leu Thr Ala Ser Val Thr Gly Ser Pro Leu Leu Val
                645                 650                 655

Gly Ala Asp Asn Val Leu Glu Leu Gln Met Asp Ala Ala Asn Glu Gly
            660                 665                 670

Glu Gly Ala Tyr Glu Ala Glu Leu Ala Val His Leu Pro Gln Gly Ala
        675                 680                 685

His Tyr Met Arg Ala Leu Ser Asn Val Glu Gly Phe Glu Arg Leu Ile
        690                 695                 700

Cys Asn Gln Lys Lys Glu Asn Glu Thr Arg Val Val Leu Cys Glu Leu
705                 710                 715                 720

Gly Asn Pro Met Lys Lys Asn Ala Gln Ile Gly Ile Ala Met Leu Val
                725                 730                 735

Ser Val Gly Asn Leu Glu Glu Ala Gly Glu Ser Val Ser Phe Gln Leu
            740                 745                 750

Gln Ile Arg Ser Lys Asn Ser Gln Asn Pro Asn Ser Lys Ile Val Leu
        755                 760                 765

Leu Asp Val Pro Val Arg Ala Glu Ala Gln Val Glu Leu Arg Gly Asn
770                 775                 780

Ser Phe Pro Ala Ser Leu Val Val Ala Ala Glu Gly Glu Arg Glu
785                 790                 795                 800

Gln Asn Ser Leu Asp Ser Trp Gly Pro Lys Val Glu His Thr Tyr Glu
                805                 810                 815

Leu His Asn Asn Gly Pro Gly Thr Val Asn Gly Leu His Leu Ser Ile
            820                 825                 830

His Leu Pro Gly Gln Ser Gln Pro Ser Asp Leu Leu Tyr Ile Leu Asp
        835                 840                 845

Ile Gln Pro Gln Gly Gly Leu Gln Cys Phe Pro Gln Pro Val Asn
        850                 855                 860

Pro Leu Lys Val Asp Trp Gly Leu Pro Ile Pro Ser Pro Ser Pro Ile
865                 870                 875                 880
```

His Pro Ala His His Lys Arg Asp Arg Arg Gln Ile Phe Leu Pro Glu
            885                 890                 895

Pro Glu Gln Pro Ser Arg Leu Gln Asp Pro Val Leu Val Ser Cys Asp
            900                 905                 910

Ser Ala Pro Cys Thr Val Val Gln Cys Asp Leu Gln Glu Met Ala Arg
            915                 920                 925

Gly Gln Arg Ala Met Val Thr Val Leu Ala Phe Leu Trp Leu Pro Ser
        930                 935                 940

Leu Tyr Gln Arg Pro Leu Asp Gln Phe Val Leu Gln Ser His Ala Trp
945                 950                 955                 960

Phe Asn Val Ser Ser Leu Pro Tyr Ala Val Pro Pro Leu Ser Leu Pro
                965                 970                 975

Arg Gly Glu Ala Gln Val Trp Thr Gln Leu Leu Arg Ala Leu Glu Glu
            980                 985                 990

Arg Ala Ile Pro Ile Trp Trp Val Leu Val Gly Val Leu Gly Gly Leu
        995                 1000                1005

Leu Leu Leu Thr Ile Leu Val Leu Ala Met Trp Lys Val Gly Phe
    1010                1015                1020

Phe Lys Arg Asn Arg Pro Pro Leu Glu Glu Asp Asp Glu Glu Gly
    1025                1030                1035

Glu

<210> SEQ ID NO 184
<211> LENGTH: 788
<212> TYPE: PRT
<213> ORGANISM: Homo sapiens

<400> SEQUENCE: 184

Met Arg Ala Arg Pro Arg Pro Arg Pro Leu Trp Ala Thr Val Leu Ala
1               5                   10                  15

Leu Gly Ala Leu Ala Gly Val Gly Val Gly Gly Pro Asn Ile Cys Thr
            20                  25                  30

Thr Arg Gly Val Ser Ser Cys Gln Gln Cys Leu Ala Val Ser Pro Met
        35                  40                  45

Cys Ala Trp Cys Ser Asp Glu Ala Leu Pro Leu Gly Ser Pro Arg Cys
    50                  55                  60

Asp Leu Lys Glu Asn Leu Leu Lys Asp Asn Cys Ala Pro Glu Ser Ile
65                  70                  75                  80

Glu Phe Pro Val Ser Glu Ala Arg Val Leu Glu Asp Arg Pro Leu Ser
                85                  90                  95

Asp Lys Gly Ser Gly Asp Ser Ser Gln Val Thr Gln Val Ser Pro Gln
            100                 105                 110

Arg Ile Ala Leu Arg Leu Arg Pro Asp Asp Ser Lys Asn Phe Ser Ile
        115                 120                 125

Gln Val Arg Gln Val Glu Asp Tyr Pro Val Asp Ile Tyr Tyr Leu Met
    130                 135                 140

Asp Leu Ser Tyr Ser Met Lys Asp Asp Leu Trp Ser Ile Gln Asn Leu
145                 150                 155                 160

Gly Thr Lys Leu Ala Thr Gln Met Arg Lys Leu Thr Ser Asn Leu Arg
                165                 170                 175

Ile Gly Phe Gly Ala Phe Val Asp Lys Pro Val Ser Pro Tyr Met Tyr
            180                 185                 190

Ile Ser Pro Pro Glu Ala Leu Glu Asn Pro Cys Tyr Asp Met Lys Thr
        195                 200                 205

```
Thr Cys Leu Pro Met Phe Gly Tyr Lys His Val Leu Thr Leu Thr Asp
    210                 215                 220

Gln Val Thr Arg Phe Asn Glu Glu Val Lys Lys Gln Ser Val Ser Arg
225                 230                 235                 240

Asn Arg Asp Ala Pro Glu Gly Gly Phe Asp Ala Ile Met Gln Ala Thr
                245                 250                 255

Val Cys Asp Glu Lys Ile Gly Trp Arg Asn Asp Ala Ser His Leu Leu
                260                 265                 270

Val Phe Thr Thr Asp Ala Lys Thr His Ile Ala Leu Asp Gly Arg Leu
                275                 280                 285

Ala Gly Ile Val Gln Pro Asn Asp Gly Gln Cys His Val Gly Ser Asp
290                 295                 300

Asn His Tyr Ser Ala Ser Thr Thr Met Asp Tyr Pro Ser Leu Gly Leu
305                 310                 315                 320

Met Thr Glu Lys Leu Ser Gln Lys Asn Ile Asn Leu Ile Phe Ala Val
                325                 330                 335

Thr Glu Asn Val Val Asn Leu Tyr Gln Asn Tyr Ser Glu Leu Ile Pro
                340                 345                 350

Gly Thr Thr Val Gly Val Leu Ser Met Asp Ser Ser Asn Val Leu Gln
                355                 360                 365

Leu Ile Val Asp Ala Tyr Gly Lys Ile Arg Ser Lys Val Glu Leu Glu
370                 375                 380

Val Arg Asp Leu Pro Glu Glu Leu Ser Leu Ser Phe Asn Ala Thr Cys
385                 390                 395                 400

Leu Asn Asn Glu Val Ile Pro Gly Leu Lys Ser Cys Met Gly Leu Lys
                405                 410                 415

Ile Gly Asp Thr Val Ser Phe Ser Ile Glu Ala Lys Val Arg Gly Cys
                420                 425                 430

Pro Gln Glu Lys Glu Lys Ser Phe Thr Ile Lys Pro Val Gly Phe Lys
                435                 440                 445

Asp Ser Leu Ile Val Gln Val Thr Phe Asp Cys Asp Cys Ala Cys Gln
450                 455                 460

Ala Gln Ala Glu Pro Asn Ser His Arg Cys Asn Asn Gly Asn Gly Thr
465                 470                 475                 480

Phe Glu Cys Gly Val Cys Arg Cys Gly Pro Gly Trp Leu Gly Ser Gln
                485                 490                 495

Cys Glu Cys Ser Glu Glu Asp Tyr Arg Pro Ser Gln Gln Asp Glu Cys
                500                 505                 510

Ser Pro Arg Glu Gly Gln Pro Val Cys Ser Gln Arg Gly Glu Cys Leu
                515                 520                 525

Cys Gly Gln Cys Val Cys His Ser Ser Asp Phe Gly Lys Ile Thr Gly
530                 535                 540

Lys Tyr Cys Glu Cys Asp Asp Phe Ser Cys Val Arg Tyr Lys Gly Glu
545                 550                 555                 560

Met Cys Ser Gly His Gly Gln Cys Ser Cys Gly Asp Cys Leu Cys Asp
                565                 570                 575

Ser Asp Trp Thr Gly Tyr Tyr Cys Asn Cys Thr Thr Arg Thr Asp Thr
                580                 585                 590

Cys Met Ser Ser Asn Gly Leu Leu Cys Ser Gly Arg Gly Lys Cys Glu
                595                 600                 605

Cys Gly Ser Cys Val Cys Ile Gln Pro Gly Ser Tyr Gly Asp Thr Cys
610                 615                 620
```

| | | | | | | | | | | | | |
|---|---|---|---|---|---|---|---|---|---|---|---|---|
| Glu | Lys | Cys | Pro | Thr | Cys | Pro | Asp | Ala | Cys | Thr | Phe | Lys | Lys | Glu | Cys |
| 625 | | | | 630 | | | | 635 | | | | 640 |

| Val | Glu | Cys | Lys | Lys | Phe | Asp | Arg | Gly | Ala | Leu | His | Asp | Glu | Asn | Thr |
|---|---|---|---|---|---|---|---|---|---|---|---|---|---|---|---|
| | | | 645 | | | | | 650 | | | | | 655 | | |

| Cys | Asn | Arg | Tyr | Cys | Arg | Asp | Glu | Ile | Glu | Ser | Val | Lys | Glu | Leu | Lys |
|---|---|---|---|---|---|---|---|---|---|---|---|---|---|---|---|
| | | | 660 | | | | | 665 | | | | | 670 | | |

| Asp | Thr | Gly | Lys | Asp | Ala | Val | Asn | Cys | Thr | Tyr | Lys | Asn | Glu | Asp | Asp |
|---|---|---|---|---|---|---|---|---|---|---|---|---|---|---|---|
| | | 675 | | | | | 680 | | | | | 685 | | | |

| Cys | Val | Arg | Phe | Gln | Tyr | Tyr | Glu | Asp | Ser | Ser | Gly | Lys | Ser | Ile |
|---|---|---|---|---|---|---|---|---|---|---|---|---|---|---|
| | 690 | | | | | 695 | | | | | 700 | | | |

| Leu | Tyr | Val | Val | Glu | Glu | Pro | Glu | Cys | Pro | Lys | Gly | Pro | Asp | Ile | Leu |
|---|---|---|---|---|---|---|---|---|---|---|---|---|---|---|---|
| 705 | | | | | 710 | | | | 715 | | | | | 720 |

| Val | Val | Leu | Leu | Ser | Val | Met | Gly | Ala | Ile | Leu | Leu | Ile | Gly | Leu | Ala |
|---|---|---|---|---|---|---|---|---|---|---|---|---|---|---|---|
| | | | | 725 | | | | 730 | | | | | 735 | | |

| Ala | Leu | Leu | Ile | Trp | Lys | Leu | Leu | Ile | Thr | Ile | His | Asp | Arg | Lys | Glu |
|---|---|---|---|---|---|---|---|---|---|---|---|---|---|---|---|
| | | | 740 | | | | | 745 | | | | 750 | | | |

| Phe | Ala | Lys | Phe | Glu | Glu | Glu | Arg | Ala | Arg | Ala | Lys | Trp | Asp | Thr | Ala |
|---|---|---|---|---|---|---|---|---|---|---|---|---|---|---|---|
| | | 755 | | | | | 760 | | | | | 765 | | | |

| Asn | Asn | Pro | Leu | Tyr | Lys | Glu | Ala | Thr | Ser | Thr | Phe | Thr | Asn | Ile | Thr |
|---|---|---|---|---|---|---|---|---|---|---|---|---|---|---|---|
| 770 | | | | | 775 | | | | | 780 | | | | | |

| Tyr | Arg | Gly | Thr |
|---|---|---|---|
| 785 | | | |

<210> SEQ ID NO 185
<211> LENGTH: 6238
<212> TYPE: DNA
<213> ORGANISM: Homo sapiens

<400> SEQUENCE: 185

```
atggccagag ctttgtgtcc actgcaagcc ctctggcttc tggagtgggt gctgctgctc      60
taccggtctc gaaacacagg tgacgttcgg gagaccgaag acctcaccca cgacgacgag     120
ttgggacctt gtgctgcccc tccagcctgg gccttgaacc tggacccagt gcagctcacc     180
aaccctggaa cacgacgggg aggtcggacc cggaacttgg acctgggtca cgtcgagtgg     240
ttctatgcag gccccaatgg cagccagttt ggattttcac tggacttcca aaggacagc      300
aagatacgtc cggggttacc gtcggtcaaa cctaaaagtg acctgaaggt gttcctgtcg     360
catgggagag tggccatcgt ggtgggcgcc cgcggaccc tggccccag ccaggaggag        420
gtaccctctc accggtagca ccacccgcgg ggcgcctggg accgggtc ggtcctcctc        480
acgggcggcg tgttcctgtg ccctggagg gcgagggcg ccagtgccc ctcgctgctc         540
tgcccgccgc acaaggacac ggggacctcc cggctcccgc cggtcacggg gagcgacgag      600
tttgacctcc gtgatgagac ccgaaatgta ggctcccaaa cttttacaaac cttcaaggcc    660
aaactggagg cactactctg ggctttacat ccgagggttt gaaatgtttg gaagttccgg     720
cgccaaggac tggggcgtc ggtcgtcagc tggagcgacg tcattgtggc ctgcgccccc       780
gcggttcctg acccccgcag ccagcagtcg acctcgctgc agtaacaccg gacgcggggg     840
tggcagcact ggaacgtcct agaaaagact gaggaggctg agaagacgcc cgtaggtagc     900
accgtcgtga ccttgcagga tcttttctga ctcctccgac tcttctgcgg gcatccatcg     960
tgctttttgg ctcagccaga gagcggccgg cgcgccgagt actccccctg tcgcgggaac    1020
acgaaaaacc gagtcggtct ctcgccggcc gcgcggctca tgagggggac agcgcccttg   1080
accctgagcc gcatttacgt ggaaaatgat tttagctggg acaagcgtta ctgtgaagcg   1140
```

```
tgggactcgg cgtaaatgca ccttttacta aaatcgaccc tgttcgcaat gacacttcgc    1200
ggcttcagct ccgtggtcac tcaggccgga gagctggtgc ttggggctcc tggcggctat    1260
ccgaagtcga ggcaccagtg agtccggcct ctcgaccacg aaccccgagg accgccgata    1320
tatttcttag gtctcctggc ccaggctcca gttgcggata ttttctcgag ttaccgccca    1380
ataaagaatc cagaggaccg ggtccgaggt caacgcctat aaaagagctc aatggcgggt    1440
ggcatccttt tgtggcacgt gtcctcccag agcctctcct ttgactccag caacccagag    1500
ccgtaggaaa acaccgtgca caggagggtc tcggagagga aactgaggtc gttgggtctc    1560
tacttcgacg gctactgggg gtactcggtg gccgtgggcg agttcgacgg ggatctcaac    1620
atgaagctgc cgatgacccc catgagccac cggcacccgc tcaagctgcc cctagagttg    1680
actacagaat atgtcgtcgg tgcccccact tggagctgga ccctgggagc ggtggaaatt    1740
tgatgtctta tacagcagcc acgggggtga acctcgacct gggaccctcg ccaccttttaa   1800 ttggattcct actaccagag gctgcatcgg ctgcgcggag agcagatggc gtcgtatttt    1860
aacctaagga tgatggtctc cgacgtagcc gacgcgcctc tcgtctaccg cagcataaaa    1920
gggcattcag tggctgtcac tgacgtcaac ggggatggga ggcatgatct gctggtgggc    1980
cccgtaagtc accgacagtg actgcagttg cccctaccct ccgtactaga cgaccacccg    2040
gctccactgt atatgagag ccgggcagac cgaaaactgg ccgaagtggg gcgtgtgtat    2100
cgaggtgaca tatacctctc ggcccgtctg gcttttgacc ggcttcaccc cgcacacata    2160
ttgttcctgc agccgcgagg cccccacgcg ctgggtgccc ccagcctcct gctgactggc    2220
aacaaggacg tcggcgctcc gggggtgcgc gacccacggg ggtcggagga cgactgaccg    2280
acacagctct atgggcgatt cggctctgcc atcgcacccc tgggcgacct cgaccgggat    2340
tgtgtcgaga taccgctaa gccgagacgg tagcgtgggg accgctgga gctggcccta    2400 ggctacaatg acattgcagt ggctgccccc tacggggtc ccagtggccg gggccaagtg    2460
ccgatgttac tgtaacgtca ccgacggggg atgcccccag ggtcaccggc cccggttcac    2520
ctggtgttcc tgggtcagag tgaggggctg aggtcacgtc cctcccaggt cctggacagc    2580
gaccacaagg acccagtctc actccccgac tccagtgcag ggagggtcca ggacctgtcg    2640
cccttcccca caggctctgc ctttggcttc tcccttcgag gtgccgtaga catcgatgac    2700
gggaaggggt gtccgagacg gaaaccgaag agggaagctc cacggcatct gtagctactg    2760
aacggatacc cagacctgat cgtgggagct tacggggcca accaggtggc tgtgtacaga    2820
ttgcctatgg gtctggacta gcaccctcga atgcccggt tggtccaccg acacatgtct    2880
gctcagccag tggtgaaggc ctctgccagc tactggtgca agattcactg aatcctgctc    2940
gagtcggtca ccacttccgg agacaggtcg atgaccacgt tctaagtgac ttaggacgag    3000
tgaagagctg tgtcctacct cagaccaaga cacccgtgag ctgcttcaac atccagatgc    3060
acttctcgac acaggatgga gtctggttct gtgggcactc gacgaagttg taggtctact    3120
gtgttggagc cactgggcac aacattcctc agaagctatc cctaaatgcc gagctgcaga    3180
cacaacctcg gtgacccgtg ttgtaaggag tcttcgatag ggatttacgg ctcgacgtcc    3240
tggaccggca gaagcccgc cagggccggc gggtgctgct gctgggctct caacaggcag    3300
acctggccgt cttcggggcg gtcccggccg cccacgacga cgacccgaga gttgtccgtg    3360
gcaccaccct gaacctggat ctgggcggaa agcacagccc catctgccac accaccatgc    3420
cgtggtggga cttggaccta gacccgcctt tcgtgtcggg gtagacggtg tggtggtacg    3480
ccttccttcg agatgaggca gacttccggg acaagctgag ccccattgtg ctcagcctcc    3540
```

| | |
|---|---|
| ggaaggaagc tctactccgt ctgaaggccc tgttcgactc ggggtaacac gagtcggaga | 3600 |
| atgtgtccct accgcccacg gaggctggaa tggcccctgc tgtcgtgctg catggagact | 3660 |
| tacacaggga tggcgggtgc ctccgacctt accgggacg acagcacgac gtacctctga | 3720 |
| cccatgtgca ggagcagaca cgaatcgtcc tggactgtgg ggaagatgac gtatgtgtgt | 3780 |
| gggtacacgt cctcgtctgt gcttagcagg acctgacacc ccttctactg catacacacc | 3840 |
| cccagcttca gctcactgcc agcgtgacgg gctccccgct cctagttggg gcagataatg | 3900 |
| gggtcgaagt cgagtgacgg tcgcactgcc cgaggggcga ggatcaaccc cgtctattag | 3960 |
| tcctggagct gcagatggac gcagccaacg agggcgaggg ggcctatgaa gcagagctgc | 4020 |
| aggacctcga cgtctacctg cgtcggttgc tcccgctccc ccggatactt cgtctcgacg | 4080 |
| ccgtgcacct gccccagggc gcccactaca tgcgggccct aagcaatgtc gagggctttc | 4140 |
| ggcacgtgga cggggtcccg cgggtgatgt acgcccggga ttcgttacag ctcccgaaag | 4200 |
| agagactcat ctgtaatcag aagaaggaga atgagaccag ggtggtgctg tgtgagctgc | 4260 |
| tctctgagta gacattagtc ttcttcctct tactctggtc ccaccacgac acactcgacg | 4320 |
| gcaaccccat gaagaagaac gcccagatag gaatcgcgat gttggtgagc gtggggaatc | 4380 |
| cgttggggta cttcttcttg cgggtctatc cttagcgcta caaccactcg cacccttac | 4440 |
| tggaagaggc tggggagtct gtgtccttcc agctgcagat acggagcaag aacagccagg | 4500 |
| accttctccg accctcaga cacaggaagg tcgacgtcta tgcctcgttc ttgtcggtca | 4560 |
| atccaaacag caagattgtg ctgctggacg tgccggtccg ggcagaggcc caagtggagt | 4620 |
| taggtttgtc gttctaacac gacgacctgc acggccaggc ccgtctccgg gttcacctcc | 4680 |
| tgcgagggaa ctcctttcca gcctccctgg tggtggcagc agaagaaggt gagagggagg | 4740 |
| acgctcccctt gaggaaaggt cggagggacc accaccgtcg tcttcttcca ctctccctcc | 4800 |
| agaacagctt ggacagctgg ggacccaaag tggagcacac ctatgagctc cacaacaatg | 4860 |
| tcttgtcgaa cctgtcgacc cctgggtttc acctcgtgtg gatactcgag gtgttgttag | 4920 |
| gccctgggac tgtgaatggt cttcacctca gcatccacct tccggacag tcccagcccc | 4980 |
| cgggaccctg acacttacca gaagtggagt cgtaggtgga aggccctgtc agggtcgggt | 5040 |
| ccgacctgct ctacatcctg gatatacagc cccagggggg ccttcagtgc ttcccacaga | 5100 |
| ggctggacga gatgtaggac ctatatgtcg gggtccccc ggaagtcacg aagggtgtcc | 5160 |
| ctcctgtcaa ccctctcaag gtggactggg ggctgcccat ccccagcccc tcccccattg | 5220 |
| gaggacagtt gggagagttc cacctgaccc ccgacgggta ggggtcgggg aggggtaac | 5280 |
| acccggccca tcacaagcgg gatcgcagac agatcttcct gccagagccc gagcagcccg | 5340 |
| tgggccgggt agtgttcgcc ctagcgtctg tctagaagga cggtctcggg ctcgtcgggt | 5400 |
| cgaggcttca ggatccagtt ctcgtaagct gcgactcggc gccctgtact gtggtgcaga | 5460 |
| gctccgaagt cctaggtcaa gagcattcga cgctgagccg cggacatga caccacgtct | 5520 |
| gtgacctgca ggagatggcg cgcgggcagc gggccatggt cacggtgctg gccttcctga | 5580 |
| cactggacgt cctctaccgc gcgcccgtcg cccggtacca gtgccacgac cggaaggact | 5640 |
| ggctgcccag cctctaccag aggcctctgg atcagtttgt gctgcagtcg cacgcatgga | 5700 |
| ccgacgggtc ggagatggtc tccggagacc tagtcaaaca cgacgtcagc gtgcgtacct | 5760 |
| tcaacgtgtc ctcctccc tatgcggtgc cccgctcag cctgcccga ggggaagcta | 5820 |
| agttgcacag gagggagggg atacgccacg ggggcgagtc ggacgggctc cccttcgaca | 5880 |

```
ggtgtggaca cagctgctcc gggccttgga ggagagggcc attccaatct ggtgggtggt      5940
ccacacctgt gtcgacgagg cccggaacct cctctcccgg taaggttaga ccacccacct      6000
ggtgggtgtg ctgggtggcc tgctgctgct caccatcctg gtcctggcca tgtggaagga      6060
ccacccacac gacccaccgg acgacgacga gtggtaggac caggaccggt acaccttcgt      6120
cggcttcttc aagcggaacc ggccacccct ggaagaagat gatgaagagg gggagtgaca      6180
gccgaagaag ttcgccttgg ccggtgggga ccttcttcta ctacttctcc ccctcact       6238

<210> SEQ ID NO 186
<211> LENGTH: 4734
<212> TYPE: DNA
<213> ORGANISM: Homo sapiens

<400> SEQUENCE: 186
atgcgagcgc gcccgcggcc ccggccgctc tgggcgactg tgctggcgct ggggggcgctg       60 tacgctcgcg cgggcgccgg ggccggcgag acccgctgac acgaccgcga ccccgcgac       120 gcgggcgttg gcgtaggagg gcccaacatc tgtaccacgc gaggtgtgag ctcctgccag      180
cgcccgcaac cgcatcctcc cgggttgtag acatggtgcg ctccacactc gaggacggtc      240
cagtgcctgg ctgtgagccc catgtgtgcc tggtgctctg atgaggccct gcctctgggc      300
gtcacggacc gacactcggg gtacacacgg accacgagac tactccggga cggagacccg      360
tcacctcgct gtgacctgaa ggagaatctg ctgaaggata actgtgcccc agaatccatc      420
agtggagcga cactggactt cctcttagac gacttcctat tgacacgggg tcttaggtag      480
gagttcccag tgagtgaggc ccgagtacta aggacaggc ccctcagcga caagggctct      540
ctcaagggtc actcactccg ggctcatgat ctcctgtccg gggagtcgct gttcccgaga      600
ggagacagct cccaggtcac tcaagtcagt ccccagagga ttgcactccg gctccggcca      660
cctctgtcga gggtccagtg agttcagtca ggggtctcct aacgtgaggc cgaggccggt      720
gatgattcga agaatttctc catccaagtg cggcaggtgg aggattaccc tgtggacatc      780
ctactaagct tcttaaagag gtaggttcac gccgtccacc tcctaatggg acacctgtag      840
tactacttga tggacctgtc ttactccatg aaggatgatc tgtggagcat ccagaacctg      900
atgatgaact acctggacag aatgaggtac ttcctactag acacctcgta ggtcttggac      960
ggtaccaagc tggccaccca gatgcgaaag ctcaccagta acctgcggat tggcttcggg     1020
ccatggttcg accggtgggt ctacgctttc gagtggtcat tggacgccta accgaagccc     1080
gcatttgtgg acaagcctgt gtcaccatac atgtatatct ccccaccaga ggccctcgaa     1140
cgtaaacacc tgttcggaca cagtggtatg tacatataga ggggtggtct ccgggagctt     1200 aaccctgct atgatatgaa gaccacctgc ttgcccatgt ttggctacaa acacgtgctg      1260
ttggggacga tactatactt ctggtggacg aacgggtaca aaccgatgtt tgtgcacgac     1320
acgctaactg accaggtgac ccgcttcaat gaggaagtga agaagcagag tgtgtcacgg     1380
tgcgattgac tggtccactg ggcgaagtta ctccttcact tcttcgtctc acacagtgcc     1440
aaccgagatg ccccagaggg tggctttgat gccatcatgc aggctacagt ctgtgatgaa     1500
ttggctctac ggggtctccc accgaaaacta cggtagtacg tccgatgtca gacactactt     1560
aagattggct ggaggaatga tgcatcccac ttgctggtgt ttaccactga tgccaagact     1620
ttctaaccga cctccttact acgtagggtg aacgaccaca aatggtgact acggttctga     1680
catatagcat tggacggaag gctggcaggc attgtccagc ctaatgacgg gcagtgtcat     1740
gtatatcgta acctgccttc cgaccgtccg taacaggtcg gattactgcc cgtcacagta     1800
```

```
gttggtagtg acaatcatta ctctgcctcc actaccatgg attatccctc tttggggctg    1860
caaccatcac tgttagtaat gagacggagg tgatggtacc taataggag aaaccccgac     1920
atgactgaga agctatccca gaaaaacatc aatttgatct ttgcagtgac tgaaaatgta    1980
tactgactct tcgataggt cttttttgtag ttaaactaga aacgtcactg acttttacat    2040
gtcaatctct atcagaacta tagtgagctc atcccaggga ccacagttgg ggttctgtcc    2100
cagttagaga tagtcttgat atcactcgag tagggtccct ggtgtcaacc caagacagg     2160
atggattcca gcaatgtcct ccagctcatt gttgatgctt atgggaaaat ccgttctaaa    2220
tacctaaggt cgttacagga ggtcgagtaa caactacgaa tacccttta ggcaagattt     2280
gtagagctgg aagtgcgtga cctccctgaa gagttgtctc tatccttcaa tgccacctgc    2340
catctcgacc ttcacgcact ggagggactt ctcaacagag ataggaagtt acggtggacg    2400
ctcaacaatg aggtcatccc tggcctcaag tcttgtatgg gactcaagat tggagacacg    2460
gagttgttac tccagtaggg accggagttc agaacatacc ctgagttcta acctctgtgc    2520
gtgagcttca gcattgaggc caaggtgcga ggctgtcccc aggagaagga gaagtccttt    2580
cactcgaagt cgtaactccg gttccacgct ccgacagggg tcctcttcct cttcaggaaa    2640
accataaagc ccgtgggctt caaggacagc ctgatcgtcc aggtcacctt tgattgtgac    2700
tggtatttcg ggcacccgaa gttcctgtcg gactagcagg tccagtggaa actaacactg    2760
tgtgcctgcc aggcccaagc tgaacctaat agccatcgct gcaacaatgg caatgggacc    2820
acacggacgg tccggggttcg acttggatta tcggtagcga cgttgttacc gttaccctgg   2880
tttgagtgtg gggtatgccg ttgtgggcct ggctggctgg gatcccagtg tgagtgctca    2940
aaactcacac cccatacggc aacacccgga ccgaccgacc ctagggtcac actcacgagt    3000
gaggaggact atcgcccttc ccagcaggac gaatgcagcc cccgggaggg tcagcccgtc    3060
ctcctcctga tagcgggaag ggtcgtcctg cttacgtcgg ggggccctccc agtcgggcag   3120
tgcagccagc ggggcgagtg cctctgtggt caatgtgtct gccacagcag tgactttggc    3180
acgtcggtcg ccccgctcac ggagacacca gttacacaga cggtgtcgtc actgaaaccg    3240
aagatcacgg gcaagtactg cgagtgtgac gacttctcct gtgtccgcta caaggggag    3300
ttctagtgcc cgttcatgac gctcacactg ctgaagagga cacaggcgat gttccccctc    3360
atgtgctcag gccatggcca gtgcagctgt ggggactgcc tgtgtgactc cgactggacc    3420
tacacgagtc cggtaccggt cacgtcgaca cccctgacgg acacactgag gctgacctgg    3480
ggctactact gcaactgtac cacgcgtact gacacctgca tgtccagcaa tgggctgctg    3540
ccgatgatga cgttgacatg gtgcgcatga ctgtggacgt acaggtcgtt acccgacgac    3600
tgcagcggcc ggggcaagtg tgaatgtggc agctgtgtct gtatccagcc gggctcctat    3660
acgtcgccgg ccccgttcac acttacaccg tcgacacaga cataggtcgg cccgaggata    3720
ggggacacct gtgagaagtg ccccacctgc ccagatgcct gcacctttaa gaaagaatgt    3780
cccctgtgga cactcttcac ggggtggacg ggtctacgga cgtggaaatt ctttcttaca    3840
gtggagtgta agaagtttga ccggggagcc ctacatgacg aaaatacctg caaccgttac    3900
cacctcacat tcttcaaact ggcccctcgg gatgtactgc tttatggac gttggcaatg    3960
tgccgtgacg agattgagtc agtgaaagag cttaaggaca ctggcaagga tgcagtgaat    4020
acggcactgc tctaactcag tcactttctc gaattcctgt gaccgttcct acgtcactta    4080
tgtacctata agaatgagga tgactgtgtc gtcagattcc agtactatga agattctagt    4140
```

```
acatggatat tcttactcct actgacacag cagtctaagg tcatgatact tctaagatca    4200
ggaaagtcca tcctgtatgt ggtagaagag ccagagtgtc ccaagggccc tgacatcctg    4260
cctttcaggt aggacataca ccatcttctc ggtctcacag ggttcccggg actgtaggac    4320
gtggtcctgc tctcagtgat gggggccatt ctgctcattg ccttgccgc cctgctcatc     4380 caccaggacg agagtcacta cccccggtaa gacgagtaac cggaacggcg ggacgagtag    4440
tggaaactcc tcatcaccat ccacgaccga aaagagttcg ctaaatttga ggaagaacgc    4500
acctttgagg agtagtggta ggtgctggct tttctcaagc gatttaaact ccttcttgcg    4560
gccagagcaa aatgggacac agccaacaac ccactgtata aagaggccac gtctaccttc    4620
cggtctcgtt ttaccctgtg tcggttgttg ggtgacatat ttctccggtg cagatggaag    4680
accaatatca cgtaccgggg cacttaatgg ttatagtgca tggccccgtg aatt          4734
```

<210> SEQ ID NO 187
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH-CDR2
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (13)..(13)
<223> OTHER INFORMATION: Any amino acid
<220> FEATURE:
<223> OTHER INFORMATION: See specification as filed for detailed
      description of substitutions and preferred embodiments

<400> SEQUENCE: 187

Glu Ile Leu Pro Gly Xaa Gly Xaa Thr Lys Tyr Asn Xaa Lys Phe Lys
1               5                   10                  15

Gly

<210> SEQ ID NO 188
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 170-loop of trypsin

<400> SEQUENCE: 188

Glu Ala Ser Tyr Pro Gly Lys
1               5

<210> SEQ ID NO 189
<211> LENGTH: 800
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE

```
<222> LOCATION: (1)..(300)
<223> OTHER INFORMATION: This region may encompass 1-100 "Gly Gly Ser"
      repeating units
<220> FEATURE:
<221> NAME/KEY: MISC_FEATURE
<222> LOCATION: (301)..(800)
<223> OTHER INFORMATION: This region may encompass 1-100 "Gly Gly Gly
      Gly Ser" repeating units

<400> SEQUENCE: 189
```

Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser Gly Gly Ser Gly Gly
            20                  25                  30

Ser Gly Gly Ser Gly Gly Ser Gly Gly Ser Gly Gly Ser Gly Gly Ser
        35                  40                  45

Gly Gly Ser Gly Gly Ser Gly Gly Ser Gly Gly Ser Gly Gly Ser Gly
        50                  55                  60

Gly Ser Gly Gly Ser Gly Gly Ser Gly Gly Ser Gly Gly Ser Gly Gly
65                  70                  75                  80

Ser Gly Gly Ser Gly Gly Ser Gly Gly Ser Gly Gly Ser Gly Gly Ser
            85                  90                  95

Gly Gly Ser Gly Gly Ser Gly Gly Ser Gly Gly Ser Gly Gly Ser Gly
            100                 105                 110

Gly Ser Gly Gly Ser Gly Gly Ser Gly Gly Ser Gly Gly Ser Gly Gly
            115                 120                 125

Ser Gly Gly Ser Gly Gly Ser Gly Gly Ser Gly Gly Ser Gly Gly Ser
    130                 135                 140

Gly Gly Ser Gly Gly Ser Gly Gly Ser Gly Gly Ser Gly Gly Ser Gly
145                 150                 155                 160

Gly Ser Gly Gly Ser Gly Gly Ser Gly Gly Ser Gly Gly Ser Gly Gly
            165                 170                 175

Ser Gly Gly Ser Gly Gly Ser Gly Gly Ser Gly Gly Ser Gly Gly Ser
            180                 185                 190

Gly Gly Ser Gly Gly Ser Gly Gly Ser Gly Gly Ser Gly Gly Ser Gly
            195                 200                 205

Gly Ser Gly Gly Ser Gly Gly Ser Gly Gly Ser Gly Gly Ser Gly Gly
        210                 215                 220

Ser Gly Gly Ser Gly Gly Ser Gly Gly Ser Gly Gly Ser Gly Gly Ser
225                 230                 235                 240

Gly Gly Ser Gly Gly Ser Gly Gly Ser Gly Gly Ser Gly Gly Ser Gly
            245                 250                 255

Gly Ser Gly Gly Ser Gly Gly Ser Gly Gly Ser Gly Gly Ser Gly Gly
            260                 265                 270

Ser Gly Gly Ser Gly Gly Ser Gly Gly Ser Gly Gly Ser Gly Gly Ser
        275                 280                 285

Gly Gly Ser Gly Gly Ser Gly Gly Ser Gly Gly Ser Gly Gly Gly Gly
            290                 295                 300

Ser Gly Gly Gly Gly Ser Gly Gly Gly Gly Ser Gly Gly Gly Gly Ser
305                 310                 315                 320

Gly Gly Gly Gly Ser Gly Gly Gly Gly Ser Gly Gly Gly Gly Ser Gly
            325                 330                 335

Gly Gly Gly Ser Gly Gly Gly Gly Ser Gly Gly Gly Gly Ser Gly Gly
            340                 345                 350

Gly Gly Ser Gly Gly Gly Gly Ser Gly Gly Gly Gly Ser Gly Gly Gly
            355                 360                 365

Gly Ser Gly Gly Gly Ser Gly Gly Gly Ser Gly Gly Gly
    370             375             380

Ser Gly Gly Gly Gly Ser Gly Gly Gly Ser Gly Gly Gly Ser
385             390             395             400

Gly Gly Gly Gly Ser Gly Gly Gly Ser Gly Gly Gly Ser Gly
            405             410             415

Gly Gly Gly Ser Gly Gly Gly Ser Gly Gly Gly Ser Gly Gly
            420             425             430

Gly Gly Ser Gly Gly Gly Ser Gly Gly Gly Ser Gly Gly Gly
        435             440             445

Gly Ser Gly Gly Gly Ser Gly Gly Gly Ser Gly Gly Gly Gly
    450             455             460

Ser Gly Gly Gly Ser Gly Gly Gly Ser Gly Gly Gly Ser
465             470             475             480

Gly Gly Gly Gly Ser Gly Gly Gly Ser Gly Gly Gly Ser Gly
            485             490             495

Gly Gly Gly Ser Gly Gly Gly Ser Gly Gly Gly Ser Gly Gly
            500             505             510

Gly Gly Ser Gly Gly Gly Ser Gly Gly Gly Ser Gly Gly Gly
        515             520             525

Gly Ser Gly Gly Gly Ser Gly Gly Gly Ser Gly Gly Gly Gly
    530             535             540

Ser Gly Gly Gly Ser Gly Gly Gly Ser Gly Gly Gly Ser
545             550             555             560

Gly Gly Gly Gly Ser Gly Gly Gly Ser Gly Gly Gly Ser Gly
            565             570             575

Gly Gly Gly Ser Gly Gly Gly Ser Gly Gly Gly Ser Gly Gly
            580             585             590

Gly Gly Ser Gly Gly Gly Ser Gly Gly Gly Ser Gly Gly Gly
        595             600             605

Gly Ser Gly Gly Gly Ser Gly Gly Gly Ser Gly Gly Gly Gly
    610             615             620

Ser Gly Gly Gly Ser Gly Gly Gly Ser Gly Gly Gly Ser
625             630             635             640

Gly Gly Gly Gly Ser Gly Gly Gly Ser Gly Gly Gly Ser Gly
            645             650             655

Gly Gly Gly Ser Gly Gly Gly Ser Gly Gly Gly Ser Gly Gly
            660             665             670

Gly Gly Ser Gly Gly Gly Ser Gly Gly Gly Ser Gly Gly Gly
        675             680             685

Gly Ser Gly Gly Gly Ser Gly Gly Gly Ser Gly Gly Gly Gly
    690             695             700

Ser Gly Gly Gly Ser Gly Gly Gly Ser Gly Gly Gly Ser
705             710             715             720

Gly Gly Gly Gly Ser Gly Gly Gly Ser Gly Gly Gly Ser Gly
            725             730             735

Gly Gly Gly Ser Gly Gly Gly Ser Gly Gly Gly Ser Gly Gly
            740             745             750

Gly Gly Ser Gly Gly Gly Ser Gly Gly Gly Ser Gly Gly Gly
        755             760             765

Gly Ser Gly Gly Gly Gly Ser Gly Gly Gly Gly Ser Gly Gly Gly Gly
    770             775             780

Ser Gly Gly Gly Gly Ser Gly Gly Gly Ser Gly Gly Gly Ser
785                 790                 795                 800

<210> SEQ ID NO 190
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Linker

<400> SEQUENCE: 190

Ser Gly Gly Ser Gly Gly Ser
1               5

<210> SEQ ID NO 191
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Linker

<400> SEQUENCE: 191

Gly Gly Ser Gly Gly Ser Gly Gly Ser Gly Gly Ser Gly Gly Gly
1               5                   10                  15

<210> SEQ ID NO 192
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Linker

<400> SEQUENCE: 192

Gly Gly Ser Gly Gly Ser Gly Gly Gly Gly Ser Gly Gly Gly Gly Ser
1               5                   10                  15

<210> SEQ ID NO 193
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Linker

<400> SEQUENCE: 193

Gly Gly Ser Gly Gly Ser Gly Gly Ser Gly Gly Ser Gly Gly Ser Gly
1               5                   10                  15

Gly Ser

<210> SEQ ID NO 194
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Linker

<400> SEQUENCE: 194

Gly Gly Gly Gly Ser Gly Gly Gly Gly Ser Gly Gly Gly Gly Ser
1               5                   10                  15

<210> SEQ ID NO 195
<211> LENGTH: 500
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Gly/Ser peptide linker
<220> FEATURE:
<221> NAME/KEY: MISC_FEATURE
<222> LOCATION: (1)..(500)
<223> OTHER INFORMATION: This sequence may encompass 1-100 'Gly Gly Gly
      Gly Ser' repeating units
<220> FEATURE:
<223> OTHER INFORMATION: See specification as filed for detailed
      description of substitutions and preferred embodiments

<400> SEQUENCE: 195

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser Gly Gly Gly Gly
    50                  55                  60

Ser Gly Gly Gly Gly Ser Gly Gly Gly Gly Ser Gly Gly Gly Gly Ser
65                  70                  75                  80

Gly Gly Gly Gly Ser Gly Gly Gly Gly Ser Gly Gly Gly Gly Ser Gly
                85                  90                  95

Gly Gly Gly Ser Gly Gly Gly Gly Ser Gly Gly Gly Gly Ser Gly Gly
            100                 105                 110

Gly Gly Ser Gly Gly Gly Gly Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Gly Gly Gly Gly Ser Gly Gly Gly Gly Ser
145                 150                 155                 160

Gly Gly Gly Gly Ser Gly Gly Gly Gly Ser Gly Gly Gly Gly Ser Gly
                165                 170                 175

Gly Gly Gly Ser Gly Gly Gly Gly Ser Gly Gly Gly Gly Ser Gly Gly
            180                 185                 190

Gly Gly Ser Gly Gly Gly Gly Ser Gly Gly Gly Gly Ser Gly Gly Gly
        195                 200                 205

Gly Ser Gly Gly Gly Gly Ser Gly Gly Gly Gly Ser Gly Gly Gly Gly
    210                 215                 220

Ser Gly Gly Gly Gly Ser Gly Gly Gly Gly Ser Gly Gly Gly Gly Ser
225                 230                 235                 240

Gly Gly Gly Gly Ser Gly Gly Gly Gly Ser Gly Gly Gly Gly Ser Gly
                245                 250                 255

Gly Gly Gly Ser Gly Gly Gly Gly Ser Gly Gly Gly Gly Ser Gly Gly
            260                 265                 270

Gly Gly Ser Gly Gly Gly Gly Ser Gly Gly Gly Gly Ser Gly Gly Gly

```
                275                 280                 285
Gly Ser Gly Gly Gly Ser Gly Gly Gly Ser Gly Gly Gly Gly
    290                 295                 300
Ser Gly Gly Gly Gly Ser Gly Gly Gly Ser Gly Gly Gly Ser
305                 310                 315                 320
Gly Gly Gly Gly Ser Gly Gly Gly Ser Gly Gly Gly Ser Gly
                325                 330                 335
Gly Gly Gly Ser Gly Gly Gly Ser Gly Gly Gly Ser Gly Gly
            340                 345                 350
Gly Gly Ser Gly Gly Gly Ser Gly Gly Gly Ser Gly Gly Gly
        355                 360                 365
Gly Ser Gly Gly Gly Ser Gly Gly Gly Ser Gly Gly Gly Gly
    370                 375                 380
Ser Gly Gly Gly Gly Ser Gly Gly Gly Ser Gly Gly Gly Ser
385                 390                 395                 400
Gly Gly Gly Gly Ser Gly Gly Gly Ser Gly Gly Gly Ser Gly
                405                 410                 415
Gly Gly Gly Ser Gly Gly Gly Ser Gly Gly Gly Ser Gly Gly
            420                 425                 430
Gly Gly Ser Gly Gly Gly Ser Gly Gly Gly Ser Gly Gly Gly
        435                 440                 445
Gly Ser Gly Gly Gly Ser Gly Gly Gly Ser Gly Gly Gly Gly
    450                 455                 460
Ser Gly Gly Gly Ser Gly Gly Gly Ser Gly Gly Gly Gly Ser
465                 470                 475                 480
Gly Gly Gly Gly Ser Gly Gly Gly Ser Gly Gly Gly Ser Gly
                485                 490                 495
Gly Gly Gly Ser
            500
```

```
<210> SEQ ID NO 196
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Gly/Ser peptide linker

<400> SEQUENCE: 196

Gly Gly Gly Gly Ser
1               5

<210> SEQ ID NO 197
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Gly/Ser peptide linker

<400> SEQUENCE: 197

Gly Gly Gly Gly Ser Gly Gly Gly Gly Ser
1               5                   10

<210> SEQ ID NO 198
<211> LENGTH: 15
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Gly/Ser peptide linker

<400> SEQUENCE: 198

Gly Gly Gly Gly Ser Gly Gly Gly Gly Ser Gly Gly Gly Gly Ser
1               5                   10                  15

<210> SEQ ID NO 199
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Gly/Ser peptide linker

<400> SEQUENCE: 199

Gly Gly Gly Gly Ser Gly Gly Gly Gly Ser Gly Gly Gly Gly Ser Gly
1               5                   10                  15

Gly Gly Gly Ser
            20

<210> SEQ ID NO 200
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Gly/Ser peptide linker

<400> SEQUENCE: 200

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 201
<211> LENGTH: 501
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Gly/Ser peptide linker
<220> FEATURE:
<221> NAME/KEY: MISC_FEATURE
<222> LOCATION: (2)..(501)
<223> OTHER INFORMATION: This region may encompass 1-100 'Gly Gly Gly
      Gly Ser' repeating units
<220> FEATURE:
<223> OTHER INFORMATION: See specification as filed for detailed
      description of substitutions and preferred embodiments

<400> SEQUENCE: 201

Ser Gly Gly Gly Gly Ser Gly Gly Gly Gly Ser Gly Gly Gly Gly Ser
1               5                   10                  15

Gly Gly Gly Gly Ser Gly Gly Gly Gly Ser Gly Gly Gly Gly Ser Gly
            20                  25                  30

Gly Gly Gly Ser Gly Gly Gly Gly Ser Gly Gly Gly Gly Ser Gly Gly
```

```
              35                  40                  45
Gly Gly Ser Gly Gly Gly Ser Gly Gly Gly Ser Gly Gly Gly
    50                  55                  60

Gly Ser Gly Gly Gly Ser Gly Gly Gly Ser Gly Gly Gly Gly
65                  70                  75                  80

Ser Gly Gly Gly Gly Ser Gly Gly Gly Ser Gly Gly Gly Ser
                85                  90                  95

Gly Gly Gly Gly Ser Gly Gly Gly Ser Gly Gly Gly Ser Gly
            100                 105                 110

Gly Gly Gly Ser Gly Gly Gly Ser Gly Gly Gly Ser Gly Gly
            115                 120                 125

Gly Gly Ser Gly Gly Gly Ser Gly Gly Gly Ser Gly Gly Gly
            130                 135                 140

Gly Ser Gly Gly Gly Ser Gly Gly Gly Ser Gly Gly Gly Gly
145                 150                 155                 160

Ser Gly Gly Gly Ser Gly Gly Gly Ser Gly Gly Gly Gly Ser
                165                 170                 175

Gly Gly Gly Ser Gly Gly Gly Ser Gly Gly Gly Ser Gly Gly
            180                 185                 190

Gly Gly Ser Gly Gly Gly Ser Gly Gly Gly Ser Gly Gly Gly
            195                 200                 205

Gly Gly Ser Gly Gly Gly Ser Gly Gly Gly Ser Gly Gly Gly
            210                 215                 220

Gly Ser Gly Gly Gly Ser Gly Gly Gly Ser Gly Gly Gly Gly
225                 230                 235                 240

Ser Gly Gly Gly Ser Gly Gly Gly Ser Gly Gly Gly Gly Ser
                245                 250                 255

Gly Gly Gly Ser Gly Gly Gly Ser Gly Gly Gly Ser Gly Gly
            260                 265                 270

Gly Gly Ser Gly Gly Gly Ser Gly Gly Gly Ser Gly Gly Gly
            275                 280                 285

Gly Gly Ser Gly Gly Gly Ser Gly Gly Gly Ser Gly Gly Gly
            290                 295                 300

Gly Ser Gly Gly Gly Ser Gly Gly Gly Ser Gly Gly Gly Gly
305                 310                 315                 320

Ser Gly Gly Gly Ser Gly Gly Gly Ser Gly Gly Gly Gly Ser
                325                 330                 335

Gly Gly Gly Ser Gly Gly Gly Ser Gly Gly Gly Ser Gly Gly
            340                 345                 350

Gly Gly Ser Gly Gly Gly Ser Gly Gly Gly Ser Gly Gly Gly
            355                 360                 365

Gly Gly Ser Gly Gly Gly Ser Gly Gly Gly Ser Gly Gly Gly
            370                 375                 380

Gly Ser Gly Gly Gly Ser Gly Gly Gly Ser Gly Gly Gly Gly
385                 390                 395                 400

Ser Gly Gly Gly Ser Gly Gly Gly Ser Gly Gly Gly Gly Ser
                405                 410                 415

Gly Gly Gly Ser Gly Gly Gly Ser Gly Gly Gly Ser Gly Gly
            420                 425                 430

Gly Gly Ser Gly Gly Gly Ser Gly Gly Gly Ser Gly Gly Gly
            435                 440                 445

Gly Gly Ser Gly Gly Gly Ser Gly Gly Gly Ser Gly Gly Gly
            450                 455                 460
```

```
Gly Ser Gly Gly Gly Gly Ser Gly Gly Gly Gly Ser Gly Gly Gly Gly
465                 470                 475                 480

Ser Gly Gly Gly Gly Ser Gly Gly Gly Gly Ser Gly Gly Gly Gly Ser
                485                 490                 495

Gly Gly Gly Gly Ser
            500

<210> SEQ ID NO 202
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Gly/Ser peptide linker

<400> SEQUENCE: 202

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 203
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Gly/Ser peptide linker

<400> SEQUENCE: 203

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser
        35

<210> SEQ ID NO 204
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Gly/Ser peptide linker

<400> SEQUENCE: 204

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser
        35                  40

<210> SEQ ID NO 205
<211> LENGTH: 45
<212> TYPE: PRT
<213> ORGANISM: Artificial Sequence
<220> FEATURE:
```

<223> OTHER INFORMATION: Description of Artificial Sequence: Synthetic
      polypeptide
<220> FEATURE:
<223> OTHER INFORMATION: Gly/Ser peptide linker

<400> SEQUENCE: 205

Gly Gly Gly Gly Ser Gly Gly Gly Ser Gly Gly Gly Gly Ser Gly
1               5                   10                  15
Gly Gly Gly Ser Gly Gly Gly Gly Ser Gly Gly Gly Gly Ser Gly Gly
            20                  25                  30
Gly Gly Ser Gly Gly Gly Gly Ser Gly Gly Gly Gly Ser
        35                  40                  45

<210> SEQ ID NO 206
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Gly/Ser peptide linker

<400> SEQUENCE: 206

Gly Gly Gly Gly Ser Gly Gly Gly Gly Ser Gly Gly Gly Gly Ser Gly
1               5                   10                  15
Gly Gly Gly Ser Gly Gly Gly Gly Ser Gly Gly Gly Gly Ser Gly Gly
            20                  25                  30
Gly Gly Ser Gly Gly Gly Gly Ser Gly Gly Gly Gly Ser Gly Gly Gly
        35                  40                  45
Gly Ser
    50

<210> SEQ ID NO 207
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Gly/Ser peptide linker

<400> SEQUENCE: 207

Ser Gly Gly Gly Gly Ser
1               5

<210> SEQ ID NO 208
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Gly/Ser peptide linker

<400> SEQUENCE: 208

Ser Gly Gly Gly Gly Ser Gly Gly Gly Gly Ser
1               5                   10

<210> SEQ ID NO 209
<211> LENGTH: 16
<212> TYPE: PRT
<213> ORGANISM: Artificial Sequence
<220> FEATURE:

<223> OTHER INFORMATION: Description of Artificial Sequence: Synthetic
      peptide
<220> FEATURE:
<223> OTHER INFORMATION: Gly/Ser peptide linker

<400> SEQUENCE: 209

Ser Gly Gly Gly Gly Ser Gly Gly Gly Gly Ser Gly Gly Gly Gly Ser
1               5                   10                  15

<210> SEQ ID NO 210
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Gly/Ser peptide linker

<400> SEQUENCE: 210

Ser Gly Gly Gly Gly Ser Gly Gly Gly Gly Ser Gly Gly Gly Gly Ser
1               5                   10                  15

Gly Gly Gly Gly Ser
            20

<210> SEQ ID NO 211
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Gly/Ser peptide linker

<400> SEQUENCE: 211

Ser Gly Gly Gly Gly Ser Gly Gly Gly Gly Ser Gly Gly Gly Gly Ser
1               5                   10                  15

Gly Gly Gly Gly Ser Gly Gly Gly Gly Ser
            20                  25

<210> SEQ ID NO 212
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Gly/Ser peptide linker

<400> SEQUENCE: 212

Ser Gly Gly Gly Gly Ser Gly Gly Gly Gly Ser Gly Gly Gly Gly Ser
1               5                   10                  15

Gly Gly Gly Gly Ser Gly Gly Gly Gly Ser Gly Gly Gly Gly Ser
            20                  25                  30

<210> SEQ ID NO 213
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Gly/Ser peptide linker

<400> SEQUENCE: 213

```
Ser Gly Gly Gly Gly Ser Gly Gly Gly Ser Gly Gly Gly Ser
1               5                  10                  15

Gly Gly Gly Gly Ser Gly Gly Gly Gly Ser Gly Gly Gly Ser Gly
            20                  25                  30

Gly Gly Gly Ser
        35
```

<210> SEQ ID NO 214
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Gly/Ser peptide linker

<400> SEQUENCE: 214

```
Ser Gly Gly Gly Gly Ser Gly Gly Gly Ser Gly Gly Gly Gly Ser
1               5                  10                  15

Gly Gly Gly Gly Ser Gly Gly Gly Gly Ser Gly Gly Gly Ser Gly
            20                  25                  30

Gly Gly Gly Ser Gly Gly Gly Gly Ser
        35                  40
```

<210> SEQ ID NO 215
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Gly/Ser peptide linker

<400> SEQUENCE: 215

```
Ser Gly Gly Gly Gly Ser Gly Gly Gly Gly Ser Gly Gly Gly Gly Ser
1               5                  10                  15

Gly Gly Gly Gly Ser Gly Gly Gly Gly Ser Gly Gly Gly Gly Ser Gly
            20                  25                  30

Gly Gly Gly Ser Gly Gly Gly Gly Ser Gly Gly Gly Gly Ser
        35                  40                  45
```

<210> SEQ ID NO 216
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Gly/Ser peptide linker

<400> SEQUENCE: 216

```
Ser Gly Gly Gly Gly Ser Gly Gly Gly Gly Ser Gly Gly Gly Gly Ser
1               5                  10                  15

Gly Gly Gly Gly Ser Gly Gly Gly Gly Ser Gly Gly Gly Gly Ser Gly
            20                  25                  30

Gly Gly Gly Ser Gly Gly Gly Gly Ser Gly Gly Gly Gly Ser Gly Gly
        35                  40                  45

Gly Gly Ser
        50
```

```
<210> SEQ ID NO 217
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: FXIa cleavage site

<400> SEQUENCE: 217

Lys Leu Thr Arg
1

<210> SEQ ID NO 218
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: FXIa cleavage site

<400> SEQUENCE: 218

Asp Phe Thr Arg
1

<210> SEQ ID NO 219
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: FXIa cleavage site

<400> SEQUENCE: 219

Thr Gln Ser Phe Asn Asp Phe Thr Arg
1               5

<210> SEQ ID NO 220
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: FXIa cleavage site

<400> SEQUENCE: 220

Ser Val Ser Gln Thr Ser Lys Leu Thr Arg
1               5                   10

<210> SEQ ID NO 221
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Thrombin cleavage site

<400> SEQUENCE: 221

Asp Phe Leu Ala Glu Gly Gly Gly Val Arg
1               5                   10
```

<210> SEQ ID NO 222
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Thrombin cleavage site

<400> SEQUENCE: 222

Thr Thr Lys Ile Lys Pro Arg
1               5

<210> SEQ ID NO 223
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Thrombin cleavage site

<400> SEQUENCE: 223

Leu Val Pro Arg Gly
1               5

<210> SEQ ID NO 224
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Thrombin cleavage site

<400> SEQUENCE: 224

Ala Leu Arg Pro Arg
1               5

<210> SEQ ID NO 225
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: ADP and PAR1 platelet receptor agonist peptide

<400> SEQUENCE: 225

Ser Phe Leu Leu Arg Asn
1               5

<210> SEQ ID NO 226
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES

```
<222> LOCATION: (4)..(4)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (16)..(16)
<223> OTHER INFORMATION: Any amino acid
<220> FEATURE:
<223> OTHER INFORMATION: See specification as filed for detailed
      description of substitutions and preferred embodiments

<400> SEQUENCE: 226

Ser Ile Xaa Xaa Gly Xaa Xaa Thr Tyr Xaa Xaa Asp Ser Val Lys Xaa
1               5                   10                  15

<210> SEQ ID NO 227
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any amino acid
<220> FEATURE:
<223> OTHER INFORMATION: See specification as filed for detailed
      description of substitutions and preferred embodiments

<400> SEQUENCE: 227

Gly Gly Asp Tyr Gly Tyr Ala Xaa Asp Tyr
1               5                   10

<210> SEQ ID NO 228
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any amino acid
<220> FEATURE:
<223> OTHER INFORMATION: See specification as filed for detailed
      description of substitutions and preferred embodiments

<400> SEQUENCE: 228

Arg Ala Ser Gln Asp Ile Xaa Asn Tyr Leu Asn
1               5                   10

<210> SEQ ID NO 229
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid
<220> FEATURE:
<223> OTHER INFORMATION: See specification as filed for detailed
      description of substitutions and preferred embodiments

<400> SEQUENCE: 229

Thr Ser Gly Xaa Gly Val Gly
1               5

<210> SEQ ID NO 230
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Any amino acid
<220> FEATURE:
<223> OTHER INFORMATION: See specification as filed for detailed
      description of substitutions and preferred embodiments

<400> SEQUENCE: 230

His Ile Trp Trp Asp Asp Asp Lys Arg Tyr Asn Pro Xaa Leu Lys Ser
1               5                   10                  15

<210> SEQ ID NO 231
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (11)..(11)
<223> OTHER INFORMATION: Any amino acid
<220> FEATURE:
<223> OTHER INFORMATION: See specification as filed for detailed
      description of substitutions and preferred embodiments

<400> SEQUENCE: 231

Ser His Tyr Xaa Gly Thr Phe Tyr Phe Asp Xaa
1               5                   10

<210> SEQ ID NO 232
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(4)
<223> OTHER INFORMATION: This region may encompass 1-4 residues
<220> FEATURE:
<221> NAME/KEY: MISC_FEATURE
<222> LOCATION: (5)..(5)
<223> OTHER INFORMATION: May or may not be present
<220> FEATURE:
<221> NAME/KEY: MISC_FEATURE
```

```
<222> LOCATION: (6)..(9)
<223> OTHER INFORMATION: This region may encompass 1-4 residues
<220> FEATURE:
<221> NAME/KEY: MISC_FEATURE
<222> LOCATION: (10)..(10)
<223> OTHER INFORMATION: May or may not be present
<220> FEATURE:
<221> NAME/KEY: MISC_FEATURE
<222> LOCATION: (11)..(14)
<223> OTHER INFORMATION: This region may encompass 1-4 residues
<220> FEATURE:
<221> NAME/KEY: MISC_FEATURE
<222> LOCATION: (15)..(15)
<223> OTHER INFORMATION: May or may not be present
<220> FEATURE:
<221> NAME/KEY: MISC_FEATURE
<222> LOCATION: (16)..(19)
<223> OTHER INFORMATION: This region may encompass 1-4 residues
<220> FEATURE:
<221> NAME/KEY: MISC_FEATURE
<222> LOCATION: (20)..(20)
<223> OTHER INFORMATION: May or may not be present
<220> FEATURE:
<221> NAME/KEY: MISC_FEATURE
<222> LOCATION: (21)..(24)
<223> OTHER INFORMATION: This region may encompass 1-4 residues
<220> FEATURE:
<221> NAME/KEY: MISC_FEATURE
<222> LOCATION: (25)..(25)
<223> OTHER INFORMATION: May or may not be present
<220> FEATURE:
<221> NAME/KEY: MISC_FEATURE
<222> LOCATION: (26)..(29)
<223> OTHER INFORMATION: This region may encompass 1-4 residues
<220> FEATURE:
<221> NAME/KEY: MISC_FEATURE
<222> LOCATION: (30)..(30)
<223> OTHER INFORMATION: May or may not be present
<220> FEATURE:
<221> NAME/KEY: MISC_FEATURE
<222> LOCATION: (31)..(34)
<223> OTHER INFORMATION: This region may encompass 1-4 residues
<220> FEATURE:
<221> NAME/KEY: MISC_FEATURE
<222> LOCATION: (35)..(35)
<223> OTHER INFORMATION: May or may not be present
<220> FEATURE:
<221> NAME/KEY: MISC_FEATURE
<222> LOCATION: (36)..(39)
<223> OTHER INFORMATION: This region may encompass 1-4 residues
<220> FEATURE:
<221> NAME/KEY: MISC_FEATURE
<222> LOCATION: (40)..(40)
<223> OTHER INFORMATION: May or may not be present
<220> FEATURE:
<221> NAME/KEY: MISC_FEATURE
<222> LOCATION: (41)..(44)
<223> OTHER INFORMATION: This region may encompass 1-4 residues
<220> FEATURE:
<221> NAME/KEY: MISC_FEATURE
<222> LOCATION: (45)..(45)
<223> OTHER INFORMATION: May or may not be present
<220> FEATURE:
<221> NAME/KEY: MISC_FEATURE
<222> LOCATION: (46)..(49)
<223> OTHER INFORMATION: This region may encompass 1-4 residues
<220> FEATURE:
<221> NAME/KEY: MISC_FEATURE
<222> LOCATION: (50)..(50)
<223> OTHER INFORMATION: May or may not be present
<220> FEATURE:
<221> NAME/KEY: MISC_FEATURE
<222> LOCATION: (51)..(54)
<223> OTHER INFORMATION: This region may encompass 1-4 residues
<220> FEATURE:
<221> NAME/KEY: MISC_FEATURE
<222> LOCATION: (55)..(55)
<223> OTHER INFORMATION: May or may not be present
<220> FEATURE:
```

```
<221> NAME/KEY: MISC_FEATURE
<222> LOCATION: (56)..(59)
<223> OTHER INFORMATION: This region may encompass 1-4 residues
<220> FEATURE:
<221> NAME/KEY: MISC_FEATURE
<222> LOCATION: (60)..(60)
<223> OTHER INFORMATION: May or may not be present
<220> FEATURE:
<221> NAME/KEY: MISC_FEATURE
<222> LOCATION: (61)..(64)
<223> OTHER INFORMATION: This region may encompass 1-4 residues
<220> FEATURE:
<221> NAME/KEY: MISC_FEATURE
<222> LOCATION: (65)..(65)
<223> OTHER INFORMATION: May or may not be present
<220> FEATURE:
<221> NAME/KEY: MISC_FEATURE
<222> LOCATION: (66)..(69)
<223> OTHER INFORMATION: This region may encompass 1-4 residues
<220> FEATURE:
<221> NAME/KEY: MISC_FEATURE
<222> LOCATION: (70)..(70)
<223> OTHER INFORMATION: May or may not be present
<220> FEATURE:
<221> NAME/KEY: MISC_FEATURE
<222> LOCATION: (71)..(74)
<223> OTHER INFORMATION: This region may encompass 1-4 residues
<220> FEATURE:
<221> NAME/KEY: MISC_FEATURE
<222> LOCATION: (75)..(75)
<223> OTHER INFORMATION: May or may not be present
<220> FEATURE:
<221> NAME/KEY: MISC_FEATURE
<222> LOCATION: (76)..(79)
<223> OTHER INFORMATION: This region may encompass 1-4 residues
<220> FEATURE:
<221> NAME/KEY: MISC_FEATURE
<222> LOCATION: (80)..(80)
<223> OTHER INFORMATION: May or may not be present
<220> FEATURE:
<221> NAME/KEY: MISC_FEATURE
<222> LOCATION: (81)..(84)
<223> OTHER INFORMATION: This region may encompass 1-4 residues
<220> FEATURE:
<221> NAME/KEY: MISC_FEATURE
<222> LOCATION: (85)..(85)
<223> OTHER INFORMATION: May or may not be present
<220> FEATURE:
<221> NAME/KEY: MISC_FEATURE
<222> LOCATION: (86)..(89)
<223> OTHER INFORMATION: This region may encompass 1-4 residues
<220> FEATURE:
<221> NAME/KEY: MISC_FEATURE
<222> LOCATION: (90)..(90)
<223> OTHER INFORMATION: May or may not be present
<220> FEATURE:
<221> NAME/KEY: MISC_FEATURE
<222> LOCATION: (91)..(94)
<223> OTHER INFORMATION: This region may encompass 1-4 residues
<220> FEATURE:
<221> NAME/KEY: MISC_FEATURE
<222> LOCATION: (95)..(95)
<223> OTHER INFORMATION: May or may not be present
<220> FEATURE:
<221> NAME/KEY: MISC_FEATURE
<222> LOCATION: (96)..(99)
<223> OTHER INFORMATION: This region may encompass 1-4 residues
<220> FEATURE:
<221> NAME/KEY: MISC_FEATURE
<222> LOCATION: (100)..(100)
<223> OTHER INFORMATION: May or may not be present
<220> FEATURE:
<221> NAME/KEY: MISC_FEATURE
<222> LOCATION: (101)..(104)
<223> OTHER INFORMATION: This region may encompass 1-4 residues
<220> FEATURE:
<221> NAME/KEY: MISC_FEATURE
<222> LOCATION: (105)..(105)
<223> OTHER INFORMATION: May or may not be present
```

-continued

```
<220> FEATURE:
<221> NAME/KEY: MISC_FEATURE
<222> LOCATION: (106)..(109)
<223> OTHER INFORMATION: This region may encompass 1-4 residues
<220> FEATURE:
<221> NAME/KEY: MISC_FEATURE
<222> LOCATION: (110)..(110)
<223> OTHER INFORMATION: May or may not be present
<220> FEATURE:
<221> NAME/KEY: MISC_FEATURE
<222> LOCATION: (111)..(114)
<223> OTHER INFORMATION: This region may encompass 1-4 residues
<220> FEATURE:
<221> NAME/KEY: MISC_FEATURE
<222> LOCATION: (115)..(115)
<223> OTHER INFORMATION: May or may not be present
<220> FEATURE:
<221> NAME/KEY: MISC_FEATURE
<222> LOCATION: (116)..(119)
<223> OTHER INFORMATION: This region may encompass 1-4 residues
<220> FEATURE:
<221> NAME/KEY: MISC_FEATURE
<222> LOCATION: (120)..(120)
<223> OTHER INFORMATION: May or may not be present
<220> FEATURE:
<221> NAME/KEY: MISC_FEATURE
<222> LOCATION: (121)..(124)
<223> OTHER INFORMATION: This region may encompass 1-4 residues
<220> FEATURE:
<221> NAME/KEY: MISC_FEATURE
<222> LOCATION: (125)..(125)
<223> OTHER INFORMATION: May or may not be present
<220> FEATURE:
<221> NAME/KEY: MISC_FEATURE
<222> LOCATION: (126)..(129)
<223> OTHER INFORMATION: This region may encompass 1-4 residues
<220> FEATURE:
<221> NAME/KEY: MISC_FEATURE
<222> LOCATION: (130)..(130)
<223> OTHER INFORMATION: May or may not be present
<220> FEATURE:
<221> NAME/KEY: MISC_FEATURE
<222> LOCATION: (131)..(134)
<223> OTHER INFORMATION: This region may encompass 1-4 residues
<220> FEATURE:
<221> NAME/KEY: MISC_FEATURE
<222> LOCATION: (135)..(135)
<223> OTHER INFORMATION: May or may not be present
<220> FEATURE:
<221> NAME/KEY: MISC_FEATURE
<222> LOCATION: (136)..(139)
<223> OTHER INFORMATION: This region may encompass 1-4 residues
<220> FEATURE:
<221> NAME/KEY: MISC_FEATURE
<222> LOCATION: (140)..(140)
<223> OTHER INFORMATION: May or may not be present
<220> FEATURE:
<221> NAME/KEY: MISC_FEATURE
<222> LOCATION: (141)..(144)
<223> OTHER INFORMATION: This region may encompass 1-4 residues
<220> FEATURE:
<221> NAME/KEY: MISC_FEATURE
<222> LOCATION: (145)..(145)
<223> OTHER INFORMATION: May or may not be present
<220> FEATURE:
<221> NAME/KEY: MISC_FEATURE
<222> LOCATION: (146)..(149)
<223> OTHER INFORMATION: This region may encompass 1-4 residues
<220> FEATURE:
<221> NAME/KEY: MISC_FEATURE
<222> LOCATION: (150)..(150)
<223> OTHER INFORMATION: May or may not be present
<220> FEATURE:
<221> NAME/KEY: MISC_FEATURE
<222> LOCATION: (151)..(154)
<223> OTHER INFORMATION: This region may encompass 1-4 residues
<220> FEATURE:
<221> NAME/KEY: MISC_FEATURE
<222> LOCATION: (155)..(155)
```

```
<223> OTHER INFORMATION: May or may not be present
<220> FEATURE:
<221> NAME/KEY: MISC_FEATURE
<222> LOCATION: (156)..(159)
<223> OTHER INFORMATION: This region may encompass 1-4 residues
<220> FEATURE:
<221> NAME/KEY: MISC_FEATURE
<222> LOCATION: (160)..(160)
<223> OTHER INFORMATION: May or may not be present
<220> FEATURE:
<221> NAME/KEY: MISC_FEATURE
<222> LOCATION: (161)..(164)
<223> OTHER INFORMATION: This region may encompass 1-4 residues
<220> FEATURE:
<221> NAME/KEY: MISC_FEATURE
<222> LOCATION: (165)..(165)
<223> OTHER INFORMATION: May or may not be present
<220> FEATURE:
<221> NAME/KEY: MISC_FEATURE
<222> LOCATION: (166)..(169)
<223> OTHER INFORMATION: This region may encompass 1-4 residues
<220> FEATURE:
<221> NAME/KEY: MISC_FEATURE
<222> LOCATION: (170)..(170)
<223> OTHER INFORMATION: May or may not be present
<220> FEATURE:
<221> NAME/KEY: MISC_FEATURE
<222> LOCATION: (171)..(174)
<223> OTHER INFORMATION: This region may encompass 1-4 residues
<220> FEATURE:
<221> NAME/KEY: MISC_FEATURE
<222> LOCATION: (175)..(175)
<223> OTHER INFORMATION: May or may not be present
<220> FEATURE:
<221> NAME/KEY: MISC_FEATURE
<222> LOCATION: (176)..(179)
<223> OTHER INFORMATION: This region may encompass 1-4 residues
<220> FEATURE:
<221> NAME/KEY: MISC_FEATURE
<222> LOCATION: (180)..(180)
<223> OTHER INFORMATION: May or may not be present
<220> FEATURE:
<221> NAME/KEY: MISC_FEATURE
<222> LOCATION: (181)..(184)
<223> OTHER INFORMATION: This region may encompass 1-4 residues
<220> FEATURE:
<221> NAME/KEY: MISC_FEATURE
<222> LOCATION: (185)..(185)
<223> OTHER INFORMATION: May or may not be present
<220> FEATURE:
<221> NAME/KEY: MISC_FEATURE
<222> LOCATION: (186)..(189)
<223> OTHER INFORMATION: This region may encompass 1-4 residues
<220> FEATURE:
<221> NAME/KEY: MISC_FEATURE
<222> LOCATION: (190)..(190)
<223> OTHER INFORMATION: May or may not be present
<220> FEATURE:
<221> NAME/KEY: MISC_FEATURE
<222> LOCATION: (191)..(194)
<223> OTHER INFORMATION: This region may encompass 1-4 residues
<220> FEATURE:
<221> NAME/KEY: MISC_FEATURE
<222> LOCATION: (195)..(195)
<223> OTHER INFORMATION: May or may not be present
<220> FEATURE:
<221> NAME/KEY: MISC_FEATURE
<222> LOCATION: (196)..(199)
<223> OTHER INFORMATION: This region may encompass 1-4 residues
<220> FEATURE:
<221> NAME/KEY: MISC_FEATURE
<222> LOCATION: (200)..(200)
<223> OTHER INFORMATION: May or may not be present
<220> FEATURE:
<221> NAME/KEY: MISC_FEATURE
<222> LOCATION: (201)..(204)
<223> OTHER INFORMATION: This region may encompass 1-4 residues
<220> FEATURE:
<221> NAME/KEY: MISC_FEATURE
```

```
<222> LOCATION: (205)..(205)
<223> OTHER INFORMATION: May or may not be present
<220> FEATURE:
<221> NAME/KEY: MISC_FEATURE
<222> LOCATION: (206)..(209)
<223> OTHER INFORMATION: This region may encompass 1-4 residues
<220> FEATURE:
<221> NAME/KEY: MISC_FEATURE
<222> LOCATION: (210)..(210)
<223> OTHER INFORMATION: May or may not be present
<220> FEATURE:
<221> NAME/KEY: MISC_FEATURE
<222> LOCATION: (211)..(214)
<223> OTHER INFORMATION: This region may encompass 1-4 residues
<220> FEATURE:
<221> NAME/KEY: MISC_FEATURE
<222> LOCATION: (215)..(215)
<223> OTHER INFORMATION: May or may not be present
<220> FEATURE:
<221> NAME/KEY: MISC_FEATURE
<222> LOCATION: (216)..(219)
<223> OTHER INFORMATION: This region may encompass 1-4 residues
<220> FEATURE:
<221> NAME/KEY: MISC_FEATURE
<222> LOCATION: (220)..(220)
<223> OTHER INFORMATION: May or may not be present
<220> FEATURE:
<221> NAME/KEY: MISC_FEATURE
<222> LOCATION: (221)..(224)
<223> OTHER INFORMATION: This region may encompass 1-4 residues
<220> FEATURE:
<221> NAME/KEY: MISC_FEATURE
<222> LOCATION: (225)..(225)
<223> OTHER INFORMATION: May or may not be present
<220> FEATURE:
<221> NAME/KEY: MISC_FEATURE
<222> LOCATION: (226)..(229)
<223> OTHER INFORMATION: This region may encompass 1-4 residues
<220> FEATURE:
<221> NAME/KEY: MISC_FEATURE
<222> LOCATION: (230)..(230)
<223> OTHER INFORMATION: May or may not be present
<220> FEATURE:
<221> NAME/KEY: MISC_FEATURE
<222> LOCATION: (231)..(234)
<223> OTHER INFORMATION: This region may encompass 1-4 residues
<220> FEATURE:
<221> NAME/KEY: MISC_FEATURE
<222> LOCATION: (235)..(235)
<223> OTHER INFORMATION: May or may not be present
<220> FEATURE:
<221> NAME/KEY: MISC_FEATURE
<222> LOCATION: (236)..(239)
<223> OTHER INFORMATION: This region may encompass 1-4 residues
<220> FEATURE:
<221> NAME/KEY: MISC_FEATURE
<222> LOCATION: (240)..(240)
<223> OTHER INFORMATION: May or may not be present
<220> FEATURE:
<221> NAME/KEY: MISC_FEATURE
<222> LOCATION: (241)..(244)
<223> OTHER INFORMATION: This region may encompass 1-4 residues
<220> FEATURE:
<221> NAME/KEY: MISC_FEATURE
<222> LOCATION: (245)..(245)
<223> OTHER INFORMATION: May or may not be present
<220> FEATURE:
<221> NAME/KEY: MISC_FEATURE
<222> LOCATION: (246)..(249)
<223> OTHER INFORMATION: This region may encompass 1-4 residues
<220> FEATURE:
<221> NAME/KEY: MISC_FEATURE
<222> LOCATION: (250)..(250)
<223> OTHER INFORMATION: May or may not be present
<220> FEATURE:
<221> NAME/KEY: MISC_FEATURE
<222> LOCATION: (1)..(250)
<223> OTHER INFORMATION: This sequence may encompass 1-50 "(Gly)x-
      (Ser)y" repeating units, wherein x is 1-4 and y is 0 or 1
```

<220> FEATURE:
<223> OTHER INFORMATION: See specification as filed for detailed
      description of substitutions and preferred embodiments

<400> SEQUENCE: 232

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser Gly Gly Gly Gly
    50                  55                  60

Ser Gly Gly Gly Ser Gly Gly Gly Ser Gly Gly Gly Ser
65                  70                  75                  80

Gly Gly Gly Gly Ser Gly Gly Gly Gly Ser Gly Gly Gly Gly Ser Gly
                85                  90                  95

Gly Gly Gly Ser Gly Gly Gly Gly Ser Gly Gly Gly Gly Ser Gly Gly
            100                 105                 110

Gly Gly Ser Gly Gly Gly Gly Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Gly Gly Gly Gly Ser Gly Gly Gly Gly Ser
145                 150                 155                 160

Gly Gly Gly Gly Ser Gly Gly Gly Gly Ser Gly Gly Gly Gly Ser Gly
                165                 170                 175

Gly Gly Gly Ser Gly Gly Gly Gly Ser Gly Gly Gly Gly Ser Gly Gly
            180                 185                 190

Gly Gly Ser Gly Gly Gly Gly Ser Gly Gly Gly Gly Ser Gly Gly Gly
        195                 200                 205

Gly Ser Gly Gly Gly Gly Ser Gly Gly Gly Gly Ser Gly Gly Gly Gly
    210                 215                 220

Ser Gly Gly Gly Gly Ser Gly Gly Gly Gly Ser Gly Gly Gly Gly Ser
225                 230                 235                 240

Gly Gly Gly Gly Ser Gly Gly Gly Gly Ser
                245                 250

<210> SEQ ID NO 233
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<223> OTHER INFORMATION: See specification as filed for detailed
      description of substitutions and preferred embodiments

<400> SEQUENCE: 233

Xaa Tyr Ala Met Ser
1               5

<210> SEQ ID NO 234
<211> LENGTH: 12
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 234

Leu Gln Gln Ser Arg Lys Val Gly Asp Ser Pro Asn
1               5                   10

<210> SEQ ID NO 235
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(20)
<223> OTHER INFORMATION: This sequence may encompass 1-20 residues

<400> SEQUENCE: 235

Gly Gly Gly Gly Gly Gly Gly Gly Gly Gly Gly Gly Gly Gly Gly Gly
1               5                   10                  15

Gly Gly Gly Gly
            20

<210> SEQ ID NO 236
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(100)
<223> OTHER INFORMATION: This sequence may encompass 1-20 "Gly Gly Gly
      Gly Ser" repeat units

<400> SEQUENCE: 236

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser Gly Gly Gly Gly
    50                  55                  60

Ser Gly Gly Gly Gly Ser Gly Gly Gly Gly Ser Gly Gly Gly Gly Ser
65                  70                  75                  80

Gly Gly Gly Gly Ser Gly Gly Gly Gly Ser Gly Gly Gly Gly Ser Gly
                85                  90                  95

Gly Gly Gly Ser
            100

<210> SEQ ID NO 237
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (2)..(101)

<223> OTHER INFORMATION: This region may encompass 1-20 "Gly Gly Gly Gly Ser" repeat units

<400> SEQUENCE: 237

```
Ser Gly Gly Gly Gly Ser Gly Gly Gly Ser Gly Gly Gly Ser
1               5                   10                  15

Gly Gly Gly Gly Ser Gly Gly Gly Ser Gly Gly Gly Ser Gly
                20                  25                  30

Gly Gly Gly Ser Gly Gly Gly Ser Gly Gly Gly Ser Gly Gly
            35                  40                  45

Gly Gly Ser Gly Gly Gly Ser Gly Gly Gly Ser Gly Gly Gly
        50                  55              60

Gly Ser Gly Gly Gly Ser Gly Gly Gly Ser Gly Gly Gly Gly
65              70                  75                  80

Ser Gly Gly Gly Gly Ser Gly Gly Gly Ser Gly Gly Gly Ser
                85                  90              95

Gly Gly Gly Gly Ser
            100
```

<210> SEQ ID NO 238
<211> LENGTH: 100
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MISC_FEATURE
<222> LOCATION: (1)..(100)
<223> OTHER INFORMATION: This sequence may encompass 1-100 residues

<400> SEQUENCE: 238

```
Gly Gly Gly Gly Gly Gly Gly Gly Gly Gly Gly Gly Gly Gly
1               5                   10                  15

Gly Gly Gly Gly Gly Gly Gly Gly Gly Gly Gly Gly Gly Gly
                20                  25                  30

Gly Gly Gly Gly Gly Gly Gly Gly Gly Gly Gly Gly Gly Gly
            35                  40                  45

Gly Gly Gly Gly Gly Gly Gly Gly Gly Gly Gly Gly Gly Gly
        50                  55              60

Gly Gly Gly Gly Gly Gly Gly Gly Gly Gly Gly Gly Gly Gly
65              70                  75                  80

Gly Gly Gly Gly Gly Gly Gly Gly Gly Gly Gly Gly Gly Gly
                85                  90              95

Gly Gly Gly Gly
            100
```

<210> SEQ ID NO 239
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 239

```
Gly Gly Gly Gly
1
```

<210> SEQ ID NO 240
<211> LENGTH: 400

<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MISC_FEATURE
<222> LOCATION: (1)..(400)
<223> OTHER INFORMATION: This sequence may encompass 1-100 "Gly Gly Gly Gly" repeating units

<400> SEQUENCE: 240

```
Gly Gly Gly Gly Gly Gly Gly Gly Gly Gly Gly Gly Gly Gly Gly
1               5                   10                  15
Gly Gly Gly Gly Gly Gly Gly Gly Gly Gly Gly Gly Gly Gly Gly
            20                  25                  30
Gly Gly Gly Gly Gly Gly Gly Gly Gly Gly Gly Gly Gly Gly Gly
        35                  40                  45
Gly Gly Gly Gly Gly Gly Gly Gly Gly Gly Gly Gly Gly Gly Gly
    50                  55                  60
Gly Gly Gly Gly Gly Gly Gly Gly Gly Gly Gly Gly Gly Gly Gly
65                  70                  75                  80
Gly Gly Gly Gly Gly Gly Gly Gly Gly Gly Gly Gly Gly Gly Gly
            85                  90                  95
Gly Gly Gly Gly Gly Gly Gly Gly Gly Gly Gly Gly Gly Gly Gly
        100                 105                 110
Gly Gly Gly Gly Gly Gly Gly Gly Gly Gly Gly Gly Gly Gly Gly
    115                 120                 125
Gly Gly Gly Gly Gly Gly Gly Gly Gly Gly Gly Gly Gly Gly Gly
130                 135                 140
Gly Gly Gly Gly Gly Gly Gly Gly Gly Gly Gly Gly Gly Gly Gly
145                 150                 155                 160
Gly Gly Gly Gly Gly Gly Gly Gly Gly Gly Gly Gly Gly Gly Gly
            165                 170                 175
Gly Gly Gly Gly Gly Gly Gly Gly Gly Gly Gly Gly Gly Gly Gly
        180                 185                 190
Gly Gly Gly Gly Gly Gly Gly Gly Gly Gly Gly Gly Gly Gly Gly
    195                 200                 205
Gly Gly Gly Gly Gly Gly Gly Gly Gly Gly Gly Gly Gly Gly Gly
210                 215                 220
Gly Gly Gly Gly Gly Gly Gly Gly Gly Gly Gly Gly Gly Gly Gly
225                 230                 235                 240
Gly Gly Gly Gly Gly Gly Gly Gly Gly Gly Gly Gly Gly Gly Gly
            245                 250                 255
Gly Gly Gly Gly Gly Gly Gly Gly Gly Gly Gly Gly Gly Gly Gly
        260                 265                 270
Gly Gly Gly Gly Gly Gly Gly Gly Gly Gly Gly Gly Gly Gly Gly
    275                 280                 285
Gly Gly Gly Gly Gly Gly Gly Gly Gly Gly Gly Gly Gly Gly Gly
290                 295                 300
Gly Gly Gly Gly Gly Gly Gly Gly Gly Gly Gly Gly Gly Gly Gly
305                 310                 315                 320
Gly Gly Gly Gly Gly Gly Gly Gly Gly Gly Gly Gly Gly Gly Gly
            325                 330                 335
Gly Gly Gly Gly Gly Gly Gly Gly Gly Gly Gly Gly Gly Gly Gly
        340                 345                 350
```

```
Gly Gly Gly Gly Gly Gly Gly Gly Gly Gly Gly Gly Gly
        355                 360                 365

Gly Gly Gly Gly Gly Gly Gly Gly Gly Gly Gly Gly Gly
        370                 375                 380

Gly Gly Gly Gly Gly Gly Gly Gly Gly Gly Gly Gly Gly Gly Gly Gly
385                 390                 395                 400

<210> SEQ ID NO 241
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 241

His His His His His His
1               5

<210> SEQ ID NO 242
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Ser Phe Phe Leu Arg Asn
1               5

<210> SEQ ID NO 243
<211> LENGTH: 16
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(16)
<223> OTHER INFORMATION: This sequence may encompass 0-4 'Gly Gly Gly
      Ser' repeating units
<220> FEATURE:
<223> OTHER INFORMATION: See specification as filed for detailed
      description of substitutions and preferred embodiments

<400> SEQUENCE: 243

Gly Gly Gly Ser Gly Gly Gly Ser Gly Gly Gly Ser Gly Gly Gly Ser
1               5                   10                  15

<210> SEQ ID NO 244
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ser or Asn
<220> FEATURE:
<221> NAME/KEY: MOD_RES
<222> LOCATION: (4)..(4)
<223> OTHER INFORMATION: Ser or Gly
<220> FEATURE:
<221> NAME/KEY: MOD_RES
<222> LOCATION: (6)..(6)
<223> OTHER INFORMATION: Ser or Gly
```

```
<220> FEATURE:
<221> NAME/KEY: MOD_RES
<222> LOCATION: (7)..(7)
<223> OTHER INFORMATION: Ser, Asn or Thr
<220> FEATURE:
<221> NAME/KEY: MOD_RES
<222> LOCATION: (10)..(10)
<223> OTHER INFORMATION: Tyr or Phe
<220> FEATURE:
<221> NAME/KEY: MOD_RES
<222> LOCATION: (11)..(11)
<223> OTHER INFORMATION: Leu or Pro
<220> FEATURE:
<221> NAME/KEY: MOD_RES
<222> LOCATION: (16)..(16)
<223> OTHER INFORMATION: Gly or Arg

<400> SEQUENCE: 244

Ser Ile Xaa Xaa Gly Xaa Xaa Thr Tyr Xaa Xaa Asp Ser Val Lys Xaa
1               5                   10                  15

<210> SEQ ID NO 245
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Thr, Ser or Ala

<400> SEQUENCE: 245

Xaa Tyr Ala Met Ser
1               5

<210> SEQ ID NO 246
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Leu or Met

<400> SEQUENCE: 246

Gly Gly Asp Tyr Gly Tyr Ala Xaa Asp Tyr
1               5                   10

<210> SEQ ID NO 247
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Ser or Thr

<400> SEQUENCE: 247

Arg Ala Ser Gln Asp Ile Xaa Asn Tyr Leu Asn
1               5                   10

<210> SEQ ID NO 248
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Met or Leu

<400> SEQUENCE: 248

Thr Ser Gly Xaa Gly Val Gly
1               5

<210> SEQ ID NO 249
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Ala or Thr

<400> SEQUENCE: 249

His Ile Trp Trp Asp Asp Asp Lys Arg Tyr Asn Pro Xaa Leu Lys Ser
1               5                   10                  15

<210> SEQ ID NO 250
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Tyr or Asn
<220> FEATURE:
<221> NAME/KEY: MOD_RES
<222> LOCATION: (11)..(11)
<223> OTHER INFORMATION: Tyr or Phe

<400> SEQUENCE: 250

Ser His Tyr Xaa Gly Thr Phe Tyr Phe Asp Xaa
1               5                   10
```

ANTI-GPIIB/IIIA ANTIBODIES OR USES THEREOF

SEQUENCE LISTING

The instant application contains a Sequence Listing which has been filed electronically in ASCII format and is hereby incorporated by reference in its entirety. Said ASCII copy, created on Sep. 12, 2018, is named 13751-0238US1_SL.txt and is 244,217 bytes in size.

BACKGROUND OF THE INVENTION

Clotting factors have been administered to patients to improve hemostasis for some time. The advent of recombinant DNA technology has significantly improved treatment for patients with clotting disorders, allowing for the development of safe and consistent protein therapeutics. For example, recombinant activated factor VII has become widely used for the treatment of major bleeding, such as that which occurs in patients having hemophilia A or B, deficiency of coagulation Factors XI or VII, defective platelet function, thrombocytopenia, or von Willebrand's disease.

Although such recombinant molecules are effective, there is a need for improved versions which localize the therapeutic to sites of coagulation, have improved pharmacokinetic properties, have improved manufacturability, have reduced thrombogenicity, or have enhanced activity, or more than one of these characteristics.

Treatment of hemophilia by replacement therapy is targeting restoration of clotting activity. There are plasma-derived and recombinant clotting factor products available to treat bleeding episodes on-demand or to prevent bleeding episodes from occurring by treating prophylactically. Based on the half-life of these products, treatment regimens require frequent intravenous administration. Such frequent administration is painful and inconvenient. Strategies to extend the half-life of clotting factors include pegylation (Rostin J, et al., *Bioconj. Chem.* 2000; 11:387-96), glycopegylation (Stennicke H R, et al., *Thromb. Haemost.* 2008; 100:920-8), formulation with pegylated liposomes (Spira J, et al., *Blood* 2006; 108:3668-3673, Pan J, et al., *Blood* 2009; 114:2802-2811) and conjugation with albumin (Schulte S., *Thromb. Res.* 2008; 122 Suppl 4:S14-9).

Recombinant FVIIa (rFVIIa; NOVOSEVEN®) is used to treat bleeding episodes in (i) hemophilia patients with neutralizing antibodies against FVIII or FIX (inhibitors), (ii) patients with FVII deficiency, or (iii) patients with hemophilia A or B with inhibitors undergoing surgical procedures. NOVOSEVEN® displays poor efficacy. Repeated doses of FVIIa at high concentration are often required to control a bleed, due to its low affinity for activated platelets, short half-life, and poor enzymatic activity in the absence of tissue factor. Accordingly, there is an unmet medical need for better treatment and prevention option for hemophilia patients with inhibitors in which the activity of the FVIIa protein is increased.

BRIEF SUMMARY OF THE INVENTION

The present disclosure provides antibodies against GPIIb/IIIa that are capable of targeting the non-active form of the receptor (see FIG. 2E). The GPIIb/IIIa antibodies and antigen-binding molecules derived from these GPIIb/IIIa antibodies can be used, for example, to target therapeutic molecules (e.g., clotting factors) to the platelet. In addition to their use as targeting moieties, GPIIb/IIIa antibodies and antigen-binding molecules thereof of the present invention can be used for diagnostics, for example, by conjugation to a detectable label.

The present invention also relates to chimeric molecules comprising the GPIIb/IIIa antibodies and antigen-binding molecules thereof disclosed herein as targeting moieties, and one or more heterologous moieties. For example, a chimeric molecule can comprise a heterologous moiety comprising a therapeutic molecule (for example, a procoagulant molecule such as the FVIIa clotting factor), and optionally a second heterologous moiety comprising, for example, a PK enhancing moiety (i.e., a molecule which can improve various pharmacokinetic properties, e.g., circulation half-life).

The present disclosure provides an antibody or antigen-binding molecule thereof which specifically binds to a GPIIb/IIIa epitope, wherein the antibody or antigen-binding molecule thereof specifically bind to the same GPIIb/IIIa epitope as an antibody selected from 34D10, 12B2, 2A2, 35D1, 36A8, 4B11, 1H6, 38G8, 21F10, 38A8, 18F7, 38F6, 13C1, 5C4, 23C10, 37C7, 28C2, 9D6, or 28F4. The invention also includes an antibody or antigen-binding molecule thereof which specifically binds to a GPIIb/IIIa epitope, wherein the antibody or antigen-binding molecule thereof competitively inhibits GPIIb/IIIa binding by an antibody selected from 34D10, 12B2, 2A2, 35D1, 36A8, 4B11, 1H6, 38G8, 21F10, 38A8, 18F7, 38F6, 13C1, 5C4, 23C10, 37C7, 28C2, 9D6, or 28F4. Also provided is an antibody or antigen-binding molecule thereof which specifically binds to a GPIIb/IIIa epitope, wherein the antibody or antigen-binding molecule thereof comprises at least one, at least two, at least three, at least four, or at least five complementarity determining regions (CDR) or variants thereof of an antibody selected from the 34D10, 12B2, 2A2, 35D1, 36A8, 4B11, 1H6, 38G8, 21F10, 38A8, 18F7, 38F6, 13C1, 5C4, 23C10, 37C7, 28C2, 9D6, or 28F4 antibodies. In some embodiments, the antibody or antigen-binding molecule thereof comprises six CDRs or variants thereof of an antibody selected from the 34D10, 12B2, 2A2, 35D1, 36A8, 4B11, 1H6, 38G8, 21F10, 38A8, 18F7, 38F6, 13C1, 5C4, 23C10, 37C7, 28C2, 9D6, or 28F4 antibodies.

The present disclosure also provides an antibody or antigen-binding molecule thereof which specifically binds to a GPIIb/IIIa epitope, comprising (i) a variable heavy chain CDR-1 (VH-CDR1) sequence at least about 60%, 70%, 80%, 90%, 95%, or 100% identical to any one of SEQ ID NOS: 25, 31, 37, 43 or 111; (ii) a variable heavy chain CDR-2 (VH-CDR2) sequence at least about 60%, 70%, 80%, 90%, 95%, or 100% identical to any one of SEQ ID NOS:26, 32, 38, 44, or 112; (iii) a variable heavy chain CDR-3 (VH-CDR3) sequence at least about 60%, 70%, 80%, 90%, 95%, or 100% identical to any one of SEQ ID NOS: 27, 33, 39, 45, or 113; (iv) a variable light chain CDR-1 (VL-CDR1) sequence at least about 60%, 70%, 80%, 90%, 95%, or 100% identical to any one of SEQ ID NOS: 28, 34, 40, 117, or 114; (v) a variable light chain CDR-2 (VL-CDR2) sequence at least about 60%, 70%, 80%, 90%, 95%, or 100% identical to any one of SEQ ID NOS: 29, 35, 41, 118, or 115; and (vi) a variable light chain CDR-3 (VL-CDR3) sequence at least about 60, 70, 80, 90, or 95% identical to any one of SEQ ID NOS: 30, 36, 42, 119, or 116.

Also provided is an antibody or antigen-binding molecule thereof which specifically binds to a GPIIb/IIIa epitope, comprising (i) a VH-CDR1 comprising the consensus sequence $X_1$YAMS (SEQ ID NO:245) wherein $X_1$ represents amino acid residues Thr (T), Ser (S), or Ala (A); (ii) a VH-CDR2 comprising the consensus sequence SIX$_2$X$_3$GX$_4$X$_5$TYX$_6$X$_7$DSVKX$_8$ (SEQ ID NO:244) wherein X2 represents amino acid residues Ser (S) or Asn (N), X$_3$ represents amino acid residues Ser (S) or Gly (G), X$_4$ represents amino acid residues Ser (S) or Gly (G), X$_5$ represents amino acid residues Ser (S), Asn (N), or Thr (T), X$_6$ represents amino acid residues Tyr (Y) or Phe (F), X$_7$ represents amino acid residues Leu (L) or Pro (P), and X$_8$ represents amino acids Gly (G) or Arg (R); (iii) a VH-CDR3 comprising the consensus sequence GGDYGYAX$_9$DY (SEQ ID NO:246), wherein X$_9$ represents amino acid residues Leu (L) or Met (M); (iv) a VL-CDR1 comprising the sequence RASSSVNYMY (SEQ ID NO: 28); (v) a VL-CDR2 comprising the sequence YTSNLAP (SEQ ID NO: 29); and, (vi) a VL-CDR3 comprising the sequence QQFSSSPWT (SEQ ID NO: 30). In some embodiments, the antibody or antigen-binding molecule thereof comprises (i) a VH-CDR1 sequence selected from SEQ ID NO: 25, 31, 37, 43, or 111; (ii) a VH-CDR2 sequence selected from SEQ ID NOS: 26, 32, 38, 44, or 112; (iii) a VH-CDR3 sequence selected from SEQ ID NOS: 27, 33, 39, 45, or 113; (iv) a VL-CDR1 sequence selected from of SEQ ID NOS: 28, 34, 40, 117, or 114; (v) a VL-CDR2 sequence selected from SEQ ID NOS: 29, 35, 41, 118, or 115; and (vi) a VL-CDR3 sequence selected from SEQ ID NOS: 30, 36, 42, 119, or 116.

The instant disclosure also provides an antibody or antigen-binding molecule thereof which specifically binds to a GPIIb/IIIa epitope, comprising a VH comprising an amino acid sequence at least about 80%, 85%, 90%, 95%, or 100% identical to any one of SEQ ID NOS: 1, 3, 5, 7, or 97, and a VL comprising an amino acid sequence at least about 80%, 85%, 90%, 95%, or 100% identical to any one of SEQ ID NOS: 2, 4, 6, 99, or 98. In some embodiments, the antibody or antigen-binding molecule thereof comprises a VH comprising the amino acid sequence of SEQ ID NO: 1 and a VL comprising the amino acid sequence of SEQ ID NO: 2.

In some embodiments, the antibody or antigen-binding molecule thereof comprises a VH comprising the amino acid sequence of SEQ ID NO: 3 and a VL comprising the amino acid sequence of SEQ ID NO: 4. In some embodiments, the antibody or antigen-binding molecule thereof comprises a VH comprising the amino acid sequence of SEQ ID NO: 5 and a VL comprising the amino acid sequence of SEQ ID NO: 6. In other embodiments, the antibody or antigen-binding molecule thereof comprises a VH comprising the amino acid sequence of SEQ ID NO: 7 and a VL comprising the amino acid sequence of SEQ ID NO: 99. In other embodiments, the antibody or antigen-binding molecule thereof comprises a VH comprising the amino acid sequence of SEQ ID NO: 97 and a VL comprising the amino acid sequence of SEQ ID NO: 98.

In some embodiments, the antibody or antigen-binding molecule thereof can bind to a GPIIb/IIIa epitope located in the extracellular domain of the alpha subunit of GPIIb/IIIa or in the extracellular domain of the GPIIb/IIIa complex. In some embodiments, the antibody or antigen-binding molecule thereof does not compete with fibrinogen for binding to GPIIb/IIIa.

The present disclosure also provides an antibody or antigen-binding molecule thereof which specifically binds to a GPIIb/IIIa epitope comprising (i) a variable heavy chain CDR-1 (VH-CDR1) sequence at least about 60%, 70%, 80%, 90%, 95%, or 100% identical to any one of SEQ ID NOS: 46, 52, 120, or 126; (ii) a variable heavy chain CDR-2 (VH-CDR2) sequence at least about 60%, 70%, 80%, 90%, 95%, or 100% identical to any one of SEQ ID NOS: 47, 53, 121, or 127; (iii) a variable heavy chain CDR-3 (VH-CDR3) sequence at least about 60%, 70%, 80%, 90%, 95%, or 100% identical to any one of SEQ ID NOS: 48, 54, 122, or 128; (iv) a variable light chain CDR-1 (VL-CDR1) sequence at least about 60%, 70%, 80%, 90%, 95%, or 100% identical to any one of SEQ ID NOS: 49, 55, 123, or 129; (v) a variable light chain CDR-2 (VL-CDR2) sequence at least about 60%, 70%, 80%, 90%, 95%, or 100% identical to any one of SEQ ID NOS: 50, 56, 124, or 130; and (vi) a variable light chain CDR-3 (VL-CDR3) sequence at least about 60%, 70%, 80%, 90%, 95%, or 100% identical to any one of SEQ ID NO: 51, 57, 125, or 131.

Also provided is an antibody or antigen-binding molecule thereof which specifically binds to a GPIIb/IIIa epitope, comprising (i) a VH-CDR1 comprising the sequence NYLIE (SEQ ID NO: 46); (ii) a VH-CDR2 comprising the sequence VINPGSGGTNYNEKFKG (SEQ ID NO: 47); (iii) a VH-CDR3 comprising the sequence GRYEWYFDV (SEQ ID NO: 48); (iv) a VL-CDR1 comprising the consensus sequence RASQDIX$_{10}$NYLN (SEQ ID NO:247) wherein X10 represents amino acid residues Ser (S) or Thr (T); (v) a VL-CDR2 comprising the sequence YTSRLHS (SEQ ID NO:50); and (vi) a VL-CDR3 comprising the sequence QQGYTLPYT (SEQ ID NO:51). In some embodiments, the antibody or antigen-binding molecule thereof comprises (i) a VH-CDR1 sequence selected from SEQ ID NO: 46, 52, 120, or 126; (ii) a VH-CDR2 sequence selected from SEQ ID NO: 47, 53, 121, or 127; (iii) a VH-CDR3 sequence selected from SEQ ID NO: 48, 54, 122, or 128; (iv) a VL-CDR1 sequence selected from SEQ ID NO: 49, 55, 123, or 129; (v) a VL-CDR2 sequence selected from SEQ ID NO: 50, 56, 124, or 130; and, (vi) a VL-CDR3 sequence selected from SEQ ID NO: 51, 57, 125, or 131.

Also provided is an antibody or antigen-binding molecule thereof which specifically binds to a GPIIb/IIIa epitope, comprising a VH comprising an amino acid sequence at least about 80%, 85%, 90%, 95%, or 100% identical to any one of SEQ ID NOS: 8, 10, 100, or 102, and a VL comprising an amino acid sequence at least about 80%, 85%, 90%, 95%, or 100% identical to any one of SEQ ID NOS: 9, 11, 101, or 103. In some embodiments, the antibody or antigen-binding molecule thereof comprises a VH comprising the amino acid sequence of SEQ ID NO: 8, and a VL comprising the amino acid sequence of SEQ ID NO: 9. In other embodiments, the antibody or antigen-binding molecule thereof comprises a VH comprising the amino acid sequence of SEQ ID NO: 10 and a VL comprising the amino acid sequence of SEQ ID NO: 11.

In some embodiments, the antibody or antigen-binding molecule thereof comprises a VH comprising the amino acid sequence of SEQ ID NO: 100 and a VL comprising the amino acid sequence of SEQ ID NO: 101. In some embodiments, the antibody or antigen-binding molecule thereof comprises a VH comprising the amino acid sequence of SEQ ID NO: 102 and a VL comprising the amino acid sequence of SEQ ID NO: 103. In some embodiments, the antibody or antigen-binding molecule thereof binds to a GPIIb/IIIa epitope located in the extracellular domain of the alpha subunit of GPIIb/IIIa. In some embodiments, the antibody or antigen-binding molecule thereof competes with fibrinogen for binding to GPIIb/IIIa.

The present disclosure also provides an antibody or antigen-binding molecule thereof which specifically binds to a gpIIb/IIIa epitope, comprising (i) a variable heavy chain CDR-1 (VH-CDR1) sequence at least about 60%, 70%, 80%, 90%, 95%, or 100% identical to SEQ ID NO: 58; (ii) a variable heavy chain CDR-2 (VH-CDR2) sequence at least about 60%, 70%, 80%, 90%, 95%, or 100% identical to SEQ ID NO: 59; (iii) a variable heavy chain CDR-3 (VH-CDR3) sequence at least about 60%, 70%, 80%, 90%, 95%, or 100% identical to SEQ ID NO: 60; (iv) a variable light chain CDR-1 (VL-CDR1) sequence at least about 60%, 70%, 80%, 90%, 95%, or 100% identical to SEQ ID NO: 61; (v) a variable light chain CDR-2 (VL-CDR2) sequence at least about 60%, 70%, 80%, 90%, 95%, or 100% identical to SEQ ID NO: 62; and, (vi) a variable light chain CDR-3 (VL-CDR3) sequence at least about 60%, 70%, 80%, 90%, 95%, or 100% identical to SEQ ID NO: 63.

Also provided is an antibody or antigen-binding molecule thereof which specifically binds to a GPIIb/IIIa epitope, comprising (i) a VH-CDR1 sequence comprising SEQ ID NO: 58; (ii) a VH-CDR2 sequence comprising SEQ ID NO: 59; (iii) a VH-CDR3 sequence comprising SEQ ID NO: 60; (iv) a VL-CDR1 sequence comprising SEQ ID NO: 61; (v) a VL-CDR2 sequence comprising SEQ ID NO: 62; and (vi) a VL-CDR3 sequence comprising SEQ ID NO: 63. The present disclosure also provides an antibody or antigen-binding molecule thereof which specifically binds to a GPIIb/IIIa epitope comprising a VH comprising an amino acid sequence at least about 80%, 85%, 90%, 95%, or 100% identical to SEQ ID NO: 12 and a VL comprising an amino acid sequence at least about 80%, 85%, 90%, 95%, or 100% identical to SEQ ID NO: 13. In some embodiments, the antibody or antigen-binding molecule thereof can bind to a GPIIb/IIIa epitope located in the extracellular domain of the alpha subunit of GPIIb/IIIa. In some embodiments, the antibody or antigen-binding molecule thereof competes with fibrinogen for binding to GPIIb/IIIa.

The instant disclosure also provides an antibody or antigen-binding molecule thereof which specifically binds to a GPIIb/IIIa epitope, comprising (i) a variable heavy chain CDR-1 (VH-CDR1) sequence at least about 60%, 70%, 80%, 90%, 95%, or 100% identical to any one of SEQ ID NOS: 64, 70, or 135; (ii) a variable heavy chain CDR-2 (VH-CDR2) sequence at least about 60%, 70%, 80%, 90%, 95%, or 100% identical to any one of SEQ ID NOS: 65, 71, or 136; (iii) a variable heavy chain CDR-3 (VH-CDR3) sequence at least about 60%, 70%, 80%, 90%, 95%, or 100% identical to any one of SEQ ID NOS: 66, 72, or 137; (iv) a variable light chain CDR-1 (VL-CDR1) sequence at least about 60%, 70%, 80%, 90%, 95%, or 100% identical to any one of SEQ ID NOS: 67, 132, or 138; (v) a variable light chain CDR-2 (VL-CDR2) sequence at least about 60%, 70%, 80%, 90%, 95%, or 100% identical to any one of SEQ ID NOS: 68, 133, or 139; and (vi) a variable light chain CDR-3 (VL-CDR3) sequence at least about 60%, 70%, 80%, 90%, 95%, or 100% identical to any one of SEQ ID NOS: 69, 134, or 140.

The invention also includes an antibody or antigen-binding molecule thereof which specifically binds to a GPIIb/IIIa epitope, comprising (i) a VH-CDR1 comprising the sequence SYWIE (SEQ ID NO: 64); (ii) a VH-CDR2 comprising the consensus sequence EILPGX$_{14}$GX$_{15}$TKYNX$_{16}$KFKG (SEQ ID NO: 187), wherein X$_{14}$ represents amino acid residues Ser (S) or Thr (T), X$_{15}$ represents amino acid residues Ile (I) or Tyr (Y), and X$_{16}$ represents amino acid residues Asp (D) or Glu (E); (iii) a VH-CDR3 comprising the sequence LISYYYAMDY (SEQ ID NO: 66); (iv) a VL-CDR1 comprising the sequence RASQDISNYLN (SEQ ID NO: 67); (v) a VL-CDR2 comprising the sequence YTSRLHS (SEQ ID NO: 68); and, (vi) a VL-CDR3 comprising the sequence QQGNTLPPT (SEQ ID NO: 69).

Also provided is an antibody or antigen-binding molecule thereof which specifically binds to a GPIIb/IIIa epitope, comprising (i) a VH-CDR1 sequence selected from SEQ ID NO: 64, 70, or 135; (ii) a VH-CDR2 sequence selected from SEQ ID NO: 65, 71, or 136; (iii) a VH-CDR3 sequence selected from SEQ ID NO: 66, 72, or 137; (iv) a VL-CDR1 sequence selected from SEQ ID NO: 67, 132, or 138; (v) a VL-CDR2 sequence selected from SEQ ID NO: 68, 133, or 139; and, (vi) a VL-CDR3 sequence selected from SEQ ID NO: 69, 134, or 140.

Also provided herein is an antibody or antigen-binding molecule thereof which specifically binds to a GPIIb/IIIa epitope, comprising a VH comprising an amino acid sequence at least about 80%, 85%, 90%, 95%, or 100% identical to any one of SEQ ID NOS: 14, 16, or 105 and a VL comprising an amino acid sequence at least about 80%, 85%, 90%, 95%, or 100% identical to any one of SEQ ID NOs: 15, 104, or 106. In some embodiments, the antibody or antigen-binding molecule thereof comprises a VH comprising the amino acid sequence of SEQ ID NO: 14 and a VL comprising the amino acid sequence of SEQ ID NO: 15. In some embodiments, the antibody or antigen-binding molecule thereof comprises a VH comprising the amino acid sequence of SEQ ID NO: 16 and a VL comprising the amino acid sequence of SEQ ID NO: 104. In other embodiments, the antibody or antigen-binding molecule thereof comprises a VH comprising the amino acid sequence of SEQ ID NO: 105 and a VL comprising the amino acid sequence of SEQ ID NO: 106. In some embodiments, the antibody or antigen-binding molecule thereof binds to a GPIIb/IIIa epitope located in the extracellular domain of the beta subunit of GPIIb/IIIa. In some embodiments, the antibody or antigen-binding molecule thereof does not compete with fibrinogen for binding to GPIIb/IIIa.

The present disclosure also provides an antibody or antigen-binding molecule thereof which specifically binds to a GPIIb/IIIa epitope, comprising (i) a variable heavy chain CDR-1 (VH-CDR1) sequence at least about 60%, 70%, 80%, 90%, 95%, or 100% identical to any one of SEQ ID NOS: 73, 76, 79, 85, or 147; (ii) a variable heavy chain CDR-2 (VH-CDR2) sequence at least about 60%, 70%, 80%, 90%, 95%, or 100% identical to any one of SEQ ID NOS: 74, 77, 80, 86, or 148; (iii) a variable heavy chain CDR-3 (VH-CDR3) sequence at least about 60%, 70%, 80%, 90%, 95%, or 100% identical to any one of SEQ ID NOS: 75, 78, 81, 87, or 149; (iv) a variable light chain CDR-1 (VL-CDR1) sequence at least about 60%, 70%, 80%, 90%, 95%, or 100% identical to any one of SEQ ID NOS: 141, 144, 82, 88, or 150; (v) a variable light chain CDR-2 (VL-CDR2) sequence at least about 60%, 70%, 80%, 90%, 95%, or 100% identical to any one of SEQ ID NOS: 142, 145, 83, 89, or 151; and, (vi) a variable light chain CDR-3 (VL-CDR3) sequence at least about 60%, 70%, 80%, 90%, 95%, or 100% identical to any one of SEQ ID NO: 143, 146, 84, 90, or 152. Also provided is an antibody or antigen-binding molecule thereof which specifically binds to a GPIIb/IIIa epitope, comprising (i) a VH-CDR1 comprising the consensus sequence TSGX$_{11}$GVG (SEQ ID NO:248), wherein X11 represents amino acid residues Met (M) or Leu (L); (ii) a VH-CDR2 comprising the consensus sequence HIWWDDDKRYNPX$_{12}$LKS (SEQ ID NO:249), wherein X12 represents amino acid residues Ala (A) or Thr (T); (iii) a VH-CDR3 comprising the consensus sequence SHYX$_{13}$GTFYFDX$_{14}$ (SEQ ID NO:250), wherein X13 represents amino acid residues Tyr (Y) or Asn (N), and X14 represents amino acid residues Tyr (Y) or Phe (F); (iv) a VL-CDR1 comprising the sequence RASKSISKYLA (SEQ ID NO: 82); (v) a VL-CDR2 comprising the sequence SGSTLQS (SEQ ID NO: 83); and, (vi) a VL-CDR3 comprising the sequence QQHIEYPWT (SEQ ID NO: 84).

In some embodiments, the antibody or antigen-binding molecule thereof comprises (i) a VH-CDR1 sequence selected from SEQ ID NOS: 73, 76, 79, 85, or 147; (ii) a VH-CDR2 sequence selected from SEQ ID NOS: 74, 77, 80, 86, or 148; (iii) a VH-CDR3 sequence selected from SEQ ID NOS: 75, 78, 81, 87, or 149; (iv) a VL-CDR1 sequence selected from SEQ ID NOS: 141, 144, 82, 88, or 150; (v) a VL-CDR2 sequence selected from SEQ ID NOS: 142, 145, 83, 89, or 151; and (vi) a VL-CDR3 sequence selected from SEQ ID NOS: 143, 146, 84, 90, or 152. Also provided is an antibody or antigen-binding molecule thereof which specifically binds to a GPIIb/IIIa epitope, comprising a VH comprising an amino acid sequence at least 80%, 85%, 90%, 95%, or 100% identical to any one of SEQ ID NOS: 17, 18, 19, 21, or 109 and a VL comprising an amino acid sequence at least 80%, 85%, 90%, 95%, or 100% identical to any one of SEQ ID NOS: 107, 108, 20, 22, or 110.

In some embodiments, the antibody or antigen-binding molecule thereof comprises a VH comprising the amino acid sequence of SEQ ID NO: 17 and a VL comprising the amino acid sequence of SEQ ID NO: 107. In other embodiments, the antibody or antigen-binding molecule thereof comprises a VH comprising the amino acid sequence of SEQ ID NO: 18 and a VL comprising the amino acid sequence of SEQ ID NO: 108. In some embodiments, the antibody or antigen-binding molecule thereof comprises a VH comprising the amino acid sequence of SEQ ID NO: 109 and a VL comprising the amino acid sequence of SEQ ID NO: 110.

In some embodiments, the antibody or antigen-binding molecule thereof comprises a VH comprising the amino acid sequence of SEQ ID NO: 19 and a VL comprising the amino acid sequence of SEQ ID NO: 20. In some embodiments, the antibody or antigen-binding molecule thereof comprises a VH comprising the amino acid sequence of SEQ ID NO: 21 and a VL comprising the amino acid sequence of SEQ ID NO: 22. In some embodiments, the antibody or antigen-binding molecule thereof binds to a GPIIb/IIIa epitope located in the extracellular domain of the beta subunit of GPIIb/IIIa. In some embodiments, the antibody or antigen-binding molecule thereof competes with fibrinogen for binding to GPIIb/IIIa.

Also provided in the present disclosure is an antibody or antigen-binding molecule thereof which specifically binds to a GPIIb/IIIa epitope, comprising (i) a variable heavy chain CDR-1 (VH-CDR1) sequence at least about 60%, 70%, 80%, 90%, 95%, or 100% identical to SEQ ID NO: 91; (ii) a variable heavy chain CDR-2 (VH-CDR2) sequence at least about 60%, 70%, 80%, 90%, 95%, or 100% identical to SEQ ID NO: 92; (iii) a variable heavy chain CDR-3 (VH-CDR3) sequence at least about 60%, 70%, 80%, 90%, 95%, or 100% identical to SEQ ID NO: 93; (iv) a variable light chain CDR-1 (VL-CDR1) sequence at least about 60%, 70%, 80%, 90%, 95%, or 100% identical to SEQ ID NO: 94; (v) a variable light chain CDR-2 (VL-CDR2) sequence at least about 60%, 70%, 80%, 90%, 95%, or 100% identical to SEQ ID NO: 95; and (vi) a variable light chain CDR-3 (VL-CDR3) sequence at least about 60%, 70%, 80%, 90%, 95%, or 100% identical to SEQ ID NO: 96.

The present disclosure also provides an antibody or antigen-binding molecule thereof which specifically binds to a GPIIb/IIIa epitope, comprising (i) a VH-CDR1 sequence comprising SEQ ID NO: 91; (ii) a VH-CDR2 sequence comprising SEQ ID NO: 92; (iii) a VH-CDR3 sequence comprising SEQ ID NO: 93; (iv) a VL-CDR1 sequence comprising SEQ ID NO: 94; (v) a VL-CDR2 sequence comprising SEQ ID NOS: 95; and (vi) a VL-CDR3 sequence comprising SEQ ID NOS: 96.

Also provided is an antibody or antigen-binding molecule thereof which specifically binds to a GPIIb/IIIa epitope, comprising a VH comprising an amino acid sequence at least about 80%, 85%, 90%, 95%, or 100% identical to SEQ ID NO: 23 and a VL comprising an amino acid sequence at least about 80%, 85%, 90%, 95%, or 100% identical to SEQ ID NO: 24. In some embodiments, the antibody or antigen-binding molecule thereof binds to a GPIIb/IIIa epitope located in the extracellular domain of the beta subunit of GPIIb/IIIa. In some embodiments, the antibody or antigen-binding molecule thereof competes with fibrinogen for binding to GPIIb/IIIa.

In some embodiments, the antibody or antigen-binding molecule thereof disclosed herein comprises or consists of (a) a single chain Fv ("scFv"); (b) a diabody; (c) a minibody; (d) a polypeptide chain of an antibody; (e) F(ab')$_2$; or (f) F(ab).

The present disclosure also provides a chimeric molecule comprising (i) a GPIIb/IIIa antibody or antigen-binding molecule thereof disclosed herein; (ii) a heterologous moiety; and, (iii) an optional linker. In some embodiments, the chimeric molecule has the formula (i) Tm-(L)-H; or (ii) H-(L)-Tm, wherein, H is a heterologous moiety; L is an optional linker; and, Tm is an anti-GPIIb/IIIa antibody or antigen-binding molecule thereof disclosed herein. In some embodiments, the heterologous moiety comprises a clotting factor. In some embodiments, the clotting factor is independently selected from the group consisting of FVII, FIX, FX, and any combinations thereof. In some embodiments, the clotting factor is FVII zymogen, activatable FVII, activated FVII (FVIIa), FIX zymogen, activatable FIX, activated FIX (FIXa), FX zymogen, activatable FX, or activated FX (FXa). In some embodiments, the chimeric molecule further comprises a second heterologous moiety.

In some embodiments, the chimeric molecule has a formula selected from (i) H1-(L1)-Tm-(L2)-H2; (ii) H2-(L2)-Tm-(L1)-H1; (iii) H1-(L1)-H2-(L2)-Tm; (iv) H2-(L2)-H1-(L1)-Tm; (v) Tm-(L1)-H1-(L2)-H2; or (vi) Tm-(L2)-H2-(L1)-H1; wherein, Tm is an anti-GPIIb/IIIa antibody or antigen-binding molecule thereof disclosed herein; H1 is a first heterologous moiety, H2 is a second heterologous moiety, L1 is a first optional linker, L2 is a second optional linker. In some embodiments, the first heterologous moiety and the second heterologous moiety are the same or different. In some embodiments, the second heterologous moiety comprises a half-life extending moiety.

In some embodiments, L1 and L2 are the same or different. In some embodiments, the first heterologous moiety comprises a clotting factor and the second heterologous moiety comprises a half-life extending moiety. In some embodiments, the second heterologous moiety comprises a low-complexity polypeptide. In some embodiments, the second heterologous moiety comprises albumin, albumin binding polypeptide or fatty acid, Fc, transferrin, PAS, the C-terminal peptide (CTP) of the β subunit of human chorionic gonadotropin, polyethylene glycol (PEG), hydroxyethyl starch (HES), albumin-binding small molecules, vWF, a clearance receptor or fragment thereof which blocks binding of the chimeric molecule to a clearance receptor or any combinations thereof. In some embodiments, the clotting factor comprises a single polypeptide chain or two polypeptide chains.

Also provided herein is a chimeric molecule comprising a first polypeptide chain and a second polypeptide chain, which are associated with each other, (1) wherein the first polypeptide chain comprises a light chain of a clotting factor and a heterologous moiety, and the second polypeptide chain comprises a heavy chain of the clotting factor and a GPIIb/IIIa antibody or antigen-binding molecule thereof disclosed herein; (2) wherein the first polypeptide chain comprises a light chain of a clotting factor and a GPIIb/IIIa antibody or antigen-binding molecule thereof disclosed herein, and the second polypeptide chain comprises a heavy chain of the clotting factor and a heterologous moiety; (3) wherein the first polypeptide chain comprises a light chain of a clotting factor and the second polypeptide chain comprises a heavy chain of the clotting factor, a GPIIb/IIIa antibody or antigen-binding molecule thereof disclosed herein, and a heterologous moiety; (4) wherein the first polypeptide chain comprises a light chain of a clotting factor and the second polypeptide chain comprises a heavy chain of the clotting factor, a heterologous moiety, and a GPIIb/IIIa antibody or antigen-binding molecule thereof disclosed herein; (5) wherein the first polypeptide chain comprises a light chain of a clotting factor, a heterologous moiety, and a GPIIb/IIIa antibody or antigen-binding molecule thereof disclosed herein, and the second polypeptide chain comprises a heavy chain of the clotting factor; or (6) wherein the first polypeptide chain comprises a light chain of a clotting factor, a GPIIb/IIa antibody or antigen-binding molecule thereof disclosed herein, and a heterologous moiety and the second polypeptide chain comprises a heavy chain of the clotting factor.

In some embodiments, the chimeric molecule comprises a first polypeptide chain and a second polypeptide chain, which are associated with each other: (1) wherein the first polypeptide chain comprises $CF_L$-H or H-$CF_L$ and the second polypeptide chain comprises $CF_H$-Tm or Tm-$CF_H$; (2) wherein the first polypeptide chain comprises $CF_L$-Tm or Tm-$CF_L$ and the second polypeptide chain comprises $CF_H$-H or H-$CF_H$; (3) wherein the first polypeptide chain comprises $CF_L$ and the second polypeptide chain comprises $CF_H$-Tm-H or H-Tm-$CF_H$; (4) wherein the first polypeptide chain comprises $CF_L$ and the second polypeptide chain comprises $CF_H$-H-Tm or Tm-H-$CF_H$; (5) wherein the first polypeptide chain comprises $CF_L$-H-Tm or Tm-H-$CF_L$ and the second polypeptide chain comprises $CF_H$; or (6) wherein the first polypeptide chain comprises $CF_L$-Tm-H or H-Tm-$CF_L$ and the second polypeptide chain comprises $CF_H$; wherein $CF_L$ is a light chain of a clotting factor; $CF_H$ is a heavy chain of the clotting factor; Tm is an anti-GPIIb/IIIa antibody or antigen-binding molecule thereof disclosed herein; or H is a heterologous moiety. In some embodiments, the clotting factor is independently selected from FVII, FIX, and FX.

In other embodiments, the chimeric molecule comprises one or more of the linkers, wherein one or more of the linkers comprise a peptide linker. In some embodiments, the peptide linker comprises at least two, at least three, at least four, at least five, at least 10, at least 20, at least 30, at least 40, at least 50, at least 60, at least 70, at least 80, at least 90, or at least 100 amino acids. In some embodiments, the peptide linker comprises at least 200, at least 300, at least 400, at least 500, at least 600, at least 700, at least 800, at least 900, at least 1000, at least 1100, at least 1200, at least 1300, at least 1400, at least 1500, at least 1600, at least 1700, at least 1800, at least 1900, or at least 2000 amino acids. In some embodiments, the peptide linker comprises a peptide having the formula $[(Gly)_x\text{-}Ser_y]_z$ where x is from 1 to 4, y is 0 or 1, and z is from 1 to 50 (SEQ ID NO:232). In other embodiments, one or more of the linkers comprise a non-peptide linker.

In some embodiments, the heterologous moiety comprises a half-life extending moiety comprising a low-complexity polypeptide. In some embodiments, the chimeric molecule comprises a half-life extending moiety comprising albumin, albumin binding polypeptide or fatty acid, Fc, transferrin, PAS, the C-terminal peptide (CTP) of the β subunit of human chorionic gonadotropin, polyethylene glycol (PEG), hydroxyethyl starch (HES), albumin-binding small molecules, vWF, a clearance receptor or fragment thereof which blocks binding of the chimeric molecule to a clearance receptor, or any combinations thereof. In some embodiments, the half-life extending moiety comprises an Fc region. In other embodiments, the half-life extending moiety comprises two Fc regions fused by a linker. In some embodiments, the chimeric molecule comprises a clotting factor comprising FVII zymogen, activatable FVII, activated FVII, FIX zymogen, activatable FIX, activated FIX, FX zymogen, activatable FX, or activated FX.

The instant disclosure also provides a chimeric molecule comprising a first polypeptide chain and a second polypeptide chain, which are associated with each other, (1) wherein the first polypeptide chain comprises a light chain of a clotting factor and a targeting moiety, which binds to a platelet, and the second polypeptide chain comprises a heavy chain of the clotting factor and a heterologous moiety; (2) wherein the first polypeptide chain comprises a light chain of a clotting factor and a heterologous moiety and the second polypeptide chain comprises a heavy chain of the clotting factor and a targeting moiety, which binds to a platelet; (3) wherein the first polypeptide chain comprises a light chain of a clotting factor, a heterologous moiety, and a targeting moiety, which binds to a platelet, and the second polypeptide comprises a heavy chain of the clotting factor; or (4) wherein the first polypeptide chain comprises a light chain of a clotting factor, a targeting moiety, which binds to a platelet, and a heterologous moiety and the second polypeptide chain comprises a heavy chain of the clotting factor, and wherein the clotting factor is FVII, FIX, or FX.

In some embodiments, the chimeric molecule comprises a first polypeptide chain and a second polypeptide chain, which are associated with each other, (1) wherein the first polypeptide chain comprises $CF_L$-H or H-$CF_L$ and the second polypeptide chain comprises $CF_H$-Tm or Tm-$CF_H$; (2) wherein the first polypeptide chain comprises $CF_L$-Tm or Tm-$CF_L$ and the second polypeptide chain comprises $CF_H$-H or H-$CF_H$; (3) wherein the first polypeptide chain comprises $CF_L$-H-Tm or Tm-H-$CF_L$ and the second polypeptide chain comprises $CF_H$; or (4) wherein the first polypeptide chain comprises $CF_L$-Tm-H or H-Tm-$CF_L$ and the second polypeptide chain comprises $CF_H$; wherein H is a heterologous moiety, $CF_H$ is a heavy chain of a clotting factor, $CF_L$ is a light chain of the clotting factor, Tm is a targeting moiety which binds to a platelet, and, L is an optional linker. In some embodiments, the chimeric molecule comprises a formula selected from (1) Tm-$CF_H$:$CF_L$-H; (2) H-$CF_H$:$CF_L$-Tm; (3) Tm-H-$CF_L$:$CF_H$; or (4) H-Tm-$CF_L$:$CF_H$; wherein, H is a heterologous moiety; $CF_H$ is a heavy chain of a clotting factor; $CF_L$ is a light chain of the clotting factor; Tm is a targeting moiety, which binds to a platelet; L is an optional linker; and: represents a covalent or non-covalent bond between $CF_H$ and $CF_L$.

In some embodiments, the association between the first polypeptide chain and the second polypeptide chain in the chimeric molecule is a covalent bond or a non-covalent bond. In other embodiment, the association between the first polypeptide chain and the second polypeptide chain in the chimeric molecule is a covalent bond between the heavy chain and the light chain of the clotting factor. In some embodiments, the covalent bond is a disulfide bond.

The present disclosure also provides a chimeric molecule comprising a single polypeptide chain, which comprises, from N terminus to C terminus, (a) a light chain of a clotting factor, a heterologous moiety, a protease cleavage site, a heavy chain of the clotting factor, and a targeting moiety which binds to a platelet or (b) a light chain of a clotting factor, a targeting moiety which binds to a platelet, a protease cleavage site, a heavy chain of the clotting factor, and a heterologous moiety, wherein the clotting factor is FVII, FIX, or FX. In some embodiments, the protease cleavage site is an intracellular processing site. In some embodiments, the intracellular processing site is processed by a proprotein convertase. In some embodiments, the proprotein convertase is selected from PC5, PACE, PC7, and any combinations thereof.

In some embodiments, the targeting moiety in the chimeric molecule is selected from: an antibody or antigen binding molecule thereof, a receptor binding portion of a receptor, and a peptide. In some embodiments, the targeting moiety selectively binds to a resting platelet or an activated platelet. In other embodiments, the targeting moiety selectively binds to a target selected from the group consisting of: GPIba, GPVI, GPIX, a nonactive form of glycoprotein IIb/IIIa ("GPIIb/IIIa"), an active form of GPIIb/IIIa, P selectin, GMP-33, LAMP-1, LAMP-2, CD40L, LOX-1, and any combinations thereof. In certain embodiments, the targeting moiety is an anti-GPIIb/IIIa antibody or antigen-binding molecule thereof. In specific embodiments, the anti-GPIIb/IIIa antibody or antigen-binding molecule thereof is a GPIIb/IIIa antibody or antigen-binding molecule thereof disclosed herein. In some embodiments, a heterologous moiety in the chimeric molecule is a half-life extending moiety. In some embodiments, the half-life extending moiety is a low-complexity polypeptide. In some embodiments, the half-life extending moiety is selected from albumin, albumin binding polypeptide or fatty acid, Fc, transferrin, PAS, the C-terminal peptide (CTP) of the β subunit of human chorionic gonadotropin, polyethylene glycol (PEG), hydroxyethyl starch (HES), albumin-binding small molecules, vWF, a clearance receptor or fragment thereof which blocks binding of the chimeric molecule to a clearance receptor, and any combinations thereof.

Also provided is a nucleic acid molecule or a set of nucleic acid molecules encoding an anti-GPIIb/IIIa antibody or antigen-binding molecule thereof disclosed herein, or any of the chimeric molecules disclosed herein, or a complement thereof. Also provided are a vector or a set of vectors comprising such nucleic acid molecule or the set of the nucleic acid molecules or a complement thereof. Also provided is a host cell comprising the vector.

The instant disclosure also provides a method for producing an anti-GPIIb/IIIa antibody or antigen-binding molecule thereof or chimeric molecule disclosed herein, such method comprising culturing the host cell disclosed herein and recovering the antibody, antigen-binding molecule thereof, or the chimeric molecule from the culture medium. Also provided is a pharmaceutical composition comprising (i) an anti-GPIIb/IIIa antibody or antigen-binding molecule thereof disclosed herein, or (ii) a chimeric molecule disclosed herein, or (iii) a nucleic acid molecule or the set of nucleic acid molecules disclosed herein, or (iv) a vector or set of vectors disclosed herein, and a pharmaceutically acceptable carrier. Also provided is method of reducing a frequency or degree of a bleeding episode in a subject in need thereof comprising administering (i) a chimeric molecule disclosed herein, (ii) a nucleic acid molecule or set of nucleic acid molecules disclosed herein, (iii) a vector or set of vectors disclosed herein, or (iii) a pharmaceutical composition disclosed herein.

Also provided is a method of reducing or preventing an occurrence of a bleeding episode in a subject in need thereof comprising administering (i) a chimeric molecule disclosed herein, (ii) a nucleic acid molecule or set of nucleic acid molecules disclosed herein, (iii) a vector or the set of vectors disclosed herein, or (iv) a pharmaceutical composition disclosed herein. In some embodiments, the subject has developed or has a tendency to develop an inhibitor against Factor VIII ("FVIII"), Factor IX ("FIX"), or both. In some embodiments, the inhibitor against FVIII or FIX is a neutralizing antibody against FVIII, FIX, or both. In some embodiments, the bleeding episode is caused by a blood coagulation disorder. In some embodiments, the blood coagulation disorder is hemophilia A or hemophilia B. In some embodiments, the bleeding episode is derived from hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, bleeding in the illiopsoas sheath, or any combinations thereof. In certain embodiments, the subject is a human subject.

The instant disclosure also provides the chimeric molecule disclosed herein, the nucleic acid molecule or the set of nucleic acid molecules disclosed herein, the vector or the set of vectors disclosed herein, or the pharmaceutical composition disclosed herein for use in reducing a frequency or degree of a bleeding episode or reducing or preventing an occurrence of a bleeding episode in a subject in need thereof. Also provided is the use of the chimeric molecule disclosed herein, the nucleic acid molecule or the set of nucleic acid molecules disclosed herein, the vector or the set of vectors disclosed herein, or the pharmaceutical composition disclosed herein for the manufacture of a medicament for reducing a frequency or degree of a bleeding episode or reducing or preventing an occurrence of a bleeding episode in a subject in need thereof.

Also provided is a method to target a therapeutic or prophylactic agent to the surface of platelets comprising fusing the agent to one of the GPIIb/IIIa antibodies or antigen-binding molecules thereof disclosed herein. Also provided is a method to increase the activity of a therapeutic or prophylactic agent comprising fusing the agent to a GPIIb/IIIa antibody or antigen-binding molecule thereof disclosed herein. In some embodiments, the therapeutic or prophylactic agent is a clotting factor.

The present disclosure also provides a method to improve the pharmacokinetic properties of a clotting factor comprising fusing the clotting factor to the GPIIb/IIIa antibody or antigen-binding molecule thereof disclosed herein. In some embodiments, the method further comprises fusing or conjugating the clotting factor and/or the GPIIb/IIIa antibody or antigen-binding molecule thereof disclosed herein to a half-life extending moiety.

The present disclosure also provides a method of measuring the level of platelets in plasma of a subject in need thereof comprising contacting the GPIIb/IIIa antibody or antigen binding molecule thereof disclosed herein with the plasma from the subject and measuring the level of platelets in plasma.

BRIEF DESCRIPTION OF THE DRAWINGS/FIGURES

FIG. 1 is a diagram summarizing the screening process used to identify the antibodies of the present disclosure.

FIG. 2A shows a diagram of an anti-GPIIb/IIIa antibody. FIGS. 2B, 2C, and 2D are schematic representations of the possible effects of the binding of antibodies to non-active GPIIb/IIIa. Antibodies can be inert (no activation) (FIG. 2B), activating (FIG. 2C), or capable of indirect activation via simultaneous interaction with GPIIb/IIIa and the FcγRIIA receptor (FIG. 2D). Also shown is a schematic representation of the nonactive (bent) and active (extended) conformations of GPIIb/IIIa (FIG. 2E). The cross over FIG. 2C indicates that platelet activating antibodies are not selected as targeting moieties for clotting factors.

FIG. 3A shows the markers detected in the X- and y-axes in the flow cytometry profiles shown in FIGS. 3B, 3C, 3D, and 3E. FIG. 3B shows flow cytometry profiles of platelets exposed to culture medium only or with an agonist in the presence or absence of an FcγRIIA inhibitory antibody. FIG. 3C shows flow cytometry profiles of platelets incubated with hybridoma clone P24H2 supernatant in the presence or absence of an FcγRIIA inhibitory antibody. FIG. 3D shows flow cytometry profiles of platelets incubated with hybridoma clone 35E2 supernatant in the presence or absence of an FcγRIIA inhibitory antibody. FIG. 3E shows flow cytometry profiles of platelets incubated with supernatants from hybridoma clones P24A4, P31G2, and P35E9, respectively, in the presence or absence of an FcγRIIA inhibitory antibody.

FIGS. 4A and 4B show identity matrices corresponding to heavy chain variable domain (VH) sequences (FIG. 4A) and light chain variable domain (VL) sequences (FIG. 4B) of antibodies against GPIIb/IIIa in which the shaded cells indicate which antibodies share identical VL or VH sequences.

FIGS. 5A and 5B show ClustalX multiple sequence alignments of the VH sequences of monoclonal antibodies 1H6, 38A8, 12B2, 38F6, 2A2, 36A8, 4B11, 34D10, 28F4, 23C10, 28C2, 5C4, 9D6, and 18F7 (FIG. 5A) (SEQ ID NOS:8, 10, 14, 16, 1, 5, 7, 3, 23, 18, 19, 17, 21 and 12, respectively, in order of appearance) and of the VL sequences of monoclonal antibodies 28C2, 9D6, 1H6, 38A8, 12B2, 18F7, 28F4, 34D10, 36A8, and 2A2 (FIG. 5B) (SEQ ID NOS:20, 22, 9, 11, 15, 13, 24, 4, 6 and 2, respectively, in order of appearance). Degree of amino acid conservation is indicating above the alignment ("*" =identical; ":" =strongly conserved; "." =poorly conserved), as well as the bars below the alignment. The ClustalX highlighting scheme, which is dependent on amino acid physicochemical and/or structural properties and conservation, was used to highlight the sequences.

FIG. 6 shows a ClustalX multiple sequence alignment of the VH sequences of the 1H6, 38A8, 12B2, 38F6, 2A2, 36A8, 4B11, 34D10, 28F4, 23C10, 28C2, 5C4, 9D6, and 18F7 antibodies (SEQ ID NOS:8, 10, 14, 16, 3, 5, 7, 1, 23, 18, 19, 17, 21 and 12, respectively, in order of appearance), indicating the location of the complementarity determining regions (CDR). The location of each CDR (CDR1, CDR2, and CDR3) according to the EU index is indicated. The location of identical, conserved and partially conserved amino acid residues is indicated below the alignment.

FIG. 7 shows a ClustalX multiple sequence alignment of the VL sequences of the 28C2, 9D6, 1H6, 38A8, 12B2, 18F7, 28F4, 34D10, 36A8, and 2A2 antibodies (SEQ ID NOS:20, 22, 9, 11, 15, 13, 24, 2, 6 and 4, respectively, in order of appearance), indicating the location of CDR1, CDR2, and CDR3 according to the EU index. The location of identical, conserved and partially conserved amino acid residues is indicated below the alignment.

FIG. 8 shows percentage identity matrices corresponding to the sequences included in the ClustalX multiple sequence alignments shown in FIG. 3 (top matrix) and FIG. 4 (bottom matrix).

FIG. 9 shows ClustalX multiple sequence alignments corresponding to the VH sequences in FIG. 2 clustered according to their specificity for the α (SEQ ID NOS:8, 10, 3, 5, 1 and 12, respectively, in order of appearance) or β (SEQ ID NOS:14, 23, 19 and 21, respectively, in order of appearance) subunit of GPIIb/IIIa.

FIG. 10 shows ClustalX multiple sequence alignments corresponding to the VL sequences in FIG. 3 clustered according to their specificity for the a (SEQ ID NOS:9, 11, 13, 2, 6 and 4, respectively, in order of appearance) or β (SEQ ID NOS:20, 22, 15 and 24, respectively, in order of appearance) subunit of GPIIb/IIIa.

FIG. 11 shows ClustalX multiple sequence alignments corresponding to the VH sequences in FIG. 2 clustered according to their ability to compete with fibrinogen for binding to GPIIb/IIIa. FIG. 11 discloses "No Fibrinogen Competition" sequences as SEQ ID NOS 3, 1, 5 and 14 and "Fibrinogen Competition" sequences as SEQ ID NOS 8, 5, 12, 23, 19 and 21, all respectively, in order of appearance.

FIG. 12 shows ClustalX multiple sequence alignments corresponding to the VL sequences in FIG. 2 clustered according to their ability to compete with fibrinogen for binding to GPIIb/IIIa. FIG. 12 discloses "No Fibrinogen Competition" sequences as SEQ ID NOS 4, 2, 6 and 15 and "Fibrinogen Competition" sequences as SEQ ID NOS 9, 13, 11, 20, 22 and 24, all respectively, in order of appearance.

Figure 14:
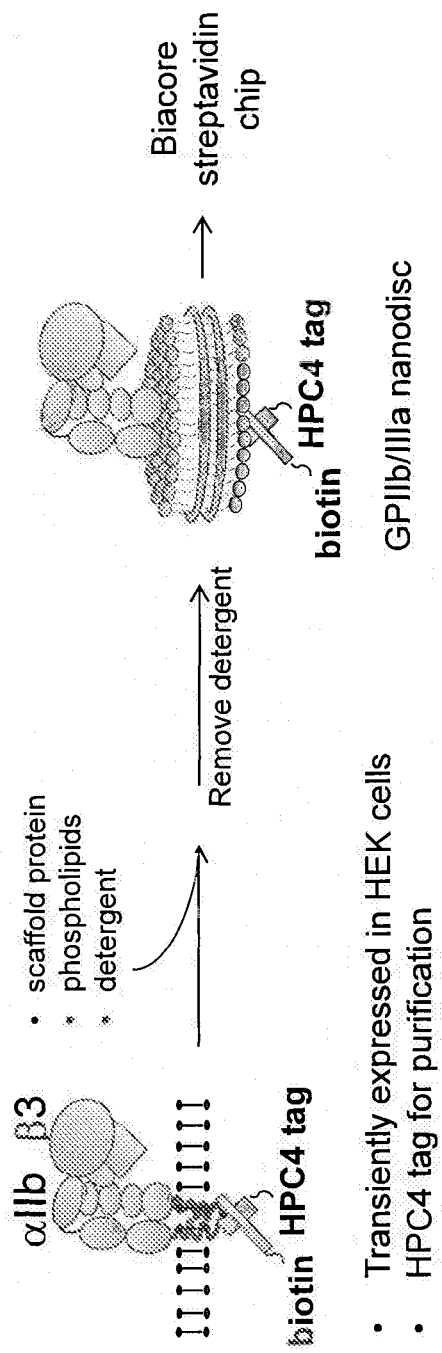

FIG. 14 is a diagram summarizing the experimental method used to study the binding kinetics and affinity of a platelet-targeted rFVIIa chimeric molecule for GPIIb/IIIa. GPIIb/IIIa constructs were doubly labeled with biotin and the HPC4 purification tag and incorporated into GPIIb/IIIa nanodiscs. Binding of the platelet-targeted rFVIIa to the nanodiscs was studied using Surface Plasmon Resonance (SPR).

Figure 15:
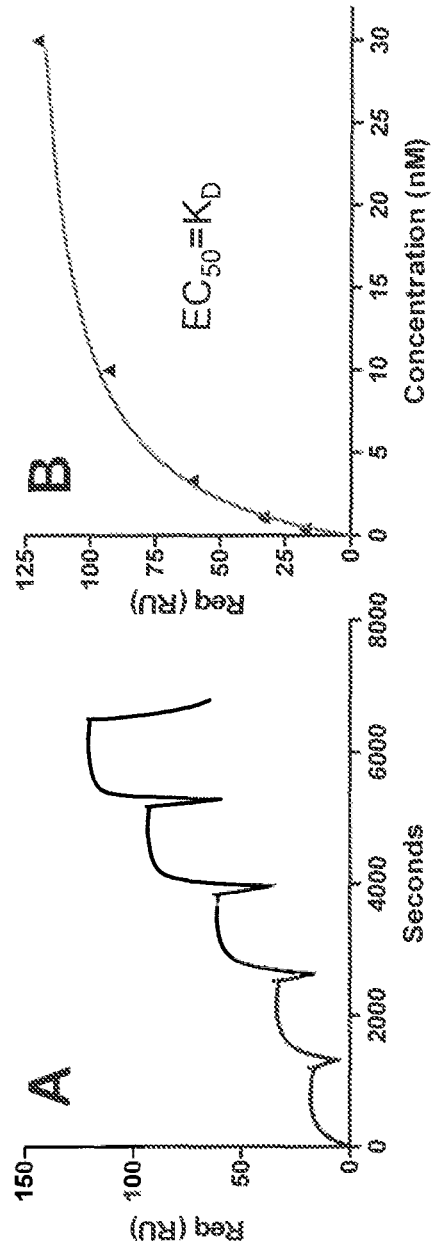

FIG. 15 shows single cycle steady-state binding of a platelet-targeted rFVIIa chimeric molecule to GPIIb/IIIa nanodiscs measured by SPR. FIG. 15A shows the binding as a function of time, and FIG. 15B shows the binding as a function of concentration.

Figure 16:
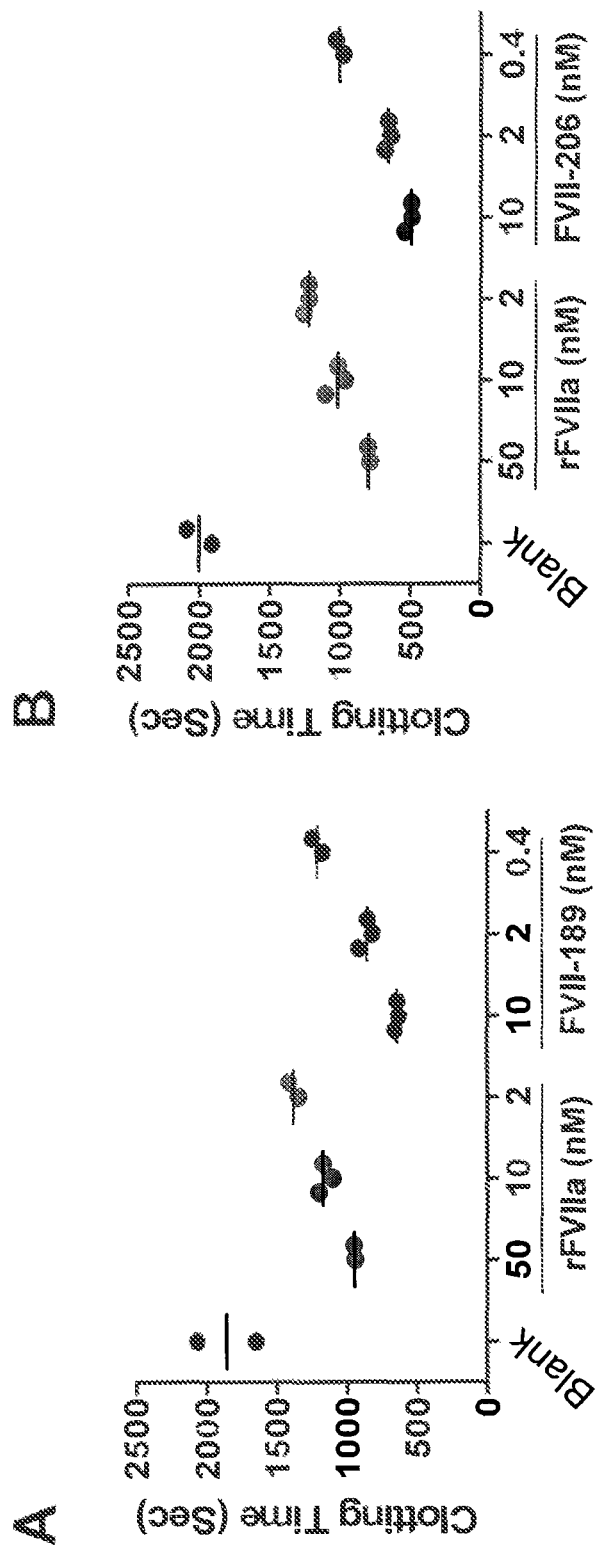

FIG. 16 shows ROTEM assay results corresponding to rFVIIa compared to FVII-189 (a platelet-targeted FVIIa chimeric molecule where the targeting moiety is an scFv derived from the 34D10 antibody) (FIG. 16A), and to rFVIIa compared to FVII-206 (a platelet-targeted FVIIa chimeric molecule where the targeting moiety is an scFv derived from the 12B2 antibody) (FIG. 16B).

FIG. 17 shows ROTEM assay results corresponding to rFVIIa compared to FVII-204 (a platelet-targeted FVIIa chimeric molecule where the targeting moiety is an scFv derived from the 38A8 antibody) (FIG. 17A), and to rFVIIa compared to FVII-163 (a platelet-targeted FVIIa chimeric molecule where the targeting moiety is an scFv derived from the PDG13 antibody) and FVII-189 (FIG. 17B).

Figure 18:
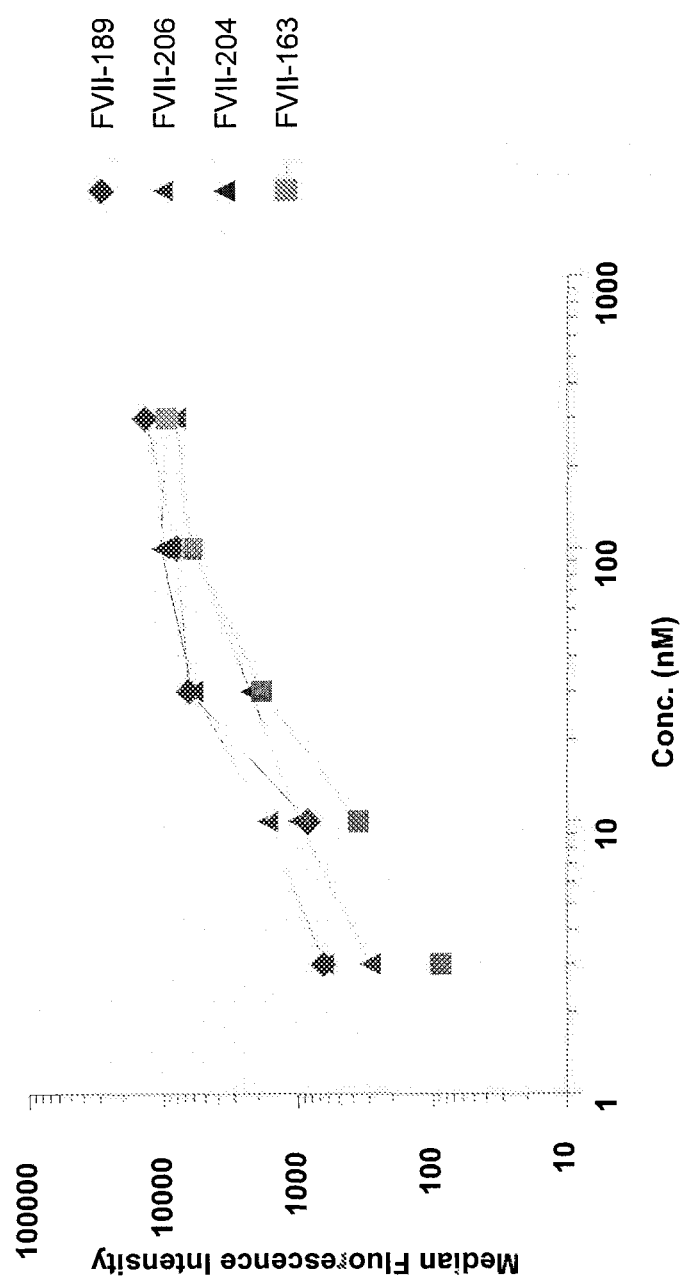

FIG. 18 shows the result of flow cytometry based platelet-binding assays, in which the median fluorescence intensity (MFI) was plotted against the concentration of the chimeric molecules spiked in blood. MFI represented the relative concentration of the chimeric molecules that bound to human platelets.

Figure 19:
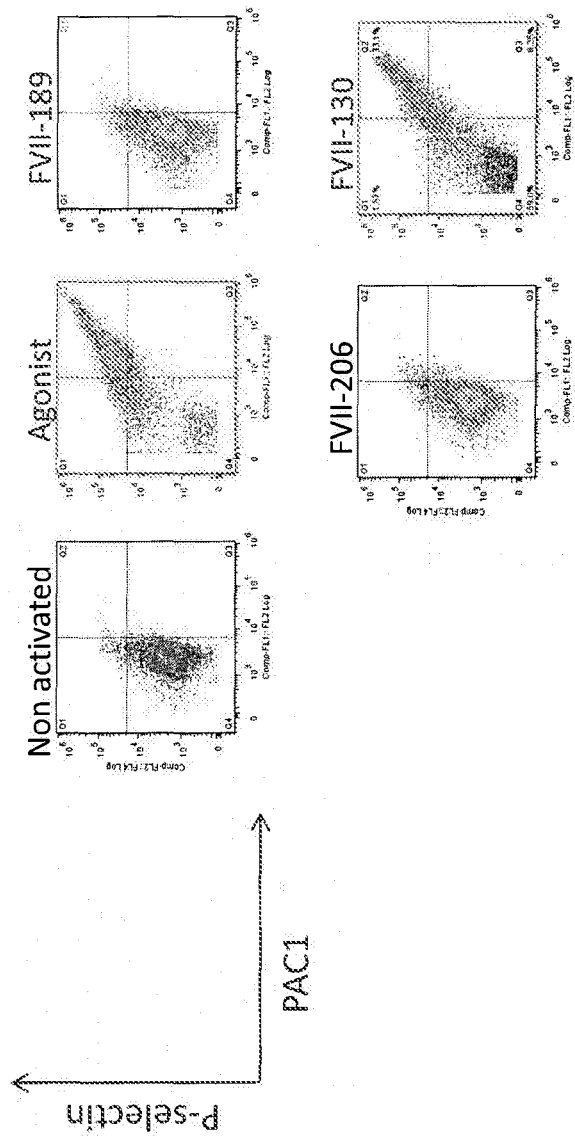

FIG. 19 shows flow cytometry profiles of the activation of gel-purified platelets. Platelets were non-activated, activated after incubation with an agonist, or incubated with chimeric molecules FVII-189, FVII-206, and FVII-130 (a platelet-targeted FVII comprising an scFv derived from the AP3 antibody and an Fc moiety).

Figure 20:
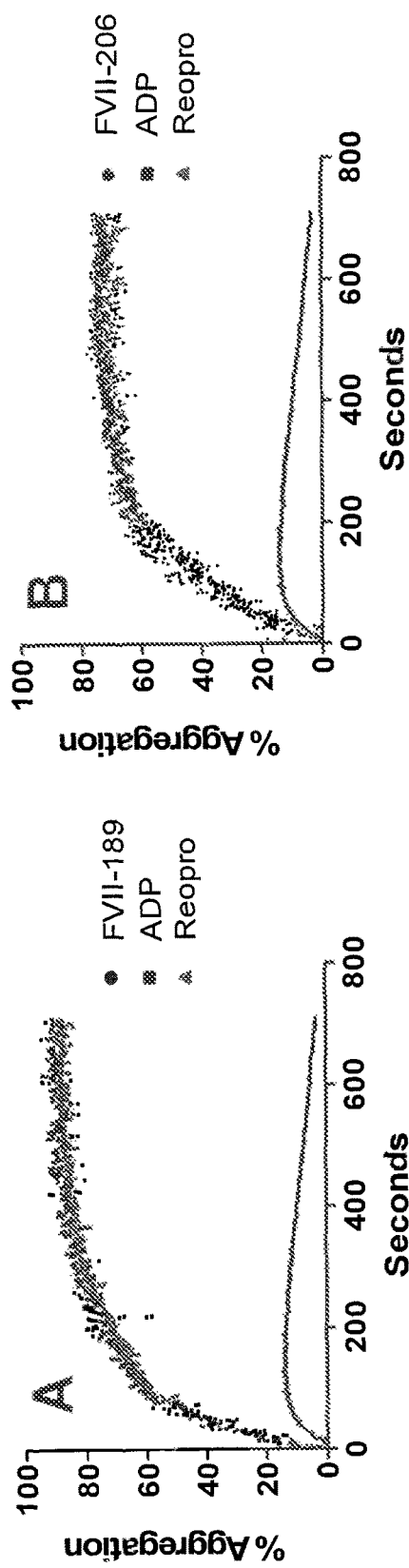

FIG. 20 shows ADP-induced aggregation of platelet-rich plasma in the presence of chimeric molecules FVII-189 (FIG. 20A) or FVII-206 (FIG. 20B). In both cases, ADP and REOPRO® (Abciximab) were used as controls.

Figure 21:
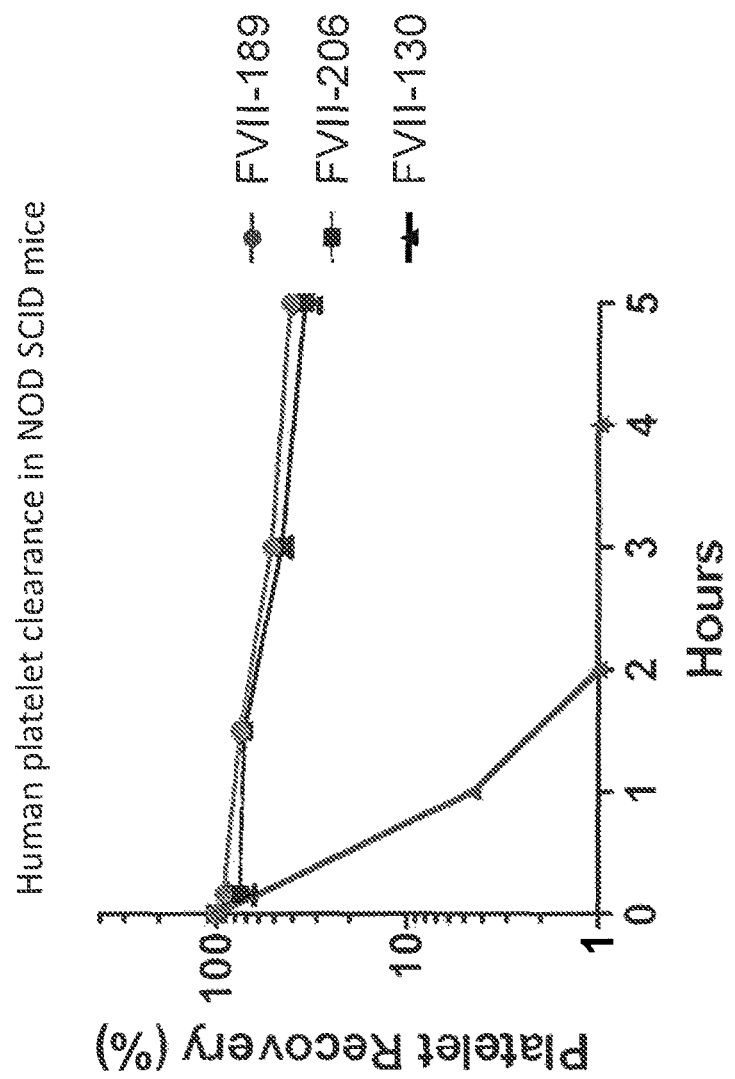

FIG. 21 shows human platelet clearance from NSG mice after administration of the chimeric molecules FVII-189, FVII-206, FVII204, or FVII-130. The NSG mice had been transfused with human platelets before treating with the chimeric molecules.

Figure 22:
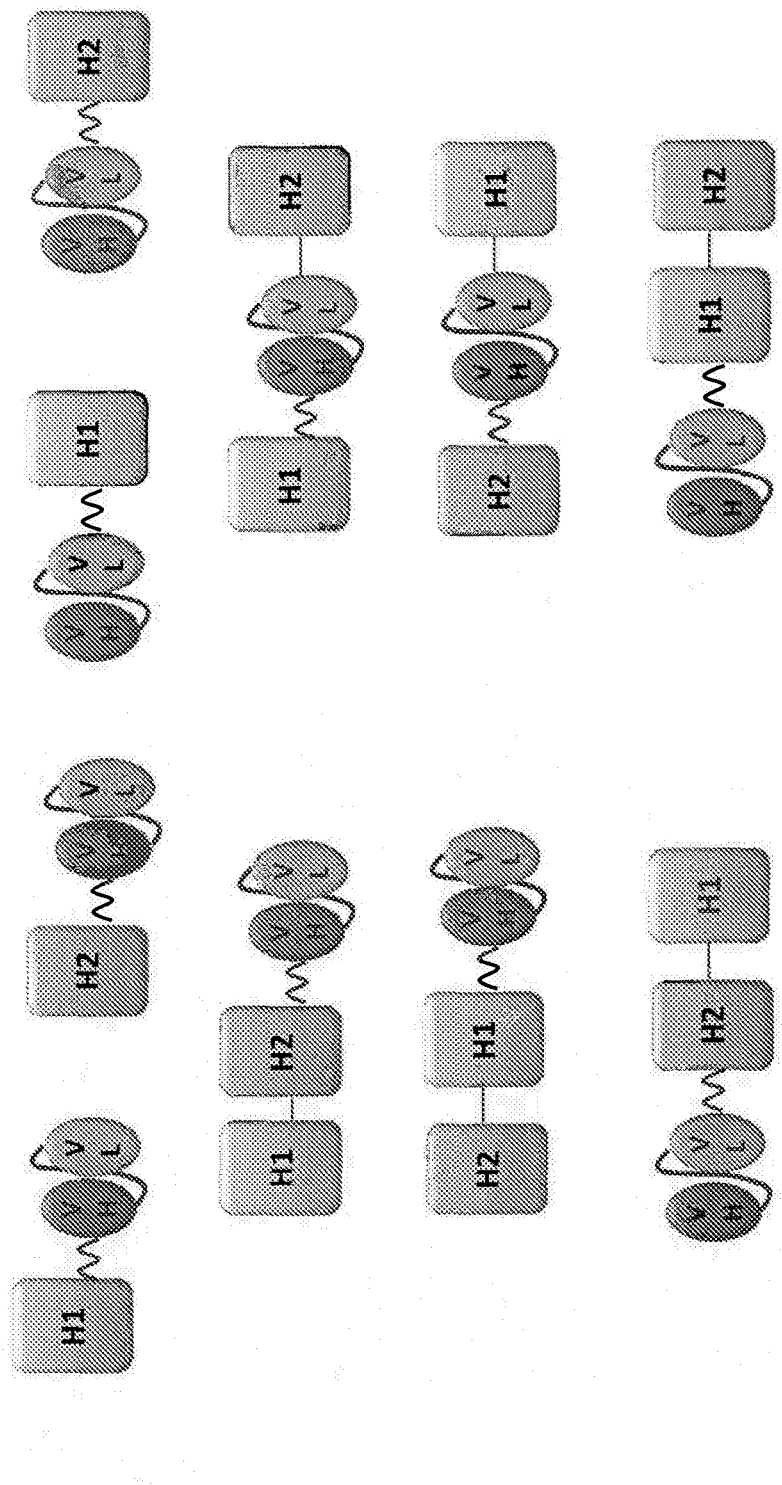

FIG. 22 shows possible configuration for chimeric molecules comprising one or two heterologous moieties (H1 and/or H2) and scFv moieties derived for GPIIb/IIIa-specific antibodies.

Figure 23:
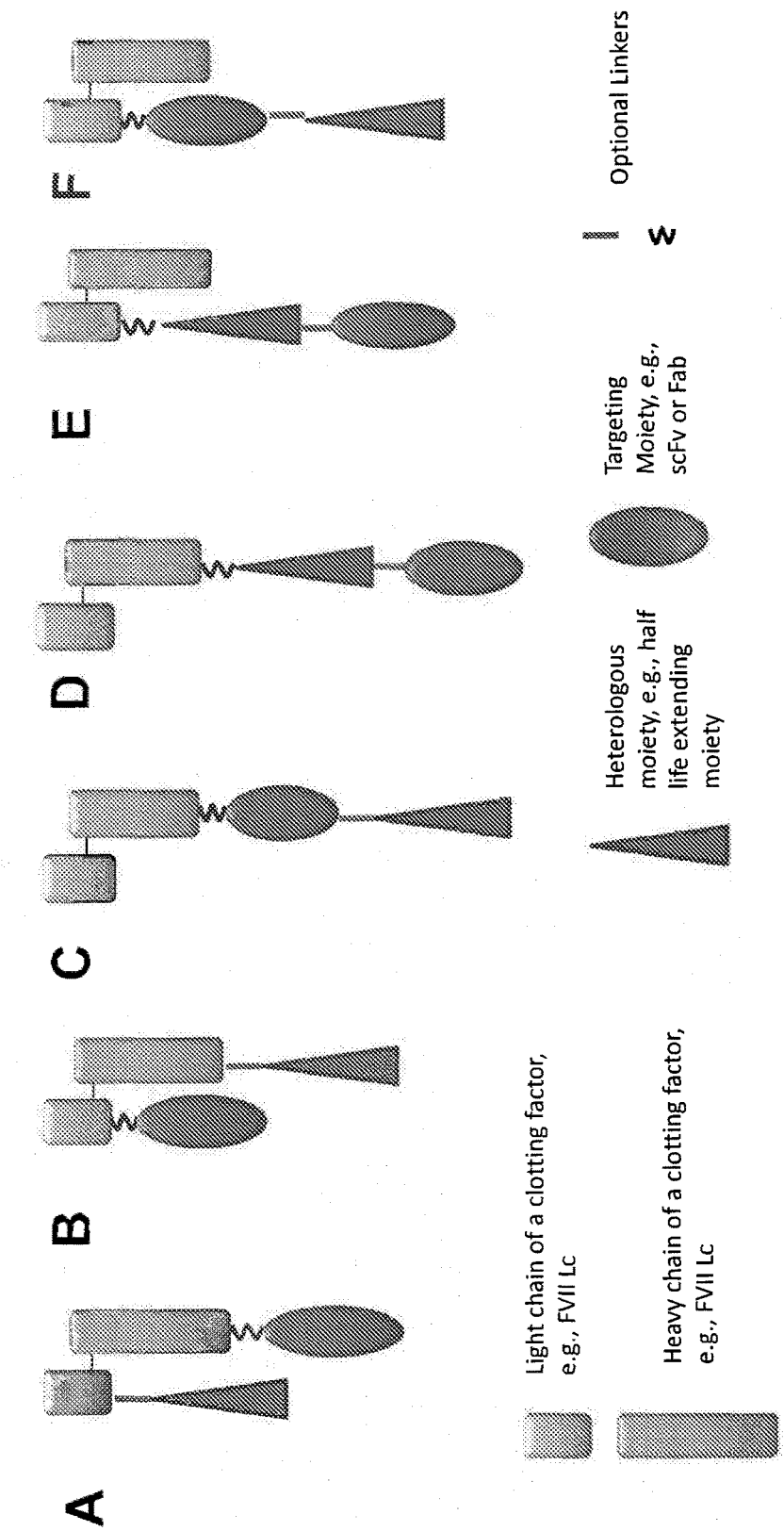

FIG. 23 shows possible configurations for chimeric molecules comprising the heavy and light chains of a clotting factor (e.g., FVII), an scFv targeting moiety (e.g., derived for GPIIb/IIIa-specific antibodies), a heterologous moiety (e.g., a half-life extending moiety), and at least one optional linker.

DETAILED DESCRIPTION

The clotting factor FVIIa has low affinity for platelets, the site of action for clot formation. Thus, a possible approach to increase activity of FVIIa is to target the clotting to platelet receptors via targeting moieties (e.g., Fab or scFv), which can increase the affinity of FVIIa for platelets thereby boosting activity. Multiple receptors are expressed exclusively on platelet. For example, GPIIb/IIIa ($\alpha$IIb$\beta$3) is an integrin specific to platelets which expressed at high levels. Activated GPIIb/IIIa receptor binds fibrinogen and modulates platelet aggregation. Upon activation, the GPIIb/IIIa receptors change from a bent low ligand affinity conformation to an extended high ligand affinity conformation. Thus, targeting strategies can be directed either the active or the non-active conformations of the receptor.

The present disclosure provides antibodies against GPIIb/IIIa that are capable of targeting the non-active form of the receptor. The GPIIb/IIIa antibodies and antigen-binding molecules derived from these antibodies can be non-activating, and be used, for example, to target therapeutic molecules (e.g., clotting factors or other molecules capable of having a pharmacological effect in platelets) to the platelet surface. In addition to their use as targeting moieties, these antibodies and antigen-binding molecules thereof can be used for diagnostics, for example, by conjugation to a detectable label.

In some embodiments, the GPIIb/IIIa antibodies and antigen-binding molecules thereof can be activating, for example, (i) by directly activating the GPIIb/IIIa receptors through binding to the $\alpha$ and/or $\beta$ subunits of the receptor, (ii) by indirectly activating the GPIIb/IIIa via simultaneous binding to the $\alpha$ and/or $\beta$ subunits of the receptor and to an Fc receptor (e.g., an Fc$\gamma$II receptor), or (iii) by interfering with the interaction between the GPIIb/IIIa receptor and fibrinogen.

In addition, the present invention relates to chimeric molecules comprising the GPIIb/IIIa antibodies and antigen-binding molecules thereof disclosed herein as targeting moieties, and one or more heterologous moieties. For example, a heterologous moiety comprising a therapeutic molecule (for example, a procoagulant molecule such as a clotting factor), and optionally a second heterologous moiety comprising, for example, a PK enhancing moiety (i.e., a molecule which can improve various pharmacokinetic properties, e.g., half-life).

Exemplary GPIIb/IIIa antibodies and antigen-binding molecules thereof, as well as exemplary constructs (chimeric molecules) comprising such antibodies and antigen-binding molecules thereof (e.g., scFv or F(ab)) are illustrated in the instant description and figures. In some embodiments, the invention pertains to chimeric molecules having the structures set forth, for example, in FIGS. 22 and 23. In other embodiments, the invention pertains to polynucleotide encoding chimeric molecule constructs disclosed herein.

In order to provide a clear understanding of the specification and claims, the following definitions are provided below.

I. Definitions

It is to be noted that the term "a" or "an" entity refers to one or more of that entity; for example, "a nucleotide sequence," is understood to represent one or more nucleotide sequences. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

It is understood that wherever embodiments are described herein with the language "comprising," otherwise analogous embodiments described in terms of "consisting of" and/or "consisting essentially of" are also provided.

The use of numerical values in the various ranges specified in this application, unless expressly indicated otherwise, are stated as approximations as though the minimum and maximum values within the stated ranges were both preceded by the word "about." In this manner, slight variations above and below the stated ranges can be used to achieve substantially the same results as values within the ranges. As used herein, the terms "about" and "approximately" when referring to a numerical value shall have their plain and ordinary meanings to one skilled in the art relevant to the range or element at issue.

The amount of broadening from the strict numerical boundary depends upon many factors. For example, some of the factors to be considered can include the criticality of the element and/or the effect a given amount of variation will have on the performance of the claimed subject matter, as well as other considerations known to those of skill in the art. Thus, as a general matter, "about" or "approximately" broaden the numerical value. For example, in some cases, "about" or "approximately" can mean±5%, or ±10%, depending on the relevant technology. Also, the disclosure of ranges is intended as a continuous range including every value between the minimum and maximum values recited.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Systeme International de Unites (SI) accepted form. Numeric ranges are inclusive of the numbers defining the range. Unless otherwise indicated, amino acid sequences are written left to right in amino to carboxy orientation. The headings provided herein are not limitations of the various embodiments of the disclosure, which can be by reference to the specification as a whole. Accordingly, the terms defined immediately below are more fully defined by reference to the specification in its entirety. Amino acids are referred to herein by either their commonly known three letter symbols or by the one-letter symbols recommended by the IUPAC-IUB Biochemical Nomenclature Commission. Nucleotides, likewise, are referred to by their commonly accepted single-letter codes.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "amino acid chain," or any other term used to refer to a chain or chains of two or more amino acids, are included within the definition of "polypeptide," and the term "polypeptide" can be used instead of, or interchangeably with any of these terms.

As used herein the term "protein" is intended to encompass a molecule comprised of one or more polypeptides, which can in some instances be associated by bonds other than amide bonds.

Polypeptides can be either monomers or multimers. For example, in one embodiment, an antibody, an antigen-binding molecule thereof, or a chimeric molecule of the invention can be a dimeric polypeptide. A dimeric antibody, an antigen-binding molecule thereof can comprise two polypeptide chains or can consist of one polypeptide chain (e.g., in the case of an scFc molecule). In one embodiment, the dimers can be a homodimer, comprising two identical monomeric subunits or polypeptides (e.g., two identical Fc moieties or two identical biologically active moieties). In another embodiment, the dimers are heterodimers, comprising two non-identical monomeric subunits or polypeptides (e.g., comprising two different clotting factors or portions thereof or one clotting factor only). See, e.g., U.S. Pat. No. 7,404,956, incorporated herein by reference.

The terms "polypeptide" and "protein" are also intended to refer to the products of post-expression modifications, including without limitation glycosylation, acetylation, phosphorylation, amidation, derivatization by known protecting/blocking groups, proteolytic cleavage, or modification by non-naturally occurring amino acids. A polypeptide or protein can be derived from a natural biological source or produced by recombinant technology, but is not necessarily translated from a designated nucleic acid sequence. It can be generated in any manner, including by chemical synthesis.

A polypeptide which is "isolated" is a polypeptide which is in a form not found in nature. Isolated polypeptides include those which have been purified to a degree that they are no longer in a form in which they are found in nature. In some embodiments, a polypeptide which is isolated is substantially pure.

"Derivatives" of GPIIb/IIIa antibodies, antigen-binding molecules thereof, or chimeric molecules of the invention are polypeptides or proteins which have been altered so as to exhibit additional features not found on the native polypeptide or protein. Also included as "derivatives" are those peptides that contain one or more naturally occurring amino acid derivatives of the twenty standard amino acids. A polypeptide or amino acid sequence "derived from" a designated polypeptide or protein refers to the origin of the polypeptide. In one embodiment, the polypeptide or amino acid sequence which is derived from a particular sequence has an amino acid sequence that is essentially identical to that sequence or a portion thereof, wherein the portion consists of at least about 10 to about 20 amino acids, at least about 20 to about 30 amino acids, or at least about 30 to about 50 amino acids, or which is otherwise identifiable to one of ordinary skill in the art as having its origin in the sequence.

Polypeptides that are "variants" of another polypeptide can have one or more mutations relative to the starting polypeptide, e.g., one or more amino acid residues which have been substituted with another amino acid residue or which has one or more amino acid residue insertions or deletions. In one embodiment, the polypeptide comprises an amino acid sequence which is not naturally occurring. Such variants necessarily have less than 100% sequence identity or similarity with the starting polypeptide. In another embodiment, the variant will have an amino acid sequence from about 75% to less than 100% amino acid sequence identity or similarity with the amino acid sequence of the starting polypeptide, for example, from about 80% to less than 100%, from about 85% to less than 100%, from about 90% to less than 100% (e.g., 91%, 92%, 93%, 94%, 95%, 96%, 97%, 98%, 99%) and from about 95% to less than 100%, e.g., over the length of the variant molecule. In one embodiment, there is one amino acid difference between a starting polypeptide sequence and the sequence derived therefrom.

The term "fragment" when referring to GPIIb/IIIa antibodies, antigen-binding molecules thereof, chimeric molecules of the invention, or clotting factors refers to any polypeptides or proteins which retain at least some of the properties of the reference polypeptide or protein. Fragments of polypeptides include proteolytic fragments, as well as deletion fragments.

The term "sequence" as used to refer to a protein sequence, a peptide sequence, a polypeptide sequence, or an amino acid sequence means a linear representation of the amino acid constituents in the polypeptide in an amino-terminal to carboxyl-terminal direction in which residues that neighbor each other in the representation are contiguous in the primary structure of the polypeptide.

The term "amino acid" includes alanine (Ala or A); arginine (Arg or R); aspar-agine (Asn or N); aspartic acid (Asp or D); cysteine (Cys or C); glutamine (Gln or Q); glutamic acid (Glu or E); glycine (Gly or G); histidine (His or H); isoleucine (Ile or I); leucine (Leu or L); lysine (Lys or K); methionine (Met or M); phenylalanine (Phe or F); proline (Pro or P); serine (Ser or S); threonine (Thr or T); tryptophan (Trp or W); tyrosine (Tyr or Y); and valine (Val or V).

Non-traditional amino acids are also within the scope of the invention and include norleucine, omithine, norvaline, homoserine, and other amino acid residue analogues such as those described in Ellman et al. Meth. Enzym. 202:301-336 (1991). To generate such non-naturally occurring amino acid residues, the procedures of Noren et al. Science 244:182 (1989) and Ellman et al., supra, can be used. Briefly, these procedures involve chemically activating a suppressor tRNA with a non-naturally occurring amino acid residue followed by in vitro transcription and translation of the RNA. Introduction of the non-traditional amino acid can also be achieved using peptide chemistries known in the art. As used herein, the term "polar amino acid" includes amino acids that have net zero charge, but have non-zero partial charges in different portions of their side chains (e.g., M, F, W, S, Y, N, Q, and C). These amino acids can participate in hydrophobic interactions and electrostatic interactions. As used herein, the term "charged amino acid" includes amino acids that can have non-zero net charge on their side chains (e.g. R, K, H, E, and D). These amino acids can participate in hydrophobic interactions and electrostatic interactions.

An "amino acid substitution" refers to the replacement of at least one existing amino acid residue in a predetermined amino acid sequence (an amino acid sequence of a starting polypeptide) with a second, different "replacement" amino acid residue. An "amino acid insertion" refers to the incorporation of at least one additional amino acid into a predetermined amino acid sequence. While the insertion will usually consist of the insertion of one or two amino acid residues, the present larger "peptide insertions", can be made, e.g. insertion of about three to about five or even up to about ten, fifteen, or twenty amino acid residues. The inserted residue(s) can be naturally occurring or non-naturally occurring as disclosed above. An "amino acid deletion" refers to the removal of at least one amino acid residue from a predetermined amino acid sequence.

A "conservative amino acid substitution" is one in which the amino acid residue is replaced with an amino acid residue having a similar side chain. Families of amino acid residues having similar side chains have been defined in the art, including basic side chains (e.g., Lys, Arg, and His), acidic side chains (e.g., Asp and Glu), uncharged polar side chains (e.g., Gly, Asn, Gnl, Ser, Thr, Tyr, and Cys), nonpolar side chains (e.g., Ala, Val, Leu, Ile, Pro, Phe, Met, and Trp), beta-branched side chains (e.g., Thr, Val, and Ile) and aromatic side chains (e.g., Tyr, Phe, Trp, and His). Thus, if an amino acid in a polypeptide is replaced with another amino acid from the same side chain family, the substitution is considered to be conservative. In another embodiment, a string of amino acids can be conservatively replaced with a structurally similar string that differs in order and/or composition of side chain family members.

Non-conservative substitutions include those in which (i) a residue having an electropositive side chain (e.g., Arg, His, or Lys) is substituted for, or by, an electronegative residue (e.g., Glu or Asp), (ii) a hydrophilic residue (e.g., Ser or Thr) is substituted for, or by, a hydrophobic residue (e.g., Ala, Leu, He, Phe, or Val), (iii) a cysteine or proline is substituted for, or by, any other residue, or (iv) a residue having a bulky hydrophobic or aromatic side chain (e.g., Val, He, Phe, or Trp) is substituted for, or by, one having a smaller side chain (e.g., Ala or Ser) or no side chain (e.g., Gly).

The term "percent sequence identity" between two polynucleotide or polypeptide sequences refers to the number of identical matched positions shared by the sequences over a comparison window, taking into account additions or deletions (i.e., gaps) that must be introduced for optimal alignment of the two sequences. A matched position is any position where an identical nucleotide or amino acid is presented in both the target and reference sequence. Gaps presented in the target sequence are not counted since gaps are not nucleotides or amino acids. Likewise, gaps presented in the reference sequence are not counted since target sequence nucleotides or amino acids are counted, not nucleotides or amino acids from the reference sequence.

The percentage of sequence identity is calculated by determining the number of positions at which the identical amino acid residue or nucleic acid base occurs in both sequences to yield the number of matched positions, dividing the number of matched positions by the total number of positions in the window of comparison and multiplying the result by 100 to yield the percentage of sequence identity. The comparison of sequences and determination of percent sequence identity between two sequences can be accomplished using readily available software both for online use and for download. Suitable software programs are available from various sources, and for alignment of both protein and nucleotide sequences.

One suitable program to determine percent sequence identity is bl2seq, part of the BLAST suite of program available from the U.S. government's National Center for Biotechnology Information BLAST web site (blast.ncbi.nlm.nih.gov). Bl2seq performs a comparison between two sequences using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and also available from the European Bioinformatics Institute (EBI) at www.ebi.ac.uk/Tools/psa.

Different regions within a single polynucleotide or polypeptide target sequence that aligns with a polynucleotide or polypeptide reference sequence can each have their own percent sequence identity. It is noted that the percent sequence identity value is rounded to the nearest tenth. For example, 80.11, 80.12, 80.13, and 80.14 are rounded down to 80.1, while 80.15, 80.16, 80.17, 80.18, and 80.19 are rounded up to 80.2. It also is noted that the length value will always be an integer.

In certain embodiments, the percentage identity "X" of a first amino acid sequence to a second sequence amino acid is calculated as 100×(Y/Z), where Y is the number of amino acid residues scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be higher than the percent identity of the second sequence to the first sequence.

One skilled in the art will appreciate that the generation of a sequence alignment for the calculation of a percent sequence identity is not limited to binary sequence-sequence comparisons exclusively driven by primary sequence data. Sequence alignments can be derived from multiple sequence alignments. One suitable program to generate multiple sequence alignments is ClustalW2, available from www.clustal.org (ClustalX is a version of the ClustalW2 program ported to the Windows environment). Another suitable program is MUSCLE, available from www.drive5.com/muscle. ClustalW2 and MUSCLE are alternatively available, e.g., from the EBI.

It will also be appreciated that sequence alignments can be generated by integrating sequence data with data from heterogeneous sources such as structural data (e.g., crystallographic protein structures), functional data (e.g., location of mutations), or phylogenetic data. A suitable program that integrates heterogeneous data to generate a multiple sequence alignment is T-Coffee, available at www.tcoffee.org, and alternatively available, e.g., from the EBI. It will also be appreciated that the final alignment used to calculate percent sequence identity can be curated either automatically or manually.

In one embodiment, the antibodies and antigen-binding molecules thereof, as well as the chimeric molecules of the invention can comprise an amino acid sequence derived from a human protein sequence. However, the antibodies and antigen-binding molecules thereof, as well as the chimeric molecules of the invention can comprise one or more amino acids from another mammalian species. In a particular embodiment, the antibodies and antigen-binding molecules thereof, as well as the chimeric molecules of the invention are not immunogenic.

As used herein, the terms "linked," "fused", or "fusion" refer to linkage via a peptide bonds (e.g., genetic fusion), chemical conjugation, or other means known in the art. For example, one way in which molecules or moieties can be linked employs peptide linkers which link the molecules or moieties via peptide bonds. The terms "genetically fused," "genetically linked," or "genetic fusion" are used interchangeably and refer to the co-linear, covalent linkage or attachment of two or more proteins, polypeptides, or fragments thereof via their individual peptide backbones, through genetic expression of a single polynucleotide molecule encoding those proteins, polypeptides, or fragments. Such genetic fusion results in the expression of a single contiguous genetic sequence.

Preferred genetic fusions are in frame, i.e., two or more open reading frames (ORFs) are fused to form a continuous longer ORF, in a manner that maintains the correct reading frame of the original ORFs. Thus, the resulting recombinant fusion protein is a single polypeptide containing two or more protein segments that correspond to polypeptides encoded by the original ORFs (which segments are not normally so joined in nature). In this case, the single polypeptide is cleaved during processing to yield dimeric molecules comprising two polypeptide chains.

As used herein the term "associated with" refers to a covalent or non-covalent bond formed between a first amino acid chain and a second amino acid chain. In one embodiment, the term "associated with" means a covalent, non-peptide bond or a non-covalent bond. In another embodiment, the term "associated with" refers to a covalent, non-peptide bond or a non-covalent bond that is not chemically crosslinked. In another embodiment, it means a covalent bond except a peptide bond. In some embodiments this association is indicated by a colon, i.e., (:). For example, when representing the structure of the clotting factor, "$CF_H$:$CF_L$" refers to a dimer comprising a heavy chain of a clotting factor ($CF_H$) disulfide bonded to a light chain of a clotting factor ($CF_L$) in a N-terminus to C-terminus orientation.

Examples of covalent bonds include, but are not limited to, a peptide bond, a metal bond, a hydrogen bond, a disulfide bond, a sigma bond, a pi bond, a delta bond, a glycosidic bond, an agnostic bond, a bent bond, a dipolar bond, a Pi backbond, a double bond, a triple bond, a quadruple bond, a quintuple bond, a sextuple bond, conjugation, hyperconjugation, aromaticity, hapticity, or antibonding. Non-limiting examples of non-covalent bond include an ionic bond (e.g., cation-pi bond or salt bond), a metal bond, an hydrogen bond (e.g., dihydrogen bond, dihydrogen complex, low-barrier hydrogen bond, or symmetric hydrogen bond), van der Walls force, London dispersion force, a mechanical bond, a halogen bond, aurophilicity, intercalation, stacking, entropic force, or chemical polarity.

As used herein, the terms "chemically crosslinked" and "conjugated" are used interchangeably and refer to chemically linking by covalent bonds between acid side chains of amino acids, either directly or via a linker, e.g., a peptide linker. Chemical crosslinking does not include intramolecular or intermolecular disulfide bonds between Fc moieties of a dimeric Fc region, or non-engineered disulfide bonds between an amino acid of the activatable clotting factor and an amino acid of the enhancer moiety. Chemical crosslinking generally takes place by addition of a cross-linking agent, e.g., a heterobifunctional crosslinking agent. Examples of chemical crosslinking includes one or more photo-reactive bonds by chemically connecting photo-Ile, photo-Met, and photo-Leu (see, Suchanek et al., (2005) *Nature Methods,* 2: 261-267).

The term "antibody" means an immunoglobulin molecule that recognizes and specifically binds to a target, such as a protein (e.g., the GPIIb/IIIa receptor, a subunit thereof, or the receptor complex), polypeptide, peptide, carbohydrate, polynucleotide, lipid, or combinations of the foregoing through at least one antigen recognition site within the variable region of the immunoglobulin molecule.

A typical antibody comprises at least two heavy (HC) chains and two light (LC) chains interconnected by disulfide bonds. Each heavy chain is comprised of a "heavy chain variable region" or "heavy chain variable domain" (abbreviated herein as VH) and a heavy chain constant region. The heavy chain constant region is comprised of three domains, CH1, CH2, and CH3. Each light chain is comprised of a "light chain variable region" or "light chain variable domain" (abbreviated herein as VL) and a light chain constant region. The light chain constant region is comprised of one domain, Cl. The VH and VL regions can be further subdivided into regions of hypervariablity, termed Complementarity Determining Regions (CDR), interspersed with regions that are more conserved, termed framework regions (FW).

Each VH and VL region is composed of three CDRs and four FWs, arranged from amino-terminus to carboxy-terminus in the following order: FW1, CDR1, FW2, CDR2, FW3, CDR3, FW4. The variable regions of the heavy and light chains contain a binding domain that interacts with an antigen. As used herein, the term "antibody" encompasses intact polyclonal antibodies, intact monoclonal antibodies, antibody fragments (such as Fab, Fab', F(ab')2, and Fv fragments), single chain Fv (scFv), minibodies, multispecific antibodies such as bispecific antibodies generated from at least two intact antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. Thus, the term "antibody" includes whole antibodies and any antigen-binding fragment or single chains thereof. Antibodies can be naked or conjugated to other molecules such as toxins, radioisotopes, etc.

There are at least two techniques for determining the location of CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al. (1997) *J. Molec. Biol.* 273:927-948)). In addition, combinations of these two approaches are sometimes used in the art to determine CDRs.

The amino acid position numbering as in Kabat, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence can contain fewer or additional amino acids corresponding to a shortening of, or insertion into, a FW or CDR of the variable domain. For example, a heavy chain variable domain can include a single amino acid insert (residue 52a according to Kabat) after residue 52 of H2 and inserted residues (e.g., residues 82a, 82b, and 82c, etc. according to Kabat) after heavy chain FW residue 82.

The Kabat numbering of residues can be determined for a given antibody by alignment at regions of homology of the sequence of the antibody with a "standard" Kabat numbered sequence. Chothia refers instead to the location of the structural loops (Chothia and Lesk, J. Mol. Biol. 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software.

IMGT (ImMunoGeneTics) also provides a numbering system for the immunoglobulin variable regions, including the CDRs. See e.g., Lefranc, M. P. et al., Dev. Comp. Immunol. 27: 55-77(2003). The IMGT numbering system was based on an alignment of more than 5,000 sequences, structural data, and characterization of hypervariable loops and allows for easy comparison of the variable and CDR regions for all species. According to the IMGT numbering schema VH-CDR1 is at positions 26 to 35, VH-CDR2 is at positions 51 to 57, VH-CDR3 is at positions 93 to 102, VL-CDR1 is at positions 27 to 32, VL-CDR2 is at positions 50 to 52, and VL-CDR3 is at positions 89 to 97.

As used throughout the specification the VH CDR sequences described herein correspond to the classical Kabat numbering locations, namely Kabat VH-CDR1 is at positions 31-35, VH-CDR2 is a positions 50-65, and VH-CDR3 is at positions 95-102. VL-CDR1, VL-CDR2, and VL-CDR3 also correspond to classical Kabat numbering locations, namely positions 14-24, 50-56 and 89-97, respectively.

The term "consensus sequence," as used herein with respect to a CDR in the light chain (VL) or heavy chain (VH) variable regions, refers to a composite or genericized amino acid sequence defined based on information as to which amino acid residues are present at a given position based in multiple sequence alignments. Thus, in a "consensus sequence" for a VL or VH chain CDR1, CDR2, or CDR3, certain amino acid positions are occupied by one of multiple possible amino acid residues at that position. For example, if an arginine (R) or a serine (S) occur at a particular position X, then that particular position within the consensus sequence can be either arginine or serine (R or S). Such occurrence would be represented, for example, as $_N\text{-}Z_1Z_2X_nZ_{t-1}Z_t\text{-}_C$, where $Z_{1>t}$ are invariant amino acids in the multiple sequence alignment, X represent a position occupied by variant amino acids (e.g., R or S), and the subindex n is an ordinal. As used herein, referring to a polypeptide sequence as consisting of or comprising a consensus sequence means that the polypeptide sequence consists of or comprises one of the of multiple possible amino acid sequences represented by the consensus sequence.

The term "antigen binding fragment" refers to a portion of an intact antibody and refers to the antigenic determining variable regions of an intact antibody. It is known in the art that the antigen binding function of an antibody can be performed by fragments of a full-length antibody. Examples of antibody fragments include, but are not limited to Fab, Fab', F(ab')2, and Fv fragments, linear antibodies, single chain antibodies, and multispecific antibodies formed from antibody fragments.

The term "Fab" refers to an antibody fragment that is essentially equivalent to that obtained by digestion of immunoglobulin (typically IgG) with the enzyme papain. The heavy chain segment of the Fab fragment is the Fd piece. Such fragments can be enzymatically or chemically produced by fragmentation of an intact antibody, recombinantly produced from a gene encoding the partial antibody sequence, or it can be wholly or partially synthetically produced.

The term "Fab'" refers to an antibody fragment that is essentially equivalent to that obtained by reduction of the disulfide bridge or bridges joining the two heavy chain pieces in the F(ab')2 fragment. Such fragments can be enzymatically or chemically produced by fragmentation of an intact antibody, recombinantly produced from a gene encoding the partial antibody sequence, or it can be wholly or partially synthetically produced.

The term "F(ab')2" refers to an antibody fragment that is essentially equivalent to a fragment obtained by digestion of an immunoglobulin (typically IgG) with the enzyme pepsin at pH 4.0-4.5. Such fragments can be enzymatically or chemically produced by fragmentation of an intact antibody, recombinantly produced from a gene encoding the partial antibody sequence, or it can be wholly or partially synthetically produced.

The term "Fv" refers to an antibody fragment that consists of one NH and one N domain held together by noncovalent interactions.

The term "monoclonal antibody" refers to a homogeneous antibody population involved in the highly specific recognition and binding of a single antigenic determinant, or epitope. This is in contrast to polyclonal antibodies that typically include different antibodies directed against different antigenic determinants. The term "monoclonal antibody" encompasses both intact and full-length monoclonal antibodies as well as antibody fragments (such as Fab, Fab', F(ab')2, or Fv), single chain (scFv) mutants, fusion proteins comprising an antibody portion, and any other modified immunoglobulin molecule comprising an antigen recognition site. Furthermore, "monoclonal antibody" refers to such antibodies made in any number of ways including, but not limited to, by hybridoma, phage selection, recombinant expression, and transgenic animals.

The term "human antibody" refers to an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide such as, for example, an antibody comprising murine light chain and human heavy chain polypeptides. The term "humanized antibody" refers to an antibody derived from a non-human (e.g., murine) immunoglobulin, which has been engineered to contain minimal non-human (e.g., murine) sequences. The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammals (e.g., mouse, rat, rabbit, etc.) with the desired specificity, affinity, and capability while the constant regions are homologous to the sequences in antibodies derived from another (usually human) to avoid eliciting an immune response in that species.

In one embodiment, an anti-GPIIa/IIIb antibody of the invention comprises an antibody variant. The term "antibody variant" or "modified antibody" includes an antibody which does not occur in nature and which has an amino acid sequence or amino acid side chain chemistry which differs from that of a naturally-derived antibody by at least one amino acid or amino acid modification as described herein. As used herein, the term "antibody variant" includes synthetic forms of antibodies which are altered such that they are not naturally occurring, e.g., antibodies that comprise at least two heavy chain portions but not two complete heavy chains (such as, domain deleted antibodies or minibodies); multispecific forms of antibodies (e.g., bispecific, trispecific, etc.) altered to bind to two or more different antigens or to different epitopes on a single antigen; heavy chain molecules joined to scFv molecules; single-chain antibodies; diabodies; triabodies; and antibodies with altered effector function and the like.

As used herein the term "scFv" or "scFv molecule" includes binding molecules which consist of one light chain variable domain (VL) or a portion thereof, and one heavy chain variable domain (VH) or a portion thereof, wherein each variable domain (or a portion thereof) is derived from the same or different antibodies. Single chain Fv molecules preferably comprise an scFv linker interposed between the VH domain and the VL domain. Exemplary scFv molecules are known in the art and are described, for example, in U.S. Pat. No. 5,892,019; Ho et al., *Gene* 77:51 (1989); Bird et al., *Science* 242:423 (1988); Pantoliano et al., *Biochemistry* 30:10117 (1991); Milenic et al., *Cancer Research* 51:6363 (1991); Takkinen et al., *Protein Engineering* 4:837 (1991).

The term "scFv linker" as used herein refers to a moiety interposed between the VL and VH domains of the scFv. The scFv linkers preferably maintain the scFv molecule in an antigen-binding conformation. In one embodiment, a scFv linker comprises or consists of an scFv linker peptide. In certain embodiments, an scFv linker peptide comprises or consists of a gly-ser peptide linker. In other embodiments, an scFv linker comprises a disulfide bond.

As used herein, the term "antigen-binding molecule" refers to a molecule comprising an anti-GPIIb/IIIa antibody fragment, variant, or derivative thereof, comprising at least one CDR from one or more of the anti-GPIIb/IIIa antibodies disclosed herein. In some embodiments, the antigen-binding molecule is a protein. In other embodiments, the antigen-binding molecule is a protein scaffold (e.g., a fibronectin type III domain) or non-protein scaffold comprising at least one CDR from one of the anti-GPIIb/IIIa antibodies disclosed herein. In some embodiments, the antigen-binding molecule is an anti-GPIIb/IIIa antibody identified according to the methods disclosed herein, comprising at least one CDR identical to one of the CDR sequences disclosed herein. The term "antigen-binding molecule" also encompasses any molecule comprising a VH and/or VL region from one or more of the anti-GPIIb/IIIa antibodies disclosed herein.

The term "polynucleotide" or "nucleotide" is intended to encompass a singular nucleic acid as well as plural nucleic acids and refers to an isolated nucleic acid molecule or construct, e.g., messenger RNA (mRNA) or plasmid DNA (pDNA). In certain embodiments, a polynucleotide comprises a conventional phosphodiester bond or a non-conventional bond (e.g., an amide bond, such as found in peptide nucleic acids (PNA)).

The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. Examples of an isolated polynucleotide include recombinant polynucleotides maintained in heterologous host cells or purified (partially or substantially) from other polynucleotides in a solution. Isolated RNA molecules include in vivo or in vitro RNA transcripts of polynucleotides of the present invention. Isolated polynucleotides or nucleic acids according to the present invention further include such molecules produced synthetically. In addition, a polynucleotide or a nucleic acid can include regulatory elements such as promoters, enhancers, ribosome binding sites, or transcription termination signals.

As used herein, a "coding region" or "coding sequence" is a portion of polynucleotide which consists of codons translatable into amino acids. Although a "stop codon" (tag, tga, or taa) is typically not translated into an amino acid, it can be considered to be part of a coding region, but any flanking sequences, for example promoters, ribosome binding sites, transcriptional terminators, introns, and the like, are not part of a coding region. The boundaries of a coding region are typically determined by a start codon at the 5' terminus, encoding the amino terminus of the resultant polypeptide, and a translation stop codon at the 3'terminus, encoding the carboxyl terminus of the resulting polypeptide.

Two or more coding regions of the present invention can be present in a single polynucleotide construct, e.g., on a single vector, or in separate polynucleotide constructs, e.g., on separate (different) vectors. It follows, then, that a single vector can contain just a single coding region, or comprise two or more coding regions, e.g., a single vector can separately encode a binding domain-A and a binding domain-B as described below. In addition, a vector, polynucleotide, or nucleic acid of the invention can encode heterologous coding regions, either fused or unfused to a nucleic acid encoding a binding domain of the invention. Heterologous coding regions include without limitation specialized elements or motifs, such as a secretory signal peptide or a heterologous functional domain.

The term "vector" or "expression vector" is used herein to mean vectors used in accordance with the present invention as a vehicle for introducing into and expressing a desired polynucleotide in a cell. As known to those skilled in the art, such vectors can easily be selected from plasmids, phages, viruses, or retroviruses. In general, vectors compatible with the instant invention will comprise a selection marker, appropriate restriction sites to facilitate cloning of the desired gene and the ability to enter and/or replicate in eukaryotic or prokaryotic cells.

Numerous expression vector systems can be employed to produce the antibody, antigen-binding molecule thereof, or a chimeric molecule of the invention. For example, one class of vector utilizes DNA elements which are derived from animal viruses such as bovine papilloma virus, polyoma virus, adenovirus, vaccinia virus, baculovirus, retroviruses (RSV, MMTV or MOMLV) or SV40 virus. Additionally, cells which have integrated the DNA into their chromosomes can be selected by introducing one or more markers which allow selection of transfected host cells. The marker can provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation. In one embodiment, an inducible expression system can be employed. Additional elements can also be needed for optimal synthesis of mRNA. These elements can include signal sequences, splice signals, as well as transcriptional promoters, enhancers, and termination signals. In one embodiment, a secretion signal, e.g., any one of several well characterized bacterial leader peptides (e.g., pelB, phoA, or ompA), can be fused in-frame to the N terminus of a polypeptide of the invention to obtain optimal secretion of the polypeptide. (Lei et al. (1988), *Nature*, 331:543; Better et al. (1988) *Science*, 240:1041; Mullinax et al., (1990). *PNAS*, 87:8095).

Certain proteins secreted by mammalian cells are associated with a secretory signal peptide which is cleaved from the mature protein once export of the growing protein chain across the rough endoplasmic reticulum has been initiated. Those of ordinary skill in the art are aware that signal peptides are generally fused to the N-terminus of the polypeptide, and are cleaved from the complete or "full-length" polypeptide to produce a secreted or "mature" form of the polypeptide. In certain embodiments, a native signal peptide, e.g., an immunoglobulin heavy chain or light chain signal peptide is used, or a functional derivative of that sequence that retains the ability to direct the secretion of the polypeptide that is operably associated with it. Alternatively, a heterologous mammalian signal peptide, e.g., a human tissue plasminogen activator (TPA) or mouse β-glucuronidase signal peptide, or a functional derivative thereof, can be used.

A "recombinant" polypeptide or protein refers to a polypeptide or protein produced via recombinant DNA technology. Recombinantly produced polypeptides and proteins expressed in host cells are considered isolated for the purpose of the invention, as are native or recombinant polypeptides which have been separated, fractionated, or partially or substantially purified by any suitable technique.

The term "host cell" refers to a cell that has been transformed with a vector constructed using recombinant DNA techniques and encoding at least one heterologous gene. In descriptions of processes for isolation of proteins from recombinant hosts, the terms "cell" and "cell culture" are used interchangeably to denote the source of protein unless it is clearly specified otherwise. In other words, recovery of protein from the "cells" can mean either from spun down whole cells, or from the cell culture containing both the medium and the suspended cells. The host cell line used for protein expression is most preferably of mammalian origin; those skilled in the art are credited with ability to preferentially determine particular host cell lines which are best suited for the desired gene product to be expressed therein. Exemplary host cell lines include, but are not limited to, CHO cell line, BHK cell line, HEK cell line, DG44 and DUXB11 (Chinese Hamster Ovary lines, DHFR minus), HELA (human cervical carcinoma), CVI (monkey kidney line), COS (a derivative of CVI with SV40 T antigen), R1610 (Chinese hamster fibroblast) BALBC/3T3 (mouse fibroblast), PerC6 cells), HAK (hamster kidney line), SP2/O (mouse myeloma), P3x63-Ag3.653 (mouse myeloma), BFA-1c1BPT (bovine endothelial cells), and RAJI (human lymphocyte). Host cell lines are typically available from commercial services, the American Tissue Culture Collection or from published literature.

II. Anti-GPIIb/IIIa Antibodies

The present invention provides antibodies and antigen-binding molecules thereof that specifically bind to GPIIb/IIIa receptors located on the surface of platelets. As used herein, the terms "GPIIb/IIIa" and "GPIIb/IIIa receptor" refer to glycoprotein IIb/IIIa (also known as integrin αIIbβ3), an integrin complex found on platelets. Integrins are composed of two chains, an α subunit and a β subunit, which are held together by noncovalent bonds in a calcium dependent manner. GPIIb constitutes the α subunit, which comprises divalent cation binding domains, whereas GPIIIa is a pro typical β subunit (β3). On each circulating platelet, there are 35,000 to 100,000 GPIIb/IIIa complexes; most are distributed on the platelet surface, with a smaller pool in an internal reserve. The GPIIb/IIIa complex does not interact with its plasma ligands until platelets have been activated by exogenous agonists such as ADP or thrombin. When this occurs, an inside-out signal is generated that results in a conformational change in the extracellular portion of the complex that renders the molecule capable of binding fibrinogen and other ligands. See Uniprot entries P05106 (ITB3_HUMAN; GPIIIa: CD61; integrin beta-3; integrin β3) and P08514 (ITA2B_HUMAN; GPIIb; CD41; integrin alpha-2b; integrin αII) as published in Universal Protein Resource (Uniprot) database release 2013_05 (May 1, 2013), which are incorporated by reference in their entireties.

The GPIIb/IIIa receptor is a target of several GpIIb/IIIa inhibitor drugs including abciximab (REOPRO®), eptifibatide (INTEGRILIN®), and tirofiban (AGGRASTAT®). GPIIb/IIIa inhibitors can be used during percutaneous coronary intervention (angioplasty with or without intracoronary stent placement) to preventing platelet aggregation and thrombus formation by inhibiting the GPIIb/IIIa receptor on the surface of the platelets. They can also be used to treat acute coronary syndromes, without percutaneous coronary intervention, depending on TIMI risk.

The terms "GPIIb/IIIa antibody," "anti-GPIIb/IIIa antibody," "anti-GPIIb/IIIa," "antibody that binds to GPIIb/IIIa" and any grammatical variations thereof refer to an antibody that is capable of specifically binding to the GPIIb/IIIa receptor with sufficient affinity such that the antibody is useful as a therapeutic agent or diagnostic reagent in targeting GPIIb/IIIa. The extent of binding of an anti-GPIIb/IIIa antibody disclosed herein to an unrelated, non-GPIIb/IIIa protein is less than about 10% of the binding of the antibody to GPIIb/IIIa as measured, e.g., by a radioimmunoassay (RIA), BIACORE™ (using recombinant GPIIb/IIIa as the analyte and antibody as the ligand, or vice versa), or other binding assays known in the art. In certain embodiments, an antibody that binds to GPIIb/IIIa has a dissociation constant ($K_D$) of ≤1 μM, ≤100 nM, ≤50 nM, ≤10 nM, ≤1 nM, ≤0.1 nM, ≤10 pM, ≤1 pM, or ≤0.1 pM.

In some embodiments, the antibody or antigen-binding molecules thereof specifically bind to a GPIIb/IIIa epitope, which comprises or overlaps with the GPIIb/IIIa binding epitope of an antibody selected from 34D10, 12B2, 2A2, 35D1, 36A8, 4B11, 1H6, 38G8, 21F10, 38A8, 18F7, 38F6, 13C1, 5C4, 23C10, 37C7, 28C2, 9D6, or 28F4 (see TABLE 1). In some embodiments, the antibody or antigen-binding molecules thereof specifically bind to a GPIIb/IIIa epitope, which is the same GPIIb/IIIa binding epitope of an antibody selected from 34D10, 12B2, 2A2, 35D1, 36A8, 4B11, 1H6, 38G8, 21F10, 38A8, 18F7, 38F6, 13C1, 5C4, 23C10, 37C7, 28C2, 9D6, or 28F4 (see TABLE 1). As used herein, the term "epitope" designates a specific amino acid sequence, modified amino acid sequence, or protein secondary or tertiary structure which is specifically recognized by an antibody. The terms "specifically recognizing," "specifically recognizes," and any grammatical variants mean that the antibody or antigen-binding molecule thereof is capable of specifically interacting with and/or binding to at least two, at least three, or at least four amino acids of an epitope, e.g., a GPIIb/IIIa epitope. Such binding can be exemplified by the specificity of a "lock-and-key-principle." Thus, specific motifs in the amino acid sequence of the antigen-binding domain the GPIIb/IIIa antibody or antigen-binding molecule thereof and the epitope bind to each other as a result of their primary, secondary or tertiary structure as well as the result of secondary modifications of the structure.

In other embodiments, the antibody or antigen-binding molecule thereof of the present invention specifically binds to GPIIb/IIIa and competitively inhibits GPIIb/IIIa binding by an antibody selected from 34D10, 12B2, 2A2, 35D1, 36A8, 4B11, 1H6, 38G8, 21F10, 38A8, 18F7, 38F6, 13C1, 5C4, 23C10, 37C7, 28C2, 9D6, or 28F4 (see TABLE 1). In some embodiments, the antibody or antigen-binding molecule thereof which specifically binds to a GPIIb/IIIa epitope comprises at least one, at least two, at least three, at least four, or at least five complementarity determining regions (CDR) or variants thereof of an antibody selected from one or more of the 34D10, 12B2, 2A2, 35D1, 36A8, 4B11, 1H6, 38G8, 21F10, 38A8, 18F7, 38F6, 13C1, 5C4, 23C10, 37C7, 28C2, 9D6, or 28F4 antibodies disclosed in TABLE 1. In other embodiments, the antibody or antigen-binding molecule thereof which specifically binds to a GPIIb/IIIa epitope comprises six CDRs or variants thereof of an antibody selected from one or more of the 34D10, 12B2, 2A2, 35D1, 36A8, 4B11, 1H6, 38G8, 21F10, 38A8, 18F7, 38F6, 13C1, 5C4, 23C10, 37C7, 28C2, 9D6, or 28F4 antibodies disclosed herein. In some embodiments, CDRs are independently selected from CDRs or variants thereof derived from the VH and/or VL region of one, two, three, four, or six antibodies selected from 34D10, 12B2, 2A2, 35D1, 36A8, 4B11, 1H6, 38G8, 21F10, 38A8, 18F7, 38F6, 13C1, 5C4, 23C10, 37C7, 28C2, 9D6, or 28F4.

In certain embodiments, the antibody or antigen-binding molecule thereof which specifically binds to a GPIIb/IIIa epitope comprises:

(i) a variable heavy chain CDR-1 (VH-CDR1) sequence at least about 60%, 70%, 80%, 90%, 95%, or 100% identical to VH-CDR1 of an antibody selected from 34D10, 12B2, 2A2, 35D1, 36A8, 4B11, 11-16, 38G8, 21F10, 38A8, 18F7, 38F6, 13C1, 5C4, 23C10, 37C7, 28C2, 9D6, or 28F4;

(ii) a variable heavy chain CDR-2 (VH-CDR2) sequence at least about 60%, 70%, 80%, 90%, 95%, or 100% identical to VH-CDR2 of an antibody selected from 34D10, 12B2, 2A2, 35D1, 36A8, 4B11, 1H6, 38G8, 21F10, 38A8, 18F7, 38F6, 13C1, 5C4, 23C10, 37C7, 28C2, 9D6, or 28F4;

(iii) a variable heavy chain CDR-3 (VH-CDR3) sequence at least about 60%, 70%, 80%, 90%, 95%, or 100% identical to VH-CDR3 of an antibody selected from 34D10, 12B2, 2A2, 35D1, 36A8, 4B11, 1H6, 38G8, 21F10, 38A8, 18F7, 38F6, 13C1, 5C4, 23C10, 37C7, 28C2, 9D6, or 28F4;

(iv) a variable light chain CDR-1 (VL-CDR1) sequence at least about 60%, 70%, 80%, 90%, 95%, or 100% identical to VL-CDR1 of an antibody selected from 34D10, 12B2, 2A2, 35D1, 36A8, 4B11, 1H6, 38G8, 21F10, 38A8, 18F7, 38F6, 13C1, 5C4, 23C10, 37C7, 28C2, 9D6, or 28F4;

(v) a variable light chain CDR-2 (VL-CDR2) sequence at least about 60%, 70%, 80%, 90%, 95%, or 100% identical to VL-CDR2 of an antibody selected from 34D10, 12B2, 2A2, 35D1, 36A8, 4B11, 1H6, 38G8, 21F10, 38A8, 18F7, 38F6, 13C1, 5C4, 23C10, 37C7, 28C2, 9D6, or 28F4, and/or (vi) a variable light chain CDR-3 (VL-CDR3) sequence at least about 60, 70, 80, 90, or 95% identical to VL-CDR3 of an antibody selected from 34D10, 12B2, 2A2, 35D1, 36A8, 4B11, 1H6, 38G8, 21F10, 38A8, 18F7, 38F6, 13C1, 5C4, 23C10, 37C7, 28C2, 9D6, or 28F4.

In certain embodiments, the antibody or antigen-binding molecule thereof which specifically binds to a GPIIb/IIIa epitope comprises:

(i) a variable heavy chain CDR-1 (VH-CDR1) sequence at least about 60%, 70%, 80%, 90%, 95%, or 100% identical to VH-CDR1 of an antibody selected from 34D10, 12B2, 2A2, 35D1, 36A8, 4B11, 1H6, 38G8, 21F10, 38A8, 18F7, 38F6, 13C1, 5C4, 23C10, 37C7, 28C2, 9D6, or 28F4;

(ii) a variable heavy chain CDR-2 (VH-CDR2) sequence at least about 60%, 70%, 80%, 90%, 95%, or 100% identical to VH-CDR2 of an antibody selected from 34D10, 12B2, 2A2, 35D1, 36A8, 4B11, 1H6, 38G8, 21F10, 38A8, 18F7, 38F6, 13C1, 5C4, 23C10, 37C7, 28C2, 9D6, or 28F4; and (iii) a variable heavy chain CDR-3 (VH-CDR3) sequence at least about 60%, 70%, 80%, 90%, 95%, or 100% identical to VH-CDR3 of an antibody selected from 4D10, 12B2, 2A2, 35D1, 36A8, 4B11, 1H6, 38G8, 21F10, 38A8, 18F7, 38F6, 13C1, 5C4, 23C10, 37C7, 28C2, 9D6, or 28F4.

In other embodiments, the antibody or antigen-binding molecule thereof which specifically binds to a GPIIb/IIIa epitope comprises:

(i) a variable light chain CDR-1 (VL-CDR1) sequence at least about 60%, 70%, 80%, 90%, 95%, or 100% identical to VL-CDR1 of an antibody selected from 34D10, 12B2, 2A2, 35D1, 36A8, 4B11, 1H6, 38G8, 21F10, 38A8, 18F7, 38F6, 13C1, 5C4, 23C10, 37C7, 28C2, 9D6, or 28F4;

(ii) a variable light chain CDR-2 (VL-CDR2) sequence at least about 60%, 70%, 80%, 90%, 95%, or 100% identical to VL-CDR2 of an antibody selected from 34D10, 12B2, 2A2, 35D1, 36A8, 4B11, 1H6, 38G8, 21F10, 38A8, 18F7, 38F6, 13C1, 5C4, 23C10, 37C7, 28C2, 9D6, or 28F4, and (iii) a variable light chain CDR-3 (VL-CDR3) sequence at least about 60, 70, 80, 90, or 95% identical to VL-CDR3 of an antibody selected from 34D10, 12B2, 2A2, 35D1, 36A8, 4B11, 1H6, 38G8, 21F10, 38A8, 18F7, 38F6, 13C1, 5C4, 23C10, 37C7, 28C2, 9D6, or 28F4.

In certain embodiments, the antibody or antigen-binding molecule thereof which specifically binds to a GPIIb/IIIa epitope comprises:

(i) a variable heavy chain CDR-1 (VH-CDR1) sequence at least about 60%, 70%, 80%, 90%, 95%, or 100% identical to VH-CDR1 of an antibody selected from 34D10, 2A2, 35D1, 36A8, 4B11, 1H6, 38G8, 21F10, 38A8, or 18F7;

(ii) a variable heavy chain CDR-2 (VH-CDR2) sequence at least about 60%, 70%, 80%, 90%, 95%, or 100% identical to VH-CDR2 of an antibody selected from 34D10, 2A2, 35D1, 36A8, 4B11, 1H6, 38G8, 21F10, 38A8, or 18F7;

(iii) a variable heavy chain CDR-3 (VH-CDR3) sequence at least about 60%, 70%, 80%, 90%, 95%, or 100% identical to VH-CDR3 of an antibody selected from 34D10, 2A2, 35D1, 36A8, 4B11, 1H6, 38G8, 21F10, 38A8, or 18F7;

(iv) a variable light chain CDR-1 (VL-CDR1) sequence at least about 60%, 70%, 80%, 90%, 95%, or 100% identical to VL-CDR1 of an antibody selected from 34D10, 2A2, 35D1, 36A8, 4B11, 1H6, 38G8, 21F10, 38A8, or 18F7;

(v) a variable light chain CDR-2 (VL-CDR2) sequence at least about 60%, 70%, 80%, 90%, 95%, or 100% identical to VL-CDR2 of an antibody selected from 34D10, 2A2, 35D1, 36A8, 4B11, 1H6, 38G8, 21F10, 38A8, or 18F7, and/or (vi) a variable light chain CDR-3 (VL-CDR3) sequence at least about 60, 70, 80, 90, or 95% identical to VL-CDR3 of an antibody selected from 34D10, 2A2, 35D1, 36A8, 4B11, 1H6, 38G8, 21F10, 38A8, or 18F7.

In some embodiments, the antibody or antigen-binding molecule thereof which specifically binds to a GPIIb/IIIa epitope comprises:

(i) a variable heavy chain CDR-1 (VH-CDR1) sequence at least about 60%, 70%, 80%, 90%, 95%, or 100% identical to VH-CDR1 of an antibody selected from 12B2, 38F6, 13C1, 5C4, 23C10, 37C7, 28C2, 9D6, or 28F4;

(ii) a variable heavy chain CDR-2 (VH-CDR2) sequence at least about 60%, 70%, 80%, 90%, 95%, or 100% identical to VH-CDR2 of an antibody selected from 12B2, 38F6, 13C1, 5C4, 23C10, 37C7, 28C2, 9D6, or 28F4;

(iii) a variable heavy chain CDR-3 (VH-CDR3) sequence at least about 60%, 70%, 80%, 90%, 95%, or 100% identical to VH-CDR3 of an antibody selected from 12B2, 38F6, 13C1, 5C4, 23C10, 37C7, 28C2, 9D6, or 28F4;

(iv) a variable light chain CDR-1 (VL-CDR1) sequence at least about 60%, 70%, 80%, 90%, 95%, or 100% identical to VL-CDR1 of an antibody selected from 12B2, 38F6, 13C1, 5C4, 23C10, 37C7, 28C2, 9D6, or 28F4;

(v) a variable light chain CDR-2 (VL-CDR2) sequence at least about 60%, 70%, 80%, 90%, 95%, or 100% identical to VL-CDR2 of an antibody selected from 12B2, 38F6, 13C1, 5C4, 23C10, 37C7, 28C2, 9D6, or 28F4, and/or (vi) a variable light chain CDR-3 (VL-CDR3) sequence at least about 60, 70, 80, 90, or 95% identical to VL-CDR3 of an antibody selected from 12B2, 38F6, 13C1, 5C4, 23C10, 37C7, 28C2, 9D6, or 28F4.

In some embodiments, the antibody or antigen-binding molecule thereof which specifically binds to a GPIIb/IIIa epitope comprises:

(i) a variable heavy chain CDR-1 (VH-CDR1) sequence at least about 60%, 70%, 80%, 90%, 95%, or 100% identical to any one of SEQ ID NOS: 25, 31, 37, 43, or 111;

(ii) a variable heavy chain CDR-2 (VH-CDR2) sequence at least about 60%, 70%, 80%, 90%, 95%, or 100% identical to any one of SEQ ID NOS:26, 32, 38, 44, or 112;

(iii) a variable heavy chain CDR-3 (VH-CDR3) sequence at least about 60%, 70%, 80%, 90%, 95%, or 100% identical to any one of SEQ ID NOS: 27, 33, 39, 45, or 113;

(iv) a variable light chain CDR-1 (VL-CDR1) sequence at least about 60%, 70%, 80%, 90%, 95%, or 100% identical to any one of SEQ ID NOS: 28, 34, 40, 117, or 114;

(v) a variable light chain CDR-2 (VL-CDR2) sequence at least about 60%, 70%, 80%, 90%, 95%, or 100% identical to any one of SEQ ID NOS: 29, 35, 41, 118, or 115; and, (vi) a variable light chain CDR-3 (VL-CDR3) sequence at least about 60, 70, 80, 90, or 95% identical to any one of SEQ ID NOS: 30, 36, 42, 119, or 116.

In some embodiments, the antibody or antigen-binding molecule thereof which specifically binds to a GPIIb/IIIa epitope, comprises:

(i) a VH-CDR1 comprising the consensus sequence $X_1YAMS$ (SEQ ID NO:233) wherein $X_1$ represents any amino acid residue, e.g., an amino acid residue with uncharged polar side chain or nonpolar side chain, e.g., Thr (T), Ser (S), or Ala (A);

(ii) a VH-CDR2 comprising the consensus sequence $SIX_2X_3GX_4X_5TYX_6X_7DSVKX_8$ (SEQ ID NO:226)

wherein $X_2$ represents any amino acid residue, e.g., an amino acid residue with uncharged polar side chain, e.g., Ser (S) or Asn (N), $X_3$ represents any amino acid residue, e.g., an amino acid residue with uncharged polar side chain, e.g., Ser (S) or Gly (G), $X_4$ represents any amino acid residue, e.g., an amino acid residue with uncharged polar side chain, e.g., Ser (S) or Gly (G), $X_5$ represents any amino acid residue, e.g., an amino acid residue with uncharged polar side chain, e.g., Ser (S), Asn (N), or Thr (T), $X_6$ represents any amino acid residue, e.g., an amino acid residue with aromatic side chain, e.g., Tyr (Y) or Phe (F), $X_7$ represents any amino acid residue, e.g., an amino acid residue with nonpolar side chains, e.g., Leu (L) or Pro (P), and $X_8$ represents any amino acid residue, e.g., an amino acid residue with basic side chains or uncharged polar side chains, e.g., Gly (G) or Arg (R);

(iii) a VH-CDR3 comprising the consensus sequence $GGDYGYAX_9DY$ (SEQ ID NO:227), wherein $X_9$ represents any amino acid residue, e.g., an amino acid residue with nonpolar side chains, e.g., Leu (L) or Met (M);

(iv) a VL-CDR1 comprising the sequence RASSSVNYMY (SEQ ID NO: 28);

(v) a VL-CDR2 comprising the sequence YTSNLAP (SEQ ID NO: 29); and, (vi) a VL-CDR3 comprising the sequence QQFSSSPWT (SEQ ID NO: 30).

In some embodiments, the antibody or antigen-binding molecule thereof which specifically binds to a GPIIb/IIIa epitope comprises:

(i) a VH-CDR1 sequence selected from SEQ ID NOS: 25, 31, 37, 43, or 111;

(ii) a VH-CDR2 sequence selected from SEQ ID NOS: 26, 32, 38, 44, or 112;

(iii) a VH-CDR3 sequence selected from SEQ ID NOS: 27, 33, 39, 45, or 113;

(iv) a VL-CDR1 sequence selected from SEQ ID NOS: 28, 34, 40, 117, or 114;

(v) a VL-CDR2 sequence selected from SEQ ID NOS: 29, 35, 41, 118, or 115; and, (vi) a VL-CDR3 sequence selected from SEQ ID NOS: 30, 36, 42, 119, or 116.

In some embodiments, the antibody or antigen-binding molecule thereof which specifically binds to a GPIIb/IIIa epitope comprises an amino acid sequence at least about 80%, 85%, 90%, 95%, or 100% identical to any one of SEQ ID NOS: 1, 3, 5, 7, or 97 and a VL region comprising an amino acid sequence at least about 80%, 85%, 90%, 95%, or 100% identical to any one of SEQ ID NOS: 2, 4, 6, 99, or 98. In some embodiments, the antibody or antigen-binding molecule thereof comprises a VH region comprising the amino acid sequence of SEQ ID NO: 1 and a VL region comprising the amino acid sequence of SEQ ID NO: 2. In other embodiments, the antibody or antigen-binding molecule thereof comprises a VH region comprising the amino acid sequence of SEQ ID NO: 3 and a VL region comprising the amino acid sequence of SEQ ID NO: 4. In some embodiments, the antibody or antigen-binding molecule thereof comprises a VH region comprising the amino acid sequence of SEQ ID NO: 5 and a VL region comprising the amino acid sequence of SEQ ID NO: 6. In some embodiments, the antibody or antigen binding molecule thereof comprises a VH region comprising the amino acid sequence of SEQ ID NO: 7 and a VL region comprising the amino acid sequence of SEQ ID NO: 99. In some embodiments, the antibody or antigen binding molecule thereof comprises a VH region comprising the amino acid sequence of SEQ ID NO: 97 and a VL region comprising the amino acid sequence of SEQ ID NO: 98. In some embodiment, the anti-GPIIb/IIIa antibody or antigen-binding molecule thereof binds to a GPIIb/IIIa epitope located in the extracellular domain of the alpha subunit of GPIIb/IIIa or to a binding site formed by the extracellular domains of the GPIIb/IIIa complex. In some embodiments, the GPIIb/IIIa antibody or antigen-binding molecule thereof does not compete with fibrinogen for binding to GPIIb/IIIa.

In some embodiments, the antibody or antigen-binding molecule thereof which specifically binds to a GPIIb/IIIa epitope comprises:
  (i) a variable heavy chain CDR-1 (VH-CDR1) sequence at least about 60%, 70%, 80%, 90%, 95%, or 100% identical to any one of SEQ ID NOS: 46, 52, 120, or 126;
  (ii) a variable heavy chain CDR-2 (VH-CDR2) sequence at least about 60%, 70%, 80%, 90%, 95%, or 100% identical to any one of SEQ ID NOS: 47, 53, 121, or 127;
  (iii) a variable heavy chain CDR-3 (VH-CDR3) sequence at least about 60%, 70%, 80%, 90%, 95%, or 100% identical to any one of SEQ ID NOS: 48, 54, 122, or 128;
  (iv) a variable light chain CDR-1 (VL-CDR1) sequence at least about 60%, 70%, 80%, 90%, 95%, or 100% identical to any one of SEQ ID NOS: 49, 55, 123, or 129;
  (v) a variable light chain CDR-2 (VL-CDR2) sequence at least about 60%, 70%, 80%, 90%, 95%, or 100% identical to any one of SEQ ID NOS: 50, 56, 124, or 130; and,
  (vi) a variable light chain CDR-3 (VL-CDR3) sequence at least about 60%, 70%, 80%, 90%, 95%, or 100% identical to any one of SEQ ID NO: 51, 57, 125, or 131.

In some embodiments. the antibody or antigen-binding molecule thereof which specifically binds to a GPIIb/IIIa epitope, comprises:
(i) a VH-CDR1 comprising the sequence NYLIE (SEQ ID NO: 46);
(ii) a VH-CDR2 comprising the sequence VINPGSGGT-NYNEKFKG (SEQ ID NO: 47);
(iii) a VH-CDR3 comprising the sequence GRYEWYFDV (SEQ ID NO: 48);
(iv) a VL-CDR1 comprising the consensus sequence RASQDIX$_{10}$NYLN (SEQ ID NO:228) wherein X$_{10}$ represents any amino acid residue, e.g., an amino acid residue with uncharged polar side chain, e.g., Ser (S) or Thr (T);
(v) a VL-CDR2 comprising the sequence YTSRLHS (SEQ ID NO:50); and,
(vi) a VL-CDR3 comprising the sequence QQGYTLPYT (SEQ ID NO:51).

In some embodiments, the antibody or antigen-binding molecule thereof comprises:
  (i) a VH-CDR1 sequence selected from SEQ ID NOS: 46, 52, 120, or 126;
  (ii) a VH-CDR2 sequence selected from SEQ ID NOS: 47, 53, 121, or 127;
  (iii) a VH-CDR3 sequence selected from SEQ ID NOS: 48, 54, 122, or 128;
  (iv) a VL-CDR1 sequence selected from SEQ ID NOS: 49, 55, 123, or 129;
  (v) a VL-CDR2 sequence selected from SEQ ID NOS: 50, 56, 124, or 130; and,
  (vi) a VL-CDR3 sequence selected from SEQ ID NOS: 51, 57, 125, or 131.

In some embodiments, the antibody or antigen-binding molecule thereof, which specifically binds to a GPIIb/IIIa epitope, comprises a VH region comprising an amino acid sequence at least about 80%, 85%, 90%, 95%, or 100% identical to any one of SEQ ID NOS: 8, 10, 100, or 102 and a VL region comprising an amino acid sequence at least about 80%, 85%, 90%, 95%, or 100% identical to any one of SEQ ID NOS: 9, 11, 101, or 103. In some embodiments, the antibody or antigen-binding molecule thereof comprises a VH region comprising the amino acid sequence of SEQ ID NO: 8 and a VL region comprising the amino acid sequence of SEQ ID NO: 9. In some embodiments, the antibody or antigen-binding molecule thereof comprises a VH region comprising the amino acid sequence of SEQ ID NO: 10 and a VL region comprising the amino acid sequence of SEQ ID NO: 11. In some embodiments, the antibody or antigen-binding molecule thereof comprises a VH region comprising the amino acid sequence of SEQ ID NO: 100 and a VL region comprising the amino acid sequence of SEQ ID NO: 101. In some embodiments, the antibody or antigen-binding molecule thereof comprises a VH region comprising the amino acid sequence of SEQ ID NO: 102 and a VL region comprising the amino acid sequence of SEQ ID NO: 103. In some embodiments, the antibody or antigen-binding molecule thereof binds to a GPIIb/IIIa epitope located in the extracellular domain of the alpha subunit of GPIIb/IIIa or to a binding site formed by the extracellular domains of the GPIIb/IIIa complex. In some embodiments, the antibody or antigen-binding molecule thereof competes with fibrinogen for binding to GPIIb/IIIa.

In some embodiments. the antibody or antigen-binding molecule thereof which specifically binds to a GPIIb/IIIa epitope comprises:
  (i) a variable heavy chain CDR-1 (VH-CDR1) sequence at least about 60%, 70%, 80%, 90%, 95%, or 100% identical to SEQ ID NO: 58;
  (ii) a variable heavy chain CDR-2 (VH-CDR2) sequence at least about 60%, 70%, 80%, 90%, 95%, or 100% identical to SEQ ID NO: 59;
  (iii) a variable heavy chain CDR-3 (VH-CDR3) sequence at least about 60%, 70%, 80%, 90%, 95%, or 100% identical to SEQ ID NO: 60;
  (iv) a variable light chain CDR-1 (VL-CDR1) sequence at least about 60%, 70%, 80%, 90%, 95%, or 100% identical to SEQ ID NO: 61;
  (v) a variable light chain CDR-2 (VL-CDR2) sequence at least about 60%, 70%, 80%, 90%, 95%, or 100% identical to SEQ ID NO: 62; and,
  (vi) a variable light chain CDR-3 (VL-CDR3) sequence at least about 60%, 70%, 80%, 90%, 95%, or 100% identical to SEQ ID NO: 63.

In some embodiments, the antibody or antigen-binding molecule thereof which specifically binds to a GPIIb/IIIa epitope comprises:
  (i) a VH-CDR1 sequence comprising SEQ ID NO: 58;
  (ii) a VH-CDR2 sequence comprising SEQ ID NO: 59;
  (iii) a VH-CDR3 sequence comprising SEQ ID NO: 60;
  (iv) a VL-CDR1 sequence comprising SEQ ID NO: 61;
  (v) a VL-CDR2 sequence comprising SEQ ID NO: 62; and,
  (vi) a VL-CDR3 sequence comprising SEQ ID NO: 63.

In some embodiments, the antibody or antigen-binding molecule thereof which specifically binds to a GPIIb/IIIa epitope comprises a VH region comprising an amino acid sequence at least about 80%, 85%, 90%, 95%, or 100% identical to SEQ ID NO: 12, and a VL region comprising an amino acid sequence at least about 80%, 85%, 90%, 95%, or 100% identical to SEQ ID NO: 13. In some embodiments, the antibody or antigen-binding molecule thereof binds to a GPIIb/IIIa epitope is located in the extracellular domain of the alpha subunit of GPIIb/IIIa. In some embodiments, the antibody or antigen-binding molecule thereof competes with fibrinogen for binding to GPIIb/IIIa.

In some embodiments, the antibody or antigen-binding molecule thereof which specifically binds to a GPIIb/IIIa epitope comprises:

(i) a variable heavy chain CDR-1 (VH-CDR1) sequence at least about 60%, 70%, 80%, 90%, 95%, or 100% identical to any one of SEQ ID NOS: 64, 70, or 135;

(ii) a variable heavy chain CDR-2 (VH-CDR2) sequence at least about 60%, 70%, 80%, 90%, 95%, or 100% identical to any one of SEQ ID NOS: 65, 71, or 136;

(iii) a variable heavy chain CDR-3 (VH-CDR3) sequence at least about 60%, 70%, 80%, 90%, 95%, or 100% identical to any one of SEQ ID NOS: 66, 72, or 137;

(iv) a variable light chain CDR-1 (VL-CDR1) sequence at least about 60%, 70%, 80%, 90%, 95%, or 100% identical to any one of SEQ ID NOS: 67, 132, or 138;

(v) a variable light chain CDR-2 (VL-CDR2) sequence at least about 60%, 70%, 80%, 90%, 95%, or 100% identical to any one of SEQ ID NOS: 68, 133, or 139; and, (vi) a variable light chain CDR-3 (VL-CDR3) sequence at least about 60%, 70%, 80%, 90%, 95%, or 100% identical to any one of SEQ ID NOS: 69, 134, or 140.

In other embodiments, the invention includes an antibody or antigen-binding molecule thereof which specifically binds to a GPIIb/IIIa epitope, comprising (i) a VH-CDR1 comprising the sequence SYWIE (SEQ ID NO: 64); (ii) a VH-CDR2 comprising the consensus sequence EILPGX$_{14}$GX$_{15}$TKYNX$_{16}$KFKG (SEQ ID NO: 187), wherein X$_{14}$ represents any amino acids, e.g., an amino acid residue with uncharged polar side chain, e.g., Ser (S) or Thr (T), X$_{15}$ represents any amino acids, e.g., an amino acid residue with uncharged polar side chains or beta-branched side chains, e.g., Ile (I) or Tyr (Y), and X$_{16}$ represents any amino acid, e.g., an amino acid residue with acidic side chains, e.g., Asp (D) or Glu (E); (iii) a VH-CDR3 comprising the sequence LISYYYAMDY (SEQ ID NO: 66); (iv) a VL-CDR1 comprising the sequence RASQDISNYLN (SEQ ID NO: 67); (v) a VL-CDR2 comprising the sequence YTSRLHS (SEQ ID NO: 68); and, (vi) a VL-CDR3 comprising the sequence QQGNTLPPT (SEQ ID NO: 69).

In some embodiments, the antibody or antigen-binding molecule thereof which specifically binds to a GPIIb/IIIa epitope comprises:

(i) a VH-CDR1 sequence selected from SEQ ID NOS: 64, 70, or 135;

(ii) a VH-CDR2 sequence selected from SEQ ID NOS: 65, 71, or 136;

(iii) a VH-CDR3 sequence selected from SEQ ID NOS: 66, 72, or 137;

(iv) a VL-CDR1 sequence selected from SEQ ID NOS: 67, 132, or 138;

(v) a VL-CDR2 sequence selected from SEQ ID NOS: 68, 133, or 139; and, (vi) a VL-CDR3 sequence selected from SEQ ID NOS: 69, 134, or 140.

In some embodiments, the antibody or antigen-binding molecule thereof which specifically binds to a GPIIb/IIIa epitope comprises a VH region comprising an amino acid sequence at least about 80%, 85%, 90%, 95%, or 100% identical to any one of SEQ ID NOS: 14, 16, or 105 and a VL region comprising an amino acid sequence at least about 80%, 85%, 90%, 95%, or 100% identical to any one of SEQ ID NOS: 15, 104, or 106. In some embodiments, the antibody or antigen-binding molecule comprises a VH region comprising the amino acid sequence of SEQ ID NO: 14 and a VL region comprising the amino acid sequence of SEQ ID NO: 15. In some embodiments, the antibody or antigen-binding molecule thereof comprises a VH region comprising the amino acid sequence of SEQ ID NO: 16 and a VL region comprising the amino acid sequence of SEQ ID NO: 104. In some embodiments, the antibody or antigen-binding molecule comprises a VH region comprising the amino acid sequence of SEQ ID NO: 105 and a VL region comprises the amino acid sequence of SEQ ID NO: 106. In some embodiments, the antibody or antigen-binding molecule thereof binds to a GPIIb/IIIa epitope located in the extracellular domain of the beta subunit of GPIIb/IIIa. In some embodiments, the antibody or antigen-binding molecule thereof does not compete with fibrinogen for binding to GPIIb/IIIa.

In some embodiments, the antibody or antigen-binding molecule thereof which specifically binds to a GPIIb/IIIa epitope comprises:

(i) a variable heavy chain CDR-1 (VH-CDR1) sequence at least about 60%, 70%, 80%, 90%, 95%, or 100% identical to any one of SEQ ID NOS: 73, 76, 79, 85, or 147;

(ii) a variable heavy chain CDR-2 (VH-CDR2) sequence at least about 60%, 70%, 80%, 90%, 95%, or 100% identical to any one of SEQ ID NOS: 74, 77, 80, 86, or 148;

(iii) a variable heavy chain CDR-3 (VH-CDR3) sequence at least about 60%, 70%, 80%, 90%, 95%, or 100% identical to any one of SEQ ID NOS: 75, 78, 81, 87, or 149;

(iv) a variable light chain CDR-1 (VL-CDR1) sequence at least about 60%, 70%, 80%, 90%, 95%, or 100% identical to any one of SEQ ID NOS: 141, 144, 82, 88, or 150;

(v) a variable light chain CDR-2 (VL-CDR2) sequence at least about 60%, 70%, 80%, 90%, 95%, or 100% identical to any one of SEQ ID NOS: 142, 145, 83, 89, or 151; and, (vi) a variable light chain CDR-3 (VL-CDR3) sequence at least about 60%, 70%, 80%, 90%, 95%, or 100% identical to any one of SEQ ID NO: 143, 146, 84, 90, or 152.

In some embodiments, the antibody or antigen-binding molecule thereof which specifically binds to a GPIIb/IIIa epitope comprises:

(i) a VH-CDR1 comprising the consensus sequence TSGX$_{11}$GVG (SEQ ID NO:229), wherein X$_{11}$ represents any amino acid residue, e.g., an amino acid residue with nonpolar side chains, e.g., Met (M) or Leu (L);

(ii) a VH-CDR2 comprising the consensus sequence HIWWDDDKRYNPX$_{12}$LKS (SEQ ID NO:230), wherein X$_{12}$ represents any amino acid residue, e.g., an amino acid residue with nonpolar side chains or beta-branched side chains, e.g., Ala (A) or Thr (T);

(iii) a VH-CDR3 comprising the consensus sequence SHYX$_{13}$GTFYFDX$_{14}$ (SEQ ID NO:231), wherein X$_{13}$ represents any amino acid residue, e.g., an amino acid residue with uncharged polar side chain, e.g., Tyr (Y) or Asn (N), and X$_{14}$ represents any amino acid residue, e.g., an amino acid residue with aromatic side chain, e.g., Tyr (Y) or Phe (F);

(iv) a VL-CDR1 comprising the sequence RASKSISKYLA (SEQ ID NO: 82);

(v) a VL-CDR2 comprising the sequence SGSTLQS (SEQ ID NO: 83); and, (vi) a VL-CDR3 comprising the sequence QQHIEYPWT (SEQ ID NO: 84).

In some embodiments, the antibody or antigen-binding molecule thereof according comprises:

(i) a VH-CDR1 sequence selected from SEQ ID NOS: 73, 76, 79, 85, or 147;

(ii) a VH-CDR2 sequence selected from SEQ ID NOS: 74, 77, 80, 86, or 148;

(iii) a VH-CDR3 sequence selected from SEQ ID NOS: 75, 78, 81, 87, or 149;

(iv) a VL-CDR1 sequence selected from SEQ ID NOS: 141, 144, 82, 88, or 150;

(v) a VL-CDR2 sequence selected from SEQ ID NOS: 142, 145, 83, 89, or 151; and, (vi) a VL-CDR3 sequence selected from SEQ ID NOS: 143, 146, 84, 90, or 152.

In some embodiments, the antibody or antigen-binding molecule thereof which specifically binds to a GPIIb/IIIa epitope comprises a VH region comprising an amino acid sequence at least 80%, 85%, 90%, 95%, or 100% identical to any one of SEQ ID NOS: 17, 18, 19, 21, or 109 and a VL region comprising an amino acid sequence at least 80%, 85%, 90%, 95%, or 100% identical to any one of SEQ ID NOS: 107, 108, 20, 22, or 110.

In some embodiments, the antibody or antigen-binding molecule thereof comprises a VH region comprising the amino acid sequence of SEQ ID NO: 17 and a VL region comprising the amino acid sequence of SEQ ID NO: 107. In other embodiments, the antibody or antigen-binding molecule thereof comprises a VH region comprising the amino acid sequence of SEQ ID NO: 18 and a VL region comprising the amino acid sequence of SEQ ID NO: 108. In some embodiments, the antibody or antigen-binding molecule thereof comprises a VH region comprising the amino acid sequence of SEQ ID NO: 109 and a VL region comprising the amino acid sequence of SEQ ID NO: 110. In other embodiments, the antibody or antigen-binding molecule thereof comprises a VH region comprising the amino acid sequence of SEQ ID NO: 19 and a VL region comprising the amino acid sequence of SEQ ID NO: 20. In other embodiments, the antibody or antigen-binding molecule thereof comprises a VH region comprising the amino acid sequence of SEQ ID NO: 21 and a VL region comprising the amino acid sequence of SEQ ID NO: 22. In some embodiments, the antibody or antigen-binding molecule thereof binds to a GPIIb/IIIa epitope located in the extracellular domain of the beta subunit of GPIIb/IIIa. In other embodiments, the antibody or antigen-binding molecule thereof competes with fibrinogen for binding to GPIIb/IIIa.

In some embodiments, the antibody or antigen-binding molecule thereof which specifically binds to a GPIIb/IIIa epitope comprises:

(i) a variable heavy chain CDR-1 (VH-CDR1) sequence at least about 60%, 70%, 80%, 90%, 95%, or 100% identical to SEQ ID NO: 91;

(ii) a variable heavy chain CDR-2 (VH-CDR2) sequence at least about 60%, 70%, 80%, 90%, 95%, or 100% identical to SEQ ID NO: 92;

(iii) a variable heavy chain CDR-3 (VH-CDR3) sequence at least about 60%, 70%, 80%, 90%, 95%, or 100% identical to SEQ ID NO: 93;

(iv) a variable light chain CDR-1 (VL-CDR1) sequence at least about 60%, 70%, 80%, 90%, 95%, or 100% identical to SEQ ID NO: 94;

(v) a variable light chain CDR-2 (VL-CDR2) sequence at least about 60%, 70%, 80%, 90%, 95%, or 100% identical to SEQ ID NO: 95; and, (vi) a variable light chain CDR-3 (VL-CDR3) sequence at least about 60%, 70%, 80%, 90%, 95%, or 100% identical to SEQ ID NO: 96.

In some embodiments, the antibody or antigen-binding molecule thereof which specifically binds to a GPIIb/IIIa epitope comprises:

(i) a VH-CDR1 sequence comprising SEQ ID NO: 91;
(ii) a VH-CDR2 sequence comprising SEQ ID NO: 92;
(iii) a VH-CDR3 sequence comprising SEQ ID NO: 93;
(iv) a VL-CDR1 sequence comprising SEQ ID NO: 94;
(v) a VL-CDR2 sequence comprising SEQ ID NOS: 95; and,
(vi) a VL-CDR3 sequence comprising SEQ ID NOS: 96.

In some embodiments, the antibody or antigen-binding molecule thereof which specifically binds to a GPIIb/IIIa epitope comprises a VH region comprising an amino acid sequence at least about 80%, 85%, 90%, 95%, or 100% identical to SEQ ID NO: 23 and a VL region comprising an amino acid sequence at least about 80%, 85%, 90%, 95%, or 100% identical to SEQ ID NO: 24. In some embodiments, the antibody or antigen-binding molecule thereof binds to a GPIIb/IIIa epitope located in the extracellular domain of the "molecule thereof competes with fibrinogen for binding to GPIIb/IIIa.

In some embodiments, the anti-GPIIb/IIIa antibody or antigen-binding molecule thereof comprises or consists of (a) a single chain Fv ("scFv"); (b) a diabody; (c) a minibody; (d) a polypeptide chain of an antibody; (e) F(ab')$_2$; or (f) F(ab).

In some embodiments, the anti-GPIIb/IIIa antibody or antigen-binding molecule thereof can be a targeting moiety. As used herein, the term "targeting moiety" refers to a moiety capable of interacting with a target molecule (e.g., the GPIIb/IIIa receptor, or a molecule comprising the α and/or β subunits of the GPIIb/IIIa receptor). Targeting moieties having limited cross-reactivity are generally preferred. In certain embodiments, suitable targeting moieties include, for example, any member of a specific binding pair, antibodies, monoclonal antibodies, or derivatives or analogs thereof, including without limitation: Fv fragments, single chain Fv (scFv) fragments, Fab'fragments, F(ab')2 fragments, single domain antibodies, camelized antibodies and antibody fragments, humanized antibodies and antibody fragments, and multivalent versions of the foregoing; multivalent binding reagents including without limitation: monospecific or bispecific antibodies, such as disulfide stabilized Fv fragments, scFv tandems ((scFv) fragments), diabodies, tribodies or tetrabodies, which typically are covalently linked or otherwise stabilized (i.e., leucine zipper or helix stabilized) scFv fragments; and other targeting moieties include for example, aptamers, receptors, ligands, and fusion proteins. In some embodiments, an anti-GPIIb/IIIa antibody or antigen-binding molecule thereof disclosed herein can target GPIIb/IIIa located on the surface of platelets.

III. Chimeric Molecules

The present disclosure also provides "chimeric molecules" comprising, for example, at least one of the GPIIb/IIIa antibodies or antigen-binding molecules thereof disclosed herein which is fused and/or conjugated and/or otherwise associated with at least one heterologous moiety. Thus, a chimeric molecule disclosed herein encompasses any molecule comprising (i) a GPIIb/IIIa antibody or antigen-binding molecule thereof disclosed herein (e.g., a scFv derived, for example, from the 34D10 antibody or the 12B2 antibody), and (ii) at least one heterologous moiety (e.g., a therapeutic moiety such as a clotting factors, and optionally a half-life extending moiety). In some embodiments, a chimeric molecule is a chimeric protein, i.e., a chimeric molecule in which all its components (heterologous moieties and/or linkers) are polypeptides. Other chimeric molecules can comprise non-polypeptide heterologous moieties (e.g., PEG, lipids, carbohydrates, nucleic acids, small molecule therapeutic agents, radionuclides, fluorescent probes, etc.) and/or non-polypeptide linkers.

In some embodiments, a chimeric molecule comprises a first amino acid sequence derived from a first source, bonded, covalently or non-covalently, to a second amino acid sequence derived from a second source, wherein the first and second source are not the same. A first source and a second source that are not the same can include two different biological entities, or two different proteins from the same biological entity, or a biological entity and a non-biological entity. A chimeric molecule can include for example, a protein derived from at least 2 different biological sources. A biological source can include any non-synthetically produced nucleic acid or amino acid sequence (e.g., a genomic or cDNA sequence, a plasmid or viral vector, a native virion or a mutant or analog, as further described herein, of any of the above). A synthetic source can include a protein or nucleic acid sequence produced chemically and not by a biological system (e.g., solid phase synthesis of amino acid sequences). A chimeric molecule can also include a protein derived from at least 2 different synthetic sources or a protein derived from at least one biological source and at least one synthetic source. A chimeric molecule can also comprise a first amino acid sequence derived from a first source, covalently or non-covalently linked to a nucleic acid, derived from any source or a small organic or inorganic molecule derived from any source. The chimeric molecule can also comprise a linker molecule between the first and second amino acid sequence or between the first amino acid sequence and the nucleic acid, or between the first amino acid sequence and the small organic or inorganic molecule.

As used herein the term "moiety" refers to a component part or constituent of a chimeric molecule of the present invention. As used herein, the term "heterologous moiety" refers to a moiety genetically fused, conjugated, and/or otherwise associated to a GPIIb/IIIa antibody or antigen-binding molecule thereof. In some embodiments, the chimeric molecule has, for example, a formula:

Tm-(L)-H or    (i)

H-(L)-Tm,    (ii)

wherein, H is a heterologous moiety; L is an optional linker; and, Tm is an anti-GPIIb/IIa antibody or antigen-binding molecule thereof disclosed herein.

In some embodiments, the chimeric molecule further comprises a second heterologous moiety. Accordingly, in some embodiments, the chimeric molecule has a formula selected from:

H1-(L1)-Tm-(L2)-H2;    (i)

H2-(L2)-Tm-(L1)-H1;    (ii)

H1-(L1)-H2-(L2)-Tm;    (iii)

H2-(L2)-H1-(L1)-Tm;    (iv)

Tm-(L1)-H1-(L2)-H2; or,    (v)

Tm-(L2)-H2-(L1)-H1;    (vi)

wherein, Tm is an anti-GPIIb/IIIa antibody or antigen-binding molecule thereof disclosed herein; H1 is a first heterologous moiety, H2 is a second heterologous moiety, L1 is a first optional linker, and L2 is a second optional linker.

In some embodiments, the first heterologous moiety and the second heterologous moiety are the same. In other embodiments, the first heterologous moiety and the second heterologous moiety are different. In some embodiments, L1 and L2 are the same. In other embodiments, L1 and L2 are different.

The chimeric molecule formulas disclosed are oriented from N-terminus (left) to C-terminus (right). One skilled in the art would understand that the chimeric molecule formulas disclosed herein are non-limiting examples of chimeric molecules comprising the disclosed GPIIb/IIIa antibodies or antigen-binding molecules thereof. For example, the formulas can comprise further sequences at their N-terminal or C-terminal ends, or inserted between elements of the formula. Accordingly, a chimeric molecule can comprise, one, two, three, four, five, or more than five heterologous moieties. In some embodiments, the hyphen (-) in a formula indicates a peptide bond or one or more amino acids. Exemplary chimeric molecules are presented in FIG. 22.

In some embodiments, a chimeric protein comprises a first polypeptide chain and a second polypeptide chain, which are associated with each other. In some embodiments, the first polypeptide chain comprises a light chain of a clotting factor (e.g., FVII) and a heterologous moiety (e.g., a half-life extending moiety), and the second polypeptide chain comprises a heavy chain of the clotting factor (e.g., FVII) and a GPIIb/IIIa antibody or antigen-binding molecule thereof disclosed herein. In other embodiments, the first polypeptide chain comprises a light chain of a clotting factor (e.g., FVII) and a GPIIb/IIIa antibody or antigen-binding molecule thereof disclosed herein, and the second polypeptide chain comprises a heavy chain of the clotting factor (e.g., FVII) and a heterologous moiety (e.g., a half-life extending moiety). In yet another embodiment, the first polypeptide chain comprises a light chain of a clotting factor (e.g., FVII) and the second polypeptide chain comprises a heavy chain of the clotting factor (e.g., FVII), a GPIIb/IIIa antibody or antigen-binding molecule thereof disclosed herein, and a heterologous moiety (e.g., a half-life extending moiety). In some embodiments, the first polypeptide chain comprises a light chain of a clotting factor (e.g., FVII) and the second polypeptide chain comprises a heavy chain of the clotting factor (e.g., FVII), a heterologous moiety (e.g., a half-life extending moiety), and a GPIIb/IIIa antibody or antigen-binding molecule thereof disclosed herein. In other embodiments, the first polypeptide chain comprises a light chain of a clotting factor (e.g., FVII), a heterologous moiety (e.g., a half-life extending moiety), and a GPIIb/IIIa antibody or antigen-binding molecule thereof disclosed herein, and the second polypeptide chain comprises a heavy chain of the clotting factor (e.g., FVII). In some embodiments, the first polypeptide chain comprises a light chain of a clotting factor (e.g., FVII), a GPIIb/IIIa antibody or antigen-binding molecule thereof disclosed herein, and a heterologous moiety (e.g., a half-life extending moiety), and the second polypeptide chain comprises a heavy chain of the clotting factor (e.g., FVII).

In some embodiments, the chimeric molecule comprises a formula:

(1) wherein the first polypeptide chain comprises $CF_L$-H or H-$CF_L$ and the second polypeptide chain comprises $CF_H$-Tm or Tm-$CF_H$;

(2) wherein the first polypeptide chain comprises $CF_L$-Tm or Tm-$CF_L$ and the second polypeptide chain comprises $CF_H$-H or H-$CF_H$;

(3) wherein the first polypeptide chain comprises $CF_L$ and the second polypeptide chain comprises $CF_H$-Tm-H or H-Tm-$CF_H$;

(4) wherein the first polypeptide chain comprises $CF_L$ and the second polypeptide chain comprises $CF_H$-H-Tm or Tm-H-$CF_H$;

(5) wherein the first polypeptide chain comprises $CF_L$-H-Tm or Tm-H-$CF_L$ and the second polypeptide chain comprises $CF_H$; or (6) wherein the first polypeptide chain comprises $CF_L$-Tm-H or H-Tm-$CF_L$ and the second polypeptide chain comprises $CF_H$;

wherein, $CF_L$ is a light chain of a clotting factor (e.g., FVII); $CF_H$ is a heavy chain of the clotting factor (e.g., FVII); Tm is an anti-GPIIb/IIIa antibody or antigen-binding molecule thereof; and H is a heterologous moiety (e.g., a half-life extending moiety). In some embodiments, the clotting factor is independently selected from the group consisting of FVII, FIX, FX, and any combinations thereof.

The instant disclosure also provides a chimeric molecule comprising a first polypeptide chain and a second polypeptide chain, which are associated with each other, (1) wherein the first polypeptide chain comprises a light chain of a clotting factor (e.g., FVII, FIX, or FX), and a targeting moiety, which binds to a platelet, and the second polypeptide chain comprises a heavy chain of the clotting factor (e.g., FVII, FIX, or FX) and a heterologous moiety (e.g., a half-life extending moiety); (2) wherein the first polypeptide chain comprises a light chain of a clotting factor (e.g., FVII) and a heterologous moiety (e.g., a half-life extending moiety), and the second polypeptide chain comprises a heavy chain of the clotting factor (e.g., FVII, FIX, or FX) and a targeting moiety, which binds to a platelet; (3) wherein the first polypeptide chain comprises a light chain of a clotting factor (e.g., FVII, FIX, or FX), a heterologous moiety (e.g., a half-life extending moiety), and a targeting moiety, which binds to a platelet, and the second polypeptide comprises a heavy chain of the clotting factor (e.g., FVII, FIX, or FX); or (4) wherein the first polypeptide chain comprises a light chain of a clotting factor (e.g., FVII, FIX, or FX), a targeting moiety, which binds to a platelet, and a heterologous moiety (e.g., a half-life extending moiety) and the second polypeptide chain comprises a heavy chain of the clotting factor (e.g., FVII, FIX, or FX). In some embodiments, the clotting factor is FVII, FIX, or FX.

As used herein, the phrases "which binds to a platelet," "binding to a platelet," and variants thereof generally refer to the specific binding of (i) a GPIIb/IIIa antibody or antigen-binding molecule thereof or (ii) a chimeric molecule of the present disclosure to an antigenic site on the surface of the platelet, e.g., an epitope on the extracellular domains of the α and/or β subunits of the GPIIb/IIIa receptor. It would be known to a person skilled in the art that GPIIb/IIIa is present in two pools, a plasma membrane pool present in the platelet's resting state and an internal pool of GPIIb/IIIa which is expressed upon platelet activation. See, for example, Quinn et al., *J Pharmacol. Exp. Ther.* 297:496-500 (2001). Accordingly, in some specific embodiments, and particularly for diagnostic uses where the platelet's plasma membrane can be permeabilized, the binding of a GPIIb/IIIa antibody or antigen-binding molecule thereof to platelets, or the binding of a chimeric molecule of the present disclosure to platelets can refer to binding to the plasma membrane pool and/or to the internal pool of GPIIb/IIIa.

In some embodiments, the chimeric molecule comprises a first polypeptide chain and a second polypeptide chain, which are associated with each other, (1) wherein the first polypeptide chain comprises $CF_L$-H or H-$CF_L$ and the second polypeptide chain comprises $CF_H$-Tm or Tm-$CF_H$; (2) wherein the first polypeptide chain comprises $CF_L$-Tm or Tm-$CF_L$ and the second polypeptide chain comprises $CF_H$-H or H-$CF_H$; (3) wherein the first polypeptide chain comprises $CF_L$-H-Tm or Tm-H-$CF_L$ and the second polypeptide chain comprises $CF_H$; or (4) wherein the first polypeptide chain comprises $CF_L$-Tm-H or H-Tm-$CF_L$ and the second polypeptide chain comprises $CF_H$; wherein, H is a heterologous moiety (e.g., a half-life extending moiety), $CF_H$ is a heavy chain of a clotting factor (e.g., FVII), $CF_L$ is a light chain of the clotting factor (e.g., FVII, FIX, or FX), Tm is a targeting moiety which binds to a platelet, and L is an optional linker.

In some embodiments, the chimeric molecule comprises a formula selected from (1) Tm-$CF_H$:$CF_L$-H; (2) H-$CF_H$:$CF_L$-Tm; (3) Tm-H-$CF_L$:$CF_H$; or (4) H-Tm-$CF_L$: $CF_H$; wherein, H is a heterologous moiety (e.g., a half-life extending moiety); $CF_H$ is a heavy chain of a clotting factor (e.g., FVII, FIX, or FX); $CF_L$ is a light chain of a clotting factor (e.g., FVII); Tm is a targeting moiety, which binds to a platelet; L is an optional linker; and: represents a covalent or non-covalent bond between $CF_H$ and $CF_L$ (e.g., a disulfide bond).

In some embodiments, the association between the first polypeptide chain and the second polypeptide chain in the chimeric molecule is a covalent bond or a non-covalent bond. Thus, in other embodiments, the association between the first polypeptide chain and the second polypeptide chain in the chimeric molecule is a covalent bond between the heavy chain and the light chain of the clotting factor (e.g., FVII, FIX, or FX). In contrast, in some other embodiments, the covalent bond is a disulfide bond.

The present disclosure also provides a chimeric molecule comprising a single polypeptide chain, which comprises, from N terminus to C terminus, (i) a light chain of a clotting factor (e.g., FVII, FIX, or FX), a heterologous moiety (e.g., a half-life extending moiety), a protease cleavage site, a heavy chain of the clotting factor (e.g., FVII, FIX, or FX), and a targeting moiety (e.g., a GPIIb/IIIa antibody or antigen-binding molecule thereof) which binds to a platelet or (ii) a light chain of a clotting factor (e.g., FVII), a targeting moiety, which binds to a platelet, a protease cleavage site, a heavy chain of the clotting factor (e.g., FVII, FIX, or FX), and a heterologous moiety (e.g., a half-life extending moiety). In some embodiments, the clotting factor is FVII. In other embodiments, the clotting factor is FIX or FX. In yet other embodiments, the clotting factor is FVII, FIX, or FX. In some embodiments, the protease cleavage site is an intracellular processing site. In some embodiments, the intracellular processing site is processed by a proprotein convertase. In some embodiments, the proprotein convertase is selected from the group consisting of PC5, PACE, PC7, and any combinations thereof.

In some embodiments, the targeting moiety in the chimeric molecule is selected from: an antibody or antigen binding molecule thereof, a receptor binding portion of a receptor, and a peptide. In some embodiments, the targeting moiety selectively binds to a resting platelet or an activated platelet. In other embodiments, the targeting moiety selectively binds to a target selected from the group consisting of: GP1ba (Uniprot: E7ES66; E7ES66_HUMAN), GPVI (Uniprot: Q9HCN6; GPVI_HUMAN), GPIX (Uniprot: P14770; GPIX_HUMAN), a nonactive form of glycoprotein IIb/IIIa ("GPIIb/IIIa"), an active form of GPIIb/IIIa, P-selectin (Uniprot: Q14242; SELPL_HUMAN), GMP-33 (see, e.g., Damas et al., *Thromb. Haemost.* 86:887-93 (2001)), LAMP-1 (Uniprot: P11279; LAMP1_HUMAN), LAMP-2 (Uniprot: P13473; LAMP2_HUMAN), CD40L (Uniprot: P29965; CD40L_HUMAN), LOX-1 (Uniprot: P78380; OLR1_HUMAN), and any combinations thereof. The above referenced Uniprot identifiers correspond the entries published in the Universal Protein Resource (Uniprot) database release 2013_05 (May 1, 2013), and are incorporated by reference in their entireties. In certain embodiments, the targeting moiety comprises a GPIIb/IIIa antibody or antigen-binding molecule thereof. In specific embodiments, the GPIIb/IIIa antibody or antigen-binding molecule thereof is a GPIIb/IIIa antibody or antigen-binding molecule thereof disclosed herein.

III.A Heterologous Moieties

The heterologous moiety or moieties of the chimeric molecules disclosed herein can comprise, consist of, or consist essentially of prophylactic and/or therapeutic agents (e.g., clotting factors), molecules capable of improving a pharmacokinetic (PK) property (e.g., plasma half-life extending moieties), detectable moieties (e.g., fluorescent molecules or radionuclides), etc.

As used herein, the term "therapeutic agent" refers to any biological or chemical agent used in the treatment of a disease or disorder. Therapeutic agents include any suitable biologically active chemical compounds, biologically derived components such as cells, peptides, antibodies, and polynucleotides, and radiochemical therapeutic agents such as radioisotopes. In some embodiments, the chimeric molecule comprises a clotting factor.

In some embodiments, a heterologous moiety can modify a physicochemical property of a chimeric molecule lacking such heterologous moiety, for example, it can increase the hydrodynamic radius of a chimeric molecule. In other embodiments, the incorporation of a heterologous moiety into a chimeric molecule can improve one or more pharmacokinetic properties without significantly affecting its biological activity or function (e.g., procoagulant activity in chimeric molecules comprising a clotting factor).

In some embodiments, the heterologous moiety is a polypeptide comprising, consisting essentially of, or consisting of at least about 10, 100, 200, 300, 400, 500, 600, 700, 800, 900, 1000, 1100, 1200, 1300, 1400, 1500, 1600, 1700, 1800, 1900, 2000, 2500, 3000, or 4000 amino acids. In other embodiments, the heterologous moiety is a polypeptide comprising, consisting essentially of, or consisting of about 100 to about 200 amino acids, about 200 to about 300 amino acids, about 300 to about 400 amino acids, about 400 to about 500 amino acids, about 500 to about 600 amino acids, about 600 to about 700 amino acids, about 700 to about 800 amino acids, about 800 to about 900 amino acids, or about 900 to about 1000 amino acids.

In other embodiments, a heterologous moiety increases stability of the chimeric molecule of the invention or a fragment thereof. As used herein, the term "stability" refers to an art-recognized measure of the maintenance of one or more physical properties of the chimeric molecule in response to an environmental condition (e.g., an elevated or lowered temperature). In certain embodiments, the physical property can be the maintenance of the covalent structure of the chimeric molecule (e.g., the absence of proteolytic cleavage, unwanted oxidation or deamidation). In other embodiments, the physical property can also be the presence of the chimeric molecule in a properly folded state (e.g., the absence of soluble or insoluble aggregates or precipitates). In one embodiment, the stability of the chimeric molecule is measured by assaying a biophysical property of the chimeric molecule, for example thermal stability, pH unfolding profile, stable removal of glycosylation, solubility, biochemical function (e.g., ability to bind to a protein, receptor or ligand), etc., and/or combinations thereof. In another embodiment, biochemical function is demonstrated by the binding affinity of the interaction. In one embodiment, a measure of protein stability is thermal stability, i.e., resistance to thermal challenge. Stability can be measured using methods known in the art, such as, HPLC (high performance liquid chromatography), SEC (size exclusion chromatography), DLS (dynamic light scattering), etc. Methods to measure thermal stability include, but are not limited to differential scanning calorimetry (DSC), differential scanning fluorimetry (DSF), circular dichroism (CD), and thermal challenge assay.

III.A.1 Clotting Factors

In some embodiments, chimeric molecules of the invention comprises at least one polypeptide heterologous moiety which is (i) a clotting factor, or (ii) a procoagulant peptide (e.g., a synthetic procoagulant peptide). In some embodiments, the clotting factor is independently selected from the group consisting of factor FVII ("FVII"), factor IX ("FIX"), or factor X ("FX"), and any combinations thereof. As discussed in detail below, the clotting factor can be, for example, FVII zymogen, activatable FVII, activated FVII (FVIIa), FIX zymogen, activatable FIX, activated FIX (FIXa), FX zymogen, activatable FX, or activated FX (FXa). In some embodiments, the clotting factor can comprise a single polypeptide chain or two polypeptide chains (e.g., the heavy chain and the light chain of FVII). The term "activatable clotting factor" refers to a clotting factor in an inactive form (e.g., in its zymogen form) that is capable of being converted to an active form.

As used herein, the term "clotting factor" refers to molecules, or analogs thereof, naturally occurring or recombinantly produced which prevent or decrease the duration of a bleeding episode in a subject. In other words, it means molecules having pro-clotting activity, i.e., are responsible for the conversion of fibrinogen into a mesh of insoluble fibrin causing the blood to coagulate or clot. The term "clotting factor," as used herein encompasses clotting factors (e.g., vWF, FV, FVa, FVII, FVIIa, FVIII, FVIIIa, FIX, FIXa, FX, FXa, FXI, FXIa, FXII, FXIIa, FXIII, or FXIIIa), fragments, variants, analogs, or derivatives thereof, naturally occurring, recombinantly produced, or synthetically produced which prevent or decrease the duration of a bleeding episode in a subject. In some embodiments, the chimeric molecule comprises a FVII or activated FVII (FVIIa) clotting factor. In some embodiments, the chimeric molecule of the invention comprises a FIX or activated FIX (FIXa) clotting factor. In other embodiments, the chimeric molecule comprises a FX or activated FX (FXa) clotting factor.

In some embodiments, the chimeric molecule comprises a single clotting factor, which in the chimeric molecule is represented by a formula as H, H1 or H2. In other embodiments, the chimeric molecule comprises two clotting factors. In some embodiments, the two clotting factors are the same, whereas in other embodiments, the two clotting factors are different. In some embodiments, one clotting factor is a fragment of a clotting factor (e.g., a heavy chain of a clotting factor such as FVII) and the second clotting factor is a fragment of the same clotting factor (e.g., a light chain of a clotting factor such as FVIII). In some embodiments, the chimeric molecule comprises more than two clotting factors.

III.A.1.a Factor VII

In some embodiments, the chimeric molecule comprises a clotting factor which is a mature form of Factor VII or a variant thereof. Factor VII (FVII, F7; also referred to as Factor 7, coagulation factor VII, serum factor VII, serum prothrombin conversion accelerator, SPCA, proconvertin and eptacog alpha) is a serine protease that is part of the coagulation cascade. FVII includes a Gla domain, two EGF domains (EGF-1 and EGF-2), and a serine protease domain (or peptidase S1 domain) that is highly conserved among all members of the peptidase S1 family of serine proteases, such as for example with chymotrypsin. FVII occurs as a single chain zymogen, an activated zymogen-like two-chain polypeptide and a fully activated two-chain form.

As used herein, a "zymogen-like" protein or polypeptide refers to a protein that has been activated by proteolytic cleavage, but still exhibits properties that are associated with a zymogen, such as, for example, low or no activity, or a conformation that resembles the conformation of the zymogen form of the protein. For example, when it is not bound to tissue factor, the two-chain activated form of FVII is a zymogen-like protein; it retains a conformation similar to the uncleaved FVII zymogen, and, thus, exhibits very low activity. Upon binding to tissue factor, the two-chain activated form of FVII undergoes conformational change and acquires its full activity as a coagulation factor.

Exemplary FVII variants include those with increased specific activity, e.g., mutations that increase the activity of FVII by increasing its enzymatic activity (Kcat or Km). Such variants have been described in the art and include, e.g., mutant forms of the molecule as described for example in Persson et al., *Proc. Natl. Acad Sci. USA* 98:13583 (2001); Petrovan and Ruf, *J. Biol. Chem.* 276:6616 (2001); Persson et al., *J. Biol. Chem.* 276:29195 (2001); Soejima et al., *J Biol. Chem.* 276:17229 (2001); Soejima et al., *J. Biol. Chem.* 247:49027 (2002).

In one embodiment, a variant form of FVII includes mutations, e.g., V158D-E296V-M298Q. In another embodiment, a variant form of FVII includes a replacement of amino acids 608-619 (LQQSRKVGDSPN (SEQ ID NO:234), corresponding to the 170- loop) from the FVII mature sequence with amino acids EASYPGK (SEQ ID NO: 188) from the 170-loop of trypsin. High specific activity variants of FVII are also known in the art. For example, Simioni et al. (*N.E. Journal of Medicine* 361:1671, 2009) describe an R338L mutation. Chang et al. (*J. Biol. Chem.* 273:12089, 1988) and Pierri et al. (*Human Gene Therapy* 20:479, 2009) describe an R338A mutation. Other mutations are known in the art and include those described, e.g., in Zogg and Brandstetter, Structure 17:1669 (2009); Sichler et al.,*J. Biol. Chem.* 278:4121 (2003); and Sturzebecher et al., *FEBS Lett.* 412:295 (1997). The contents of these references are incorporated herein by reference.

Full activation, which occurs upon conformational change from a zymogen-like form, occurs upon binding to its co-factor, i.e., tissue factor. Also, mutations can be introduced that result in the conformation change in the absence of tissue factor. Hence, reference to FVIIa includes both two-chain forms thereof: the zymogen-like form, and the fully activated two-chain form.

III.A.1.b Factor IX

In one embodiment, the chimeric molecule comprises a clotting factor which is a mature form of Factor IX or a variant thereof. Factor IX circulates as a 415 amino acid, single chain plasma zymogen. See, Vysotchin et al., *J Biol. Chem.* 268:8436 (1993). The zymogen of FIX is activated by FXIa or by the tissue factor/FVIIa complex. Specific cleavages between arginine-alanine 145-146 and arginine-valine 180-181 result in a light chain and a heavy chain linked by a single disulfide bond between cysteine 132 and cysteine 289 (Bajaj et al., *Biochemistry* 22:4047 (1983)).

The structural organization of FIX is similar to that of the vitamin K-dependent blood clotting proteins FVII, FX and protein C. The approximately 45 amino acids of the amino terminus comprise the gamma-carboxyglutamic acid, or Gla, domain. This is followed by two epidermal growth factor homology domains (EGF), an activation peptide and the catalytic "heavy chain" which is a member of the serine protease family (Vysotchin et al., *J. Biol. Chem.* 268:8436 (1993); Spitzer et al., *Biochemical Journal* 265:219 (1990); Brandstetter et al., *Proc. Natl. Acad Sci. USA* 92:9796 (1995)).

III.A.1.c Factor X

In one embodiment, the chimeric molecule comprises a clotting factor which is a mature form of Factor X. Factor X is a vitamin-K dependent glycoprotein with a molecular weight of 58.5 kDa, which is secreted from liver cells into the plasma as a zymogen. Initially factor X is produced as a prepropeptide with a signal peptide consisting in total of 488 amino acids. The signal peptide is cleaved off by signal peptidase during export into the endoplasmatic reticulum. The propeptide sequence is cleaved off after gamma carboxylation took place at the first 11 glutamic acid residues at the N-terminus of the mature N-terminal chain. A further processing step occurs by cleavage between Arg182 and Ser183. This processing step also leads concomitantly to the deletion of the tripeptide Arg180-Lys181-Arg182. The resulting secreted factor X zymogen consists of an N-terminal light chain of 139 amino acids (M, 16,200) and a C-terminal heavy chain of 306 amino acids (M, 42,000) which are covalently linked via a disulfide bridge between Cys172 and Cys342. Further posttranslational processing steps include the β-hydroxylation of Asp103 as well as N- and O-type glycosylation.

It will be understood that in addition to wild type (WT) versions of these clotting factors or biologically active portions thereof, the heterologous moieties in the chimeric molecules disclosed herein can also comprise precursor truncated forms thereof that have activity, allelic variants and species variants, variants encoded by splice variants, and other variants, including polypeptides that have at least 40%, 45%, 50%, 55%, 65%, 70%, 75%, 80%, 85%, 90%, 95%, 96%, 97%, 98%, 99% or more sequence identity to the mature form of the clotting factor and which retain the ability to promote clot formation. For example, modified FVII polypeptides and variants thereof which retain at least one activity of FVII, such as TF binding, factor X binding, phospholipid binding, and/or coagulant activity of FVII can be employed. By retaining activity, the activity can be altered, such as reduced or increased, as compared to a wild-type clotting factor so long as the level of activity retained is sufficient to yield a detectable effect.

Exemplary modified polypeptides include, but are not limited to, tissue-specific isoforms and allelic variants thereof, synthetic molecules prepared by translation of nucleic acids, proteins generated by chemical synthesis, such as syntheses that include ligation of shorter polypeptides, through recombinant methods, proteins isolated from human and non-human tissue and cells, chimeric polypeptides and modified forms thereof. The instant clotting factors can also consist of fragments or portions of WT molecules that are of sufficient length or include appropriate regions to retain at least one activity (upon activation if needed) of a full-length mature polypeptide. Exemplary clotting factor variants are known in the art.

As used herein, the term "Gla domain" refers to the conserved membrane binding motif which is present in vitamin K-dependent proteins, such as prothrombin, coagulation factors VII, IX and X, proteins C, S, and Z. These proteins require vitamin K for the posttranslational synthesis of γ-carboxyglutamic acid, an amino acid clustered in the N-terminal Gla domain of these proteins. All glutamic residues present in the domain are potential carboxylation sites and many of them are therefore modified by carboxylation. In the presence of calcium ions, the Gla domain interacts with phospholipid membranes that include phosphatidylserine. The Gla domain also plays a role in binding to the FVIIa cofactor, tissue factor (TF). Complexed with TF, the Gla domain of FVIIa is loaded with seven $Ca^{2+}$ ions, projects three hydrophobic side chains in the direction of the cell membrane for interaction with phospholipids on the cell surface, and has significant contact with the C-terminal domain of TF.

The Gla domain of factor VII comprises the uncommon amino acid γ-carboxyglutamic acid (Gla), which plays a vital role in the binding of clotting factors to negatively charged phospholipid surfaces. The Gla domain is responsible for the high-affinity binding of calcium ions. It starts at the N-terminal extremity of the mature form of proteins and ends with a conserved aromatic residue. A conserved Gla-x(3)-Gla-x-Cys motif is found in the middle of the domain which seems to be important for substrate recognition by the carboxylase. Using stopped-flow fluorescence kinetic measurements in combination with surface plasmon resonance analysis, the Gla domain has been found to be important in the sequence of events whereby the protease domain of FVIIa initiates contact with sTF (Osterlund et al., *Biochem. Biophys. Res. Commun.* 337:1276 (2005)). In addition, clearance of clotting factors can be significantly mediated through Gla interactions, e.g., on liver cells and clearance receptors, e.g., EPCR.

In one embodiment, the chimeric molecule comprises a heterologous moiety comprising a clotting factor modified to lack a Gla domain. The Gla domain is responsible for mediating clearance of clotting factors via multiple pathways, such as binding to liver cells, clearance receptors such as EPCR, etc. Thus, eliminating the Gla domain has beneficial effects on half life of clotting factors. Though Gla domain is also generally required for activity by localizing clotting factors to sites of coagulation, the inclusion of a platelet targeting domain moiety (e.g., a GPIIb/IIIa antibody or antigen-binding molecule thereof) targets the Gla deleted clotting factor to platelets. Accordingly, in one embodiment, the chimeric molecule comprises a targeting moiety (e.g., a GPIIb/IIIa antibody or antigen-binding molecule thereof) and a heterologous moiety comprising a clotting factor that lacks a Gla domain. For example, in the case of Factor VII, the Gla domain is present at the amino terminus of the light chain and consists of amino acids 1-35. The Gla domains of the exemplary clotting factors disclosed herein are known in the art. The Gla domain can be removed using standard molecular biology techniques, replaced with a targeting domain, and the modified light chain incorporated into a construct of the invention. In one embodiment, a cleavage site can be introduced into constructs lacking a Gla domain to facilitate activation of the molecule. For example, in one embodiment, such a cleavage site can be introduced between the amino acids that are cleaved when the clotting factor is activated (e.g., between amino acids 152 and 153 in the case of Factor VII).

In one embodiment, a cleavage site can be introduced into chimeric molecules comprising a clotting factor that lacks a Gla domain to facilitate activation of the molecule. For example, in one embodiment, such a cleavage site can be introduced between the amino acids that are cleaved when the clotting factor is activated (e.g., between amino acids 152 and 153 in the case of Factor VII). Exemplary clotting factors lacking a Gla domain are known in the art. Exemplary clotting factors are those of mammalian, e.g., human, origin.

III.A.2 Half-life Extending Moieties

In some embodiments, the chimeric molecule comprises at last one heterologous moiety that is a "half-life extending moiety." As used herein, the term "half-life extending moiety" refers to a heterologous moiety which increases the in vivo half-life of a protein, for example, a chimeric molecule. The term "half-life" refers to a biological half-life of a particular protein or polypeptide (e.g., a clotting factor or a chimeric molecule disclosed herein) in vivo. Half-life can be represented by the time required for half the quantity administered to a subject to be cleared from the circulation and/or other tissues in the animal. When a clearance curve of a given polypeptide or chimeric molecule of the invention is constructed as a function of time, the curve is usually biphasic with a rapid α-phase and longer β-phase. The α-phase typically represents an equilibration of the administered Fc polypeptide between the intra- and extra-vascular space and is, in part, determined by the size of the polypeptide. The β-phase typically represents the catabolism of the polypeptide in the intravascular space. In some embodiments, procoagulant compounds of the invention are monophasic, and thus do not have an alpha phase, but just the single beta phase. In certain embodiments, the term half-life as used herein refers to the half-life of the procoagulant compound in the β-phase. The typical β phase half-life of a human antibody in humans is 21 days. In vivo half-life of a chimeric molecule can be determined by any method known to those of skill in the art. In certain embodiments, the half-life extending moiety can comprise an attachment site for a non-polypeptide moiety (e.g., PEG).

Half-life extending moieties, as discussed below in detail, can comprise, for example, (i) low complexity peptides, (ii) albumin, (iii) albumin binding polypeptide or fatty acid, (iv) Fc, (v) transferrin, (vi) PAS, (vii) the C-terminal peptide (CTP) of the β subunit of human chorionic gonadotropin, (viii) polyethylene glycol (PEG), (ix) hydroxyethyl starch (HES), (x) albumin-binding small molecules, (xi) vWF, (xii) a clearance receptor or fragment thereof which blocks binding of the chimeric molecule to a clearance receptor, or (xiii) any combinations thereof. In some embodiments, the half-life extending moiety comprises an Fc region. In other embodiments, the half-life extending moiety comprises two Fc regions fused by a linker. Exemplary heterologous moieties also include, e.g., FcRn binding moieties (e.g., complete Fc regions or portions thereof which bind to FcRn), single chain Fc regions (scFc regions, e.g., as described in U.S. Publ. No. 2008-0260738, and Intl. Publ. Nos. WO 2008-012543 and WO 2008-1439545), or processable scFc regions. In some embodiments, a heterologous moiety can include an attachment site for a non-polypeptide moiety such as polyethylene glycol (PEG), hydroxyethyl starch (HES), polysialic acid, or any derivatives, variants, or combinations of these moieties.

In certain embodiments, a chimeric molecule of the invention comprises at least one half-like extending moiety which increases the in vivo half-life of the chimeric molecule with respect to the in vivo half-life of the corresponding chimeric molecule lacking such heterologous moiety. In vivo half-life of a chimeric molecule can be determined by any method known to those of skill in the art, e.g., activity assays (chromogenic assay or one stage clotting aPTT assay), ELISA, etc.

In some embodiments, the presence of one or more half-life extending moiety results in the half-life of the chimeric molecule to be increased compared to the half-life of the corresponding chimeric molecule lacking such one or more half-life extending moieties. The half-life of the chimeric molecule comprising a half-life extending moiety is at least about 1.5 times, at least about 2 times, at least about 2.5 times, at least about 3 times, at least about 4 times, at least about 5 times, at least about 6 times, at least about 7 times, at least about 8 times, at least about 9 times, at least about 10 times, at least about 11 times, or at least about 12 times longer than the in vivo half-life of the corresponding chimeric molecule lacking such half-life extending moiety.

In one embodiment, the half-life of the chimeric molecule comprising a half-life extending moiety is about 1.5-fold to about 20-fold, about 1.5 fold to about 15 fold, or about 1.5 fold to about 10 fold longer than the in vivo half-life of the corresponding chimeric molecule lacking such half-life extending moiety. In another embodiment, the half-life of chimeric molecule comprising a half-life extending moiety is extended about 2-fold to about 10-fold, about 2-fold to about 9-fold, about 2-fold to about 8-fold, about 2-fold to about 7-fold, about 2-fold to about 6-fold, about 2-fold to about 5-fold, about 2-fold to about 4-fold, about 2-fold to about 3-fold, about 2.5-fold to about 10-fold, about 2.5-fold to about 9-fold, about 2.5-fold to about 8-fold, about 2.5-fold to about 7-fold, about 2.5-fold to about 6-fold, about 2.5-fold to about 5-fold, about 2.5-fold to about 4-fold, about 2.5-fold to about 3-fold, about 3-fold to about 10-fold, about 3-fold to about 9-fold, about 3-fold to about 8-fold, about 3-fold to about 7-fold, about 3-fold to about 6-fold, about 3-fold to about 5-fold, about 3-fold to about 4-fold, about 4-fold to about 6 fold, about 5-fold to about 7-fold, or about 6-fold to about 8 fold as compared to the in vivo half-life of the corresponding chimeric molecule lacking such half-life extending moiety.

III.A.2.a Fc Region

In certain embodiments, the chimeric molecule comprises at least a heterologous moiety comprising a Fc region. "Fc" or "Fe region" as used herein means a functional neonatal Fc receptor (FcRn) binding partner comprising an Fc domain, variant, or fragment thereof, unless otherwise specified. An FcRn binding partner is any molecule that can be specifically bound by the FcRn receptor with consequent active transport by the FcRn receptor of the FcRn binding partner. Thus, the term Fc includes any variants of IgG Fc that are functional. The region of the Fc portion of IgG that binds to the FcRn receptor has been described based on X-ray crystallography (Burmeister et al., Nature 372:379 (1994), incorporated herein by reference in its entirety). The major contact area of the Fc with the FcRn is near the junction of the CH2 and CH3 domains. Fc-FcRn contacts are all within a single Ig heavy chain. FcRn binding partners include, but are not limited to, whole IgG, the Fc fragment of IgG, and other fragments of IgG that include the complete binding region of FcRn. An Fc can comprise the CH2 and CH3 domains of an immunoglobulin with or without the hinge region of the immunoglobulin. Also included are Fc fragments, variants, or derivatives which maintain the desirable properties of an Fc region in a chimeric molecule, e.g., an increase in half-life, e.g., in vivo half-life. Myriad mutants, fragments, variants, and derivatives are described, e.g., in PCT Publication Nos. WO2011/069164, WO2012/006623, WO2012/006635, or WO 2012/006633, all of which are incorporated herein by reference in their entireties.

In some embodiments, the chimeric molecule comprises a clotting factor (e.g., FVII), a targeting moiety (e.g., a (GPIIb/IIIa antibody or antigen-binding molecule thereof), and an Fe region.

III.A.2.b scFc (Single Chain Fc) Region

In one embodiment, the chimeric molecule comprises a heterologous moiety comprising one genetically fused Fc region or a portion thereof within a single polypeptide chain (i.e., a single-chain Fc (scFc) region). The unprocessed polypeptides comprise at least two immunoglobulin constant regions or portions thereof (e.g., Fc moieties or domains (e.g., 2, 3, 4, 5, 6, or more Fc moieties or domains)) within the same linear polypeptide chain that are capable of folding (e.g., intramolecularly or intermolecularly folding) to form one functional scFc region which is linked by an Fc peptide linker. For example, in one embodiment, a polypeptide of the invention is capable of binding, via its scFc region, to at least one Fc receptor (e.g., an FcRn, an FcγR receptor (e.g., FcγRIII), or a complement protein (e.g., C1q)) in order to improve half-life or trigger an immune effector function (e.g., antibody-dependent cytotoxicity (ADCC), phagocytosis, or complement-dependent cytotoxicity (CDCC) and/or to improve manufacturability).

In some embodiments, the chimeric molecule comprises a clotting factor (e.g., FVII), a targeting moiety (e.g., a GPIIb/IIIa antibody or antigen-binding molecule thereof), and an scFc region.

III.A.2.c Albumins

In certain embodiments, the chimeric molecule comprises a heterologous moiety comprising albumin or a functional fragment thereof. Human serum albumin (HSA, or HA), a protein of 609 amino acids in its full-length form, is responsible for a significant proportion of the osmotic pressure of serum and also functions as a carrier of endogenous and exogenous ligands. The term "albumin" as used herein includes full-length albumin or a functional fragment, variant, derivative, or analog thereof. Examples of albumin or the fragments or variants thereof are disclosed in US Pat. Publ. Nos. US2008/0194481, US2008/0004206, US2008/0161243, US2008/0261877, or US2008/0153751 or PCT Appl. Publ. Nos. WO2008/033413, WO2009/058322, or WO2007/021494, which are incorporated herein by reference in their entireties.

In some embodiments, the chimeric molecule comprises a clotting factor (e.g., FVII), a targeting moiety (e.g., a GPIIb/IIIa antibody or antigen-binding molecule thereof), and an albumin.

III.A.2.d Albumin Binding Polypeptides and Lipids

In certain embodiments, a heterologous moiety can comprise an albumin binding moiety, which comprises an albumin binding peptide, a bacterial albumin binding domain, an albumin-binding antibody fragment, or any combinations thereof. For example, the albumin binding protein can be a bacterial albumin binding protein, an antibody or an antibody fragment including domain antibodies (see, e.g., U.S. Pat. No. 6,696,245). An albumin binding protein, for example, can be a bacterial albumin binding domain, such as the one of streptococcal protein G (Konig and Skerra (1998) *J. Immunol. Methods* 218, 73-83). Other examples of albumin binding peptides that can be used as conjugation partner are, for instance, those having a Cys-$Xaa_1$-$Xaa_2$-$Xaa_3$-$Xaa_4$-Cys consensus sequence, wherein $Xaa_1$ is Asp, Asn, Ser, Thr, or Trp; $Xaa_2$ is Asn, Gln, His, Ile, Leu, or Lys; $Xaa_3$ is Ala, Asp, Phe, Trp, or Tyr; and $Xaa_4$ is Asp, Gly, Leu, Phe, Ser, or Thr as described in U.S. Pub. No. US2003/0069395 or Dennis et al. (2002) *J. Biol. Chem.* 277, 35035-35043.

Domain 3 from streptococcal protein G, as disclosed by Kraulis et al., FEBS Lett. 378:190-194 (1996) and Linhult et al., Protein Sci. 11:206-213 (2002) is an example of a bacterial albumin-binding domain. Examples of albumin-binding peptides include a series of peptides having the core sequence DICLPRWGCLW (SEQ ID NO: 162). See, e.g., Dennis et al., *J. Biol. Chem.* 2002, 277: 35035-35043 (2002). Examples of albumin-binding antibody fragments are disclosed in Muller and Kontermann, *Curr. Opin. Mol. Ther.* 9:319-326 (2007); Roovers et al., *Cancer Immunol. Immunother.* 56:303-317 (2007), and Holt et al., *Prot. Eng. Design Sci.*, 21:283-288 (2008), which are incorporated herein by reference in their entireties. An example of such albumin binding moiety is 2-(3-maleimidopropanamido)-6-(4-(4-iodophenyl)butanamido) hexanoate ("Albu" tag) as disclosed by Trussel et al., *Bioconjugate Chem.* 20:2286-2292 (2009). Fatty acids, in particular long chain fatty acids (LCFA) and long chain fatty acid-like albumin-binding compounds can be used to extend the in vivo half-life of chimeric molecules of the invention. An example of a LCFA-like albumin-binding compound is 16-(1-(3-(9-(((2, 5-dioxopyrrolidin-1-yloxy)carbonyloxy)-methyl)-7-sulfo-9H-fluoren-2-ylamino)-3-oxopropyl)-2,5-dioxopyrrolidin-3-ylthio) hexadecanoic acid (see, e.g., WO 2010/140148).

In some embodiments, the chimeric molecule comprises a clotting factor (e.g., FVII), a targeting moiety (e.g., a GPIIb/IIIa antibody or antigen-binding molecule thereof), and an albumin binding polypeptide or lipid.

III.A.2.e CTP

In certain embodiments, a chimeric molecule disclosed herein comprises at least one heterologous moiety comprising one β subunit of the C-terminal peptide (CTP) of human chorionic gonadotropin or fragment, variant, or derivative thereof. The insertion of one or more CTP peptides into a recombinant protein is known to increase the in vivo half-life of that protein. See, e.g., U.S. Pat. No. 5,712,122, incorporated by reference herein in its entirety.

Exemplary CTP peptides include DPRFQDSSSSKAP-PPSLPSPSRLPGPSDTPIL (SEQ ID NO: 153) or SSSSKAPPPSLPSPSRLPGPSDTPILPQ (SEQ ID NO: 154). See, e.g., U.S. Patent Appl. Publ. No. US 2009/0087411, incorporated by reference. In some embodiments, the chimeric molecule comprises two heterologous moieties that are CTP sequences. In some embodiments, three of the heterologous moieties are CTP sequences. In some embodiments, four of the heterologous moieties are CTP sequences. In some embodiments, five of the heterologous moieties are CTP sequences. In some embodiments, six or more of the heterologous moieties are CTP sequences.

In some embodiments, the chimeric molecule comprises a clotting factor (e.g., FVII), a targeting moiety (e.g., a GPIIb/IIIa antibody or antigen-binding molecule thereof), and a CTP.

III.A.2.f PAS

In other embodiments, at least one heterologous moiety is a PAS sequence. A PAS sequence, as used herein, means an amino acid sequence comprising mainly alanine and serine residues or comprising mainly alanine, serine, and proline residues, the amino acid sequence forming random coil conformation under physiological conditions. Accordingly, the PAS sequence is a building block, an amino acid polymer, or a sequence cassette comprising, consisting essentially of, or consisting of alanine, serine, and proline which can be used as a part of the heterologous moiety in the chimeric molecule. Yet, the skilled person is aware that an amino acid polymer also can form random coil conformation when residues other than alanine, serine, and proline are added as a minor constituent in the PAS sequence.

The term "minor constituent" as used herein means that amino acids other than alanine, serine, and proline can be added in the PAS sequence to a certain degree, e.g., up to about 12%, i.e., about 12 of 100 amino acids of the PAS sequence, up to about 10%, i.e., about 10 of 100 amino acids of the PAS sequence, up to about 9%, i.e., about 9 of 100 amino acids, up to about 8%, i.e., about 8 of 100 amino acids, about 6%, i.e., about 6 of 100 amino acids, about 5%, i.e., about 5 of 100 amino acids, about 4%, i.e., about 4 of 100 amino acids, about 3%, i.e., about 3 of 100 amino acids, about 2%, i.e., about 2 of 100 amino acids, about 1%, i.e., about 1 of 100 of the amino acids.

The amino acids different from alanine, serine and proline can be selected from Arg, Asn, Asp, Cys, Gln, Glu, Gly, His, Ile, Leu, Lys, Met, Phe, Thr, Trp, Tyr, or Val.

Under physiological conditions, the PAS sequence stretch forms a random coil conformation and thereby can mediate an increased in vivo and/or in vitro stability to the chimeric molecule. Since the random coil domain does not adopt a stable structure or function by itself, the biological activity mediated by the activatable clotting factor in the chimeric molecule is essentially preserved. In other embodiments, the PAS sequences that form random coil domain are biologically inert, especially with respect to proteolysis in blood plasma, immunogenicity, isoelectric point/electrostatic behavior, binding to cell surface receptors or internalization, but are still biodegradable, which provides clear advantages over synthetic polymers such as PEG.

Non-limiting examples of the PAS sequences forming random coil conformation comprise an amino acid sequence selected from the group consisting of ASPAAPAPASPAA-PAPSAPA (SEQ ID NO: 155), AAPASPAPAAPSAPA-PAAPS (SEQ ID NO: 156), APSSPSPSAPSSPSPASPSS (SEQ ID NO: 157), APSSPSPSAPSSPSPASPS (SEQ ID NO: 158), SSPSAPSPSSPASPSPSSPA (SEQ ID NO: 159), AASPAAPSAPPAAASPAAPSAPPA (SEQ ID NO: 160) and ASAAAPAAASAAASAPSAAA (SEQ ID NO: 161) or any combinations thereof. Additional examples of PAS sequences are known from, e.g., US Pat. Publ. No. 2010/0292130 and PCT Appl. Publ. No. WO2008/155134 A1.

In some embodiments, the chimeric molecule comprises a clotting factor (e.g., FVII), a targeting moiety (e.g., a GPIIb/IIIa antibody or antigen-binding molecule thereof), and a PAS.

III.A.2.g HAP

In certain embodiments, at least one heterologous moiety is a glycine-rich homo-amino-acid polymer (HAP). The HAP sequence can comprise a repetitive sequence of glycine, which has at least 50 amino acids, at least 100 amino acids, 120 amino acids, 140 amino acids, 160 amino acids, 180 amino acids, 200 amino acids, 250 amino acids, 300 amino acids, 350 amino acids, 400 amino acids, 450 amino acids, or 500 amino acids in length. In one embodiment, the HAP sequence is capable of extending half-life of a moiety fused to or linked to the HAP sequence. Non-limiting examples of the HAP sequence includes, but are not limited to $(Gly)_n$ (SEQ ID NO:235), $(Gly_4Ser)_n$ (SEQ ID NO:236) or $S(Gly_4Ser)_n$ (SEQ ID NO:237), wherein n is 1, 2, 3, 4, 5, 6, 7, 8, 9, 10, 11, 12, 13, 14, 15, 16, 17, 18, 19, or 20. In one embodiment, n is 20, 21, 22, 23, 24, 25, 26, 26, 28, 29, 30, 31, 32, 33, 34, 35, 36, 37, 38, 39, or 40. In another embodiment, n is 50, 60, 70, 80, 90, 100, 110, 120, 130, 140, 150, 160, 170, 180, 190, or 200. See, e.g., Schlapschy M et al., *Protein Eng. Design Selection,* 20: 273-284 (2007).

In some embodiments, the chimeric molecule comprises a clotting factor (e.g., FVII), a targeting moiety (e.g., a GPIIb/IIIa antibody or antigen-binding molecule thereof), and a HAP.

III.A.2.h Transferrin

In certain embodiments, at least one heterologous moiety is transferrin or a peptide or fragment, variant, or derivative thereof. Any transferrin can be used to make the chimeric molecules of the invention. As an example, wild-type human TF (TF) is a 679 amino acid protein, of approximately 75 KDa (not accounting for glycosylation), with two main domains, N (about 330 amino acids) and C (about 340 amino acids), which appear to originate from a gene duplication. N domain comprises two subdomains, N1 domain and N2 domain, and C domain comprises two subdomains, C1 domain and C2 domain. See GenBank accession numbers NM001063, XM002793, M12530, XM039845, XM 039847 and S95936 (www.ncbi.nlm.nih.gov), all of which are herein incorporated by reference in their entirety. In one embodiment, the transferrin heterologous moiety includes a transferrin splice variant. In one example, a transferrin splice variant can be a splice variant of human transferrin, e.g., Genbank Accession AAA61140. In another embodiment, the transferrin portion of the chimeric molecule includes one or more domains of the transferrin sequence, e.g., N domain, C domain, N1 domain, N2 domain, C1 domain, C2 domain or any combinations thereof.

Transferrin transports iron through transferrin receptor (TfR)-mediated endocytosis. After the iron is released into an endosomal compartment and Tf-TfR complex is recycled to cell surface, the Tf is released back extracellular space for next cycle of iron transporting. Tf possesses a long half-life that is in excess of 14-17 days (Li et al., Trends Pharmacol. Sci. 23:206-209 (2002)). Transferrin fusion proteins have been studied for half-life extension, targeted deliver for cancer therapies, oral delivery and sustained activation of proinsulin (Brandsma et al., Biotechnol. Adv., 29: 230-238 (2011); Bai et al., Proc. Natl. Acad. Sci. USA 102:7292-7296 (2005); Kim et al., J. Pharmacol. Exp. Ther., 334:682-692 (2010); Wang et al., J. Controlled Release 155:386-392 (2011)).

In some embodiments, the chimeric molecule comprises a clotting factor (e.g., FVII), a targeting moiety (e.g., a GPIIb/IIIa antibody or antigen-binding molecule thereof), and a transferrin.

III.A.2.i PEG

In some embodiments, at least one heterologous moiety is a soluble polymer known in the art, including, but not limited to, polyethylene glycol, ethylene glycol/propylene glycol copolymers, carboxymethylcellulose, dextran, or polyvinyl alcohol. In some embodiments, the chimeric molecule comprising a PEG heterologous moiety further comprises a heterologous moiety selected from an immunoglobulin constant region or portion thereof (e.g., an Fc region), a PAS sequence, HES, and albumin, fragment, or variant thereof. In still other embodiments, the chimeric molecule comprises an activatable clotting factor or fragment thereof and a PEG heterologous moiety, wherein the chimeric molecule further comprises a heterologous moiety selected from an immunoglobulin constant region or portion thereof (e.g., an Fc moiety), a PAS sequence, HES, and albumin, fragment, or variant thereof. In yet other embodiments, the chimeric molecule comprises a clotting factor or fragment thereof, a second clotting factor or fragment thereof, and a PEG heterologous moiety, wherein the chimeric molecule further comprises a heterologous moiety selected from an immunoglobulin constant region or portion thereof (e.g., an Fc moiety), a PAS sequence, HES, and albumin, fragment, or variant thereof.

In other embodiments, the chimeric molecule comprises a clotting factor or fragment thereof, a synthetic procoagulant polypeptide, and a PEG heterologous moiety, wherein the chimeric molecule further comprises a heterologous moiety selected from an immunoglobulin constant region or portion thereof (e.g., an Fc region), a PAS sequence, HES, and albumin, fragment, or variant thereof. In other embodiments, the chimeric molecule comprises two synthetic procoagulant peptides and a PEG heterologous moiety, wherein the chimeric molecule further comprises a heterologous moiety selected from the group consisting of an immunoglobulin constant region or portion thereof (e.g., an Fc region), a PAS sequence, HES, and albumin, fragment, or variant thereof. In yet another embodiment, the chimeric molecule comprises a clotting factor or fragment thereof, a clotting factor cofactor (e.g., Tissue Factor if the clotting factor is Factor VII), and a PEG heterologous moiety, wherein the chimeric molecule further comprises a heterologous moiety selected from an immunoglobulin constant region or portion thereof (e.g., an Fc region), a PAS sequence, HES, and albumin, fragment, or variant thereof.

The polymer can be of any molecular weight, and can be branched or unbranched. For polyethylene glycol, in one embodiment, the molecular weight is between about 1 kDa and about 100 kDa for ease in handling and manufacturing. Other sizes can be used, depending on the desired profile (e.g., the duration of sustained release desired, the effects, if any on biological activity, the ease in handling, the degree or lack of antigenicity and other known effects of the polyethylene glycol to a protein or analog). For example, the polyethylene glycol can have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 45,000, 50,000, 55,000, 60,000, 65,000, 70,000, 75,000, 80,000, 85,000, 90,000, 95,000, or 100,000 kDa.

In some embodiments, the polyethylene glycol can have a branched structure. Branched polyethylene glycols are described, for example, in U.S. Pat. No. 5,643,575; Morpurgo et al., *Appl. Biochem. Biotechnol.* 56:59-72 (1996); Vorobjev et al., *Nucleosides Nucleotides* 18:2745-2750 (1999); and Caliceti et al., *Bioconjug. Chem.* 10:638-646 (1999), each of which is incorporated herein by reference in its entirety.

The number of polyethylene glycol moieties attached to each chimeric molecule of the invention (i.e., the degree of substitution) can also vary. For example, the PEGylated chimeric molecule can be linked, on average, to 1, 2, 3, 4, 5, 6, 7, 8, 9, 10, 12, 15, 17, 20, or more polyethylene glycol molecules. Similarly, the average degree of substitution within ranges such as 1-3, 2-4, 3-5, 4-6, 5-7, 6-8, 7-9, 8-10, 9-11, 10-12, 11-13, 12-14, 13-15, 14-16, 15-17, 16-18, 17-19, or 18-20 polyethylene glycol moieties per protein molecule. Methods for determining the degree of substitution are discussed, for example, in Delgado et al., *Crit. Rev. Thera. Drug Carrier Sys.* 9:249-304 (1992).

In some embodiments, the chimeric molecule can be PEGylated. A PEGylated chimeric molecule comprises at least one polyethylene glycol (PEG) molecule. In other embodiments, the polymer can be water-soluble. Non-limiting examples of the polymer can be poly(alkylene oxide), poly(vinyl pyrrolidone), poly(vinyl alcohol), polyoxazoline, or poly(acryloylmorpholine). Additional types of polymer-conjugation to clotting factors are disclosed in U.S. Pat. No. 7,199,223. See also, Singh et al. Curr. Med. Chem. 15:1802-1826 (2008).

There are a number of PEG attachment methods available to those skilled in the art, for example Malik F et al., *Exp. Hematol.* 20:1028-35 (1992); Francis, *Focus on Growth*

Factors 3(2):4-10 (1992); European Pat. Pub. Nos. EP0401384, EP0154316, and EP0401384; and International Pat. Appl. Pub. Nos. WO92/16221 and WO95/34326.

In some embodiments, the chimeric molecule comprises a clotting factor (e.g., FVII), a targeting moiety (e.g., a GPIIb/IIIa antibody or antigen-binding molecule thereof), and a PEG.

III.A.2.j HES

In certain embodiments, at least one heterologous moiety is a polymer, e.g., hydroxyethyl starch (HES) or a derivative thereof. Hydroxyethyl starch (HES) is a derivative of naturally occurring amylopectin and is degraded by alpha-amylase in the body. HES is a substituted derivative of the carbohydrate polymer amylopectin, which is present in corn starch at a concentration of up to 95% by weight. HES exhibits advantageous biological properties and is used as a blood volume replacement agent and in hemodilution therapy in the clinics (Sommermeyer et al., *Krankenhauspharmazie*, 8(8), 271-278 (1987); and Weidler et al., *Arzneim.-Forschung/Drug Res.*, 41, 494-498 (1991)).

Amylopectin contains glucose moieties, wherein in the main chain alpha-1,4-glycosidic bonds are present and at the branching sites alpha-1,6-glycosidic bonds are found. The physical-chemical properties of this molecule are mainly determined by the type of glycosidic bonds. Due to the nicked alpha-1,4-glycosidic bond, helical structures with about six glucose-monomers per turn are produced. The physico-chemical as well as the biochemical properties of the polymer can be modified via substitution. The introduction of a hydroxyethyl group can be achieved via alkaline hydroxyethylation. By adapting the reaction conditions it is possible to exploit the different reactivity of the respective hydroxy group in the unsubstituted glucose monomer with respect to a hydroxyethylation. Owing to this fact, the skilled person is able to influence the substitution pattern to a limited extent.

HES is mainly characterized by the molecular weight distribution and the degree of substitution. The degree of substitution, denoted as DS, relates to the molar substitution, is known to the skilled people. See Sommermeyer et al., *Krankenhauspharmazie*, 8(8), 271-278 (1987), as cited above, in particular p. 273.

In one embodiment, hydroxyethyl starch has a mean molecular weight (weight mean) of from 1 to 300 kD, from 2 to 200kD, from 3 to 100 kD, or from 4 to 70kD. Hydroxyethyl starch can further exhibit a molar degree of substitution of from 0.1 to 3, preferably 0.1 to 2, more preferred, 0.1 to 0.9, preferably 0.1 to 0.8, and a ratio between C2:C6 substitution in the range of from 2 to 20 with respect to the hydroxyethyl groups. A non-limiting example of HES having a mean molecular weight of about 130 kD is a HES with a degree of substitution of 0.2 to 0.8 such as 0.2, 0.3, 0.4, 0.5, 0.6, 0.7, or 0.8, preferably of 0.4 to 0.7 such as 0.4, 0.5, 0.6, or 0.7. In a specific embodiment, HES with a mean molecular weight of about 130 kD is VOLUVEN® from Fresenius. VOLUVEN® is an artificial colloid, employed, e.g., for volume replacement used in the therapeutic indication for therapy and prophylaxis of hypovolemia. The characteristics of VOLUVEN® are a mean molecular weight of 130,000+/−20,000 D, a molar substitution of 0.4 and a C2:C6 ratio of about 9:1. In other embodiments, ranges of the mean molecular weight of hydroxyethyl starch are, e.g., 4 to 70 kD or 10 to 70 kD or 12 to 70 kD or 18 to 70 kD or 50 to 70 kD or 4 to 50 kD or 10 to 50 kD or 12 to 50 kD or 18 to 50 kD or 4 to 18 kD or 10 to 18 kD or 12 to 18 kD or 4 to 12 kD or 10 to 12 kD or 4 to 10 kD. In still other embodiments, the mean molecular weight of hydroxyethyl starch employed is in the range of from more than 4 kD and below 70 kD, such as about 10 kD, or in the range of from 9 to 10 kD or from 10 to 11 kD or from 9 to 11 kD, or about 12 kD, or in the range of from 11 to 12 kD) or from 12 to 13 kD or from 11 to 13 kD, or about 18 kD, or in the range of from 17 to 18 kD or from 18 to 19 kD or from 17 to 19 kD, or about 30 kD, or in the range of from 29 to 30, or from 30 to 31 kD, or about 50 kD, or in the range of from 49 to 50 kD or from 50 to 51 kD or from 49 to 51 kD.

In certain embodiments, the heterologous moiety can be a mixture of hydroxyethyl starches having different mean molecular weights and/or different degrees of substitution and/or different ratios of C2: C6 substitution. Therefore, mixtures of hydroxyethyl starches can be employed having different mean molecular weights and different degrees of substitution and different ratios of C2: C6 substitution, or having different mean molecular weights and different degrees of substitution and the same or about the same ratio of C2:C6 substitution, or having different mean molecular weights and the same or about the same degree of substitution and different ratios of C2:C6 substitution, or having the same or about the same mean molecular weight and different degrees of substitution and different ratios of C2:C6 substitution, or having different mean molecular weights and the same or about the same degree of substitution and the same or about the same ratio of C2:C6 substitution, or having the same or about the same mean molecular weights and different degrees of substitution and the same or about the same ratio of C2:C6 substitution, or having the same or about the same mean molecular weight and the same or about the same degree of substitution and different ratios of C2: C6 substitution, or having about the same mean molecular weight and about the same degree of substitution and about the same ratio of C2:C6 substitution.

In some embodiments, the chimeric molecule comprises a clotting factor (e.g., FVII), a targeting moiety (e.g., a GPIIb/IIIa antibody or antigen-binding molecule thereof), and a HES.

III.A.2.k PSA

In certain embodiments, at least one heterologous moiety is a polymer, e.g., polysialic acids (PSAs) or a derivative thereof. Polysialic acids (PSAs) are naturally occurring unbranched polymers of sialic acid produced by certain bacterial strains and in mammals in certain cells Roth J., et al. (1993) in *Polysialic Acid. From Microbes to Man*, eds Roth J., Rutishauser U., Troy F. A. (Birkhiuser Verlag, Basel, Switzerland), pp 335-348. They can be produced in various degrees of polymerisation from n=about 80 or more sialic acid residues down to n=2 by limited acid hydrolysis or by digestion with neuraminidases, or by fractionation of the natural, bacterially derived forms of the polymer. The composition of different polysialic acids also varies such that there are homopolymeric forms i.e. the alpha-2,8-linked polysialic acid comprising the capsular polysaccharide of *E. coli* strain K1 and the group-B meningococci, which is also found on the embryonic form of the neuronal cell adhesion molecule (N-CAM). Heteropolymeric forms also exist— such as the alternating alpha-2,8 alpha-2,9 polysialic acid of *E. coli* strain K92 and group C polysaccharides of *N. meningitidis*. Sialic acid can also be found in alternating copolymers with monomers other than sialic acid such as group W135 or group Y of *N. meningitidis*. Polysialic acids have important biological functions including the evasion of the immune and complement systems by pathogenic bacteria and the regulation of glial adhesiveness of immature neurons during foetal development (wherein the polymer has an anti-adhesive function) Cho and Troy, *P.N.A.S., USA,* 91 (1994) 11427-11431, although there are no known receptors for polysialic acids in mammals. The alpha-2,8-linked polysialic acid of *E. coli* strain K1 is also known as 'colominic acid' and is used (in various lengths) to exemplify the present invention. Various methods of attaching or conjugating polysialic acids to a polypeptide have been described (for example, see U.S. Pat. No. 5,846,951; WO-A-0187922, and US 2007/0191597 A1, which are incorporated herein by reference in their entireties.

In some embodiments, the chimeric molecule comprises a clotting factor (e.g., FVII), a targeting moiety (e.g., a GPIIb/IIIa antibody or antigen-binding molecule thereof), and a PSA.

III.A.2.1 Clearance Receptors

In certain embodiments, the in vivo half-life of a chimeric molecule of the invention can be extended where the chimeric molecule comprises at least one heterologous molecule comprising a clearance receptor, fragment, variant, or derivative thereof. In specific embodiments wherein the chimeric molecule comprises Factor X, soluble forms of clearance receptors, such as the low density lipoprotein-related protein receptor LRP1, or fragments thereof, can block binding of Factor X to clearance receptors and thereby extend its in vivo half-life.

LRP1 is a 600 kDa integral membrane protein that is implicated in the receptor-mediate clearance of a variety of proteins, such as FVIII or X. See, e.g., Narita et al., Blood 91:555-560 (1998); Lenting et al., Haemophilia 16:6-16 (2010). Other suitable clearance receptors are, e.g., LDLR (low-density lipoprotein receptor), VLDLR (very low-density lipoprotein receptor), and megalin (LRP-2), or fragments thereof. See, e.g., Bovenschen et al., Blood 106:906-912 (2005); Bovenschen, Blood 116:5439-5440 (2010); Martinelli et al., Blood 116:5688-5697 (2010).

In some embodiments, the chimeric molecule comprises a clotting factor (e.g., FVII), a targeting moiety (e.g., a GPIIb/IIIa antibody or antigen-binding molecule thereof), and a clearance receptor, fragment, variant, or derivative thereof.

III.B Linkers

As used herein, the term "linker" or "linker moiety" (represented as L, L1, or L2 in the formulas disclosed herein) refers to a peptide or polypeptide sequence (e.g., a synthetic peptide or polypeptide sequence), or a non-peptide linker for which its main function is to connect two domains in a linear amino acid sequence of a polypeptide chain, for example, two heterologous moieties in a chimeric molecule of the invention. Accordingly, in some embodiments, linkers are interposed between two heterologous moieties, between a heterologous moiety and a targeting moiety, which binds to a platelet (e.g., an anti-GPIIb/IIIa antibody or antigen-binding molecule thereof disclosed herein), between a clotting factor (either the heavy chain or the light chain) and a targeting moiety, which binds to a platelet (e.g., an anti-GPIIb/IIIa antibody or antigen-binding molecule thereof disclosed herein), or between a clotting factor (either the heavy chain or the light chain) and a heterologous moiety.

When multiple linkers are present in a chimeric molecule of the invention, each of the linkers can be the same or different. Generally, linkers provide flexibility to the chimeric molecule. Linkers are not typically cleaved; however in certain embodiments, such cleavage can be desirable. Accordingly, in some embodiments a linker can comprise one or more protease-cleavable sites, which can be located within the sequence of the linker or flanking the linker at either end of the sequence of the linker.

In some embodiments, the chimeric molecule comprises one or more linkers, wherein one or more of the linkers comprise a peptide linker. In other embodiments, one or more of the linkers comprise a non-peptide linker. In some embodiments, the peptide linker can comprise at least two amino, at least three, at least four, at least five, at least 10, at least 20, at least 30, at least 40, at least 50, at least 60, at least 70, at least 80, at least 90, or at least 100 amino acids. In other embodiments, the peptide linker can comprise at least 200, at least 300, at least 400, at least 500, at least 600, at least 700, at least 800, at least 900, or at least 1,000 amino acids. In some embodiments, the peptide linker can comprise at least about 10, 20, 30, 40, 50, 60, 70, 80, 90, 100, 150, 200, 300, 400, 500, 600, 700, 800, 900, 1000, 1100, 1200, 1300, 1400, 1500, 1600, 1700, 1800, 1900, or 2000 amino acids.

The peptide linker can comprise 1-5 amino acids, 1-10 amino acids, 1-20 amino acids, 10-50 amino acids, 50-100 amino acids, 100-200 amino acids, 200-300 amino acids, 300-400 amino acids, 400-500 amino acids, 500-600 amino acids, 600-700 amino acids, 700-800 amino acids, 800-900 amino acids, 900-1000, 1000-1100, 1100-1200, 1200-1300, 1300-1400, 1400-1500, 1500-1600, 1600-1700, 1700-1800, 1800-1900, or 1900-2000 amino acids.

Examples of peptide linkers are well known in the art, for example peptide linkers according to the formula $[(Gly)_x\text{-}Ser_y]_z$ where x is from 1 to 4, y is 0 or 1, and z is from 1 to 50 (SEQ ID NO:232). In one embodiment, the peptide linker comprises the sequence $G_n$, where n can be an integer from 1 to 100 (SEQ ID NO:238). In a specific embodiment, the specific embodiment, the sequence of the peptide linker is GGGG (SEQ ID NO:239). The peptide linker can comprise the sequence $(GA)_n$. The peptide linker can comprise the sequence $(GGS)_n$. In other embodiments, the peptide linker comprises the sequence $(GGGS)_n$ (SEQ ID NO: 166). In still other embodiments, the peptide linker comprises the sequence $(GGS)_n(GGGGS)_n$ (SEQ ID NO: 189). In these instances, n can be an integer from 1-100. In other instances, n can be an integer from 1-20, i.e., 1, 2, 3, 4, 5, 6, 7, 8, 9, 10, 11, 12, 13, 14, 15, 16, 17, 18, 19, or 20. Examples of linkers include, but are not limited to, GGG, SGGSGGS (SEQ ID NO: 190), GGSGGSGGSGGSGGG (SEQ ID NO: 191), GGSGGSGGGGSGGGGS (SEQ ID NO: 192), GGSGGSGGSGGSGGGS (SEQ ID NO: 193), or GGGGSGGGGSGGGGS (SEQ ID NO: 194). In other embodiments, the linker is a poly-G sequence $(GGGG)_n$, where n can be an integer from 1-100 (SEQ ID NO:240).

An exemplary Gly/Ser peptide linker comprises the amino acid sequence $(Gly_4Ser)_n$ (SEQ ID NO: 195), wherein n is an integer that is the same or higher than 1, 2, 3, 4, 5, 6, 7, 8, 9, 10, 15, 20, 25, 30, 35, 40, 46, 50, 55, 60, 70, 80, 90, or 100. In one embodiment, n=1, i.e., the linker is $(Gly_4Ser)$ (SEQ ID NO: 196). In one embodiment, n=2, i.e., the linker is $(Gly_4Ser)_2$ (SEQ ID NO: 197). In another embodiment, n=3, i.e., the linker is $(Gly_4Ser)_3$ (SEQ ID NO: 198). In another embodiment, n=4, i.e., the linker is $(Gly_4Ser)_4$ (SEQ ID NO: 199). In another embodiment, n=5, i.e., the linker is $(Gly_4Ser)_5$ (SEQ ID NO: 200). In yet another embodiment, n=6, i.e., the linker is $(Gly_4Ser)_6$ (SEQ ID NO: 202). In another embodiment, n=7, i.e., the linker is $(Gly_4Ser)_7$ (SEQ ID NO: 203). In yet another embodiment, n=8, i.e., the linker is $(Gly_4Ser)_8$ (SEQ ID NO: 204). In another embodiment, n=9, i.e., the linker is $(Gly_4Ser)_9$ (SEQ ID NO: 205). In yet another embodiment, n=10, i.e., the linker is $(Gly_4Ser)_{10}$ (SEQ ID NO: 206).

Another exemplary Gly/Ser peptide linker comprises the amino acid sequence $Ser(Gly_4Ser)_n$ (SEQ ID NO: 201), wherein n is an integer that is the same or higher than 1, 2, 3, 4, 5, 6, 7, 8, 9, 10, 15, 20, 25, 30, 35, 40, 46, 50, 55, 60, 70, 80, 90, or 100. In one embodiment, n=1, i.e., the linker is Ser(Gly$_4$Ser) (SEQ ID NO: 207). In one embodiment, n=2, i.e., the linker is Ser(Gly$_4$Ser)$_2$ (SEQ ID NO: 208). In another embodiment, n=3, i.e., the linker is Ser(Gly$_4$Ser)$_3$ (SEQ ID NO: 209). In another embodiment, n=4, i.e., the linker is Ser(Gly$_4$Ser)$_4$ (SEQ ID NO: 210). In another embodiment, n=5, i.e., the linker is Ser(Gly$_4$Ser)$_5$ (SEQ ID NO: 211). In yet another embodiment, n=6, i.e., the linker is Ser(Gly$_4$Ser)$_6$ (SEQ ID NO: 212). In yet another embodiment, n=7, i.e., the linker is Ser(Gly$_4$Ser)$_7$ (SEQ ID NO: 213). In yet another embodiment, n=8, i.e., the linker is Ser(Gly$_4$Ser)$_8$ (SEQ ID NO: 214). In yet another embodiment, n=9, i.e., the linker is Ser(Gly$_4$Ser)$_9$ (SEQ ID NO: 215). In yet another embodiment, n=10, i.e., the linker is Ser(Gly$_4$Ser)$_{10}$ (SEQ ID NO: 216).

In certain embodiments, said Gly/Ser peptide linker can be inserted between two other sequences of the peptide linker (e.g., any of the peptide linker sequences described herein). In other embodiments, a Gly/Ser peptide linker is attached at one or both ends of another sequence of the peptide linker (e.g., any of the peptide linker sequences described herein). In yet other embodiments, two or more Gly/Ser linkers are incorporated in series in a peptide linker. In one embodiment, a peptide linker of the invention comprises at least a portion of an upper hinge region (e.g., derived from an IgG1, IgG2, IgG3, or IgG4 molecule), at least a portion of a middle hinge region (e.g., derived from an IgG1, IgG2, IgG3, or IgG4 molecule) and a series of Gly/Ser amino acid residues (e.g., a Gly/Ser linker such as (Gly$_4$Ser)$_n$) (SEQ ID NO: 195)).

A particular type of linker which can be present in an heterologous moiety, for example an activatable clotting factor, is herein referred to as a "cleavable linker" which comprises a heterologous protease-cleavage site (e.g., a factor XIa or thrombin cleavage site) that is not naturally occurring in the clotting factor and which can include additional linkers on either the N terminal of C terminal or both sides of the cleavage site. Exemplary locations for such sites include, e.g., placement between a heavy chain of a clotting factor zymogen and a light chain of a clotting factor zymogen.

Peptide linkers can be introduced into polypeptide sequences using techniques known in the art. Modifications can be confirmed by DNA sequence analysis. Plasmid DNA can be used to transform host cells for stable production of the polypeptides produced.

III.C Protease Cleavage Site

In some embodiments, a chimeric molecule can comprise a protease cleavage site linking, for example, a light chain of a clotting factor zymogen and a heavy chain of the clotting factor zymogen (e.g., FVII). A protease-cleavage site linking a light chain of a clotting factor zymogen and a heavy chain of the clotting factor zymogen can be selected from any protease-cleavage site known in the art. In one embodiment, the protease-cleavage site is cleaved by a protease selected from the group consisting of factor XIa, factor XIIa, kallikrein, factor VIIa, factor IXa, factor Xa, factor IIa (thrombin), and any combinations thereof. The protease-cleavage sites allow the light chain and the heavy chain of the clotting factor to be cleaved and dissociated from each other at the site of injury. Exemplary FXIa cleavage sites include, e.g., KLTR (SEQ ID NO: 217), DFTR (SEQ ID NO: 218), TQSFNDFTR (SEQ ID NO: 219) and SVSQTSKLTR (SEQ ID NO: 220). Exemplary thrombin cleavage sites include, e.g., DFLAEGGGVR (SEQ ID NO: 221), TTKIKPR (SEQ ID NO: 222), LVPRG (SEQ ID NO: 223) and ALRPR (SEQ ID NO: 224).

In some embodiments, the protease-cleavage site can be combined with an intracellular processing site for efficient cleavage and activation. For example, an activatable clotting factor in the chimeric molecule can comprise a heterodimer, which comprises a light chain of a clotting factor associated with a heavy chain of the clotting factor by a covalent bond, wherein the N-terminus of the heavy chain of the clotting factor is linked to a protease-cleavage site. The protease-cleavage site can be cleaved off at the site of coagulation, thus activating the clotting factor. Such constructs can be designed by inserting an intracellular processing site between the light chain of the clotting factor zymogen and the protease-cleavage site, which is linked to the heavy chain of the clotting factor zymogen. The intracellular processing site inserted therein can be processed (cleaved) by an intracellular processing enzyme upon expression in a host cell, thereby allowing formation of a zymogen-like heterodimer.

Examples of the intracellular processing enzymes include furin, a yeast Kex2, PCSK1 (also known as PC1/Pc3), PCSK2 (also known as PC2), PCSK3 (also known as furin or PACE), PCSK4 (also known as PC4), PCSK5 (also known as PC5 or PC6), PCSK6 (also known as PACE4), or PCSK7 (also known as PC7/LPC, PC8, or SPC7). Other processing sites are known in the art. In constructs that include more than one processing or cleavage site, it will be understood that such sites can be the same or different.

IV. Methods of Preparation

The present disclosure also provides a nucleic acid molecule or a set of nucleic acid molecules encoding (i) a GPIIb/IIIa antibody or antigen-binding molecule thereof disclosed herein, or (ii) any of the chimeric molecules disclosed herein, or (iii) a complement thereof.

In one embodiment, the invention includes a nucleic acid molecule encoding a polypeptide chain, which comprises a light chain of a clotting factor (e.g., FVII, FIX, or FX), a heterologous moiety (e.g., a half-life extending moiety), an intracellular processing site, a heavy chain of the clotting factor (e.g., FVII, FIX, or FX), and a targeting moiety which binds to a platelet (e.g., an anti-GPIIb/IIIa antibody or antigen-binding molecule thereof). In another embodiment, the nucleic acid molecule of the invention encodes a polypeptide chain comprising a light chain of a clotting factor (e.g., FVII, FIX, or FX), a targeting moiety which binds to a platelet (e.g., an anti-GPIIb/IIIa antibody or antigen-binding molecule thereof), an intracellular processing site, a heavy chain of the clotting factor (e.g., FVII, FIX, or FX), and a heterologous moiety (e.g., a half-life extending moiety). In other embodiments, the nucleic acid molecule encodes a polypeptide chain comprising a light chain of a clotting factor (e.g., FVII, FIX, or FX), an intracellular processing site, a heavy chain of the clotting factor (e.g., FVII, FIX, or FX), a heterologous moiety (e.g., a half-life extending moiety), and a targeting moiety which binds to a platelet (e.g., an anti-GPIIb/IIIa antibody or antigen-binding molecule thereof). In some embodiments, the nucleic acid molecule encodes a polypeptide chain comprising a light chain of a clotting factor (e.g., FVII, FIX, or FX), an intracellular processing site, a heavy chain of the clotting factor (e.g., FVII, FIX, or FX), a targeting moiety which binds to a platelet (e.g., an anti-GPIIb/IIIa antibody or antigen-binding molecule thereof), and a heterologous moiety (e.g., a half-life extending moiety).

In some embodiments, the nucleic acid molecule comprises a set of nucleotide sequences, a first nucleotide sequence encoding a first polypeptide chain comprising a light chain of a clotting factor (e.g., FVII, FIX, or FX) and a heterologous moiety (e.g., a half-life extending moiety) and a second nucleotide sequence encoding a second polypeptide chain comprising a heavy chain of the clotting factor (e.g., FVII, FIX, or FX) and a targeting moiety which binds to a platelet (e.g., an anti-GPIIb/IIIa antibody or antigen-binding molecule thereof). In other embodiments, the nucleic acid molecule comprises a set of nucleotide sequences, a first nucleotide sequence encoding a first polypeptide chain comprising a light chain of a clotting factor (e.g., FVII, FIX, or FX) and a targeting moiety which binds to a platelet (e.g., an anti-GPIIb/IIIa antibody or antigen-binding molecule thereof) and a second nucleotide sequence encoding a second polypeptide chain comprising a heavy chain of the clotting factor (e.g., FVII, FIX, or FX) and a heterologous moiety (e.g., a half-life extending moiety). In other embodiments, the nucleic acid molecule comprises a set of nucleotide sequences, a first nucleotide sequence encoding a light chain of a clotting factor (e.g., FVII, FIX, or FX) and a second nucleotide sequence encoding a heavy chain of the clotting factor (e.g., FVII, FIX, or FX), a heterologous moiety (e.g., a half-life extending moiety), and a targeting moiety which binds to a platelet (e.g., an anti-GPIIb/IIIa antibody or antigen-binding molecule thereof). In some embodiments, the nucleic acid molecule comprises a set of nucleotide sequences, a first nucleotide sequence encoding a light chain of a clotting factor (e.g., FVII, FIX, or FX) and a second nucleotide sequence encoding a heavy chain of the clotting factor (e.g., FVII, FIX, or FX), a targeting moiety which binds to a platelet (e.g., an anti-GPIIb/IIIa antibody or antigen-binding molecule thereof), and a heterologous moiety (e.g., a half-life extending moiety).

Also provided are a vector or a set of vectors comprising such nucleic acid molecule or the set of the nucleic acid molecules or a complement thereof, as well as a host cell comprising the vector.

The instant disclosure also provides a method for producing a GPIIb/IIIa antibody or antigen-binding molecule thereof or chimeric molecule disclosed herein, such method comprising culturing the host cell disclosed herein and recovering the antibody, antigen-binding molecule thereof, or the chimeric molecule from the culture medium.

A variety of methods are available for recombinantly producing a GPIIb/IIIa antibody or antigen-binding molecule thereof disclosed herein, or a chimeric molecule disclosed herein. It will be understood that because of the degeneracy of the code, a variety of nucleic acid sequences will encode the amino acid sequence of the polypeptide. The desired polynucleotide can be produced by de novo solid-phase DNA synthesis or by PCR mutagenesis of an earlier prepared polynucleotide.

Oligonucleotide-mediated mutagenesis is one method for preparing a substitution, in-frame insertion, or alteration (e.g., altered codon) to introduce a codon encoding an amino acid substitution (e.g., into a GPIIb/IIIa antibody variant). For example, the starting polypeptide DNA is altered by hybridizing an oligonucleotide encoding the desired mutation to a single-stranded DNA template. After hybridization, a DNA polymerase is used to synthesize an entire second complementary strand of the template that incorporates the oligonucleotide primer. In one embodiment, genetic engineering, e.g., primer-based PCR mutagenesis, is sufficient to incorporate an alteration, as defined herein, for producing a polynucleotide encoding a GPIIb/IIIa antibody or antigen-binding molecule thereof disclosed herein, or any of the chimeric molecules disclosed herein.

For recombinant production, a polynucleotide sequence encoding a polypeptide (e.g., a GPIIb/IIIa antibody or antigen-binding molecule thereof disclosed herein, or any of the chimeric molecules disclosed herein) is inserted into an appropriate expression vehicle, i.e., a vector which contains the necessary elements for the transcription and translation of the inserted coding sequence, or in the case of an RNA viral vector, the necessary elements for replication and translation.

The nucleic acid encoding the polypeptide (e.g., a GPIIb/IIIa antibody or antigen-binding molecule thereof disclosed herein, or any of the chimeric molecules disclosed herein) is inserted into the vector in proper reading frame. The expression vector is then transfected into a suitable target cell which will express the polypeptide. Transfection techniques known in the art include, but are not limited to, calcium phosphate precipitation (Wigler et al. 1978, *Cell* 14:725) and electroporation (Neumann et al. 1982, *EMBO J.* 1:841). A variety of host-expression vector systems can be utilized to express the polypeptides described herein (e.g., a GPIIb/IIIa antibody or antigen-binding molecule thereof disclosed herein, or any of the chimeric molecules disclosed herein) in eukaryotic cells. In one embodiment, the eukaryotic cell is an animal cell, including mammalian cells (e.g., 293 cells, PerC6, CHO, BHK, Cos, HeLa cells). When the polypeptide is expressed in a eukaryotic cell, the DNA encoding the polypeptide (e.g., a GPIIb/IIIa antibody or antigen-binding molecule thereof disclosed herein, or any of the chimeric molecules disclosed herein) can also code for a signal sequence that will permit the polypeptide to be secreted. One skilled in the art will understand that while the polypeptide is translated, the signal sequence is cleaved by the cell to form the mature chimeric molecule. Various signal sequences are known in the art, e.g., native FVII signal sequence, native FIX signal sequence, native FX signal sequence, native GPIIb signal sequence, native GPIIIa signal sequence, and the mouse IgK light chain signal sequence. Alternatively, where a signal sequence is not included, the polypeptide (e.g., a GPIIb/IIIa antibody or antigen-binding molecule thereof disclosed herein, or any of the chimeric molecules disclosed herein) can be recovered by lysing the cells.

The GPIIb/IIIa antibody or antigen-binding molecule thereof disclosed herein, or any of the chimeric molecules disclosed herein can be synthesized in a transgenic animal, such as a rodent, goat, sheep, pig, or cow. The term "transgenic animals" refers to non-human animals that have incorporated a foreign gene into their genome. Because this gene is present in germline tissues, it is passed from parent to offspring. Exogenous genes are introduced into single-celled embryos (Brinster et al. 1985, *Proc. Natl. Acad. Sci. USA* 82:4438). Methods of producing transgenic animals are known in the art including transgenics that produce immunoglobulin molecules (Wagner et al. 1981, *Proc. Natl. Acad. Sci. USA* 78:6376; McKnight et al. 1983, *Cell* 34:335; Brinster et al. 1983, *Nature* 306:332; Ritchie et al. 1984, *Nature* 312:517; Baldassarre et al. 2003, *Theriogenology* 59:831; Robl et al. 2003, *Theriogenology* 59:107; Malassagne et al. 2003, *Xenotransplantation* 10: 267).

The expression vectors can encode for tags that permit for easy purification or identification of the recombinantly produced polypeptide. Examples include, but are not limited to, vector pUR278 (Ruther et al. 1983, *EMBO J.* 2:1791) in which the polypeptide (e.g., a GPIIb/IIIa antibody or antigen-binding molecule thereof disclosed herein, or any of the chimeric molecules disclosed herein) coding sequence can be ligated into the vector in frame with the lac z coding region so that a hybrid polypeptide is produced; pGEX vectors can be used to express proteins with a glutathione S-transferase (GST) tag. These proteins are usually soluble and can easily be purified from cells by adsorption to glutathione-agarose beads followed by elution in the presence of free glutathione. The vectors include cleavage sites, e.g., for PreCission Protease (Pharmacia, Peapack, N. J.) for easy removal of the tag after purification.

For the purposes of this invention, numerous expression vector systems can be employed. These expression vectors are typically replicable in the host organisms either as episomes or as an integral part of the host chromosomal DNA. Expression vectors can include expression control sequences including, but not limited to, promoters (e.g., naturally-associated or heterologous promoters), enhancers, signal sequences, splice signals, enhancer elements, and transcription termination sequences. Preferably, the expression control sequences are eukaryotic promoter systems in vectors capable of transforming or transfecting eukaryotic host cells. Expression vectors can also utilize DNA elements which are derived from animal viruses such as bovine papilloma virus, polyoma virus, adenovirus, vaccinia virus, baculovirus, retroviruses (RSV, MMTV or MOMLV), cytomegalovirus (CMV), or SV40 virus. Others involve the use of polycistronic systems with internal ribosome binding sites.

Commonly, expression vectors contain selection markers (e.g., ampicillin-resistance, hygromycin-resistance, tetracycline resistance or neomycin resistance) to permit detection of those cells transformed with the desired DNA sequences (see, e.g., Itakura et al., U.S. Pat. No. 4,704,362). Cells which have integrated the DNA into their chromosomes can be selected by introducing one or more markers which allow selection of transfected host cells. The marker can provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation.

An exemplary expression vector is NEOSPLA (U.S. Pat. No. 6,159,730). This vector contains the cytomegalovirus promoter/enhancer, the mouse beta globin major promoter, the SV40 origin of replication, the bovine growth hormone polyadenylation sequence, neomycin phosphotransferase exon 1 and exon 2, the dihydrofolate reductase gene and leader sequence. This vector has been found to result in very high level expression of antibodies upon incorporation of variable and constant region genes, transfection in cells, followed by selection in G418 containing medium and methotrexate amplification. Vector systems are also taught in U.S. Pat. Nos. 5,736,137 and 5,658,570, each of which is incorporated by reference in its entirety herein. This system provides for high expression levels, e.g., >30 pg/cell/day. Other exemplary vector systems are disclosed e.g., in U.S. Pat. No. 6,413,777.

In other embodiments, polypeptides of the invention (e.g., a GPIIb/IIIa antibody or antigen-binding molecule thereof disclosed herein, or any of the chimeric molecules disclosed herein) can be expressed using polycistronic constructs. In these expression systems, multiple gene products of interest such as multiple polypeptides of multimer binding protein can be produced from a single polycistronic construct. These systems advantageously use an internal ribosome entry site (IRES) to provide relatively high levels of polypeptides of the invention in eukaryotic host cells. Compatible IRES sequences are disclosed in U.S. Pat. No. 6,193,980 which is also incorporated herein. Those skilled in the art will appreciate that such expression systems can be used to effectively produce the full range of polypeptides disclosed in the instant application.

More generally, once the vector or DNA sequence encoding a polypeptide has been prepared, the expression vector can be introduced into an appropriate host cell. That is, the host cells can be transformed. Introduction of the plasmid into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, and infection with intact virus. See, Ridgway, A. A. G. "*Mammalian Expression Vectors*" Chapter 24.2, pp. 470-472 Vectors, Rodriguez and Denhardt, Eds. (Butterworths, Boston, Mass. 1988). Most preferably, plasmid introduction into the host is via electroporation. The transformed cells are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), flow cytometry, immunohistochemistry, and the like.

As used herein, the term "transformation" refers in a broad sense to the introduction of DNA into a recipient host cell that changes the genotype and consequently results in a change in the recipient cell.

Along those same lines, "host cells" refers to cells that have been transformed with vectors constructed using recombinant DNA techniques and encoding at least one heterologous gene. In descriptions of processes for isolation of polypeptides from recombinant hosts, the terms "cell" and "cell culture" are used interchangeably to denote the source of polypeptide unless it is clearly specified otherwise. In other words, recovery of polypeptide from the "cells" can mean either from spun down whole cells, or from the cell culture containing both the medium and the suspended cells.

In one embodiment, a host cell endogenously expresses an enzyme (or the enzymes) necessary to cleave a scFc linker (e.g., if such a linker is present and contains intracellular processing site(s)) during processing to form the mature polypeptide. During this processing, the scFc linker can be substantially removed to reduce the presence of extraneous amino acids. In another embodiment of the invention, a host cell is transformed to express one or more enzymes which are exogenous to the cell such that processing of a scFc linker occurs or is improved.

In one embodiment an enzyme which can be endogenously or exogenously expressed by a cell is a member of the furin family of enzymes. Complete cDNA and amino acid sequences of human furin (i.e., PACE) were published in 1990, Van den Ouweland A M et al. (1990) Nucleic Acids Res. 18:664; Erratum in: Nucleic Acids Res. 18:1332 (1990). U.S. Pat. No. 5,460,950, issued to Barr et al., describes recombinant PACE and the coexpression of PACE with a substrate precursor polypeptide of a heterologous protein to improve expression of active, mature heterologous protein. U.S. Pat. No. 5,935,815, likewise describes recombinant human furin (i.e., PACE) and the coexpression of furin with a substrate precursor polypeptide of a heterologous protein to improve expression of active, mature heterologous protein. Possible substrate precursors disclosed in this patent include a precursor of Factor IX. Other family members in the mammalian furin/subtilisin/Kex2p- like proprotein convertase (PC) family in addition to PACE are reported to include PCSK1 (also known as PC1/Pc3), PCSK2 (also known as PC2), PCSK3 (also known as furin or PACE), PCSK4 (also known as PC4), PCSK5 (also known as PC5 or PC6), PCSK6 (also known as PACE4), or PCSK7 (also known as PC7/LPC, PC8, or SPC7). While these various members share certain conserved overall structural features, they differ in their tissue distribution, subcellular localization, cleavage specificities, and preferred substrates. For a review, see Nakayama K (1997) Biochem J. 327:625-35. Similar to PACE, these proprotein convertases generally include, beginning from the amino terminus, a signal peptide, a propeptide (that can be autocatalytically cleaved), a subtilisin-like catalytic domain characterized by Asp, His, Ser, and Asn/Asp residues, and a Homo B domain that is also essential for catalytic activity and characterized by an Arg-Gly-Asp (RGD) sequence. PACE, PACE4, and PC5 also include a Cys-rich domain, the function of which is unknown. In addition, PC5 has isoforms with and without a transmembrane domain; these different isoforms are known as PC5B and PC5A, respectively. Comparison between the amino acid sequence of the catalytic domain of PACE and the amino acid sequences of the catalytic domains of other members of this family of proprotein convertases reveals the following degrees of identity: 70 percent for PC4; 65 percent for PACE4 and PC5; 61 percent for PC1/PC3; 54 percent for PC2; and 51 percent for LPC/PC7/PC8/SPC7. Nakayama K (1997) Biochem J. 327:625-35.

PACE and PACE4 have been reported to have partially overlapping but distinct substrates. In particular, PACE4, in striking contrast to PACE, has been reported to be incapable of processing the precursor polypeptide of FIX. Wasley et al. (1993) J. Biol. Chem. 268:8458-65; Rehemtulla et al. (1993) Biochemistry. 32:11586-90. U.S. Pat. No. 5,840,529, discloses nucleotide and amino acid sequences for human PC7 and the notable ability of PC7, as compared to other PC family members, to cleave HIV gp160 to gp120 and gp41.

Nucleotide and amino acid sequences of rodent PC5 were first described as PC5 by Lusson et al. (1993) Proc Natl Acad Sci USA 90:6691-5 and as PC6 by Nakagawa et al. (1993) J Biochem (Tokyo) 113:132-5. U.S. Pat. No. 6,380,171 discloses nucleotide and amino acid sequences for human PC5A, the isoform without the transmembrane domain. The sequences of these enzymes and method of cloning them are known in the art.

Genes encoding the polypeptides of the invention (e.g., a GPIIb/IIIa antibody or antigen-binding molecule thereof disclosed herein, or any of the chimeric molecules disclosed herein) can also be expressed in non-mammalian cells such as bacteria or yeast or plant cells. In this regard it will be appreciated that various unicellular non-mammalian microorganisms such as bacteria can also be transformed; i.e., those capable of being grown in cultures or fermentation. Bacteria, which are susceptible to transformation, include members of the enterobacteriaceae, such as strains of *Escherichia coli* or *Salmonella*; Bacillaceae, such as *Bacillus subtilis; Pneumococcus; Streptococcus*, and *Haemophilus influenzae*. It will further be appreciated that, when expressed in bacteria, the polypeptides typically become part of inclusion bodies. The polypeptides must be isolated, purified and then assembled into functional molecules.

In addition to prokaryates, eukaryotic microbes can also be used. *Saccharomyces cerevisiae*, or common baker's yeast, is the most commonly used among eukaryotic microorganisms although a number of other strains are commonly available.

For expression in *Saccharomyces*, the plasmid YRp7, for example, (Stinchcomb et al., Nature, 282:39 (1979); Kingsman et al., Gene, 7:141 (1979); Tschemper et al., Gene, 10:157 (1980)) is commonly used. This plasmid already contains the TRP1 gene which provides a selection marker for a mutant strain of yeast lacking the ability to grow in tryptophan, for example ATCC No. 44076 or PEP4-1 (Jones, Genetics, 85:12 (1977)). The presence of the trp1 lesion as a characteristic of the yeast host cell genome then provides an effective environment for detecting transformation by growth in the absence of tryptophan.

Other yeast hosts such *Pichia* can also be employed. Yeast expression vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for methanol, maltose, and galactose utilization.

Alternatively, polypeptide-coding nucleotide sequences can be incorporated in transgenes for introduction into the genome of a transgenic animal and subsequent expression in the milk of the transgenic animal (see, e.g., U.S. Pat. Nos. 5,741,957; 5,304,489; and 5,849,992). Suitable transgenes include coding sequences for polypeptides in operable linkage with a promoter and enhancer from a mammary gland specific gene, such as casein or beta lactoglobulin.

In vitro production allows scale-up to give large amounts of the desired polypeptides. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose or (immuno-)affinity chromatography, e.g., after preferential biosynthesis of a synthetic hinge region polypeptide or prior to or subsequent to the HIC chromatography step described herein. An affinity tag sequence (e.g. a His(6) tag (SEQ ID NO:241)) can optionally be attached or included within the polypeptide sequence to facilitate downstream purification.

Once expressed, the chimeric molecules can be purified according to standard procedures of the art, including ammonium sulfate precipitation, affinity column chromatography, HPLC purification, gel electrophoresis and the like (see generally Scopes, Protein Purification (Springer-Verlag, N.Y., (1982)) and see specifically the methods used in the instant Examples. Substantially pure proteins of at least about 90 to 95% homogeneity are preferred, and 98 to 99% or more homogeneity most preferred, for pharmaceutical uses.

V. Methods of use

The present disclosure also provides is a pharmaceutical composition comprising (i) a GPIIb/IIIa antibody or antigen-binding molecule thereof disclosed herein;

(ii) a chimeric molecule disclosed herein;

(iii) a nucleic acid molecule or the set of nucleic acid molecules disclosed herein;

(iv) a vector or set of vectors disclosed herein; or (v) any combinations thereof, and a pharmaceutically acceptable carrier.

In some embodiments, administering (i) a chimeric molecule disclosed herein, (ii) a nucleic acid molecule or a set of nucleic acid molecules disclosed herein, (iii) a vector or a set of vectors disclosed herein, or (iii) a pharmaceutical composition disclosed herein, can be used, for example, to reduce the frequency or degree of a bleeding episode in a subject in need, and/or reducing or preventing an occurrence of a bleeding episode in a subject in need thereof. In some embodiments, the subject has developed or has a tendency to develop an inhibitor against treatment with FVIII, FIX, or both. In some embodiments, the inhibitor against FVIII or FIX is a neutralizing antibody against FVIII, FIX, or both.

In some embodiments, the bleeding episode can be caused by a blood coagulation disorder, for example, hemophilia A or hemophilia B. In other embodiments, the bleeding episode can be derived from hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, bleeding in the illiopsoas sheath, or any combinations thereof. In certain embodiments, the subject is a human subject.

The instant disclosure also provides:

(a) a method to target a therapeutic or prophylactic agent (e.g., a clotting factor such as FVII) to the surface of platelets, wherein the method comprises fusing the agent to one of the GPIIb/IIIa antibodies or antigen-binding molecules thereof disclosed herein;

(b) a method to increase the activity of a therapeutic or prophylactic agent (e.g., a clotting factor such as FVII) comprising fusing the agent to a GPIIb/IIIa antibody or antigen-binding molecule thereof disclosed herein; or, (c) a method to improve the pharmacokinetic properties of a clotting factor comprising fusing the clotting factor to the GPIIb/IIIa antibody or antigen-binding molecule thereof disclosed herein.

In some embodiments, these methods further comprise fusing or conjugating the clotting factor and/or the GPIIb/IIIa antibody or antigen-binding molecule thereof disclosed herein to a half-life extending moiety. In some embodiments, the therapeutic or prophylactic agent is FVII, FIX, or FX.

The present disclosure also provides a method of measuring the level of platelets in plasma of a subject in need thereof comprising contacting the GPIIb/IIIa antibody or antigen binding molecule thereof disclosed herein with the plasma from the subject and measuring the level of platelets in plasma. This method can further comprise fusing or conjugating the clotting factor and/or the GPIIb/IIIa antibody or antigen-binding molecule thereof disclosed herein to a detectable heterologous moiety, for example, a fluorescent molecule or a radionuclide.

The invention also relates to a method of treating, ameliorating, or preventing a hemostatic disorder to a subject comprising administering a therapeutically effective amount of a chimeric molecule of the invention which comprises a clotting factor. The treatment, amelioration, and prevention by the chimeric molecule can be a bypass therapy. The subject in the bypass therapy can have already developed an inhibitor to a clotting factor, e.g., FVIII or FIX, or is subject to developing a clotting factor inhibitor. Compositions for administration to a subject include nucleic acid molecules which comprise a nucleotide sequence encoding a chimeric molecule the invention.

In one embodiment, a chimeric molecule composition of the invention is administered in combination with at least one other agent that promotes hemostasis. As an example, but not as a limitation, hemostatic agent can include FV, FVII, FVIII, FIX, FX, FXI, FXII, FXIII, prothrombin, or fibrinogen or activated forms of any of the preceding. The clotting factor or hemostatic agent can also include antifibrinolytic drugs, e.g., epsilon-amino-caproic acid, tranexamic acid.

In one embodiment, the composition (e.g., the polypeptide or nucleic acid molecule encoding the polypeptide) is one in which the clotting factor is present in activatable form when administered to a subject. Such an activatable molecule can be activated in vivo at the site of clotting after administration to a subject.

The chimeric molecule of the invention can be administered intravenously, subcutaneously, intramuscularly, or via any mucosal surface, e.g., orally, sublingually, buccally, sublingually, nasally, rectally, vaginally or via pulmonary route. The chimeric molecule can be implanted within or linked to a biopolymer solid support that allows for the slow release of the chimeric molecule to the desired site.

For oral administration, the pharmaceutical composition can take the form of tablets or capsules prepared by conventional means. The composition can also be prepared as a liquid for example a syrup or a suspension. The liquid can include suspending agents (e.g., sorbitol syrup, cellulose derivatives or hydrogenated edible fats), emulsifying agents (lecithin or acacia), non-aqueous vehicles (e.g., almond oil, oily esters, ethyl alcohol, or fractionated vegetable oils), and preservatives (e.g., methyl or propyl-p-hydroxybenzoates or sorbic acid). The preparations can also include flavoring, coloring and sweetening agents. Alternatively, the composition can be presented as a dry product for constitution with water or another suitable vehicle. For buccal and sublingual administration the composition can take the form of tablets, lozenges or fast dissolving films according to conventional protocols. For administration by inhalation, the chimeric molecules for use according to the present invention are conveniently delivered in the form of an aerosol spray from a pressurized pack or nebulizer (e.g., in PBS), with a suitable propellant.

In one embodiment, the route of administration of the polypeptides of the invention is parenteral. The term parenteral as used herein includes intravenous, intraarterial, intraperitoneal, intramuscular, subcutaneous, rectal or vaginal administration. The intravenous form of parenteral administration is preferred. While all these forms of administration are clearly contemplated as being within the scope of the invention, a form for administration would be a solution for injection, in particular for intravenous or intraarterial injection or drip. Usually, a suitable pharmaceutical composition for injection can comprise a buffer (e.g., acetate, phosphate or citrate buffer), a surfactant (e.g. polysorbate), optionally a stabilizer agent (e.g., human albumin), etc. However, in other methods compatible with the teachings herein, the polypeptides can be delivered directly to the site of the adverse cellular population thereby increasing the exposure of the diseased tissue to the therapeutic agent.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. In the subject invention, pharmaceutically acceptable carriers include, but are not limited to, 0.01-0.1M and preferably 0.05M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives can also be present such as for example, antimicrobials, antioxidants, chelating agents, and inert gases and the like.

More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants.

Prevention of the action of microorganisms can be achieved by various antibacterial and antifungal agents, for example, parabens, chlorobutanol, phenol, ascorbic acid, thimerosal and the like. In many cases, it will be preferable to include isotonic agents, for example, sugars, polyalcohols, such as mannitol, sorbitol, or sodium chloride in the composition. Prolonged absorption of the injectable compositions can be brought about by including in the composition an agent which delays absorption, for example, aluminum monostearate and gelatin.

In any case, sterile injectable solutions can be prepared by incorporating an active compound (e.g., a polypeptide by itself or in combination with other active gents) in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations can be packaged and sold in the form of a kit. Such articles of manufacture will preferably have labels or package inserts indicating that the associated compositions are useful for treating a subject suffering from, or predisposed to clotting disorders.

The pharmaceutical composition can also be formulated for rectal administration as a suppository or retention enema, e.g., containing conventional suppository bases such as cocoa butter or other glycerides.

Effective doses of the compositions of the present invention, for the treatment of conditions vary depending upon many different factors, including means of administration, target site, physiological state of the patient, whether the patient is human or an animal, other medications administered, and whether treatment is prophylactic or therapeutic. Usually, the patient is a human but non-human mammals including transgenic mammals can also be treated. Treatment dosages can be titrated using routine methods known to those of skill in the art to optimize safety and efficacy.

In one embodiment, the dose of a biologically active moiety (e.g., comprising FVII), can range from about 90 to 270 µg/kg or 0.090 to 0.270 mg/kg. In another embodiment, the dose of a biologically active moiety (e.g., comprising FX), can range from about 1 µg/kg to 400 mg/kg.

Dosages can range from 1000 µg/kg to 0.1 ng/kg body weight. In one embodiment, the dosing range is 1 ug/kg to 100 µg/kg. The protein can be administered continuously or at specific timed intervals. In vitro assays can be employed to determine optimal dose ranges and/or schedules for administration. In vitro assays that measure clotting factor activity are known in the art, e.g., STA-CLOT VIIa-rTF clotting assay, Additionally, effective doses can be extrapolated from dose-response curves obtained from animal models, e g., a hemophiliac dog (Mount et al. 2002, *Blood* 99: 2670).

Doses intermediate in the above ranges are also intended to be within the scope of the invention. Subjects can be administered such doses daily, on alternative days, weekly or according to any other schedule determined by empirical analysis. An exemplary treatment entails administration in multiple dosages over a prolonged period, for example, of at least six months. In some methods, two or more polypeptides can be administered simultaneously, in which case the dosage of each polypeptide administered falls within the ranges indicated.

Polypeptides of the invention can be administered on multiple occasions. Intervals between single dosages can be daily, weekly, monthly or yearly. Intervals can also be irregular as indicated by measuring blood levels of modified polypeptide or antigen in the patient. Alternatively, polypeptides can be administered as a sustained release formulation, in which case less frequent administration is required. Dosage and frequency vary depending on the half-life of the polypeptide in the patient.

The dosage and frequency of administration can vary depending on whether the treatment is prophylactic or therapeutic. In prophylactic applications, compositions containing the polypeptides of the invention or a cocktail thereof are administered to a patient not already in the disease state to enhance the patient's resistance or minimize effects of disease. Such an amount is defined to be a "prophylactic effective dose." A relatively low dosage is administered at relatively infrequent intervals over a long period of time. Some patients continue to receive treatment for the rest of their lives.

Polypeptides of the invention can optionally be administered in combination with other agents that are effective in treating the disorder or condition in need of treatment (e.g., prophylactic or therapeutic).

As used herein, the administration of polypeptides of the invention in conjunction or combination with an adjunct therapy means the sequential, simultaneous, coextensive, concurrent, concomitant or contemporaneous administration or application of the therapy and the disclosed polypeptides. Those skilled in the art will appreciate that the administration or application of the various components of the combined therapeutic regimen can be timed to enhance the overall effectiveness of the treatment. A skilled artisan (e.g., a physician) would be readily be able to discern effective combined therapeutic regimens without undue experimentation based on the selected adjunct therapy and the teachings of the instant specification.

It will further be appreciated that the polypeptides of the instant invention can be used in conjunction or combination with an agent or agents (e.g., to provide a combined therapeutic regimen). Exemplary agents with which a polypeptide of the invention can be combined include agents that represent the current standard of care for a particular disorder being treated. Such agents can be chemical or biologic in nature. The term "biologic" or "biologic agent" refers to any pharmaceutically active agent made from living organisms and/or their products which is intended for use as a therapeutic.

The amount of agent to be used in combination with the polypeptides of the instant invention can vary by subject or can be administered according to what is known in the art. See for example, Bruce A Chabner et al., Antineoplastic Agents, in Goodman & Gilman's The Pharmacological Basis of Therapeutics 1233-1287 ((Hardman et al., eds., 9th ed. 1996). In another embodiment, an amount of such an agent consistent with the standard of care is administered.

As previously discussed, the polypeptides of the present invention, can be administered in a pharmaceutically effective amount for the in vivo treatment of clotting disorders. In this regard, it will be appreciated that the polypeptides of the invention can be formulated to facilitate administration and promote stability of the active agent. Preferably, pharmaceutical compositions in accordance with the present invention comprise a pharmaceutically acceptable, non-toxic, sterile carrier such as physiological saline, non-toxic buffers, preservatives and the like. Of course, the pharmaceutical compositions of the present invention can be administered in single or multiple doses to provide for a pharmaceutically effective amount of the polypeptide.

In one embodiment, a chimeric molecule of the invention is administered as a nucleic acid molecule. Nucleic acid molecules can be administered using techniques known in the art, including via vector, plasmid, liposome, DNA injection, electroporation, gene gun, intravenously injection or hepatic artery infusion. Vectors for use in gene therapy embodiments are known in the art.

In keeping with the scope of the present disclosure, the chimeric molecule of the invention can be administered to a human or other animal in accordance with the aforementioned methods of treatment in an amount sufficient to produce a therapeutic or prophylactic effect.

The chimeric molecules of the invention have many uses as will be recognized by one skilled in the art, including, but not limited to methods of treating a subject with a disease or condition. The disease or condition can include, but is not limited to, hemostatic disorders.

In one embodiment, the invention relates to a method of treating a subject having a hemostatic disorder comprising administering a therapeutically effective amount of at least one chimeric molecule of the invention.

The chimeric molecules of the invention treat or prevent a hemostatic disorder by promoting the formation of a fibrin clot. The chimeric molecule of the invention can activate any member of a coagulation cascade. The clotting factor can be a participant in the extrinsic pathway, the intrinsic pathway or both. A chimeric molecule of the invention can be used to treat hemostatic disorders, e.g., those known to be treatable with the particular clotting factor present in the chimeric molecule. The hemostatic disorders that can be treated by administration of the chimeric molecule of the invention include, but are not limited to, hemophilia A, hemophilia B, von Willebrand's disease, Factor XI deficiency (PTA deficiency), Factor XII deficiency, as well as deficiencies or structural abnormalities in fibrinogen, prothrombin, Factor V, Factor VII, Factor X, or Factor XIII.

In one embodiment, the hemostatic disorder is an inherited disorder. In one embodiment, the subject has hemophilia A, and the chimeric molecule comprises activated or protease-activatable FVII linked to or associated with a GPIIb/IIIa antibody or antigen-binding molecule thereof and a half-life extending heterologous moiety. In another embodiment, the subject has hemophilia A and the chimeric molecule comprises activated or protease-activatable FVII linked to or associated with a GPIIb/IIIa antibody or antigen-binding molecule thereof and a half-life extending heterologous moiety. In other embodiments, the subject has hemophilia B and the chimeric molecule comprises activated or protease-activatable FVII or FX linked to or associated with a GPIIb/IIIa antibody or antigen-binding molecule thereof and a half-life extending heterologous moiety. In some embodiments, the subject has inhibitory antibodies to FVIII or FVIIIa and the chimeric molecule comprises activated or protease-activatable FVII linked to or associated with a GPIIb/IIIa antibody or antigen-binding molecule thereof and a half-life extending heterologous moiety. In yet other embodiments, the subject has inhibitory antibodies against FIX or FIXa and the chimeric molecule comprises activated or protease-activatable FVII linked to or associated with a GPIIb/IIIa antibody or antigen-binding molecule thereof and a half-life extending heterologous moiety. In still other embodiments, the subject has inhibitory antibodies to FVIII or FVIIIa and the chimeric molecule comprises activated or protease-activatable FX linked to or associated with a GPIIb/IIIa antibody or antigen-binding molecule thereof and a half-life extending heterologous moiety. In certain embodiments, the subject has inhibitory antibodies against FIX or FIXa and the chimeric molecule comprises activated or protease-activatable FX linked to or associated with a GPIIb/IIIa antibody or antigen-binding molecule thereof and a half-life extending heterologous moiety.

Chimeric molecules of the invention comprising a clotting factor (e.g., FVII) can be used to prophylactically treat a subject with a hemostatic disorder. Chimeric molecules of the invention comprising a clotting factor (e.g., FVII) can be used to treat an acute bleeding episode in a subject with a hemostatic disorder.

In one embodiment, the hemostatic disorder is the result of a deficiency in a clotting factor, e.g., FVII, FIX, or FVIII. In another embodiment, the hemostatic disorder can be the result of a defective clotting factor. In another embodiment, the hemostatic disorder can be an acquired disorder. The acquired disorder can result from an underlying secondary disease or condition. The unrelated condition can be, as an example, but not as a limitation, cancer, an autoimmune disease, or pregnancy. The acquired disorder can result from old age or from medication to treat an underlying secondary disorder (e.g. cancer chemotherapy).

The invention also relates to methods of treating a subject who does not have a hemostatic disorder or a secondary disease or condition resulting in acquisition of a hemostatic disorder. The invention thus relates to a method of treating a subject in need of a general hemostatic agent comprising administering a therapeutically effective amount of at least one chimeric molecule of the invention. For example, in one embodiment, the subject in need of a general hemostatic agent is undergoing, or is about to undergo, surgery. The chimeric molecule of the invention can be administered prior to or after surgery as a prophylactic. The chimeric molecule of the invention can be administered during or after surgery to control an acute bleeding episode. The surgery can include, but is not limited to, liver transplantation, liver resection, or stem cell transplantation. In another embodiment, the chimeric molecule of the invention can be used to treat a subject having an acute bleeding episode who does not have a hemostatic disorder. The acute bleeding episode can result from severe trauma, e.g., surgery, an automobile accident, wound, laceration gun shot, or any other traumatic event resulting in uncontrolled bleeding.

Having now described the present invention in detail, the same will be more clearly understood by reference to the following examples, which are included herewith for purposes of illustration only and are not intended to be limiting of the invention. All patents and publications referred to herein are expressly incorporated by reference in their entireties.

EXAMPLES

General Materials and Methods

In general, the practice of the present invention employs, unless otherwise indicated, conventional techniques of chemistry, biophysics, molecular biology, recombinant DNA technology, immunology (especially, e.g., antibody technology), and standard techniques in electrophoresis. See, e.g., Sambrook, Fritsch and Maniatis, Molecular Cloning: Cold Spring Harbor Laboratory Press (1989); Antibody Engineering Protocols (Methods in Molecular Biology), 510, Paul, S., Humana Pr (1996); Antibody Engineering: A Practical Approach (Practical Approach Series, 169), McCafferty, Ed., Irl Pr (1996); Antibodies: A Laboratory Manual, Harlow et al., CS.H.L. Press, Pub. (1999); and Current Protocols in Molecular Biology, eds. Ausubel et al., John Wiley & Sons (1992).

Example 1

Identification and Characterization of Platelet-Targeted Antibodies

Figure 1:
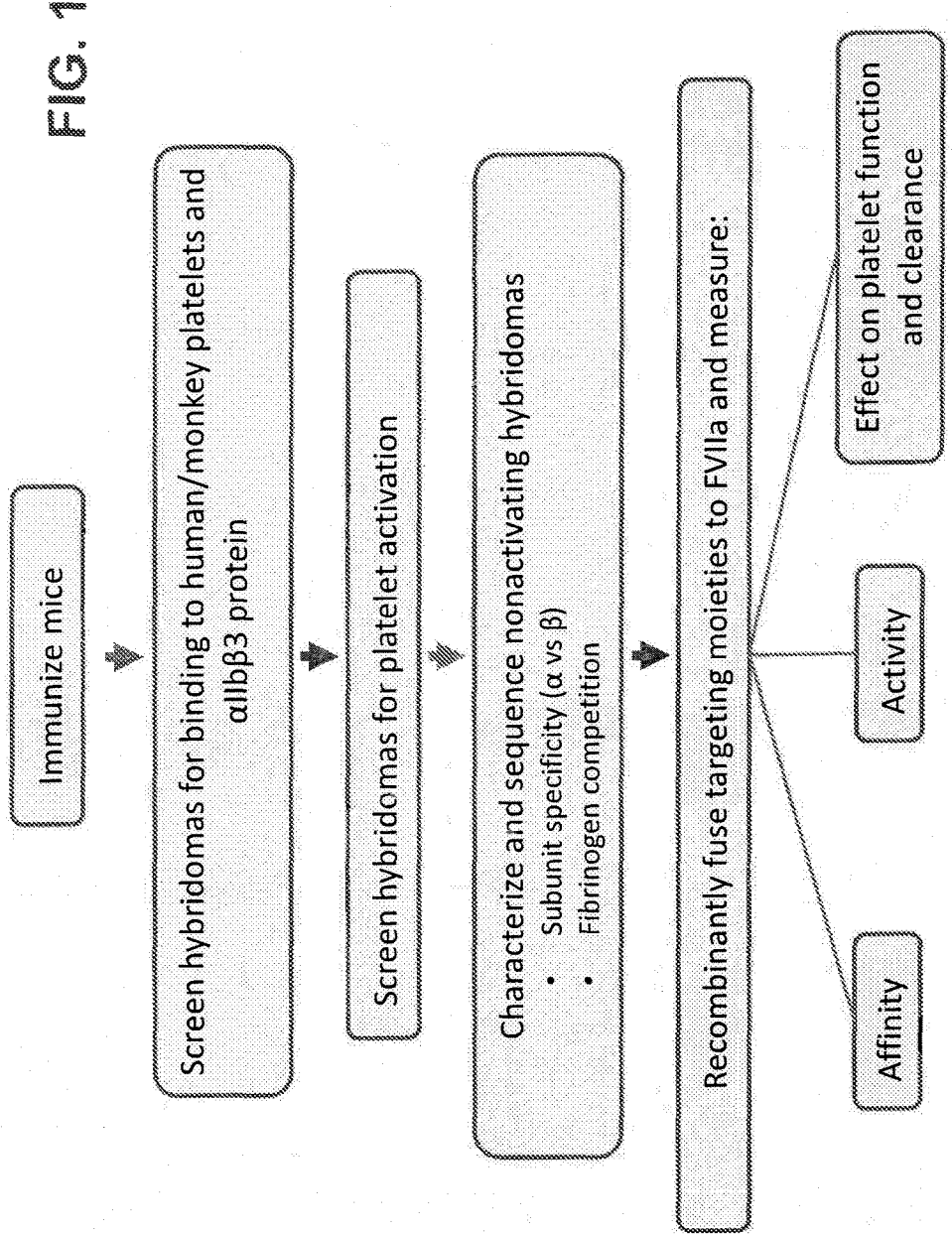

A summary of the process used for production, identification, and characterization of antibodies against GPIIb/IIIa disclosed herein, and constructs derived from these antibodies is presented in FIG. 1.

Hybridomas were generated from BALB/C mice immunized with plasmids containing DNA sequences encoding GPIIb/IIIa (SEQ ID NOs: 183 and 184) according to methods known in the art. Hybridomas were then screened for binding to human and cynomolgus monkey platelets using flow cytometry, and for binding to GPIIb/IIIa using Enzyme-linked immunosorbent assays (ELISA). To determine binding to human and money platelets, gel-purified human or monkey (cynomolgus) platelets in Tyrode's buffer were incubated with hybridoma supernatant. Following a 30 minute incubation, cells were fixed in 1% formaldehyde. Following fixation, cells were washed in Tyrode's buffer and a detection antibody was added (Jackson Immunoresearch goat anti-mouse IgG-PE conjugated). Antibody binding was detected by flow cytometry.

The binding of supernatants from hybridomas to human GPIIb/IIIa (αIIbβ) was determined by using ELISA as follows., Costar plates (Cat. No. 3590) were coated with 100 µl/well of 5 µg/mL human GPIIb/IIIa (Calbiochem Cat No. 528240) in measuring buffer (20 mM Tris, pH 7.4, 150 mM NaCl, 1 mM $MgCl_2$, and 1 mM $MnCl_2$) and incubated for 1 hour at 37° C. with shaking. Wells were washed three times with TBST using a plate washer. Blocking was performed using 200 µl of measuring buffer containing 5% BSA (Bovine Serum albumin, Jackson Cat No 001 000 173) per well, and incubating 1 hour at 37° C. with shaking. 100 µl of hybridoma supernatant were added assay wells, incubated for 1 hour at 37° C. with shaking, and washed three times with TBST. A 1:10,000 dilution of goat anti mouse IgGHRP (Southern Biotech (Cat. No. 1010 05) in measuring buffer was added, incubated for 1 hour at 37° C. with shaking, and washed three times with TBST. HRP presence was developed using TMB and O.D. read at 450 nm using a Molecular Devices plate reader.

The supernatants from hybridomas which tested positive in the ELISA assays were mixed with platelets and screened for platelet activation using flow cytometry as follows.

(a) Reagents: Citrated human whole blood; Sepharose 2B beads (GE Healthcare); Tyrode's buffer with 1 mg/mL BSA (no calcium); Tyrode's buffer with 5 mM $CaCl_2$ and 1 mg/mL BSA; 32% paraformaldehyde (PFA) (EM Sciences); PAC1 FITC antibody (BD Cat. No. 340507); CD62 PE antibody (BD Cat. No. 555524); ADP; SFFLRN peptide (SEQ ID NO:242) (Anaspec, Cat. No. 24191); IV.3 Fabb anti CD32 (StemCell, Cat. No. 01470).

(b) Platelet purification: A 10 mL Sepharose 2B bead column was packed and equilibrated with 30 mL of Tyrode's buffer containing 1 mg/mL BSA. A volume of 1 to 1.5 mL of platelet-rich plasma (PRP) was loaded onto the equilibrated Sepharose column and allowed to enter the packed beads by gravity, followed with approximately 5 mL of Tyrode's buffer. The turbid drops, which contained the platelets, were collected.

(c) Assay: First, 50µL aliquots of hybridoma supernatant were added to assay wells of a 96 well round bottom plate. 10 µL of PAC1 FITC and 10 µL of CD62PE were added to all control and assay wells. 10 µL of ADP and 10 µL of SFFLRN (SEQ ID NO:242) were added to all control wells (no hybridoma supernatant). 10 µL of IV.3 inhibitor (antibody to FcγRIIA) were added wells to see if activation was Fc or antibody mediated. Next, a 50 µL aliquot of concentrated resting platelets, which was purified as described above, was added to all wells. Plates were incubated for 30 minutes in the dark and at room temperature. Cells were fixed with 1% PFA (final concentration) for 10 minutes at room temperature (a volume of 2% PFA equal to the content of each well was added). After fixation, samples were analyzed by flow cytometry.

Figure 2:
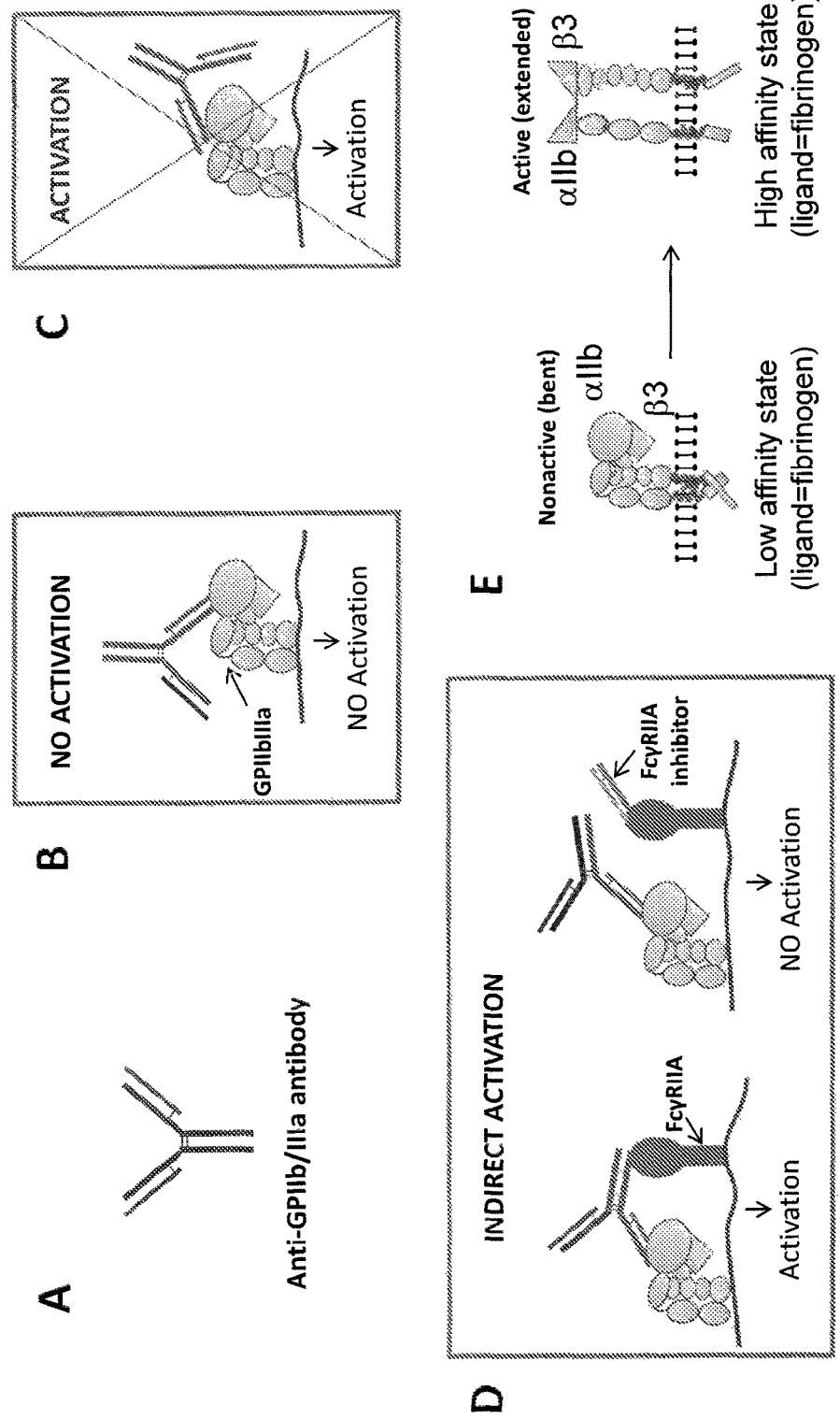

The antibodies that did not activate platelets upon binding to GPIIb/IIIa (see FIG. 2B) were selected as candidates for clotting factor targeting moieties. The antibodies that activate platelets upon binding to GPIIb/IIIa were excluded from selection (see FIG. 2C)

Antibodies can also activate platelets by binding to the FcγRIIA receptor via the Fc region (see FIG. 2D), which were not excluded from the selection because their antigen binding portion contain no Fc region and therefore not bind to the FcγRIIA receptor. These antibodies can be identified by blocking the FcγRIIA receptor with an inhibitor.

Figure 3:
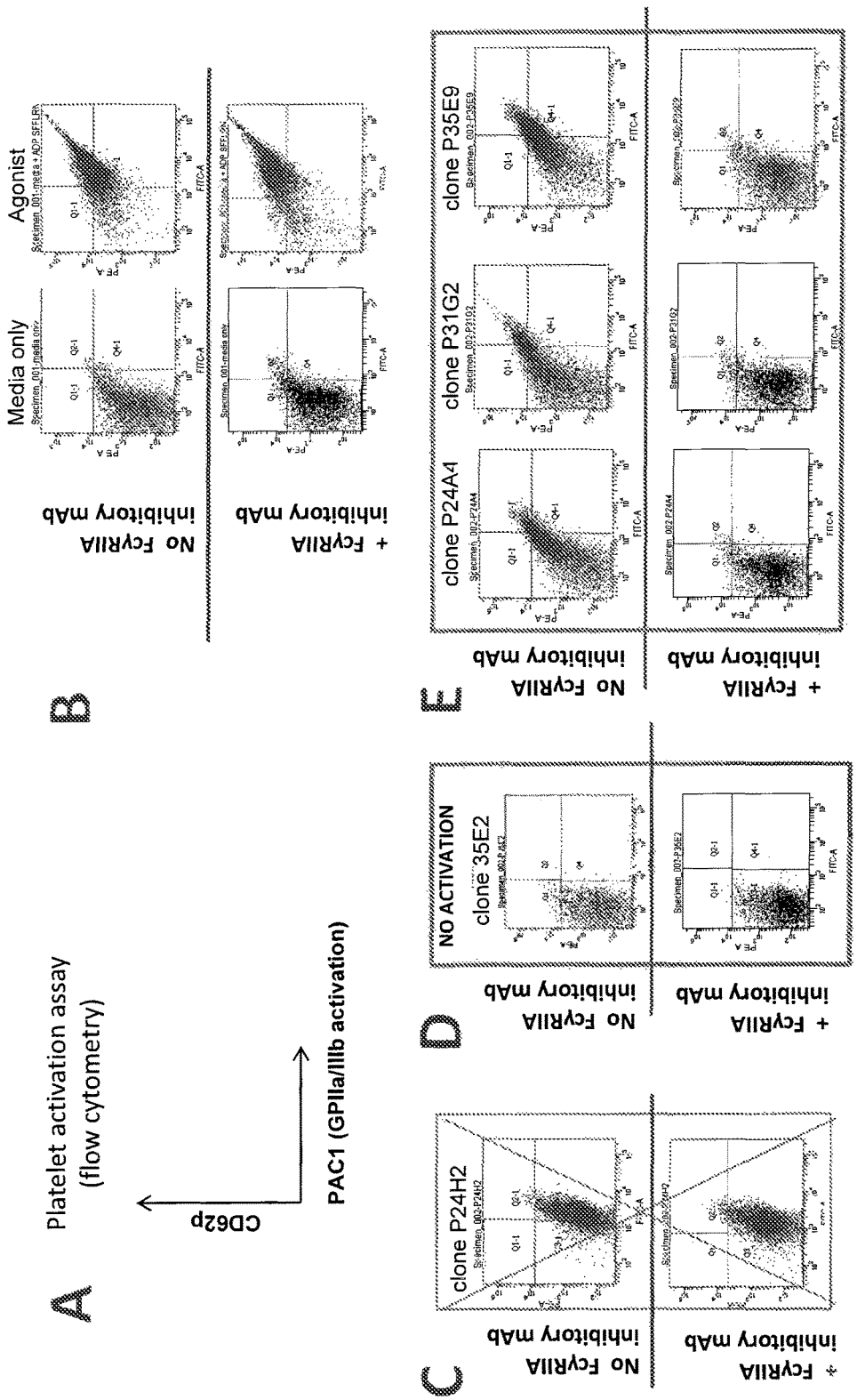

FIG. 3 shows flow cytometry profiles from platelet activation assays in which CD62p and PAC1 were detected (FIG. 3A). CD62p, also known as P-selectin, is expressed on the platelet surface upon platelet activation. PAC1 is a pentameric IgM that binds to agonist-stimulated platelets, and PAC1 binding is therefore indicative of GPIIb/IIIa-mediated activation. Experiments were performed in the absence and presence of an FcγRIIA receptor inhibitor (IV.3 Fab; see Naik et al., *Biochem. J.* 310:155-162 (1995)) in order to detect antibodies capable of activating platelets indirectly via simultaneous binding to GPIIb/IIIa and to the FcγRIIA receptor (see FIGS. 3B, 3C, 3D, and 3E).

FIG. 3B shows flow cytometry profiles observed when only cell culture medium was present, and when ADP and a PAR1 platelet receptor agonist peptide with amino sequence SFLLRN (SEQ ID NO: 225) were present. FIG. 3C shows flow cytometry profiles corresponding to an antibody capable of activating platelets both in the presence and absence of the FcγRIIA inhibitor monoclonal antibody. Thus, the antibody activates platelets by direct binding to GPIIb/IIIa. FIG. 3D shows flow cytometry profiles corresponding to an antibody not capable of activating platelets both in the presence and absence of the FcγRIIA inhibitor monoclonal antibody. FIG. 3E shows flow cytometry profiles corresponding to antibodies indirectly activating platelets, i.e., the antibodies bind simultaneously to GPIIa/IIIb and to the FcγRIIA receptor.

The supernatants from non-activating hybridomas were subject to additional characterization assays (i) to confirm antibody binding to human and cynomolgus platelets, (ii) to determine antibody binding specificity for the α and/or β subunit of GPIIb/IIIa, and (iii) to determine whether the antibodies can compete with fibrinogen for binding to platelets. Fibrinogen is the natural ligand of GPIIb/IIIa and its binding to GPIIbIIIa is essential to mediate platelet aggregation. Thus, the antibodies that compete with the binding of fibrinogen to GPIIb/IIIa were excluded from the selection.

Antibody binding to the α and/or β subunit of GPIIb/IIIa was assessed using ELISA, whereas antibody competition with fibrinogen was assessed using flow cytometry. Antibodies determined to be non-activating (e.g., clones 34D10, 2A2, 35D1, 36A8, 4B11, 1H6, 38G8, 21F10, 38A8, 18F7, 12B2, 38F6, 13C1, 5C4, 23C10, 37C7, 28C2, 9D6, 13A1) were clustered into 6 different groups according to the VH domain sequence similarity, α or β subunit specificity, ability to compete with fibrinogen, and relative strength of the signals measured via ELISA and flow cytometry (see TABLE 1).

TABLE 1

Platelet Specific Non-Activating Anti-GPIIb/IIIa Monoclonal Antibodies

| Group/Antibody Characteristics | Antibody/Chain | | SEQ ID | CDR SEQ IDs | | |
|---|---|---|---|---|---|---|
| | | | | CDR1 | CDR2 | CDR3 |
| 1/α subunit specific No fibrinogen competition | 2A2 | HC | 3 | 25 | 26 | 27 |
| | | LC | 4 | 28 | 29 | 30 |
| | 34D10# | HC | 1 | 31 | 32 | 33 |
| | | LC | 2 | 34 | 35 | 36 |
| | 35D1 | HC | 97 | 111 | 112 | 113 |
| | | LC | 98 | 114 | 115 | 116 |
| | 36A8 | HC | 5 | 37 | 38 | 39 |
| | | LC | 6 | 40 | 41 | 42 |
| | 4B11 | HC | 7 | 43 | 44 | 45 |
| | | LC | 99 | 117 | 118 | 119 |
| 2/α subunit specific. Fibrinogen competition | 1H6 | HC | 8 | 46 | 47 | 48 |
| | | LC | 9 | 49 | 50 | 51 |
| | 38G8 | HC | 100 | 120 | 121 | 122 |
| | | LC | 101 | 123 | 124 | 125 |
| | 21F10 | HC | 102 | 126 | 127 | 128 |
| | | LC | 103 | 129 | 130 | 131 |
| | 38A8 | HC | 10 | 52 | 53 | 54 |
| | | LC | 11 | 55 | 56 | 57 |
| 3/α subunit specific. Fibrinogen competition. Low ELISA signal v flow cytometry | 18F7 | HC | 12 | 58 | 59 | 60 |
| | | LC | 13 | 61 | 62 | 63 |
| 4/β subunit specific. No fibrinogen competition | 12B2$ | HC | 14 | 64 | 65 | 66 |
| | | LC | 15 | 67 | 68 | 69 |
| | 38F6 | HC | 16 | 70 | 71 | 72 |
| | | LC* | 104 | 132 | 133 | 134 |
| | 13C1 | HC | 105 | 135 | 136 | 137 |
| | | LC* | 106 | 138 | 139 | 140 |
| 5/β subunit specific. Fibrinogen competition | 5C4 | HC | 17 | 73 | 74 | 75 |
| | | LC* | 107 | 141 | 142 | 143 |
| | 23C10 | HC | 18 | 76 | 77 | 78 |
| | | LC* | 108 | 144 | 145 | 146 |
| | 37C7 | HC | 109 | 147 | 148 | 149 |
| | | LC* | 110 | 150 | 151 | 152 |
| | 28C2 | HC | 19 | 79 | 80 | 81 |
| | | LC | 20 | 82 | 83 | 84 |
| | 9D6 | HC | 21 | 85 | 86 | 87 |
| | 9D6 | LC | 22 | 88 | 89 | 90 |
| 6/β subunit specific. Fibrinogen competition. Low ELISA signal v flow cytometry | 28F4 | HC | 23 | 91 | 92 | 93 |
| | | LC | 24 | 94 | 95 | 96 |

*= Not sequenced.
HC = Heavy Chain (i.e., VH).
LC = Light Chain (i.e., VL)
α subunit or complex specific
$β subunit specific Several non-activating antibodies identified using the screening method described above shared the same VH or VL domains, as show in FIG. 4. For example, 35D1 and 34D10 shared the same VH domain.

Unique VH and VL sequences were aligned using the ClustalX program using standard parameters (FIG. 5). Sequence designators in FIG. 5, which are also used in the sequence alignments of FIGS. 6 to 12, follow the schema "SEQ ID NO-Antibody-BindingDomain." Accordingly "SEQ22-9D6LC" corresponds to SEQ ID NO:22, which is the Light Chain variable domain (i.e., VL) of the 9D6 antibody. Similarly, "SEQ08-1H6HC" corresponds to SEQ ID NO:8, which is the Heavy Chain variable domain (i.e., VH) of the 1H6 antibody.

The character "*" in the multiple sequence alignments indicates positions which have a single, fully conserved amino acid residue. The character ":" indicates that one strong conservation group is fully conserved. Strong conservation amino acid groups are STA, NEQK, NHQK, NDEQ, QHRK, MILV, MILF, HY, and FYW. The character "." indicates that one weaker conservation group is fully conserved. Weaker conservation amino acid groups are CSA, ATV, SAG, STNK, STPA, SGND, SNDEQK, NDEQHK, NEQHRK, FVLIM, and HFY. Amino acids are shaded in FIG. 5 according to the rules set out below. Rules are specified according to the formula: (A, C, and D): {50%, P,Q,RSTV} {85%, W,Y}, where amino acid residue or residues in the alignment column are given first in the round brackets. More than one amino acid can be specified between the round brackets, in which case the rules apply to each of these amino acid residues. Next, the rule or rules to assign a given color are provided between curly braces. Only one rule has to be met for the color to be applied. The minimum percentage of occurrence in the alignment column is given first, followed by the amino acid residue or residues which must meet or exceed this percentage within the column. If a group of amino acid residues is concatenated together, such as "RSTV," then any combination of these residues in total must meet or exceed the given percentage for the color to be applied. For amino acid residues or residue groups separated by commas, at least one of these must by itself exceed the percentage.

Highlighting (shading) rules in FIG. 5 are based on conservation and common physicochemical and/or structural properties. For example, tiny residues (G) and prolines (P) are always highlighted when present. The follow highlighting rules were applied:

W, L, V, I, M, F, A, and C amino acid residues are highlighted according to the following set of rules: (W, L, V, I, M, F): {50%, P} {60%, WLVIMAFCYHP}; (A): {50%, P} {60%, WLVIMAFCYHP} {85%, T, S, G}; and (C): {50%, P} {60%, WLVIMAFCYHP} {85%, S}.

K and R amino acid residues are highlighted according to the following set of rules: (K, R): {60%, KR} {85%, Q}.

T, S, N, and Q amino acid residues are highlighted according to the following set of rules: (T): {50%, TS} {60%, WLVIMAFCYHP}; (S): {50%, TS} {80%, WLVIMAFCYHP}; (N): {85%, N} {85%, D}; and, (Q): {50%, QE} {60%, KR}.

C amino acid residues are highlighted according to the following rule: (C): {85%, C}.

D and E amino acid residues are highlighted according to the following set of rules: (D): {50%, DE, N}; and (E): {50%, DE, QE}.

G amino acid residues are highlighted in according to the following rule: (G): {Always}.

H and Y amino acid residues highlighted according to the following set of rules: (H,Y): {50%, P}{60%, WLVIMAFCYHP}.

P amino acid residues are highlighted according to the following rule: (P): {Always}.

Multiple sequence alignments corresponding to the VH and VL domains of the above identified antibodies are shown in FIG. 6 and FIG. 7, respectively. The multiple sequence alignments show the location of the complementarity determining regions CDR1, CDR2, and CDR3 in the VH and VL domain and their location according to the EU numbering system (Kabat, E. A., Wu, T. T., Perry, H., Gottesman, K., and Foeller, C. (1991) "Sequences of Proteins of Immunological Interest," 4th ed., U.S. Govt. Printing Off. No. 165-492, Nethesda, MD).

FIG. 8 shows percent identity matrices showing the percentage of sequence identity among each pair of the VH and VL sequences shown in the multiple sequence alignments of FIGS. 6 and 7. Column designations correspond to the designation applied to each row in the matrix. For example, column 2 corresponds to "2: SEQ 22-9D6LC." The sequences aligned in FIG. 6 and FIG. 7 were clustered according to the specificity of the antibodies for the α or β subunits of GPIIb/IIIa (see FIG. 9 and FIG. 10), and according to their ability to compete with fibrinogen for binding to GPIIb/IIIa (see FIG. 11 and FIG. 12).

Example 2

Figure 13:
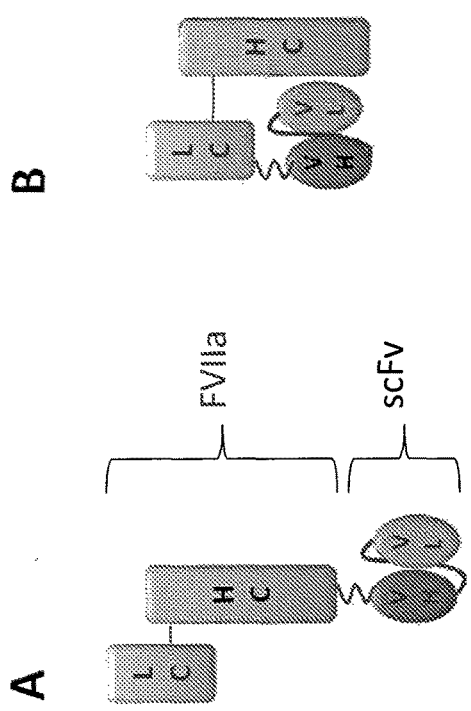
FIGS. 13A and 13B are schematic representations of an anti-GPIIb/IIIa antibody in scFv format recombinantly fused to the FVIIa clotting factor heavy chain (FIG. 13A) or light chain (FIG. 13B) for platelet targeting.

Platelet-Targeted Chimeric Molecules Comprising Anti-GPIIb/IIIa Antibodies and FVIIa The above described monoclonal antibodies against GPIIb/IIIa were used to target the FVIIa clotting factor to the surface of platelets. Accordingly, scFv's derived from the platelet-specific monoclonal antibodies identified according to the methods disclosed in Example 1 were recombinantly fused to FVIIa using molecular biology methods known in the art. In the resulting chimeric molecules, the C-terminus of the heavy chain of FVIIa was fused to the N-terminus of an scFv comprising a VH and a VL domain derived from non-activating platelet-targeting antibodies identified in Example 1 (see FIG. 13). A chimeric molecule comprising an scFv derived from the GPIIb/IIIa α subunit/complex-specific 34D10 antibody was designated "FVII-189". A second chimeric molecule comprising an scFv derived from the GPIIb/IIa β subunit-specific 12B2 monoclonal antibody was designated "FVII-206". A chimeric molecule comprising an scFv from a known antibody (PDG13) was designated as "FVII-163". A chimeric molecule containing an scFV from 38A8 monoclonal antibody was designated as "FVII-204", These platelet-targeted FVIIa variants were characterized for their affinity to GPIIb/IIIa receptor, their ability to bind to platelets, their procoagulant activity, their effect on platelet activation and platelet function, and their effect on platelet clearance in animals.

The affinity of platelet-targeted FVII-189, FVII-206, FVII-163 chimeric molecules to GPIIb/IIIa receptor was measured using surface plasmon resonance (SPR). GPIIb/IIIa was modified to incorporate a tag for in vivo biotinylation, and an HPC4 tag for purification (see FIG. 14). The GPIIb/IIIa protein were transiently expressed in HEK293 cells and subsequently purified. GPIIb/IIIa nanodiscs were formed by first combining the GPIIb/IIIa protein with the scaffold protein, phospholipids, and detergent, followed with the removal of the detergent (FIG. 14). (see, Zhu et al., Sci. Transl. Med. 4, 125ra32 (2012), which is hereby incorporated by reference in its entirety).

The nanodiscs, which contained the biotinylated GPIIb/IIIa receptor, were bound to BIACORE® streptavidin chips, and binding of the FVII-189, FVII-206, and FVII-163 chimeric molecules was measured using SPR (see FIG. 15 and TABLE 2).

TABLE 2

Affinity of FVII-189 and FVII-206 Chimeric Molecules to GPIIb/IIIa receptor as measured by SPR

| FVIIa Variant | Antibody (scFv) Moiety | Affinity (nM) |
|---|---|---|
| FVII-189 | 34D10 | 5.2 |
| FVII-206 | 12B2 | 5.3 |
| FVII-163 | PDG13 | 8.8 |
| Recombinant FVIIa | None | No binding observed |

SPR results indicate that both α-targeted and β-targeted chimeric molecules bound to GPIIb/IIIa with similar affinity. Compared to the known antibody (PDG13), the 34D10 and 12B2 antibodies provide stronger GPIIb/IIIa affinity to FVIIa.

The ability of the FVIIa chimeric molecules to bind to platelets was measured in a flow cytometry-based platelet-binding assay. Briefly, the FVIIa chimeric molecules were spiked into a citrated human whole blood and incubated for 30 mins. The blood was then stained with an APC-conjugated anti-human CD42b antibody and a FITC-conjugated anti-FVII polyclonal antibody to label the platelets and FVII protein, respectively. After fixing with paraformadyhyde, the stained blood was analyzed by flow cytometry. The platelets were identified by scatter gating followed by APC-fluorescence gating; and relative FVII concentration was represented by the median fluorescent value of FITC-fluorescence gating on gated platelets. As shown in FIG. 18, all platelet-targeted FVII chimeric molecules described above (FVII-163, FVII-189, FVII-204, and FVII-206) were capable of binding to human platelets. No binding was observed to human platelets for recombinant FVIIa alone (in the absence of a targeting moiety). See also Table 2.

The procoagulant activity of the platelet-targeted FVIIa chimeric molecules was measured using a FVIIa specific soluble tissue factor prothrombin time (sTF-PT) and rotational thromboelastometry (ROTEM) assays. The specific activity of the platelet-targeted rFVIIa variants FVII-189, FVII-206, and FVII-204, as measured by sTF-PT assays, was found to be comparable to that of rFVIIa, indicating that linking of the platelet-targeting moiety does not affect rFVIIa's catalytic activity. In the presence of platelets, such as the ROTEM assays using the whole blood from human Hemophila A donors, the platelet-targeted rFVIIa variants showed improved clotting activities. Specifically, FVII-189 and FVII-206 displayed a 25-50 fold increase in activity compared to rFVIIa (FIGS. 16A, 16B, 17B). Improvement in activity was also observed in FVII-204 (FIG. 17A).

Platelet activation was measured using flow cytometry as described in Example 1. FIG. 19 shows that platelets were not activated by either the platelet-targeted FVII-189 chimeric molecule (targeting the α chain/complex) or the platelet-targeted FVII-206 chimeric molecule (targeting the β chain). FVII-130 is a platelet-targeted chimeric molecule known to activate platelets and was used as a positive control using the same experimental conditions (see FIG. 19).

FVII-189 (FIG. 20A) and FVII-206 (FIG. 20B) did not inhibit ADP-induced platelet aggregation in platelet-rich plasma, indicating that none of these chimeric molecules inhibited platelet function. REOPRO® (abciximab), a monoclonal antibody that blocks the pathway to platelet aggregation, was used as a control. Accordingly, platelet-targeted chimeric molecules comprising targeting moieties derived from the anti-GPIIb/IIIa antibodies disclosed herein did not activate or inhibit platelet function.

The effect of platelet-targeting rFVIIa chimeric molecules on platelet clearance in vivo was investigated in the NOD SCID gamma (NSG) mice with circulating human platelets since none of the targeting moieties is capable of binding mouse platelets. Human platelet-rich plasma (PRP) was prepared from the citrated whole blood. The PRP was concentrated and administrated via retro-orbital into NSG mice. After 30 minutes, the clotting factors were dosed at 5 nmol/kg by tail-vein injection, and the blood samples were collected via tail laceration at 5 minutes before, and at various times after clotting factor dosing. To quantify the human platelets, the blood was stained with a cocktail containing PE-conjugated anti-mouse CD61, APC-conjugated anti-human CD42b to visualize by flow cytometry the mouse platelets and human platelet, respectively. The relative human platelet counts was obtained by the scattering gating for platelets, and the PE, APC fluorescent gating for mouse and human platelets, respectively. As shown in FIG. 21, a control protein FVII-130, which is known to promote platelet clearance and cause thrombocytopenia, led a rapid human platelet clearance in this model; more than 90% of injected human platelets were cleared within 1 hour following the administration of FVII-130. On the contrary, no effect on human platelet clearance can be detected when treated the mice with FVII-189, FVII-206, and FVII-204, indicating that these platelet-targeted rFVIIa chimeric molecules do not affect the human platelet clearance in vivo.

The present invention has been described above with the aid of functional building blocks illustrating the implementation of specified functions and relationships thereof. The boundaries of these functional building blocks have been arbitrarily defined herein for the convenience of the description. Alternative boundaries can be defined so long as the specified functions and relationships thereof are appropriately performed.

The present application claims benefit to U.S. Provisional Application No. 61/827,165, filed May 24, 2014, which is incorporated herein by reference in its entirety.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents. Other embodiments of the invention will be apparent to those skilled in the art from consideration of the specification and practice of the invention disclosed herein.

All patents and publications cited herein are incorporated by reference herein in their entirety.

SEQUENCE LISTING:

>SEQ_ID_NO: 1 34D10 HC
EVKLVESGGGLVKFGGSLKLSCAASGFTFSAYAMSWVRQTPEKRLEWVAS
ISSGGTTYYPDSVKRRFTISRNARNILYLQMSSLRSEDTAMYYCTRGGDY
GYALDYWGQGTSVTVSS

>SEQ_ID_NO: 2 34D10 LC
ENVLTQSPAIMSASLGEKVTMSCRASSSVNYMYWYQQKSDASPKLWIYYT
SNLAPGVPARFSGSGSGNSYSLTISSMEGEDAATYYCQQFSSSPWTFGGG
TKLEIKR

>SEQ_ID_NO: 3 2A2 HC
EVKLVESGGGLVKPGGSLKLSCAASGFTFRTYAMSWVRQTPEKRLEWVAS
ISSGSSTYYLDSVKGRFTISRDNARNILYLQMSSLRSEDTAMYYCARGGD
YGYALDYWGQGTSVTVSS

>SEQ_ID_NO: 4 2A2 LC
ENVLTQSPAIMSASLGEKVTMSCRASSSVNYMYWYQQKSDASPKLWIYYT
SNLAPGVPTRFSGSGSGNSYSLTISSLEGEDAGTYYCQQFSSSPWTFGGG
TKLEIKR

>SEQ_ID_NO: 5 36A8 HC
EVRLVESGGGLVKPGGSLKLSCAASGFTFSTYAMSWVRQTPEKRLEWVAS
INGGGSTYYPDSVKGRFTISRDNARNILYLQMRSLRSEDTAMYYCARGGD
YGYALDYWGQGTSVTVSS

>SEQ_ID_NO: 6 36A8 LC
ENVLTQSPAIMSASLGEKVTMNCRASSSVNYMYWYQQKSDASPKLWIFYT
SNLAPGVPARFSGSGSGNSYSLTISSMEGEDAATYYCQQFSSSPWTFGGG
SKLEIKR

>SEQ_ID_NO: 7 4B11 LC
EVKLVESGGGLVKPGGSLKLSCAASGFTFSSYAMSWVRQTPEKRLAWVAS
ISSGGNIYFPDSVKGRFTISRDDARNILYLQMRSLRSEDTAMYYCARGGD
YGYAMDYWGQGTSVTVSS

>SEQ_ID_NO: 8 1H6 HC
QVQLQQSGAELVRPGTSVKVSCKASGYAFTNYLIEWVKQRPGQGLEWIGV
INPGSGGTNYNEKFKGKATLTADKSSSTAYMHLSSLTSDDSAVYFCARGR
YEWYFDVWGAGTTVTVSS

>SEQ_ID_NO: 9 1H6 LC
DIQMTQTTSSLSASLGDRVTISCRASQDITNYLNWYQRKPDGTVKLLIYY
TSRLHSGVPSRFSGSGSGTDYSLTISNLEQEDIATYFCQQGYTLPYTFGG
GTKLEIKR

>SEQ_ID_NO: 10 38A8 HC
QVQLQQSGAELVRPGTSVKVSCKASGYAFTNYLIEWIKQRPGQGLEWIGV
INPGSGGTNYNEKFKGKATLTADKSSSTAYMQLSSLTSDDSAVYFCARGR
YEWYFDVWGAGTTVTVSS

>SEQ_ID_NO: 11 38A8 LC
DIQMTQTTSSLSASLGDRVTISCRASQDISNYLNWYLQKPDGTVKLLIYY
TSRLHSGVPSRFSGSGSGTDYSLISNLEQEDIATYFCQQGYTLPYTFGG
GTKLEIKR

>SEQ_ID_NO: 12 18F7 HC
QVQLKESGPGLVAPSQSLSITCTVSGFSLTSYGVSWVRQPPGKGLEWLGI
IWGDGSTNYHSVLKSRLSISKDNSKSQVFLKLNSLQTDDTATYYCAKQDF
DVWGAGTTVTVSS

>SEQ_ID_NO: 13 18F7 LC
DVQMIQSPFSLSASLGDIVTMTCQASQGTSINLNWFQQKPGKAPKLLIYG
VSNLEDGVPSRFSGSRYGTDFTLTIGSLEDEDMATYFCLQHSYLPYTFGG
GTKLEIKR

>SEQ_ID_NO: 14 12B2 HC
QVQLQQSGAELTKPGASVKISCKATGYTFSSYWIEWVKQRPGHGLEWIGE
ILPGSGITKYNDKFKGKATFTADTSSNTAYMQLSSLTSEDSAVYSCARLI
SYYYAMDYWGQGTSVTVSS

>SEQ_ID_NO: 15 12B2 LC
DIQMTQTTSSLSASLGDRVTISCRASQDISNYLNWYQQKPDGTVKLLIYY
TSRLHSGVPSRFSGSGSGTDYSLTISNLEQEDIATYFCQQGNTLPPTFGG
GTKLEIKR

>SEQ_ID_NO: 16 38F6 HC
QVQLQQSGAELMRPGASVKISCKATGYTFSSYWIEWVKQRPGHGLEWIGE
ILPGTGYTKYNEKPFKGKATFTAETSSNTASMQVSSLTSEDSAVYFCARLI
SYYYAMDYWGQGTSVTVSS

>SEQ_ID_NO: 17 5C4 hc
QVTLKASGPGILQPSQTLSLTCSFSGFSLNTSGLGVGWIRQPSGKGLEWL
AHIWWDDDKRYNPALKSRLTISKDTSNNQIFLKIASVDTADTATYYCARS
HYYGTFYFDYWGQGTTLTVSS

>SEQ_ID_NO: 18 23C10 HC
FLLLIVPAYVLSQVTLKASGPGIVQPSQTLSLTCSFSGFSLNTSGMGVGW
IRQPSGKGLEWLAHIWWDDDKRYNPALKSRLTISKDTSNNQIFLKIASVD
TADTATYYCARSHYYGTFYFDYWGQGTTLTVSS

>SEQ_ID_NO: 19 28C2 HC
QVTLKASEPGIVQPSQTLSLTCSFSGFSLNTSGMGVGWIRQPSGKGLEWL
AHIWWDDDKRYNPALKSRLTISKDTSNNQIFLKIASVDTADTATYYCARS
HYYGTFYFDYWGQGTTLTVSS

>SEQ_ID_NO: 20 28C2 LC
DVQITQSPSYLAASPGETITINCRASKSISKYLAWYQEKPGTTYKLLIYS
GSTLQSGIPSRFSGSGSGTDFTLTISSLEPEDFAMYYCQQHIEYPWTFGG
GTKLEIKR

>SEQ_ID_NO: 21 9D6 HC
QVTLKESGPGILQPSQTLSLTCSFSGFSLSTSGMGVGWIRQSSGKGLEWL
AHIWWDDDKRYNPTLKSRLTISKDTSNNQVFLKIANMDTADIATYYCARS
HYNGTFYFDFWGQGITLTVSS

>SEQ_ID_NO: 22 9D6 LC
DVQITQSPSYLAASPGETITINCRASKSISKYLAWYQEKPGKTNKLLIYS
GSTLQSGIPSRFSGSGSGTDFTLTISTLEPEDFAMYYCQQHIEYPWTFGG
GTKLEIKR

>SEQ_ID_NO: 23 28F4 HC
EVQLVESGGDLVKPGGSLKLSCAASGFTFSNYGMSWVRQTPDKRLEWVAT
ISSGGTYTYYPDSVKGQFTIFRDNAKNTLYLQMSSLKSEDTAMYYCTRRD
YDYEGFAYWGQGTLVTVS

>SEQ_ID_NO: 24 28F4 LC
DIVLTQSPATLSVTPGDSVSLSCRASQSISNNLHWYQQKSHESPRLLIKY
ASHSIGIPSRFSGSGSGTDFTLSINSVETEDFGMYFCQQSNNWPFTFGS
GTKLEIKR

>SEQ_ID_NO: 25 2A2 HC CDR1
TYAMS

>SEQ_ID_NO: 26 2A2 HC CDR2
SISSGSSTYYLDSVKG

>SEQ_ID_NO: 27 2A2 HC CDR3
GGDYEYAEDY

>SEQ_ID_NO: 28 2A2 LC CDR1
RASSSVNYMY

>SEQ_ID_NO: 29 2A2 LC CDR2
YTSNLAP

>SEQ_ID_NO: 30 2A2 LC CDR3
QQFSSSPWT

>SEQ_ID_NO: 31 34D10 HC CDR1
AYAMS

>SEQ_ID_NO: 32 34D10 HC CDR2
SISSEGTTYYPDSVKR

>SEQ_ID_NO: 33 34D10 HC CDR3
GGDYGYALDY

```
>SEQ_ID_NO: 34 34D10 LC CDR1
RASSSVNYMY

>SEQ_ID_NO: 35 34D10 LC CDR2
YTSNLAP

>SEQ_ID_NO: 36 34D10 LC CDR3
QQFSSSPWT

>SEQ_ID_NO: 37 36A8 HC CDR1
TYAMS

>SEQ_ID_NO: 38 36A8 HC CDR2
SINGGGSTYYPDSVKG

>SEQ_ID_NO: 39 36A8 HC CDR3
GGDYGYALDY

>SEQ_ID_NO: 40 36A8 LC CDR1
RASSSVNYMY

>SEQ_ID_NO: 41 36A8 LC CDR2
YTSNLAP

>SEQ_ID_NO: 42 36A8 LC CDR3
QQFSSSPWT

>SEQ_ID_NO: 43 4B11 HC CDR1
SYAMS

>SEQ_ID_NO: 44 4B11 HC CDR2
SISSGGNIYFPDSVKG

>SEQ_ID_NO: 45 4B11 HC CDR3
GGDYGYAMDY

>SEQ_ID_NO: 46 1H6 HC CDR1
NYLIE

>SEQ_ID_NO: 47 1H6 HC CDR2
VINPGSGGTNYNEKFKG

>SEQ_ID_NO: 48 1H6 HC CDR3
GRYEWYFDV

>SEQ_ID_NO: 49 1H6 LC CDR1
RASQDITNYLN

>SEQ_ID_NO: 50 1H6 LC CDR2
YTSRLHS

>SEQ_ID_NO: 51 1H6 LC CDR3
QQGYTLPYT

>SEQ_ID_NO: 52 38A8 HC CDR1
NYLIE

>SEQ_ID_NO: 53 38A8 HC CDR2
VINPGSGGTNYNEKFKG

>SEQ_ID_NO: 54 38A8 HC CDR3
GRYEWYFDV

>SEQ_ID_NO: 55 38A8 LC CDR1
RASQDISNYLN

>SEQ_ID_NO: 56 38A8 LC CDR2
YTSRLHS

>SEQ_ID_NO: 57 38A8 LC CDR3
QQGYTLPYT

>SEQ_ID_NO: 58 18F7 HC CDR1
SYGVS

>SEQ_ID_NO: 59 18F7 HC CDR2
IIWGDGSTNYHSVLKS

>SEQ_ID_NO: 60 18F7 HC CDR3
QDFDV

>SEQ_ID_NO: 61 18F7 LC CDR1
QASQGTSINLN

>SEQ_ID_NO: 62 18F7 LC CDR2
GVSNLED

>SEQ_ID_NO: 63 18F7 LC CDR3
LQHSYLPYT

>SEQ_ID_NO: 64 12B2 HC CDR1
SYWIE

>SEQ_ID_NO: 65 12B2 HC CDR2
EILPGSGITKYNDKFKG

>SEQ_ID_NO: 66 12B2 HC CDR3
LISYYYAMDY

>SEQ_ID_NO: 67 12B2 LC CDR1
RASQDISNYLN

>SEQ_ID_NO: 68 12B2 LC CDR2
YTSRLHS

>SEQ_ID_NO: 69 12B2 LC CDR3
QQGNTLPPT

>SEQ_ID_NO: 70 38F6 HC CDR1
SYWIE

>SEQ_ID_NO: 71 38F6 HC CDR2
EILPGTGYTKYNEKFKG

>SEQ_ID_NO: 72 38F6 HC CDR3
LISYYYAKIIDY

>SEQ_ID_NO: 73 5C4 HC CDR1
TSGLGVG

>SEQ_ID_NO: 74 5C4 HC CDR2
HIWWDDDKRYNPALKS

>SEQ_ID_NO: 75 5C4 HC CDR3
SHYYaTFYFDY

>SEQ_ID_NO: 76 23C10 HC CDR1
TSGMGVG

>SEQ_ID_NO: 77 23C10 HC CDR2
HIWWDDDKRYNPALKS

>SEQ_ID_NO: 78 23C10 HC CDR3
SHYYGTFYFDY

>SEQ_ID_NO: 79 28C2 HC CDR1
TSGMGVG

>SEQ_ID_NO: 80 28C2 HC CDR2
HIWWDDDKRYNPALKS

>SEQ_ID_NO: 81 2802 HC CDR3
SHYYETFYFDY

>SEQ_ID_NO: 82 28C2 LC CDR1
RASKISKYLA

>SEQ_ID_NO: 83 28C2 LC CDR2
SGSTLQS
```

SEQUENCE LISTING:

>SEQ_ID_NO: 84 2802 LC CDR3
QQHIEYPWT

>SEQ_ID_NO: 85 9D6 HC CDR1
TSGMGVG

>SEQ_ID_NO: 86 9D6 HC CDR2
HIWWEDDKRYNPILKS

>SEQ_ID_NO: 87 9D6 HC CDR3
SHYNGTFYFDF

>SEQ_ID_NO: 88 9D6 LC CDR1
RASKSISKYLA

>SEQ_ID_NO: 89 9D6 LC CDR2
SGSTLQS

>SEQ_ID_NO: 90 9D6 LC CDR3
QQHIEYPWT

>SEQ_ID_NO: 91 28F4 HC CDR1
NYGMS

>SEQ_ID_NO: 92 28F4 HC CDR2
TISSGGTTTYYPDSVKG

>SEQ_ID_NO: 93 28F4 HC CDR3
RDYDYEGFAY

>SEQ_ID_NO: 94 28F4 LC CDR1
RASQSISNNLH

>SEQ_ID_NO: 95 28F4 LC CDR2
YASHSIS

>SEQ_ID_NO: 96 28F4 LC CDR3
QQSNNWPFT

>SEQ_ID_NO: 97 35D1 HC
EVKLVESEGGLVKPGGSLKLSCAASGFTFSAYAMSWVRQTPEKRLEWVAS
ISSGGTTYYPDSVKRRFTISRDNARNILYLQMSSLRSEDTAMYYCTRGGD
YGYALDYWGQGTSVIVSS

>SEQ_ID_NO: 98 35D1 LC
ENVLIQSPAIMSASLGEKVTMSCRASSSVNYMYWYQQKSDASPKLWIYYT
SNLAPGVPARFSGSGSGNSYSLTISSMEGEDAATYYCQQFSSSPWTFGGG
TKLEIKR

>SEQ_ID_NO: 99 4B11 LC
ENVLTQSPAIMSASLGEKVTMNCRASSSVNYMYWYQQKSDASPKLWIFYT
SNLAPGVPARFSGSGSGNSYSLTISSMEGEDAATYYCQQFSSSPWTFGGG
SKLEIKR

>SEQ_ID_NO: 100 38G8 HC
QVQLQQSGAELVRPGTSVKVSCKASGYAFTNYLIEWVKQRPGQGLEWIGV
INPGSGGTNYNEKFKGKATLTADKSSSTAYMHLSSLTSDDSAVYFCARGR
YEWYFDVWGAGTIVTVSS

>SEQ_ID_NO: 101 38G8 LC
DIQMTQTTSSLSASLGDRVTISCRASQDITNYLNWYQRKRDGTVKLLIYY
TSRLHSGVPSRFSGSGSGTDYSLTISNLEQEDIATYFCQQGYTLPYTFGG
GTKLEIKR

>SEQ_ID_NO: 102 21F10 HC
DIQMTQTTSSLSASLGDRVTISCRASQDITNYLNWYQRKPDGTVKLLIYY
TSRLHSGVPSRFSGSGSGTDYSLTISNLEQEDIATYFCQQGYTLPYTFGG
GTKLEIKR

>SEQ_ID_NO: 103 21F10 LC
DIQMTQTTSSLSASLGDRVTISCRASQDITNYLNWYQRKPDGTVKLLIYY
TSRLHSGVPSRFSGSGSGTDYSLTISNLEQEDIATYFCQQGYTLPYTFGG
GTKLEIKR

>SEQ_ID_NO: 104 38F6 LC*
sequencing_pending

>SEQ_ID_NO: 105 13C1 HC
QVQLQQSGAELTKPGASVKISCKATGYTFSSYWIEWVKQRPGHGLEWIGE
ILPGSGITKYNDKFKGKATFTADTSSNTAYMQLSSLTSEDSAVYSCARLI
SYYYAMDYWGQGTSVTVSS

>SEQ_ID_NO: 106 13C1 LC
sequencing_pending

>SEQ_ID_NO: 107 5C4 LC*
sequencing_pending

>SEQ_ID_NO: 108 23C10 LC*
sequencing_pending

>SEQ_ID_NO: 109 37C7 HC
FLLLIVPAYVLSQVTLKASGPGIVQPSQTLSLTCSFSGFSLNTSGMGVGW
IRQPSGKGLEWLAHIWWDDDKRYNPALKSRLTISKDTSNNQIFLKIASVD
TADTATYYCARSHYYGTFYFDYWGQGTTLTVSS

>SEQ_ID_NO: 110 37C7 LC*
sequencing_pending

>SEQ_ID_NO: 111 35D1 HC CDR1
AYAMS

>SEQ_ID_NO: 112 35D1 HC CDR2
SISSGGTTYYPDSVKR

>SEQ_ID_NO: 113 35D1 HC CDR3
GGDYGYALDY

>SEQ_ID_NO: 114 35D2 LC CDR1
RASSSVNYMY

>SEQ_ID_NO: 115 35D2 LC CDR2
YTSNLAP

>SEQ_ID_NO: 116 35D2 LC CDR3
QQFSSSPWT

>SEQ_ID_NO: 117 4B11 LC CDR1
RASSSVNYMY

>SEQ_ID_NO: 118 4B11 LC CDR2
YTSNLAP

>SEQ_ID_NO: 119 4B11 LC CDR3
QQFSSSPWT

>SEQ_ID_NO: 120 38G8 HC CDR1
NYLIE

>SEQ_ID_NO: 121 38G8 HC CDR2
VINPGSGGTNYNEKFKG

>SEQ_ID_NO: 122 38G8 HC CDR3
GRYEWYFDV

>SEQ_ID_NO: 123 38G8 LC CDR1
RASQDITNYLN

>SEQ_ID_NO: 124 38G8 LC CDR2
YTSRLHS

>SEQ_ID_NO: 125 38G8 LC CDR3
QQGYTLPYT

>SEQ_ID_NO: 126 21F10 HC CDR1
NYLIE

>SEQ_ID_NO: 127 21F10 HC CDR2
VINPGSGGTNYNEKFKG

>SEQ_ID_NO: 128 21F10 HC CDR3
GRYEWYFDV

>SEQ_ID_NO: 129 21F10 LC CDR1
RASQDITRYLN

>SEQ_ID_NO: 130 21F10 LC CDR2
YTSRLHS

>SEQ_ID_NO: 131 21F10 LC CDR3
QQGYTLPYT

>SEQ_ID_NO: 132 38F6 LC* CDR1
sequencing_pending

>SEQ_ID_NO: 133 38F6 LC* CDR2
sequencing_pending

>SEQ_ID_NO: 134 38F6 LC* CDR3
sequencing_pending

>SEQ_ID_NO: 135 13C1 HC CDR1
SYWIE

>SEQ_ID_NO: 136 13C1 HC CDR2
EILPGSGITKYNDKFKG

>SEQ_ID_NO: 137 13C1 HC CDR3
LISYYYAMDY

>SEQ_ID_NO: 138 13C1 LC* CDR1
sequencing_pending

>SEQ_ID_NO: 139 13C1 LC* CDR2
sequencing_pending

>SEQ_ID_NO: 140 13C1 LC* CDR3
sequencing_pending

>SEQ_ID_NO: 141 5C4 LC* CDR1
sequencing_pending

>SEQ_ID_NO: 142 5C4 LC* CDR2
sequencing_pending

>SEQ_ID_NO: 143 5C4 LC* CDR3
sequencing_pending

>SEQ_ID_NO: 144 23C10 LC* CDR1
sequencing_pending

>SEQ_ID_NO: 145 23C10 LC* CDR2
sequencing_pending

>SEQ_ID_NO: 146 23010 LC* CDR3
sequencing_pending

>SEQ_ID_NO: 147 37C7 HC CDR1
TSGMGVG

>SEQ_ID_NO: 148 37C7 HC CDR2
HIWWDDDKRYNPALKS

>SEQ_ID_NO: 149 3707 HC CDR3
SHYYGTFYFDY

>SEQ_ID_NO: 150 3707 LC* CDR1
sequencing_pendlng

>SEQ_ID_NO: 151 37C7 LC* CDR2
sequencing_pending

>SEQ_ID_NO: 152 37C7 LC* CDR3
sequencing,pending

>CTP peptide 1
SEQ ID NO: 153
DPRFQDSSSSKAPPPSLPSPSRLPGPSDTPIL

>CTP peptide 2
SEQ ID NO: 154
SSSSKAPPPSLPSPSRLPGPSDTPILPQ

>PAS peptide 1
SEQ ID NO: 155
ASPAAPAPASPAAPAPSAPA

>PAS peptide 2
SEQ ID NO: 156
AAPASPAPAAPSAPAPAAPS

>PAS peptide 3
SEQ ID NO: 157
APSSPSPSAPSSPSPASPSS

>PAS peptide 4
SEQ ID NO: 158
APSSPSPSAPSSPSPASPS

>PAS peptide 5
SEQ ID NO: 159
SSPSAPSPSSPASPSPSSPA

>PAS peptide 6
SEQ ID NO: 160
AASPAAPSAPPAAASPAAPSAPPA

>PAS peptide 7
SEQ ID NO: 161
ASAAAPAAASAAASAPSAk

>Albumin Binding Peptide Core Sequence
SEQ ID NO: 162
DICLPRWGCLW

>GFP protein sequence (Genbank ID AAG34521.1)
SEQ ID NO: 163
MSKGEELFTGVVPILVELDGDVNGHKFSVSGEGEGDATYGELTLKFIC

TTGKLPVPWPTLVTTFGYGVQCFARYPDHMKQEDFFKSAMPEGYVQER

TIFFKDDGNYKTRAEVKFEGDTLVNRIELKGIDFKEDGNILGHKLEYN

YNSHNVYIMADKQKNGIKVNFKIRHNIEDGSVQLADHYQQNTPIGDGP

VLLPDNHYLSTQSALSKDPNEKRDHMVLLEFVTAAGITHGMDELYKSR

TSGSPGLQEFDIKLIDTVDLESCN

>Example: Single-chain Human IgG1 Fc.
(Fc sequences with Gly/Ser linker underlined.)
SEQ ID NO: 164
DKTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLNG

KEYKCKVSNKALPAPIEKTISKAKGQPREPQVYTLPPSRDELTKNQVS

LICLVKGFYPSDIAVEWESNGQPENNYKTIPPVLDSDGSFFLYSKLTV

DKSRWQQGNVFSCSVMHEALHNHYTQKSLSLSPGKGGGGSGGGGSGGG

GSGGGGSDKIHTCPPCPAPELLGGPSVFLFPPKPKDTLMISRTPEVIC

VVVDVSHEDPEVKFNWYVDGVEVHNAKTKPREEQYNSTYRVVSVLTVL

HQDWLNGKEYKCKVSNKALPAPIEKTISKAKGQPREPQVYTLPPSRDE

LTKNQVSLTCLVKGFYPSDIAVEWESNGQPENNYKTTPPVLDSDGSFF

LYSKLTVDKSRWQQGNVFSCSVMHEALHNHYTQKSLSLSPGK

SEQUENCE LISTING:

>Mature human albumin protein sequence
(derived from NCBI Ref. Sequence NP_000468);
SEQ ID NO: 165
RGVFRRDAHKSEVAHRFKDLGEENFKALVLIAFAQYLQQCPFEDHVKL

VNEVIEFAKTCVADESAENCDKSLHTLFGDKLCTVATLRETYGEMADC

CAKQEPERNECFLQHKDDNPNLPRLVRPEVDVMCTAFHDNEETFLKKY

LYEIARRHPYFYAPELLFFAKRYKAAFTECCQAADKAACLLPKLDELR

DEGKASSAKQRLKCASLQKFGERAFKAWAVARLSQRFPKAEFAEVSKL

VTDLIKVHTECCHGDLLECADDRADLAKYICENQDSISSKLKECCEKP

LLEKSHCIAEVENDEMPADLPSLAADFVESKDVCKNYAEAKDVFLGMF

LYEYARRHPDYSVVLLLRLAKTYETTLEKCCAAADPHECYAKVFDEFK

PLVEEPQNLIKQNCELFEQLGEYKFQNALLVRYTKKVPQVSTPTLVEV

SRNLGKVGSKCCKHPEAKRMPCAEDYLSVVLNQLCVLHEKTPVSDRVT

KCCTESLVNRRPCFSALEVDETYVPKEFNAETFTFHADICTLSEKERQ

IKKQTALVELVKHKPKATKEQLKAVMDDFAAFVEKCCKADDKETCFAE

EGKKLVAASQAALGL

>Linker, n = 0, 1, 2, 3, 4 or more
SEQ ID NO: 166
(GGGS)$_n$

>Albumin binding peptide 1
SEQ ID NO: 167
RLIEDICLPRWGCLWEDD

>Albumin binding peptide 2
SEQ ID NO: 168
QRLMEDICLPRWGCLWEDDF

>Albumin binding peptide 3
SEQ ID NO: 169
QGLIGDICLPRWGCLWGDSVK

>Albumin binding peptide 4
SEQ ID NO: 170
GEWWEDICLPRWGCLWEEED

>Cysteine-containing peptide
SEQ ID NO: 171
GGGSGCGGGS

>Human LRP1 sequence (signal peptide and
transmembrane segment underlined; NCBI
Reference Sequence: CAA32112)
SEQ ID NO: 172
<u>MLTPPLLLLLPLLSALVAA</u>AIDAPKTCSPKQFACRDQITCISKGWRCDG

ERDCPDGSDEAPEICPQSKAQRCQPNEHNCLGTELCVPMSRLCMGVQDC

MDGSDEGPHCRELQGNCSRLGCQHHCVPTLDGPTCYCNSSFQLQADGKI

CKDFDECSVYGTCSQLCTNIDGSFICGCVEGYLLQPDNRSCKAKNEPVD

RPPVLLIANSQNILATYLSGAQVSTITPTSTRQTTAMDFSYANETVCWV

HVGDSAAQTQLKCARMPGLKGFVDEHTINISLSLHHVEQMAIDWLTGNF

YFVDDIDDRIFVCNRNGDTCVTLLDLELYNPKGIALDPAMGKVFFTDYG

QIPKVERCDMDGQNRIKLVDSKIVFPHGITLDLVSRLVYWADAYLDYIE

VVDYEGKGRQIIIQGILIEHLYGLTVFENYLYAINSDNANAQQKTSVIR

VNRFNSTEYQVVTRVDKGGALHIYHQRRQPRVRSHACENDQYGKPGGCS

DICLLANSHKARTCRCRSGFSLGSDGKSCKKPEHELFLVYGKGRPGIIR

GMDMGAKVPDEHMIPIENLMNPRALDFHAETGFIYFADTTSYLIGRQKI

DGTERETILKDGIHNVEGVAVDWMGDNLYWIDDGPKKTISVARLEKAAQ

TRKTLIEGKMTHPRAIVVDPLNGWMYWTDWEEDPKDSRRGRLERAWMDG

SNRDIFVISKTVLWPNGLSLDIPAGRLYWVDAFYDRIETILLNGTDRKI

VYEGPELNHAFGLCHHGNYLFWTEYRSGSVYRLERGVGGAPPTVTLLIS

ERPPIFEIRMYDAQQQQVGINKCRVNNGGCSSLCLATPGSRQCACAEDQ

VLDADGVICLANPSYVPPPQCQPGEFACANSRCIQERWKCDGDNDCLDN

SDEAPALCHQHTCPSDRFKCENNRCIPNRWLCDGDNDCGNSEDESNATC

SARTCPPNQFSCASGRCIPISWTCDLDDDCGDRSDESASCAYPTCFPLT

QFTCNNGRCININWRCDNDNDCGDNSDEAGCSHSCSSTQFKCNSGRCIP

EHWTCDGDNDCGDYSDETHANCINQATRPPGGCHTDEFQCRLDGLCIPL

RWRCDGDTDCMDSSDEKSCEGVIHVCDPSVKFGCKDSARCISKAWVCDG

DNDCEDNSDEENCESLACRPPSHPCANNTSVCLPPDKLCDGNDDCGDGS

DEGELCDQCSLNNGGCSHNCSVAPGEGIVCSCPLGMELGPDNHTCQIQS

YCAKHLKCSQKDQNKFSVKCSCYEGWVLEPDGESCRSLDPFKPFIIFSN

RHEIRRIDLHKGDYSVLVPGLRNTIALDFHLSQSALYWIDVVEDKIYRG

KLLDNGALTSFEVVIQYGLATPEGLAVDWIAGNIYWVESNLDQIEVAKL

DGILRTILLAGDIEHPRAIALDPRDGIDFWTDWDASLPRIEAASMSGAG

RRIVHREIGSGGWPNGLIVDYLEKRILWIDARSDAIYSARYDGSGHMEV

LRGHEFLSHPFAVTLYGGEVYWIDWRINTLAKANKWIGHNVTVVQRTNI

QPFDLQVYHPSRUMAPNPCEANGGQGPCSHLCLINYNRIVSCACPHLNI

KLHKDNITCYEFKKFLLYARQMEIRGVDLDAPYYNYIISFTVPDIDNVI

VLDYDAREQRVYWSDVRTQAIKRAFINGTGVETVVSADLPNAHGLAVDW

VSRNLFWTSYDINKKQINVARLDGSFKNAVVQGLEQPHGLVVHPLRGKL

YWIDGDNISMANMDGSNRILLFSGQKGPVGLAIDFPESKLYWISSGNHT

INRCNLDGSGLEVIDAMRSQLGKATALAIMGDKLWADQVSEKMGICSKA

DGSGSVVLRNSTILVMHMKVYDESIQLDHKGINPCSVNNGDCSQLCLPT

SETTRSCMCIAGYSLRSGQQACEGVGSFLLYSVHEGIRGIPLDPNDKSD

ALVPVSGTSLAVGIDFHAENDTIYWVDMGLSTISRAKRDQTWREDVVIN

GIGRVEGIAVDWIAGNIYWIDQGFDVIEVARLNGSFRYVVISQGLDKPR

AITVHPEKGYLFWTEWGQYPRIERSRLDGTERVVLVNVSISWPNGISVD

YQDGKLYWCDARTDKIERIDLETGENREVVLSSNNMDMFSVSVFEDFIY

WSDRIHANGSIKRGSKDNATDSVPLRIGIGVQLKDIKVFNRDRQKGINV

CAVANGGCQQLCLYRGRGQRACAHGMLAEDGASCREYAGYLLYSERT

ILKSIHLSDERNLNAPVQPFEDPEHMKNVTALAFDYRAGTSPGTPNRIF

FSDIHFGNIQQINDDGSRRITIVENVGSVEGLAYHRGWDTLYWTSYTTS

TITRHTVDQTRPGAFERETVITMSGDDHPRAFVLDECQNLMFWINWNEQ

SEQUENCE LISTING:

HPSIMRAALSGANVLTLIEKDIRTPNGLAIDHRAEKLYFSDATLDKIER
CEYDGSHRYVILKSEPVHPFGLAVYGEHIFWIDWVRRAVQRANKHVGSN
MKLLRVDIPQQPMGIIAVANDINSCELSPCRINNGGCQDLCLLTHQGHV
NCSCRGGRILQDDLICRAVNSSCRAQDEFECANGECINFSLTCDGVPHC
KDKSDEKPSYCNSRRCKKTFRQCSNGRCVSNMLWCNGADDCGDGSDEIP
CNKTACGVGEFRCRDGICIGNSSRCNQFVDCEDASDEMNCSATDCSSYF
RLGVKGVLFQPCERTSLCYAPSWVCDGANDCGYSDERDCPGVKRPRCP
LNYFACPSGRCIPMSWTCDKEDDCEHGEDETHCNKFCSEAQFECQNHRC
ISKQWLCDGSDDCGDGSDEAAHCEGKTCGPSSFSCPGTHVCVPERWLCD
GDKDCADGADESIAAGCLYNSTCDDREFMCQNRQCIPKHFVCDHDRDCA
DGSDESPECEYPTCGPSEFRCANGRCLSSRQWECDGENDCHDQSDEAPK
NPHCTSPEHKCNASSQFLCSSGRCVAEALLCNGQDDCGDSSDERGCHIN
ECLSRKLSGCSQDCEDLKIGFKCRCRPGFRLKDDGRICADVDECSTIFP
CSQRCINTHGSYKCLCVEGYAPRGGDPHSCKAVIDEERFLIFANRYYLR
KLNLDGSNYILLKQGLNNAVALDFDYREQMIYWIDVITQGSMIRRMHLN
GSNVQVLHRTGLSNPDGLAVDWVGGNLYWCDKGRDTIEVSKINGAYFTV
LVSSGLREPRALVVDVQNGYLYWIDWGDHSLIGRIGMDGSSRSVIVDTK
ITWPNGLILDYVTERIYWADAREDYIEFASLDGSNRHVVLSQDIPHIFA
LTLFEDYVYWTDWETKSINRAHKITGINKILLISTLHRPMDLEVFHALR
QPDVPNHPCKVNNGGCSNLCLLSPGGGHKCACPINFYLGSDGRICVSNC
TASQFVCKNDKCIPFWWKCDTEDDCGDHSDEPPDCPEFKCRPGQFQCST
GICTNPAFICDGDNDCQDNSDEANCDIHVCLPSQFKCININRCIPGIFR
CNGQDNCGDGEDERDCPEVICAPNQFQCSITKRCIPRVWVCDRDNDCVD
GSDEPANCIQMTCGVDEFRCKDSGRCIPARWKCDGEDDCGDGSDEPKEE
CDERICEPYQFRCKNNRCVPGRWQCDYDNDCGDNSDEESCIPRPCSESE
FSCANGRCIAGRWKCDGDHDCADGSDEKDCTPRCDMDQFQCKSGHCIPL
RWRCDADADCMDGSDEEACGTGVRTCPLDEFQCNNTLCKPLAWKCDGED
DCGDNSDENPEECARFVCPPNRPFRCKNDRVCLWIGRQCDGIDNCGDGI
DEEDCEPPTAHTTHCKDKKEFLCRNQRCLSSSLRCNMFDDCGDGSDEED
CSIDPKLTSCATNASICGDEARCVRTEKAAYCACRSGFHTVPGQPGCQD
INECLRFGICSQLCNNTKGGHLCSCARNFMKIHNTCKAEGSEYQVLYIA
DDNEIRSLFPGHPHSAYEQAFQGDESVRIDAMDVHVKAGRVYWINWHIG
TISYRSLPPAAPPITSNRHRRQIDRGVTHLNISGLKMPRGIAIDWVAGN
VYWIDSGRDVIEVAQMKGENRKTLISGMIDEPHAIVVDPLRGIMYWSDW
GNHPKIETAAMDGILFETLVQDNIQWPTGLAVDYHNERLYWADAKLSVI
GSIRLNGTDPIVAADSKRGLSHPFSIDVFEDYIYGVIYINWRVFKIHKF
GHSPLVNLIGGLSHASDVVLYHQHKQPEVINPCDRKKCEWLCLLSPSGP
VCTCPNGKRLDNGTCVPVPSPIPPPDAPRPGICNLQCFNGGSCFLNARR

QPKCRCQPRYTGDKCELDQCWEHCRNGGICAASPSGMPTCRCPTGFIGP
KCIQQVCAGYCANNSTCTVNQGNQPWRCLPGFLGDRCQYRQCSGYCENF
GTCQMAADGSRQCRCTAYFEGSRCEVNKCSRCLEGACVVNKQSGDVICN
CIDGRVAPSCLICVGHCSNGGSCIMNSKMMPECQCPPHMTGPRCEEHVF
SQQQPGHIAS<u>ILIPLLLLLLLVLVAGVVF</u>WYKRRVQGAKGFQHQRMING
AMNVEIGNPTYKMYEGGEPDDVGGLLDADFALDPDKRINFINPVYATLY
MGGHGSRHSLASTDEKRELLGRGPEDEIGDPLA

>Biotin Acceptor Peptide (BAP)
SEQ ID NO: 173
LNDIFEAQKTEWH

>Lipoate Acceptor Peptide 2 (LAP2)
SEQ ID NO: 174
GFEIDKVWYDLDA

>HAPylation motif, n = 1 to 400
SEQ ID NO: 175
(Gly4Ser)n

>Alternative linker
SEQ ID NO: 176
PEAPTDPEAPTD

>CTP
SEQ ID NO: 177
DSSSSKAPPPSLPSPSRLPGPSDTPILPQ

>FVII-HC
SEQ ID NO: 178
IVGGKVCP KGECPWQVLL LVNGAQLCGG TLINTIWVVS
AAHCFDKIKN WRNLIAVLGE HDLSEHDGDE QSRRVAQVII
PSTYVPGTTN HDIALLRLHQ PVVLTDHVVP LCLPERTFSE
RTLAFVRFSL VSGWGQLLDR GATALELMVL NVPRLMTQDC
LQQSRKVGDS PNITEYMFCA GYSDGSKDSC KGDSGGPHAT
HYRGTWYLTG IVSWGQGCAT VGHFGVYTRV SQYIEWLQKL
MRSEPRPGVL LRAPFP

>FVII-LC
SEQ ID NO: 179
ANAFLEELRP GSLERECKEE QCSFEEAREI FKDAERTKLF
WISYSDGDQC ASSPCQNGGS CKDQLQSYIC FCLPAFEGRN
CETHKDDQLI CVNENGGCEQ YCSDHTGTKR SCRCHEGYSL
LADGVSCTPT VEYPCGKIPI LEKRNASKPQ GR

>FVII zymogen.
SEQ ID NO: 180
MVSQALRLLC LLLGLQGCLA AGGVAKASGG ETRDMPWKPG
PHRVFVTQEE AHGVLHRRRR ANAFLEELRP GSLERECKEE
QCSFEEAREI FKDAERTKLF WISYSDGDQC ASSPCQNGGS
CKDQLQSYIC FCLPAFEGRN CETHKDDQLI CVNENGGCEQ
YCSDHTGTKR SCRCHEGYSL LADGVSCTPT VEYPCGKIPI
LEKRNASKPQ GRIVGGKVCP KGECPWQVLL LVNGAQLCGG
TLINTIWVVS AAHCFDKIKN WRNLIAVLGE HDLSEHDGDE QSRRVAQVII PSTYVPGTTN HDIALLRLHQ PVVLTDHVVP
LCLPERTESE RTLAFVRFSL VSGWGQLLDR GATALELMVL
NVPRLMTQDC LQQSRKVGDS PNITEYMFCA GYSDGSKDSC
KGDSGGPHAT HYRGTWYLTG IVSWGQGCAT VGHFGVYTRV
SQYIEWLQKL MRSEPRPGVL LRAPPFP >FIX zymogen- Signal sequence (1-28), Propeptide
(29-46)
SEQ ID NO: 181
MQRVNMIMAESPGLITICLLGYLLSAECTVFLDHENANKILNRPKRYNSG
KLEEEVQGNLERECMEEKCSFEEAREVFENTERTTEFWKQYVDGDQCESN
PCLNGGSCKDDINSYECWCPFGFEGKNCELDVTCNIKNGRCEQFCKNSAD
NKVVCSCTEGYRLAENQKSCEPAVPFPCGRVSVSQTSKLTRAETVEPDVD
YVNSTEAETILDNITQSTQSENDFTRVVGGEDAKPGQFPWQVVLNGKVDA
FCGGSIVNEKWIVTAAHCVETGVKITVVAGEHNIEETEHTEQKRNVIRII
PHHNYNAAINKYNHDIALLELDEPLVLNSYVTPICIADKEYTNIFLKFGS
GYVSGWGRVFHKGRSALVDQYLRVPLVDRATCLRSTKFTIYNNMFCAGFH
EGGRDSCQGDSGGPHVTEVEGTSFLTGIISWGEECAMKGKYGIYTKVSRY
VNWIKEKTKLT >FX zymogen. Signal sequence (1-23), Propeptide
(24-40)
SEQ ID NO: 182
MGRPLHLVLLSASLAGLLLLGESLFIRREQANNILARVTRANSFLEEMKK
GHLERECMEETCSYEEAREVFEDSDKTNEFWNKYKDGDQCETSPCQNQGK
CKDGLGEYTCTCLEGFEGKNCELFTRKLCSLDNGDCDQFCHEEQNSVVCS
CARGYTLADNGKACIPTGPYPCGKQTLERRKRSVAQATSSSGEAPDSITW
KPYDAADLDPTENPEDLLDFNQTQPERGDNNLTRIVGGQECKDGECPWQA
LLINEENEGFCGGTILSEFYILTAAHCLYQAKREKVRVGDRNTEQEEGGE
AVHEVEVVIKHNRETKETYDFDIAVLRLKTPITERMNVAPACLPERDWAE
STLMTQKTGIVSGFGRTHEKGRQSTRLKMLEVPYVDRNSCKLSSSFIITQ
NMECAGYDTKQEDACQGDSGGPHVTREKDTYFVTGIVSWGEGCARKGKY
IYTKVTAFLKWIDRSMKTRGLPKAKSHAPEVITSSPLK >Human GPIIb. Signal sequence (1-31). Trans-
membrane (981-1019). Cytoplasmic (1020-1039)
SEQ ID NO: 183
MARALCPLQALWLLEWVLLLLGPCAAPPAWALNLDPVQLTFYAGPNGSQF
GESLDFHKDSHGRVAIVVGAPRTLGPSQEETGGVELCPWRAEGGQCPSLL
FDLRDETRNVGSQTLQTPKARQGLGASVVSWSDVIVACAPWQHWNVLEKT
EEAEKTPVGSCFLAQPESGRRAEYSPCRGNTLSRIYVENDFSWDKRYCEA
GESSVVTQAGELVLGAPGGYYFLGLLAQAPVADIFSSYRPGILLWHVSSQ
SLSEDSSNPEYFDGYWGYSVAVGEFDGDLNTTEYVVGAPTWSWTLGAVEI
LDSYYQRLHRLRGEQMASYFGHSVAVTDVNGDGRHDLLVGAPLYMESRAD
RKLAEVGRVYLFLQPRGPHALGAPSLLLTGTQLYGREGSAIAPLGDLDRD
GYNDIAVAAPYGGPSGRGQVLVFLGQSEGLRSRPSQVLDSPEPTGSAFGF SLRGAVDIDDNGYPDLIVGAYGANQVAVYRAQPVVKASVQLLVQDSLNPA
VKSCVLPQTKTPVSCFNIQMCVGATGHNIPQKLSLNAELQLDRQKPRQGR
RVLLLGSQQAGTTLNLDLGGKHSPICHTTMAFLRDEADFRDKLSPIVLSL
NVSLPPTEAGMAPAVVLHGDTHVQEQTRIVLDCGEDDVCVPQLQLTASVT
GSPLLVGADNVLELQMDAANEGEGAYEAELAVHLPQGAHYMRALSNVEGF
ERLICNQKKENETRVVLCELGNPMKKNAQIGIAMLVSVGNLEEAGESVSF
QLQIRSKNSQNPNSKIVLLDVPVRAEAQVELRGNSFPASLVVAAEEGERE
QNSLDSWGPKVEHTYELHNNGPGTVNGLHLSIHLPGQSQPSDLLYILDIQ
PQGGLQCFPQPPVNPLKVDWGDPIPSPSPIHPAHHKRDRRQIFLPEPEQP
SRLQDPVLVSCDSAPCTVVQCDLQEMARGQRAMVTVLAFLWLPSLYQRPL
DQFVLQSHAWFNVSSLPYAVPPLSLPRGEAQVWTQLLRALEERAIPIWWV
LVGVLGGLLLLTILVLAMWKVGFFKRNRPPLEEDDEEGE >Human GPIIIa. Signal sequence (1-26),
Transmembrane (719-747). Cytoplasmic (748-788)
SEQ ID NO: 184
MRARPRPRPLWATVLALGALAGVGVGGPNICTTRGVSSCQQCLAVSPMCA
WCSDEALPLGSPRCDLKENLLKDNCAPESIEFPVSEARVLEDRPLSDKGS
GDSSQVTQVSPQRIALRLRPDDSKNFSIQVRQVEDYPVDIYYLMDLSYSM
KDDLWSIQNLGTKLATQMRKLTSNLRIGFGAFVDKPVSPYMYISPPEALE
NPCYDMKTTCLPMFGYKHVLTLTDQVTRFNEEVKKQSVSRNRDAPEGGFD
AIMQATVCDEKIGWRNDASHLLVETTDAKTHIALDGRLAGIVQPNDGQCH
VGSDNHYSASTTMDYPSLGLMTEKLSQKNINLIFAVTENVVNLYQNYSEL
IPGTTVGVLSMDSSNVLQLIVDAYGKIRSKVELEVRDLPEELSLSFNATC
LNNEVIPGLKSCMGLKIGDTVSFSIEAKVRGCPQEKEKSFTIKPVGFKDS
LIVQVTEDCDCACQAQAEPNSHRCNNGNGTFECGVCRCGPGWLGSQCECS
EEDYRPSQQDECSPREGQPVCSQRGECLCGQCVCHSSDFGKITGKYCECD
DFSCVRYKGEMCSGHGQCSCGDCLCDSDWTGYYCNCTTRTDTCMSSNGLL
CSGRGKCECGSCVCIQPGSYGDTCEKCPTCPDACTFKKECVECKKFDRGA
LHDENTCNRYCRDEIESVKELKDTGKDAVNCTYKNEDDCVVREQYYEDSS
GKSILYVVEEPECPKGPDILVVLLSVMGAILLIGLAALLIWKLLITIHDR
KEFAKFEEERARAKWDTANNPLYKEATSTFTNITYRGT >Human GPIIb DNA.
SEQ ID NO: 185
ATGGCCAGAGCTTTGTGTCCACTGCAAGCCCTCTGGCTTCTGGAGTGGGT
GCTGCTGCTCTACCGGTCTCGAAACACAGGTGACGTTCGGGAGACCGAAG
ACCTCACCCACGACGACGAGTTGGGACCTTGTGCTGCCCCTCCAGCCTGG
GCCTTGAACCTGGACCCAGTGCAGCTGACCAACCCTGGAACACGACGGGG
AGGTCGGACCCGGAACTTGGACCTGGGTCACGTCGAGTGGTTCTATGCAG
GCCCCAATGGCAGCCAGTTTGGATTTTCACTGGACTTCCACAAGGACAGC
AAGATACGTCCGGGGTTACCGTCGGTCAAACCTAAAAGTGACCTGAAGGT
GTTCCTGTCGCATGGGAGAGTGGCCATCGTGGTGGGCGCCCCGCGGACCC

SEQUENCE LISTING:

TGGGCCCCAGCCAGGAGGAGGTACCCTCTCACCGGTAGCACCACCCGCGG

GGCGCCTGGGACCCGGGGTCGGTCCTCCTCACGGGCGGCGTGTTCCTGTG

CCCCTGGAGGGCCGAGGGCGGCCAGTGCCCCTCGCTGCTCTGCCCGCCGC

ACAAGGACACGGGGACCTCCCGGCTCCCGCCGGTCACGGGGAGCGACGAG

TTTGACCTCCGTGATGAGACCCGAAATGTAGGCTCCCAAACTTTACAAAC

CTTCAAGGCCAAACTGGAGGCACTACTCTGGGGTTTACATCCGAGGGTTT

GAAATGTTTGGAAGTTCCGGCGCCAAGGACTGGGGCGTCGGTCGTCAGC

TGGAGCGACGTCATTGTGGCCTGCGCCCCCGCGGTTCCTGACCCCCGCAG

CCAGCAGTCGACCTCGCTGCAGTAACACCGGACGCGGGGGTGGCAGCACT

GGAACGTCCTAGAAAAGACTGAGGAGGCTGAGAAGACGCCCGTAGGTAGC

ACCGTCGTGACCTTGCAGGATCTTTTCTGACTCCTCCGACTCTTCTGCGG

GCATCCATCGTGCTTTTTGGCTCAGCCAGAGAGCGGCCGGCGCGCCGAGT

ACTCCCCCTGTCGCGGGAACACGAAAAACCGAGTCGGTCTCTCGCCGGCC

GGGCGGCTCATGAGGGGGACAGCGCCCTTGACCCTGAGCCGCATTTACGT

GGAAAATGATTTTAGCTGGGACAAGCGTTACTGTGAAGCGTGGGACTCGG

CGTAAATGCACCTTTTACTAAAATCGACCCTGTTCGCAATGACACTTCGC

GGCTTCAGCTCCGTGGTCACTCAGGCCGGAGAGCTGGTGCTTGGGGCTCC

TGGCGGCTATCCGAAGTCGAGGCACCAGTGAGTCCGGCCTCTCGACCACG

AACCCCGAGGACCGCCGATATATTTGTTAGGTCTCCTGGCCCAGGCTCCA

GTTGCGGATATTTTCTCGAGTTACCGCCCAATAAAGAATCCAGAGGACCG

GGTCCGAGGTCAACGCCTATAAAGAGCTCAATGGCGGGTGGCATCCTTT

TGTGGCACGTGTCCTCCCAGAGCCTCTCCTTTGACTCCAGCAACCCAGAG

CCGTAGGAAAACACCGTGCACAGGAGGGTCTCGGAGAGGAAACTGAGGTC

GTTGGGTCTCTACTTCGACGGCTACTGGGGGTACTCGGTGGCCGTGGGCG

AGTTCGACGGGGATCTCAACATGAAGCTGCCGATGACCCCCATGAGCCAC

CGGCACCCGCTCAAGCTGCCCCTAGAGTTGACTACAGAATATGTCGTCGG

TGCCCCCACTTGGAGCTGGACCCTGGGAGCGGTGGAAATTTGATGTCTTA

TACAGCAGCCACGGGGTGAACCTCGACCTGGGACCCTCGCCACCTTTAA

TTGGATTCCTACTACCAGAGGCTGCATCGGCTGCGCGGAGAGCAGATGGC

GTCGTATTTTAACCTAAGGATGATGGTCTCCGACGTAGCCGACGCGCCTC

TCGTCTACCGCAGCATAAAAGGGCATTCAGTGGCTGTCACTGACGTCAAC

GGGGATGGGAGGCATGATCTGCTGGTGGGCCCCGTAAGTCACCGACAGTG

ACTGCAGTTGCCCCTACCCTCCGTACTAGACGACCACCCGGCTCCACTGT

ATATGGAGAGCCGGGCAGACCGAAAACTGGCCGAAGTGGGGCGTGTGTAT

CGAGGTGACATATACCTCTCGGCCCGTCTGGCTTTTGACCGGCTTCACCC

CGCACACATATTGTTCCTGCAGCCGCGAGGCCCCCACGCGCTGGGTGCCC

CCAGCCTCCTGCTGACTGGCAACAAGGACGTCGGCGCTCCGGGGGTGCGC

GACCCACGGGGGTCGGAGGACGACTGACCGACACAGCTCTATGGGCGATT

CGGCTCTGCCATCGCACCCCTGGGCGACCTCGACCGGGATTGTGTCGAGA

TACCCGCTAAGCCGAGACGGTAGCGTGGGGACCCGCTGGAGCTGGCCCTA

GGCTACAATGACATTGCAGTGGCTGCCCCCTACGGGGGTCCCAGTGGCCG

GGGCCAAGTGCCGATGTTACTGTAACGTCACCGACGGGGATGCCCCCAG

GGTCACCGGCCCCGGTTCACCTGGTGTTGCTGGGTCAGAGTGAGGGGCTG

AGGTCACGTCCCTCCCAGGTCCTGGACAGCGACCACAAGGACCCAGTCTC

AGTCCCCGACTCCAGTGCAGGGAGGGTCCAGGACCTGTCGCCCTTCCCA

CAGGCTCTGCCTTTGGCTTCTCCCTTCGAGGTGCCGTAGACATCGATGAC

GGGAAGGGGTGTCCGAGACGGAAACCGAAGAGGGAAGCTCCACGGCATCT

GTAGCTACTGAACGGATACCCAGACCTGATCGTGGGAGCTTACGGGGCCA

ACCAGGTGGCTGTGTACAGATTGCCTATGGGTCTGGACTAGCACCCTCGA

ATGCCCCGTTGGTCCACCGACACATGTCTGCTCAGCCAGTGGTGAAGGC

CTTTCCAGCTACTGGTGCAAGATTCACTGAATCCTGCTCGAGTCGGTCAC

CACTTCCGGAGACAGGTCGATGACCACGTTCTAAGTGACTTAGGACGAGT

GAAGAGCTGTGTCCTACCTCAGACCAAGACACCCGTGAGCTGCTTCAACA

TCCAGATGCACTTCTCGACACAGGATGGAGTCTGGTTCTGTGGGCACTCG

ACGAAGTTGTAGGTCTACTGTGTTGGAGCCACTGGGCACAACATTCCTCA

GAAGGTATCCCTAAATGCCGAGCTGCAGACACAACCTCGGTGACCCGTGT

TGTAAGGAGTCTTCGATAGGGATTTACGGCTCGACGTCCTGGACCGGCAG

AAGCCCGCCAGGGCCGGCGGGTGCTGCTGCTGGGCTCTCAACAGGCAGA

CCTGGCCGTCTTCGGGGCGGTCCCGGCCGCCCACGACGACGACCCGAGAG

TTGTCCGTGGCACCACCCTGAACCTGGATCTGGGCGGAAAGCACAGCCCC

ATGTGCCACACCACCATGCCGTGGTGGGACTTGGACCTAGACCCGCCTTT

CGTGTCGGGGTAGACGGTGTGGTGGTACGCCTTCCTTCGAGATGAGGCAG

ACTTCCGGGACAAGCTGAGCCCCATTGTGCTCAGCCTCCGGAAGGAAGCT

CTACTCCGTCGAAGGCCCTGTTCGACTCGGGGTAACACGAGTCGGAGAA

TGTGTCCCTACCGCCCACGGAGGCTGGAATGGCCCCTGCTGTCGTGCTGC

ATGGAGACTTACACAGGGATGGCGGGTGCCTCCGACCTTACCGGGGACGA

CAGCACGACGTACCTCTGACCCATGTGCAGGAGCAGACACGAATCGTCCT

GGACTGTGGGGAAGATGACGTATGTGTGTGGGTACACGTCCTCGTGTGTG

CTTAGCAGGACCTGACACCCGTTCTACTGCATACACACCCCCAGCTTCAG

CTCACTGCCAGCGTGACGGGCTCCCCGCTCCTAGTTGGGGCAGATAATGG

GGTCGAAGTCGAGTGACGGTCGCACTGCCCGAGGGGCGAGGATCAACCCC

GTCTATTAGTCCTGGAGCTGCAGATGGACGCAGCCAACGAGGGCGAGGGG

GCCTATGAAGCAGAGCTGCAGGACCTCGACGTCTACCTGCGTGGGTTGGT

CCCGCTCCCCCGGATACTTCGTCTCGACGCCGTGCACCTGCCCCAGGGCG

CCCACTACATGCGGGCCCTAAGGAATGTCGAGGGCTTTGGGCACGTGGAC

GGGGTCCCGCGGGTGATGTACGCCCGGGATTCGTTACAGCTCCCGAAAGA

GAGACTCATCTGTAATCAGAAGAAGGAGAATGAGACCAGGGTGGTGCTGT

SEQUENCE LISTING:

```
GTGAGCTGCTCTCTGAGTAGACATTAGTCTTCTTCCTCTTACTCTGGTCC
CACCACGACACACTCGACGGCAACCCCATGAAGAAGAACGCCCAGATAGG
AATCGCGATGTTGGTGAGCGTGGGGAATCCGTTGGGGTACTTCTTGTTGC
GGGTCTATCCTTAGCGCTACAACCACTCGCACCGCTTACTGGAAGAGGCT
GGGGAGTGTGTCGTTCCAGCTGCAGATACGGAGGAAGAACAGCCAGGA
CCTTCTCCGACCCCTCAGACACAGGAAGGTGGACGTCTATGCCTCGTTCT
TGTGGGTCAATCCAAACGCAAGATTGTGCTGCTGGACGTGCCGGTCCGGG
CAGAGGCCCAAGTGGAGTTAGGTTTGTCGTTGTAACACGACGACCTGCAC
GGCCAGGCCCGTCTCCGGGTTCACCTCCTGCGAGGGAACTCCTTTCCAGC
CTGCCTGGTGGTGGCAGCAGAAGAAGGTGAGAGGGAGGACGCTCGCTTGA
GGAAAGGTCGGAGGGACCAGGACGGTGGTGTTGTTCCACTCTCCCTCCAG
AACAGGTTGGACAGCTGGGACCCAAAGTGGAGCACACCTATGAGCTGGA
CAACAATGTCTTGTCGAAGCTGTGGACCCCTGGGTTTCACGTCGTGTGGA
TACTCGAGGTGTTGTTAGGCCCTGGGACTGTGAATGGTCTTCACCTCAGC
ATCCACCTTCCGGGACAGTGGCAGCCCGCGGGAGGCTGACACTTAGCAGA
AGTGGAGTCGTAGGTGGAAGGCCGTGTCAGGGTCGGGTCCGACCTGCTCT
ACATCCTGGATATACAGCCCCAGGGGGCCTTCAGTGGTTCCCACAGAGG
CTGGACGAGATGTAGGAGCTATATGTCGGGGTGGCCCGGGAAGTCACGAA
GGGTGTCCCTGCTGTCAACCGTGTCAAGGTGGACTGGGGCTGCCCATCC
CCAGCCCCTCGCCCATTGGAGGACAGTTGGGAGAGTTCCACCTGACCGCC
GACGGGTAGGGTCGGGGAGGGGGTAACAGGGGGGGATCACAAGGGGGA
TCGCAGACAGATCTTCCTGCGAGAGCCGGAGCAGCCCGTGGGCCGGGTAG
TGTTGGGCCTAGCGTCTGTCTAGAAGGACGGTGTGGGGCTCGTCGGGTCG
AGGCTTCAGGATCCAGTTCTCGTAAGCTGCGACTCGGCGCCCTGTACTGT
GGTGCAGAGCTCCGAAGTCCTAGGTCAAGAGCATTCGACGCTGAGGGGGG
GGACATGACACCACGTCTGTGACCTGCAGGAGATGGCGCGCGGGCAGGGG
GCCATGGTCACGGTGCTGGCCTTGCTGACACTGGACGTCCTCTACCGCGC
GCCCGTCGCCGGGTACCAGTGCCACGACCGGAAGGACTGGCTGCCCAGCC
TCTAGCAGAGGCGTGTGGATGAGTTTGTGCTGGAGTCGCACGCATGGACC
GAGGGGTCGGAGATGGTCTCCGGAGACCTAGTCAAACACGACGTCAGCGT
GCGTACCTTCAACGTGTCGTCCGTCCCCTATGCGGTGCGCCCGCTCAGCC
TGCGCCGAGGGGAAGCTAAGTTGGACAGGAGGGAGGGGATACGCCACGGG
GGCGAGTCGGACGGGCTCCCCTTCGACAGGTGTGGAGACAGCTGCTCCGG
GCCTTGGAGGAGAGGGCCATTCCAATCTGGTGGGTGGTCCACACGTGTGT
GGACGAGGCCCGGAACCTCCTCTCCCGGTAAGGTTAGACCACCCACCTGG
TGGGTGTGCTGGGTGGCCTGGTGGTGGTGACCATCCTGGTGGTGGCGATG
TGGAAGGAGCACCCAGAGGACCCAGGGGACGACGAGGAGTGGTAGGACCA
GGACCGGTACACCTTCGTCGGCTTGTTCAAGCGGAACCGGCCACCCCTGG
AAGAAGATGATGAAGAGGGGGAGTGACAGCCGAAGAAGTTCGCCTTGGCC
GGTGGGGACCTTCTTCTACTACTTCTCCCCCTCACT

>Human GPIIIa DNA
                                    SEQ ID NO: 186
ATGCGAGCGCGCCCGCGGCCGCGGGCGCTCTGGGCGACTGTGCTGGCGCT
GGGGGCGCTGTACGCTCGCGGGGGGGGGGGGCCGGCGAGACCCGCTGAC
ACGACCGCGACCCCCGCGACGCGGGCGTTGGCGTAGGAGGGCCCAACATC
TGTACCACGCGAGGTGTGAGCTCCTGCCAGCGCCCGCAACCGCATCCTCC
CGGGTTGTAGACATGGTGCGCTCCACACTCGAGGACGGTCCAGTGCCTGG
CTGTGAGCCCCATGTGTGCCTGGTGCTCTGATGAGGCCCTGCCTCTGGGC
GTCACGGACCGACACTCGGGGTACACACGGACCACGAGACTACTCCGGGA
CGGAGACCCGTCACCTCGCTGTGACCTGAAGGAGAATCTGCTGAAGGATA
ACTGTGCCCCAGAATCCATCAGTGGAGCGACACTGGACTTCCTCTTAGAC
GACTTCCTATTGACACGGGGTCTTAGGTAGGAGTTCCCAGTGAGTGAGGC
CCGAGTACTAGAGGACAGGCCCCTCAGCGACAAGGGCTCTCTCAAGGGTC
ACTCACTCCGGCTCATGATCTCCTGTCCGGGGAGTCGCTGTTCCCGAGA
GGAGTTGAGCTCCCAGGTCACTCAAGTCAGTCCCCAGAGGATTGCACTCC
GGCTCCGGCCACCTCTGTCGAGGGTCCAGTGAGTTCAGTCAGGGGTCTCC
TAAGGTGAGGCCGAGGCGGGTGATGATTCGAAGAATTTCTCCATGGAAGT
GCGGCAGGTGGAGGATTACCGTGTGGACATCCTACTAAGGTTCTTAAAGA
GGTAGGTTCACGGGGTCCAGGTCCTAATGGGACACGTGTAGTACTACTTG
ATGGAGGTGTCTTACTCCATGAAGGATGATCTGTGGAGGATCCAGAACCT
GATGATGAACTACCTGGACAGAATGAGGTACTTCCTACTAGACACCTCGT
AGGTCTTGGACGGTACGAAGCTGGCCACCCAGATGGGAAAGCTCACCAGT
AACCTGCGGATTGGCTTGGGGCCATGGTTCGACCGGTGGGTCTACGCTTT
GGAGTGGTCATTGGACGCCTAACCGAAGCCCGCATTTGTGGACAAGCCTG
TGTCACCATACATGTATATCTCCCCACCAGAGGCCCTCGAACGTAAACAC
CTGTTCGGACACAGTGGTATGTACATATAGAGGGGTGGTCTCCGGGAGCT
TAACCCCTGCTATGATATGAAGACCACCTGCTTGCCCATGTTTGGCTACA
AAGACGTGCTGTTGGGGACGATACTATACTTGTGGTGGACGAACGGGTAC
AAACCGATGTTTGTGCACGACACGCTAACTGACCAGGTGACCCGCTTCAA
TGAGGAAGTGAAGAAGCAGAGTGTGTCACGGTGCGATTGACTGGTGCACT
GGGCGAAGTTACTCCTTCACTTCTTCGTCTCACACAGTGCCAACCGAGAT
GCCCCAGAGGGTGGCTTTGATGCCATCATGCAGGCTACAGTGTGTGATGA
ATTGGCTCTACGGGGTCTCGGACGGAAACTACGGTAGTAGGTCCGATGTC
AGACTTGTACTTAAGATTGGCTGGAGGAATGATGCATCCCACTTGTGGTG
TTTACCACTGATGCCAAGACTTTCTAACCGACGTCCTTACTACGTAGGGT
GAACGACCACAAATGGTGACTACGGTTCTGACATATAGCATTGGACGGAA
GGCTGGCAGGCATTGTCCAGCCTAATGACGGGCAGTGTCATGTATATCGT
```

SEQUENCE LISTING:

AACCTGCCTTCCGACCGTCCGTAAGAGGTCGGATTACTGCCCGTCACAGT

AGTTGGTAGTGACAATCATTACTGTGCCTCCACTACCATGGATTATCCCT

CTTTGGGGCTGCAAGCATCACTGTTAGTAATGAGACGGAGGTGATGGTAC

CTAATAGGGAGAAACCCGGACATGACTGTTAAGCTATCCCAGAAAACAT

CAATTTGATGTTTGGAGTGACTGAAAATGTATACTGACTCTTCGATAGGG

TGTTTTTGTAGTTAAACTAGAAACGTCACTGACTTTTAGATGTCAATGTC

TATCAGAACTATAGTGAGCTCATCCCAGGGACCACAGTTGGGGTTCTGTC

CCAGTTAGAGATAGTCTTGATATCACTCGAGTAGGGTCCCTGGTGTCAAC

CCGAAGACAGGATGGATTCCAGCAATGTCCTCCAGCTCATTGTTGATGCT

TATGGGAAAATCCGTTCTAAATACCTAAGGTCGTTACAGGAGGTGGAGTA

ACAACTACGAATACCCTTTTAGGCAAGATTTGTAGAGCTGGAAGTGCGTG

ACCTCGGTGAAGAGYTGTGTGTATCCTTCAATGCCACCTGCCATCTGGAC

CTTCACGCACTGGAGGGACTTCTCAACAGAGATAGGAAGTTACGGTGGAC

GGTCAAGAATGAGGTCATGCGTGGGCTCAAGTCTTGTATGGGACTCAAGA

TTGGAGACACGGAGTTGTTACTCCAGTAGGGACCGGAGTTCAGAAGATAC

CGTGAGTTCTAACCTCTGTGGGTGAGCTTCAGCATTGAGGCCAAGGTGCG

AGGCTGTTTTAGGAGAAGGAGAAGTGGTTTCAGTCGAAGTCGTAACTCCG

GTTCGACGCTGCGACAGGGGTCCTCTTCGTCTTCAGGAAAACCATAAAGC

CGGTGGGCTTCAAGGACAGCCTGATCGTCCAGGTCAGCTTTGATTGTGAC

TGGTATTTGGGGCAGCCGAAGTTCCTGTCGGACTAGCAGGTCCAGTGGAA

ACTAACACTGTGTGCCTGCCAGGCCCAAGCTGAACCTAATAGCCATCGCT

GCAACAATGGCAATGGGACCAGACGGACGGTGCGGGTTCGACTTGGATTA

TCGGTAGCGAGGTTGTTAGCGTTACCCTGGTTTGAGTGTGGGGTATGCCG

TTGTGGGCCTGGCTGGCTGGGATCGGFTGTGTGAGTGGTCAAAACTCACA

CCCCATACGGCAACACCCGGACCGACCGACCCTAGGGTCACACTCACGAG

TGAGGAGGACTATCGGCCTTCCCAGCAGGACGAATGCAGCCCGCGGGAGG

GTCAGCCCGTCCTGCTCCTGATAGCGGGAAGGGTCGTCCTGCTTACGTCG

GGGGCCCTCCCAGTCGGGCAGTGCAGCCAGCGGGGCGAGTGCCTCTGTGG

TCAATGTGTCTGCCACAGCAGTGACTTTGGCACGTCGGTCGCCCCGCTCA

CGGAGACACCAGTTACACAGACGGTGTCGTCACTGAAACCGAAGATCACG

GGCAAGTACTGCGAGTGTGACGACTTCTCCTGTGTCCGCTACAAGGGGGA

GTTCTAGTGCCCGTTCATGACGCTCACACTGCTGAAGAGGACACAGGCGA

TGTTCCCCCTCATGTGCTCAGGCCATGGCCAGTGCAGCTGTGGGGACTGC

CTGTGTGACTCCGACTGGACCTACACGAGTCCGGTACCGGTCACGTCGAC

ACCCCTGACGGACACACTGAGGCTGACCTGGGGCTACTACTGCAACTGTA

CCACGCGTACTGACACCTGCATGTCCAGCAATGGGCTGCTGCCGATGATG

ACGTTGACATGGTGCGCATGACTGTGGACGTACAGGTCGTTACCCGACGA

CTGCAGCGGCCGGGCAAGTGTGAATGTGGCAGCTGTGTCTGTATCCAGC

CGGGCTCCTATACGTCGCCGGCCCCGTTCACACTTACACCGTCGACACAG

ACATAGGTCGGCCCGAGGATAGGGGACACCTGTGAGAAGTGCCCCACCTG

CCCAGATGCCTGCACCTTTAAGAAAGAATGTCCCCTGTGGACACTCTTCA

CGGGGTGGACGGGTCTACGGACGTGGAAATTCTTTCTTACAGTGGAGTGT

AAGAAGTTTGACCGGGAGCCCTACATGACGAAAATACCTGCAACCGTTA

CCACCTCACATTCTTCAAACTGGCCCCTCGGGATGTACTGCTTTTATGGA

CGTTGGCAATGTGCCGTGACGAGATTGAGTCAGTGAAAGAGCTTAAGGAC

ACTGGCAAGGATGCAGTGAATACGGCACTGCTCTAACTCAGTCACTTTCT

CGAATTCCTGTGACCGTTCCTACGTCACTTATGTACCTATAAGAATGAGG

ATGACTGTGTCGTCAGATTCCAGTACTATGAAGATTCTAGTACATGGATA

TTCTTACTCCTACTGACACAGCAGTCTAAGGTCATGATACTTCTAAGATC

AGGAAAGTCCATCCTGTATGTGGTAGAAGAGCCAGAGTGTCCCAAGGGCC

CTGACATCCTGCCTTTCAGGTAGGACATACACCATCTTCTCGGTCTCACA

GGGTTCCCGGGACTGTAGGACGTGGTCCTGCTCTCAGTGATGGGGCCAT

TCTGCTCATTGGCCTTGCCGCCCTGCTCATCCACCAGGACGAGAGTCACT

ACCCCCGGTAAGACGAGTAACCGGAACGGCGGGACGAGTAGTGGAAACTC

CTCATCACCATCCACGACCGAAAAGAGTTCGCTAAATTTGAGGAAGAACG

CACCTTTGAGGAGTAGTGGTAGGTGCTGGCTTTTCTCAAGCGATTTAAAC

TCCTTCTTGCGGCCAGAGCAAAATGGGACACAGCCAACAACCCACTGTAT

AAAGAGGCCACGTCTACCTTCCGGTCTCGTTTTACCCTGTGTCGGTTGTT

GGGTGACATATTTCTCCGGTGCAGATGGAAGACCAATATCACGTACCGGG

GCACTTAATGGTTATAGTGCATGGCCCCGTGAATT

What is claimed is:

1. An antibody or antigen-binding fragment thereof that binds to glycoprotein IIb/IIIa (GPIIb/IIIa), wherein the antibody or the antigen-binding fragment thereof comprises a heavy chain variable region (VH) comprising VH complementarity determining region (CDR)1, VH CDR2, and VH CDR3, wherein:
the VH CDR1 comprises the amino acid sequence AYAMS (SEQ ID NO:31);
the VH CDR2 comprises the amino acid sequence SISSGGTTYYPDSVKR (SEQ ID NO:32); and
the VH CDR3 comprises the amino acid sequence GGDYGYALDY (SEQ ID NO:33); and
wherein the antibody or the antigen-binding fragment thereof comprises a light chain variable region (VL) comprising VL CDR1, VL CDR2, and VL CDR3, wherein:
the VL CDR1 comprises the amino acid sequence RASSSVNYMY (SEQ ID NO:34);
the VL CDR2 comprises the amino acid sequence YTSNLAP (SEQ ID NO:35); and
the VL CDR3 comprises the amino acid sequence QQFSSSPWT (SEQ ID NO:36).

2. The antibody or antigen-binding fragment thereof of claim 1, wherein the VH comprises the amino acid sequence set forth in SEQ ID NO:1 and the VL comprises the amino acid sequence set forth in SEQ ID NO:2.

3. The antibody or antigen-binding fragment thereof of claim 1, wherein the antibody or antigen-binding molecule thereof comprises or consists of a single chain Fv, a diabody, a minibody, a polypeptide chain of an antibody, an F(ab')$_2$, or, an F(ab).

4. The antibody or antigen-binding fragment thereof of claim 2, wherein the antibody or antigen-binding molecule thereof comprises or consists of a single chain Fv, a diabody, a minibody, a polypeptide chain of an antibody, an F(ab')$_2$, or, an F(ab).

5. A pharmaceutical composition comprising the antibody or antigen-binding molecule thereof of claim 1 and a pharmaceutically acceptable carrier.

6. A pharmaceutical composition comprising the antibody or antigen-binding molecule thereof of claim 2 and a pharmaceutically acceptable carrier.

7. A pharmaceutical composition comprising the antibody or antigen-binding molecule thereof of claim 3 and a pharmaceutically acceptable carrier.

8. A pharmaceutical composition comprising the antibody or antigen-binding molecule thereof of claim 4 and a pharmaceutically acceptable carrier.

* * * * *